(12) United States Patent
Reed et al.

(10) Patent No.: US 12,360,114 B2
(45) Date of Patent: *Jul. 15, 2025

(54) METHODS AND COMPOSITIONS FOR PROTEIN SEQUENCING

(71) Applicant: Quantum-Si Incorporated, Branford, CT (US)

(72) Inventors: Brian Reed, Madison, CT (US); Jeremy Lackey, Foster City, CA (US); Haidong Huang, Madison, CT (US)

(73) Assignee: Quantum-Si Incorporated, Branford, CT (US)

( * ) Notice: Subject to any disclaimer, the term of this patent is extended or adjusted under 35 U.S.C. 154(b) by 38 days.

This patent is subject to a terminal disclaimer.

(21) Appl. No.: 16/709,024

(22) Filed: Dec. 10, 2019

(65) Prior Publication Data

US 2020/0209255 A1 Jul. 2, 2020

Related U.S. Application Data

(63) Continuation of application No. 16/686,028, filed on Nov. 15, 2019.

(60) Provisional application No. 62/907,507, filed on Sep. 27, 2019, provisional application No. 62/768,076, filed on Nov. 15, 2018.

(51) Int. Cl.

| | | |
|---|---|---|
| *G01N 33/58* | (2006.01) | |
| *C07K 14/47* | (2006.01) | |
| *C07K 19/00* | (2006.01) | |
| *C12Q 1/6806* | (2018.01) | |
| *G01N 1/28* | (2006.01) | |
| *G01N 21/64* | (2006.01) | |
| *G01N 33/68* | (2006.01) | |
| *G16B 25/10* | (2019.01) | |
| *G16B 30/00* | (2019.01) | |
| *G16B 40/00* | (2019.01) | |
| *G16B 40/10* | (2019.01) | |
| *G16B 50/00* | (2019.01) | |
| *G16B 50/30* | (2019.01) | |

(52) U.S. Cl.
CPC ........... *G01N 33/581* (2013.01); *C07K 14/47* (2013.01); *C07K 19/00* (2013.01); *C12Q 1/6806* (2013.01); *G01N 1/28* (2013.01); *G01N 21/6428* (2013.01); *G01N 33/58* (2013.01); *G01N 33/582* (2013.01); *G01N 33/6821* (2013.01); *G01N 33/6824* (2013.01); *G16B 25/10* (2019.02); *G16B 40/00* (2019.02); *G16B 40/10* (2019.02); *G16B 50/30* (2019.02); *G01N 2021/6439* (2013.01); *G01N 2458/00* (2013.01); *G16B 30/00* (2019.02); *G16B 50/00* (2019.02)

(58) Field of Classification Search
None
See application file for complete search history.

(56) References Cited

U.S. PATENT DOCUMENTS

| | | |
|---|---|---|
| 5,707,804 A | 1/1998 | Mathies et al. |
| 5,851,840 A | 12/1998 | Sluka et al. |
| 6,153,442 A | 11/2000 | Pirio et al. |
| 6,248,518 B1 | 6/2001 | Parkhurst et al. |
| 6,255,083 B1 | 7/2001 | Williams |
| 6,762,048 B2 | 7/2004 | Williams |
| 6,787,308 B2 | 9/2004 | Balasubramanian et al. |
| 6,846,638 B2 | 1/2005 | Shipwash |
| 6,869,764 B2 | 3/2005 | Williams et al. |
| 6,936,702 B2 | 8/2005 | Williams et al. |
| 7,052,847 B2 | 5/2006 | Korlach et al. |
| 7,056,661 B2 | 6/2006 | Korlach et al. |
| 7,229,799 B2 | 6/2007 | Williams |
| 7,361,466 B2 | 4/2008 | Korlach et al. |
| 7,968,702 B2 | 6/2011 | Wegener et al. |
| 8,034,623 B2 | 10/2011 | Oh et al. |
| 8,084,734 B2 | 12/2011 | Vertes et al. |
| 8,153,375 B2 | 4/2012 | Travers et al. |
| 8,192,961 B2 | 6/2012 | Williams |
| 8,252,910 B2 | 8/2012 | Korlach et al. |
| 8,257,954 B2 | 9/2012 | Clark et al. |
| 8,309,330 B2 | 11/2012 | Travers et al. |
| 8,354,252 B2 | 1/2013 | Wegener et al. |
| 8,420,366 B2 | 4/2013 | Clark et al. |

(Continued)

FOREIGN PATENT DOCUMENTS

| | | |
|---|---|---|
| AU | 2003-282832 A1 | 5/2004 |
| AU | 2009251881 A1 | 12/2009 |

(Continued)

OTHER PUBLICATIONS

Witze et al., "Mapping protein post-translational modifications with mass spectrometry" 4(10 Nature Methods 798-806 (Year: 2007).*

(Continued)

*Primary Examiner* — Nancy J Leith
(74) *Attorney, Agent, or Firm* — Wolf, Greenfield & Sacks, P.C.

(57) ABSTRACT

Aspects of the application provide methods of identifying and sequencing proteins, polypeptides, and amino acids, and compositions useful for the same. In some aspects, the application provides methods of obtaining data during a degradation process of a polypeptide, and outputting a sequence representative of the polypeptide. In some aspects, the application provides amino acid recognition molecules comprising a shielding element that enhances photostability in polypeptide sequencing reactions.

22 Claims, 77 Drawing Sheets

Specification includes a Sequence Listing.

(56) References Cited

U.S. PATENT DOCUMENTS

| | | | |
|---|---|---|---|
| 8,455,193 | B2 | 6/2013 | Travers et al. |
| 8,530,154 | B2 | 9/2013 | Williams |
| 8,581,179 | B2 | 11/2013 | Franzen |
| 8,586,006 | B2 | 11/2013 | Hood |
| 8,608,929 | B2 | 12/2013 | Marziali et al. |
| 8,846,881 | B2 | 9/2014 | Korlach et al. |
| 8,906,614 | B2 | 12/2014 | Wegener et al. |
| 8,927,212 | B2 | 1/2015 | Kong et al. |
| 8,980,584 | B2 | 3/2015 | Williams |
| 9,062,091 | B2 | 6/2015 | Bjornson et al. |
| 9,238,822 | B2 | 1/2016 | Baum et al. |
| 9,404,146 | B2 | 8/2016 | Travers et al. |
| 9,435,810 | B2 | 9/2016 | Havranek et al. |
| 9,464,107 | B2 | 10/2016 | Wegener et al. |
| 9,542,527 | B2 | 1/2017 | Travers et al. |
| 9,551,031 | B2 | 1/2017 | Korlach et al. |
| 9,551,660 | B2 | 1/2017 | Kong et al. |
| 9,566,335 | B1 | 2/2017 | Emili et al. |
| 9,582,640 | B2 | 2/2017 | Travers et al. |
| 9,600,626 | B2 | 3/2017 | Travers et al. |
| 9,678,080 | B2 | 6/2017 | Bjornson et al. |
| 9,719,073 | B2 | 8/2017 | Emig et al. |
| 9,759,658 | B2 | 9/2017 | Rothberg et al. |
| 9,845,501 | B2 | 12/2017 | Williams |
| 9,879,319 | B2 | 1/2018 | Korlach et al. |
| 9,885,657 | B2 | 2/2018 | Rothberg et al. |
| 9,910,956 | B2 | 3/2018 | Travers et al. |
| 9,957,291 | B2 | 5/2018 | Sebo et al. |
| 10,023,605 | B2 | 7/2018 | Bjornson et al. |
| 10,048,208 | B2 | 8/2018 | Rothberg et al. |
| 10,066,258 | B2 | 9/2018 | Kong et al. |
| 10,138,291 | B2 | 11/2018 | Chhabra et al. |
| 10,150,872 | B2 | 12/2018 | Zheng et al. |
| 10,161,002 | B2 | 12/2018 | Korlach et al. |
| 10,246,742 | B2 | 4/2019 | Rothberg et al. |
| 10,481,162 | B2 | 11/2019 | Emili et al. |
| 10,544,449 | B2 | 1/2020 | Shen et al. |
| 10,545,153 | B2 | 1/2020 | Marcotte et al. |
| 10,551,624 | B2 | 2/2020 | Rothberg et al. |
| 10,570,445 | B2 | 2/2020 | Kong et al. |
| 10,592,121 | B2 | 3/2020 | Malladi et al. |
| 10,676,788 | B2 | 6/2020 | Shen et al. |
| 10,745,750 | B2 | 8/2020 | Korlach et al. |
| 10,787,573 | B2 | 9/2020 | Zheng et al. |
| 10,845,308 | B2 | 11/2020 | Rothberg et al. |
| 11,237,326 | B2 | 2/2022 | Rothberg et al. |
| 11,573,238 | B2 | 2/2023 | Callewaert et al. |
| 11,959,920 | B2 | 4/2024 | Reed et al. |
| 12,000,835 | B2 * | 6/2024 | Reed ............... C07K 19/00 |
| 12,055,548 | B2 | 8/2024 | Reed et al. |
| 12,065,466 | B2 | 8/2024 | Reed et al. |
| 12,174,196 | B2 | 12/2024 | Reed et al. |
| 2005/0042633 | A1 | 2/2005 | Williams |
| 2005/0266456 | A1 | 12/2005 | Williams et al. |
| 2006/0014212 | A1 | 1/2006 | Benkovic et al. |
| 2007/0072196 | A1 | 3/2007 | Xu et al. |
| 2007/0219367 | A1 | 9/2007 | Shchepinov et al. |
| 2009/0028832 | A1 | 1/2009 | Chung et al. |
| 2009/0105341 | A1 | 4/2009 | Stanton |
| 2009/0263802 | A1 | 10/2009 | Drmanac |
| 2010/0009872 | A1 | 1/2010 | Eid et al. |
| 2010/0029494 | A1 | 2/2010 | Cherkasov et al. |
| 2010/0035254 | A1 | 2/2010 | Williams |
| 2010/0311098 | A1 | 12/2010 | Heck et al. |
| 2011/0003343 | A1 | 1/2011 | Nikiforov et al. |
| 2011/0281776 | A1 | 11/2011 | Eshoo et al. |
| 2012/0178676 | A1 | 7/2012 | Barrack et al. |
| 2012/0322692 | A1 | 12/2012 | Pham et al. |
| 2013/0316912 | A1 | 11/2013 | Bjornson et al. |
| 2014/0273004 | A1 | 9/2014 | Havranek et al. |
| 2017/0037462 | A1 | 2/2017 | Turner et al. |
| 2017/0052194 | A1 | 2/2017 | Havranek et al. |
| 2017/0136433 | A1 | 5/2017 | Sun et al. |
| 2017/0204401 | A1 | 7/2017 | Brevnova et al. |
| 2017/0212126 | A1 | 7/2017 | Emili et al. |
| 2017/0276686 | A1 | 9/2017 | Marcotte et al. |
| 2017/0336419 | A1 | 11/2017 | Tran et al. |
| 2018/0172906 | A1 | 6/2018 | Rothberg et al. |
| 2018/0211003 | A1 | 7/2018 | Travers et al. |
| 2018/0299460 | A1 | 10/2018 | Emili |
| 2018/0320224 | A1 | 11/2018 | Guablomme et al. |
| 2018/0326412 | A1 | 11/2018 | Rothberg et al. |
| 2018/0346507 | A1 | 12/2018 | Sebo et al. |
| 2019/0010183 | A1 | 1/2019 | Bjornson et al. |
| 2019/0024168 | A1 | 1/2019 | Rothberg et al. |
| 2019/0025511 | A1 | 1/2019 | Rothberg et al. |
| 2019/0145982 | A1 | 5/2019 | Chee et al. |
| 2019/0194709 | A1 | 6/2019 | Church et al. |
| 2019/0249153 | A1 | 8/2019 | Kamtekar et al. |
| 2019/0285644 | A1 | 9/2019 | Regev et al. |
| 2020/0141944 | A1 | 5/2020 | Emili et al. |
| 2020/0148727 | A1 | 5/2020 | Tullman et al. |
| 2020/0209249 | A1 | 7/2020 | Reed et al. |
| 2020/0209253 | A1 | 7/2020 | Reed et al. |
| 2020/0209254 | A1 | 7/2020 | Reed et al. |
| 2020/0209256 | A1 | 7/2020 | Reed et al. |
| 2020/0209257 | A1 | 7/2020 | Reed et al. |
| 2020/0217853 | A1 | 7/2020 | Estandian et al. |
| 2020/0219590 | A1 | 7/2020 | Reed et al. |
| 2020/0231956 | A1 | 7/2020 | Callewaert et al. |
| 2020/0300861 | A1 | 9/2020 | Mena et al. |
| 2020/0348307 | A1 | 11/2020 | Beierle et al. |
| 2020/0348308 | A1 | 11/2020 | Chee et al. |
| 2020/0395099 | A1 | 12/2020 | Meyer et al. |
| 2020/0400677 | A1 | 12/2020 | Boyden et al. |
| 2021/0071162 | A1 | 3/2021 | Franzetti et al. |
| 2021/0139973 | A1 | 5/2021 | Dyer et al. |
| 2021/0147474 | A1 | 5/2021 | Dyer et al. |
| 2021/0148921 | A1 | 5/2021 | Reed et al. |
| 2021/0148922 | A1 | 5/2021 | Dyer et al. |
| 2021/0354134 | A1 | 11/2021 | Rothberg et al. |
| 2021/0364527 | A1 | 11/2021 | Reed et al. |
| 2021/0396762 | A1 | 12/2021 | Chee et al. |
| 2022/0221467 | A1 | 7/2022 | Kirschner et al. |
| 2023/0021352 | A1 | 1/2023 | Callewaert et al. |
| 2023/0213527 | A1 | 7/2023 | Reed et al. |
| 2024/0272169 | A1 | 8/2024 | Reed et al. |
| 2024/0272170 | A1 | 8/2024 | Reed et al. |
| 2024/0295562 | A1 | 9/2024 | Reed et al. |
| 2024/0344122 | A1 | 10/2024 | Dyer et al. |

FOREIGN PATENT DOCUMENTS

| | | | |
|---|---|---|---|
| AU | 2013226090 A1 | 9/2014 | |
| CN | 109923216 A | 6/2019 | |
| CN | 110199019 A | 9/2019 | |
| EP | 3008094 A1 | 4/2016 | |
| JP | 2019-531715 A | 11/2019 | |
| WO | WO 2005/044836 A2 | 5/2005 | |
| WO | WO 2007/070572 A2 | 6/2007 | |
| WO | WO 2007/123708 A1 | 11/2007 | |
| WO | WO 2010/044892 A1 | 4/2010 | |
| WO | WO 2010/065322 A1 | 6/2010 | |
| WO | WO 2010/065531 A1 | 6/2010 | |
| WO | WO 2010/115016 A2 | 10/2010 | |
| WO | WO 2013/112745 A1 | 8/2013 | |
| WO | WO 2013/130683 A2 | 9/2013 | |
| WO | WO 2014/014347 A1 | 1/2014 | |
| WO | WO 2014/205401 A1 | 12/2014 | |
| WO | WO 2016/069124 A1 | 5/2016 | |
| WO | WO 2016/164530 A1 | 10/2016 | |
| WO | WO 2016/193980 A1 | 12/2016 | |
| WO | WO 2017/024049 A1 | 2/2017 | |
| WO | WO 2017/192633 A1 | 11/2017 | |
| WO | WO 2018/045186 A1 | 3/2018 | |
| WO | WO 2019/040825 A1 | 2/2019 | |
| WO | WO 2019/063827 A1 * | 4/2019 | ......... G01N 33/6824 |
| WO | WO 2019/089836 A1 | 5/2019 | |
| WO | WO 2019/089846 A1 | 5/2019 | |
| WO | WO 2020/014586 A1 | 1/2020 | |
| WO | WO 2020/023488 A1 | 1/2020 | |
| WO | WO 2020/037205 A1 | 2/2020 | |
| WO | WO 2020/072907 A1 | 4/2020 | |
| WO | WO 2020/102741 A1 | 5/2020 | |

(56) References Cited

FOREIGN PATENT DOCUMENTS

| WO | WO 2020/154307 A1 | 7/2020 |
| WO | WO 2020/201350 A1 | 10/2020 |
| WO | WO 2020/219365 A1 | 10/2020 |
| WO | WO 2020/252345 A1 | 12/2020 |
| WO | WO 2021/051011 A1 | 3/2021 |
| WO | WO 2021/086913 A1 | 5/2021 |
| WO | WO 2021/236983 A2 | 11/2021 |
| WO | WO 2022/125973 A1 | 6/2022 |

OTHER PUBLICATIONS

International Search Report and Written Opinion for Application No. PCT/US2019/061831, mailed Mar. 23, 2020.
International Preliminary Report on Patentability for Application No. PCT/US2019/061831, mailed May 27, 2021.
International Search Report and Written Opinion for Application No. PCT/US2020/057638, mailed Feb. 16, 2021.
Invitation to Pay Additional Fees for Application No. PCT/US2020/057647, mailed Feb. 25, 2021.
International Search Report and Written Opinion for Application No. PCT/US2020/057647, mailed Apr. 20, 2021.
Invitation to Pay Additional Fees for Application No. PCT/US2020/057656, mailed Feb. 23, 2021.
International Search Report and Written Opinion for Application No. PCT/US2020/057656, mailed Apr. 13, 2021.
Invitation to Pay Additional Fees for Application No. PCT/US2020/057669, mailed Feb. 12, 2021.
International Search Report and Written Opinion for Application No. PCT/US2020/057669, mailed Apr. 7, 2021.
Addlagatta et al., Structural basis for the unusual specificity of *Escherichia coli* aminopeptidase N. Biochemistry. May 13, 2008;47(19):5303-11. doi: 10.1021/bi7022333. Epub Apr. 17, 2008.
Astruc et al., Dendrimers designed for functions: from physical, photophysical, and supramolecular properties to applications in sensing, catalysis, molecular electronics, photonics, and nanomedicine. Chem Rev. Apr. 14, 2010;110(4):1857-959. doi: 10.1021/cr900327d.
Bladergroen et al., Solid-phase extraction strategies to surmount body fluid sample complexity in high-throughput mass spectrometry-based proteomics. J Anal Methods Chem. 2015;2015:250131. doi: 10.1155/2015/250131. Epub Jan. 27, 2015.
Borgo et al., Computer-aided design of a catalyst for Edman degradation utilizing substrate-assisted catalysis. Protein Sci. Apr. 2015; 24(4): 571-579. https://doi.org/10.1002/pro.2633. Epub Dec. 16, 2014.
Borgo et al., Strategies for Computational Protein Design with Application to the Development of a Biomolecular Tool-kit for Single Molecule Protein Sequencing. Dissertation presented at Washington University in St. Louis. May 2014; 203 pages.
Chin et al., Addition of p-azido-L-phenylalanine to the genetic code of *Escherichia coli*. J Am Chem Soc. Aug. 7, 2002;124(31):9026-7. doi: 10.1021/ja027007w.
Cong et al., Site-specific PEGylation at histidine tags. Bioconjug Chem. Feb. 15, 2012;23(2):248-63. doi: 10.1021/bc200530x. Epub Feb. 6, 2012.
Corey et al., Generation of a hybrid sequence-specific single-stranded deoxyribonuclease. Science. Dec. 4, 1987;238(4832):1401-3. doi: 10.1126/science.3685986.
Debets et al., Aza-dibenzocyclooctynes for fast and efficient enzyme PEGylation via copper-free (3+2) cycloaddition. Chem Commun (Camb). Jan. 7, 2010;46(1):97-9. doi: 10.1039/b917797c. Epub Nov. 6, 2009.
Garcia-Guerrero et al. Crystal structure and mechanism of human carboxypeptidase O: Insights into its specific activity for acidic residues. PNAS. Apr. 24, 2018;115(17):E3932-E3939. doi: 10.1073/pnas.1803685115. Epub Apr. 10, 2018.
Giansanti et al., Six alternative proteases for mass spectrometry-based proteomics beyond trypsin. Nat Protoc. May 2016;11(5):993-1006. doi: 10.1038/nprot.2016.057. Epub Apr. 28, 2016.
Gurupriya et al., Proteases and Protease Inhibitors in Male Reproduction. In: Proteases in Physiology and Pathology. Chakraborti et al., Eds. 2017:195-216. https://doi.org/10.1007/978-981-10-2513-6_10.
Hamaguchi et al., Aptamer beacons for the direct detection of proteins. Anal Biochem. Jul. 15, 2001;294(2):126-31. doi: 10.1006/abio.2001.5169.
Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.
Kukolka et al., Synthesis of fluorescent oligonucleotide—EYFP conjugate: towards supramolecular construction of semisynthetic biomolecular antennae. Org Biomol Chem. Aug. 7, 2004;2(15):2203-6. doi: 10.1039/b406492e. Epub Jul. 8, 2004.
Lee et al., Aptamer/ISET-MS: a new affinity-based MALDI technique for improved detection of biomarkers. Anal Chem. Aug. 5, 2014;86(15):7627-34. doi: 10.1021/ac501488b. Epub Jul. 11, 2014.
Malyshev et al., Efficient and sequence-independent replication of DNA containing a third base pair establishes a functional six-letter genetic alphabet. Proc Natl Acad Sci U S A. Jul. 24, 2012;109(30):12005-10. doi: 10.1073/pnas.1205176109. Epub Jul. 6, 2012.
Mattson et al., A practical approach to crosslinking. Mol Biol Rep. Apr. 1993;17(3):167-83. doi: 10.1007/BF00986726.
Needleman et al., A general method applicable to the search for similarities in the amino acid sequence of two proteins. J Mol Biol. Mar. 1970;48(3):443-53. doi: 10.1016/0022-2836(70)90057-4.
Pearson et al., Improved tools for biological sequence comparison. PNAS. Apr. 1, 1988;85(8):2444-8. https://doi.org/10.1073/pnas.85.8.2444.
Radko et al., Evaluation of Aptamers as Affinity Reagents for an Enhancement of SRM-Based Detection of Low-Abundance Proteins in Blood Plasma. Biomedicines. May 24, 2020;8(5):133. doi: 10.3390/biomedicines8050133.
Reid et al., Application of aptamers as molecular recognition elements in lateral flow assays. Anal Biochem. Mar. 15, 2020;593:113574. doi: 10.1016/j.ab.2020.113574. Epub Jan. 3, 2020.
Richards et al., Aptamer based peptide enrichment for quantitative analysis of gonadotropin-releasing hormone by LC-MS/MS. Talanta. Apr. 1, 2016;150:671-80. doi: 10.1016/j.talanta.2016.01.006. Epub Jan. 7, 2016.
Rosen et al., Template-directed covalent conjugation of DNA to native antibodies, transferrin and other metal-binding proteins. Nat Chem. Sep. 2014;6(9):804-9. doi: 10.1038/nchem.2003. Epub Jul. 20, 2014.
Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.
Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.
Shi et al., Advancing the sensitivity of selected reaction monitoring-based targeted quantitative proteomics. Proteomics. Apr. 2012;12(8):1074-92. doi: 10.1002/pmic.201100436.
Smith et al., Comparison of biosequences. Adv Appl Math. Dec. 1981;2(4):482-9. https://doi.org/10.1016/0196-8858(81)90046-4.
Smith et al., Proteoform: a single term describing protein complexity. Nat Methods. Mar. 2013;10(3):186-7. doi: 10.1038/nmeth.2369. Author Manuscript, 4 pages.
Smith et al., Proteoforms as the next proteomics currency. Science. Mar. 9, 2018;359(6380):1106-7. doi: 10.1126/science.aat1884. Epub Mar. 8, 2018. Author Manuscript, 4 pages.
Speicher et al., UNIT 11.10 N-terminal sequence analysis of proteins and peptides. Curr Protoc Protein Sci. May 2001;Chapter:Unit 11.10. doi: 10.1002/0471140864.ps1110s08. Author Manuscript, 41 pages.
Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.

(56) References Cited

OTHER PUBLICATIONS

Swaminathan et al. A theoretical justification for single molecule peptide sequencing. PLoS Comput Biol. Feb. 25, 2015;11(2):e1004080. doi: 10.1371/journal.pcbi.1004080. eCollection Feb. 2015.
Takeda et al., Site-specific conjugation of oligonucleotides to the C-terminus of recombinant protein by expressed protein ligation. Bioorg Med Chem Lett. May 17, 2004;14(10):2407-10. doi: 10.1016/j.bmcl.2004.03.023.
Tanaka et al., Identification of low-abundance proteins in serum via the isolation of HSP72 complexes. J Proteomics. Mar. 16, 2016;136:214-21. doi: 10.1016/j.jprot.2016.01.008. Epub Jan. 15, 2016.
Thakur et al., Real-time measurement of protein-protein interactions at single-molecule resolution using a biological nanopore. Nat. Biotechnol. Jan. 2019; 37(1):96-101.
Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.
Yang et al., DNA Nanostructures as Programmable Biomolecular Scaffolds. Bioconjug Chem. Aug. 19, 2015;26(8):1381-95. doi: 10.1021/acs.bioconjchem.5b00194. Epub May 22, 2015.
Yao et al. Single-molecule protein sequencing through fingerprinting: computational assessment. Phys Biol. Aug. 12, 2015;12(5):055003. doi: 10.1088/1478-3975/12/5/055003.
Zhao et al., Modification-specific proteomics: strategies for characterization of post-translational modifications using enrichment techniques. Proteomics. Oct. 2009;9(20):4632-41. doi: 10.1002/pmic.200900398.
Kim, Probing structures of membrane proteins and their inhibitors. 2005 (Doctoral dissertation, University of Oxford), 258 pages.
Third Party Observation for European Application No. 19817882.4 mailed Dec. 20, 2021.
Callahan et al. Strategies for Development of a Next-Generation Protein Sequencing Platform. Trends Biochem Sci. Jan. 2020;45(1):76-89. doi: 10.1016/j.tibs.2019.09.005. Epub Oct. 30, 2019.
Costa et al., Fusion tags for protein solubility, purification and immunogenicity in *Escherichia coli*: the novel Fh8 system. Front Microbiol. Feb. 19, 2014;5:63. doi: 10.3389/fmicb.2014.00063.
Tullman et al., A ClpS-based N-terminal amino acid binding reagent with improved thermostability and selectivity. Biochemical Engineering Journal. Feb. 15, 2020;154:107438.
Uniprot Accession No. A0A0K1RWM1, ATP-dependent Clp protease adapter protein CLPS, XP55836295, Nov. 11, 2015. 4 pages.
Bostrom, High-throughput protein analysis using mass spectrometry-based methods (Doctoral dissertation, KTH Royal Institute of Technology). 2014. 135 pages.
Jekel et al., Use of endoproteinase Lys-C from Lysobacter enzymogenes in protein sequence analysis. Anal Biochem. Oct. 15, 1983;134(2):347-54. doi: 10.1016/0003-2697(83)90308-1.
Samyn et al., A case study of de novo sequence analysis of N-sulfonated peptides by Maldi TOF/TOF mass spectrometry. J Am Soc Mass Spectrom. Dec. 2004;15(12):1838-52. doi: 10.1016/j.jasms.2004.08.010.
Steinhardt et al., Rational design of a trispecific antibody targeting the HIV-1 Env with elevated anti-viral activity. Nat Commun. Feb. 28, 2018;9(1):877. doi: 10.1038/s41467-018-03335-4.
Wagner et al., Specificity of Aeromonas aminopeptidase toward amino acid amides and dipeptides. J Biol Chem. Feb. 25, 1972;247(4):1208-10.
U.S. Appl. No. 18/598,854, filed Mar. 7, 2024, Reed et al.
U.S. Appl. No. 18/598,736, filed Mar. 7, 2024, Reed et al.
U.S. Appl. No. 18/365,185, filed Aug. 3, 2023, Reed et al.
U.S. Appl. No. 18/145,815, filed Dec. 22, 2022, Reed et al.
U.S. Appl. No. 18/491,719, filed Oct. 20, 2023, Reed et al.
U.S. Appl. No. 18/59,9113, filed Mar. 7, 2024, Dyer et al.
Choi et al., Structural basis for the recognition of N-end rule substrates by the UBR box of ubiquitin ligases. Nat Struct Mol Biol. Oct. 2010;17(10):1175-81. doi: 10.1038/nsmb.1907. Epub Sep. 12, 2010.
Munoz-Escobar et al., Bound Waters Mediate Binding of Diverse Substrates to a Ubiquitin Ligase. Structure. May 2, 2017;25(5):719-729.e3. doi: 10.1016/j.str.2017.03.004. Epub Apr. 6, 2017.
Stein et al., Structural Basis of an N-Degron Adaptor with More Stringent Specificity. Structure. Feb. 2, 2016;24(2):232-42. doi: 10.1016/j.str.2015.12.008. Epub Jan. 21, 2016.
Tullman et al., Engineering ClpS for selective and enhanced N-terminal amino acid binding. Appl Microbiol Biotechnol. Mar. 2019;103(6):2621-2633. doi: 10.1007/s00253-019-09624-2. Epub Jan. 24, 2019.
Brownstein et al., Paired single residue-transposed Lys-N and Lys-C digestions for label-free identification of N-terminal and C-terminal MS/MS peptide product ions: ultrahigh resolution Fourier transform ion cyclotron resonance mass spectrometry and tandem mass spectrometry for peptide de novo sequencing. Rapid Communications in Mass Spectrometry. Apr. 15, 2015;29(7):659-66.

\* cited by examiner

S. elongatus ClpS2 mean pulse duration distribution
Leu human GID4
distribution of median pulse durations
Proline (QP64: PGLWAADDDW)(SEQ ID NO: 166)

DBCO-Cy3

Determining the Degree of Labeling for K287pAzF-Cy3 yPIP

Degree of Labeling (DOL) = 103%

|  | N pulses | mean pulse width (s) | median pulse width (s) | pulse rate (pulses/min) |
|---|---|---|---|---|
| atClpS1 | 98 | 1.3 | 0.63 | 8.1 |
| atClpS2-V1 | 169 | 1.0 | 0.35 | 14.1 |

SEQUENCE LISTING

<160> NUMBER OF SEQ ID NOS: 166

<210> SEQ ID NO 1
<211> LENGTH: 103
<212> TYPE: PRT
<213> ORGANISM: Agrobacterium tumifaciens

<400> SEQUENCE: 1

Met Ser Asp Ser Pro Val Asp Leu Lys Pro Lys Pro Lys Val Lys Pro
1               5                   10                  15

Lys Leu Glu Arg Pro Lys Leu Tyr Lys Val Met Leu Leu Asn Asp Asp
            20                  25                  30

Tyr Thr Pro Met Ser Phe Val Thr Val Val Leu Lys Ala Val Phe Arg
        35                  40                  45

Met Ser Glu Asp Thr Gly Arg Arg Val Met Met Thr Ala His Arg Phe
    50                  55                  60

Gly Ser Ala Val Val Val Cys Glu Arg Asp Ile Ala Glu Thr Lys
65                  70                  75                  80

Ala Lys Glu Ala Thr Asp Leu Gly Lys Glu Ala Gly Phe Pro Leu Met
                85                  90                  95

Phe Thr Thr Glu Pro Glu Glu
            100

<210> SEQ ID NO 2
<211> LENGTH: 103
<212> TYPE: PRT
<213> ORGANISM: Agrobacterium tumifaciens

<400> SEQUENCE: 2

Met Ser Asp Ser Pro Val Asp Leu Lys Pro Lys Pro Lys Val Lys Pro
1               5                   10                  15

Lys Leu Glu Arg Pro Lys Leu Tyr Lys Val Met Leu Leu Asn Asp Asp
            20                  25                  30

Tyr Thr Pro Arg Glu Phe Val Thr Val Val Leu Lys Ala Val Phe Arg
        35                  40                  45

Met Ser Glu Asp Thr Gly Arg Arg Val Met Met Thr Ala His Arg Phe
    50                  55                  60

Gly Ser Ala Val Val Val Cys Glu Arg Asp Ile Ala Glu Thr Lys
65                  70                  75                  80

Ala Lys Glu Ala Thr Asp Leu Gly Lys Glu Ala Gly Phe Pro Leu Met
                85                  90                  95

Phe Thr Thr Glu Pro Glu Glu
            100

<210> SEQ ID NO 3
<211> LENGTH: 103
<212> TYPE: PRT
<213> ORGANISM: Agrobacterium tumifaciens

<400> SEQUENCE: 3

Met Ser Asp Ser Pro Val Asp Leu Lys Pro Lys Pro Lys Val Lys Pro
1               5                   10                  15

Lys Leu Glu Arg Pro Lys Leu Tyr Lys Val Met Leu Leu Asn Asp Asp
            20                  25                  30

Tyr Thr Pro Arg Glu Phe Val Thr Val Val Leu Lys Ala Val Phe Arg
            35                  40                  45

Met Ser Glu Asp Thr Gly Arg Arg Val Met Met Thr Ala His Arg Phe
 50                  55                  60

Gly Ser Ala Val Val Val Ser Glu Arg Asp Ile Ala Glu Thr Lys
 65                  70                  75                  80

Ala Lys Glu Ala Thr Asp Leu Gly Lys Glu Ala Gly Phe Pro Leu Met
                85                  90                  95

Phe Thr Thr Glu Pro Glu Glu
            100

<210> SEQ ID NO 4
<211> LENGTH: 117
<212> TYPE: PRT
<213> ORGANISM: Agrobacterium tumifaciens

<400> SEQUENCE: 4

Met Ile Ala Glu Pro Ile Cys Met Gln Gly Glu Gly Asp Gly Glu Asp
 1               5                  10                  15

Gly Gly Thr Asn Arg Gly Thr Ser Val Ile Thr Arg Val Lys Pro Lys
                20                  25                  30

Thr Lys Arg Pro Asn Leu Tyr Arg Val Leu Leu Asn Asp Asp Tyr
            35                  40                  45

Thr Pro Met Glu Phe Val Ile His Ile Leu Glu Arg Phe Phe Gln Lys
 50                  55                  60

Asp Arg Glu Ala Ala Thr Arg Ile Met Leu His Val His Gln His Gly
 65                  70                  75                  80

Val Gly Glu Cys Gly Val Phe Thr Tyr Glu Val Ala Glu Thr Lys Val
                85                  90                  95

Ser Gln Val Met Asp Phe Ala Arg Gln His Gln His Pro Leu Gln Cys
                100                 105                 110

Val Met Glu Lys Lys
            115

<210> SEQ ID NO 5
<211> LENGTH: 103
<212> TYPE: PRT
<213> ORGANISM: Agrobacterium tumifaciens

<400> SEQUENCE: 5

Met Ser Asp Ser Pro Val Asp Leu Lys Pro Lys Pro Lys Val Lys Pro
 1               5                  10                  15

Lys Leu Glu Arg Pro Lys Leu Tyr Lys Val Met Leu Leu Asn Asp Asp
                20                  25                  30

Tyr Thr Pro Met Ser Phe Val Thr Val Val Leu Lys Ala Val Phe Arg
            35                  40                  45

Met Ser Glu Asp Thr Gly Arg Arg Val Met Met Thr Ala His Arg Phe
 50                  55                  60

Gly Ser Ala Val Val Val Ser Glu Arg Asp Ile Ala Glu Thr Lys
 65                  70                  75                  80

Ala Lys Glu Ala Thr Asp Leu Gly Lys Glu Ala Gly Phe Pro Leu Met
                85                  90                  95

Phe Thr Thr Glu Pro Glu Glu
            100

<210> SEQ ID NO 6
<211> LENGTH: 117

```
<212> TYPE: PRT
<213> ORGANISM: Agrobacterium tumifaciens

<400> SEQUENCE: 6

Met Ile Ala Glu Pro Ile Ser Met Gln Gly Glu Gly Asp Gly Glu Asp
1               5                   10                  15

Gly Gly Thr Asn Arg Gly Thr Ser Val Ile Thr Arg Val Lys Pro Lys
            20                  25                  30

Thr Lys Arg Pro Asn Leu Tyr Arg Val Leu Leu Asn Asp Asp Tyr
        35                  40                  45

Thr Pro Met Glu Phe Val Ile His Ile Leu Glu Arg Phe Phe Gln Lys
    50                  55                  60

Asp Arg Glu Ala Ala Thr Arg Ile Met Leu His Val His Gln His Gly
65                  70                  75                  80

Val Gly Glu Cys Gly Val Phe Thr Tyr Glu Val Ala Glu Thr Lys Val
                85                  90                  95

Ser Gln Val Met Asp Phe Ala Arg Gln His Gln His Pro Leu Gln Cys
            100                 105                 110

Val Met Glu Lys Lys
        115

<210> SEQ ID NO 7
<211> LENGTH: 117
<212> TYPE: PRT
<213> ORGANISM: Agrobacterium tumifaciens

<400> SEQUENCE: 7

Met Ile Ala Glu Pro Ile Ser Met Gln Gly Glu Gly Asp Gly Glu Asp
1               5                   10                  15

Gly Gly Thr Asn Arg Gly Thr Ser Val Ile Thr Arg Val Lys Pro Lys
            20                  25                  30

Thr Lys Arg Pro Asn Leu Tyr Arg Val Leu Leu Asn Asp Asp Tyr
        35                  40                  45

Thr Pro Met Glu Phe Val Ile His Ile Leu Glu Arg Phe Phe Gln Lys
    50                  55                  60

Asp Arg Glu Ala Ala Thr Arg Ile Met Leu His Val His Gln His Gly
65                  70                  75                  80

Val Gly Glu Ser Gly Val Phe Thr Tyr Glu Val Ala Glu Thr Lys Val
                85                  90                  95

Ser Gln Val Met Asp Phe Ala Arg Gln His Gln His Pro Leu Gln Ser
            100                 105                 110

Val Met Glu Lys Lys
        115

<210> SEQ ID NO 8
<211> LENGTH: 103
<212> TYPE: PRT
<213> ORGANISM: Agrobacterium tumifaciens

<400> SEQUENCE: 8

Met Ser Asp Ser Pro Val Asp Leu Lys Pro Lys Pro Lys Val Lys Pro
1               5                   10                  15

Lys Leu Glu Arg Pro Lys Leu Tyr Lys Val Ile Leu Leu Asn Asp Asp
            20                  25                  30

Tyr Thr Pro Met Glu Phe Val Val Glu Val Leu Lys Arg Val Phe Asn
        35                  40                  45

Met Ser Glu Glu Gln Ala Arg Arg Val Met Met Thr Ala His Lys Lys
```

```
                50                  55                  60
Gly Lys Ala Val Val Gly Val Cys Pro Arg Asp Ile Ala Glu Thr Lys
 65                  70                  75                  80

Ala Lys Gln Ala Thr Asp Leu Ala Arg Glu Ala Gly Phe Pro Leu Met
                 85                  90                  95

Phe Thr Thr Glu Pro Glu Glu
            100

<210> SEQ ID NO 9
<211> LENGTH: 103
<212> TYPE: PRT
<213> ORGANISM: Agrobacterium tumifaciens

<400> SEQUENCE: 9

Met Ser Asp Ser Pro Val Asp Leu Lys Pro Lys Pro Lys Val Lys Pro
 1               5                  10                  15

Lys Leu Glu Arg Pro Lys Leu Tyr Lys Val Ile Leu Leu Asn Asp Asp
                20                  25                  30

Tyr Thr Pro Met Glu Phe Val Val Glu Val Leu Lys Arg Val Phe Asn
                35                  40                  45

Met Ser Glu Glu Gln Ala Arg Arg Val Met Met Thr Ala His Lys Lys
     50                  55                  60

Gly Lys Ala Val Val Gly Val Ser Pro Arg Asp Ile Ala Glu Thr Lys
 65                  70                  75                  80

Ala Lys Gln Ala Thr Asp Leu Ala Arg Glu Ala Gly Phe Pro Leu Met
                 85                  90                  95

Phe Thr Thr Glu Pro Glu Glu
            100

<210> SEQ ID NO 10
<211> LENGTH: 95
<212> TYPE: PRT
<213> ORGANISM: Synechococcus elongatus

<400> SEQUENCE: 10

Met Ala Val Glu Thr Ile Gln Lys Pro Glu Thr Thr Thr Lys Arg Lys
 1               5                  10                  15

Ile Ala Pro Arg Tyr Arg Val Leu Leu His Asn Asp Asp Phe Asn Pro
                20                  25                  30

Met Glu Tyr Val Val Met Val Leu Met Gln Thr Val Pro Ser Leu Thr
                35                  40                  45

Gln Pro Gln Ala Val Asp Ile Met Met Glu Ala His Thr Asn Gly Thr
     50                  55                  60

Gly Leu Val Ile Thr Cys Asp Ile Glu Pro Ala Glu Phe Tyr Cys Glu
 65                  70                  75                  80

Gln Leu Lys Ser His Gly Leu Ser Ser Ile Glu Pro Asp Asp
                85                  90                  95

<210> SEQ ID NO 11
<211> LENGTH: 136
<212> TYPE: PRT
<213> ORGANISM: Synechococcus elongatus

<400> SEQUENCE: 11

Met Ser Pro Gln Pro Asp Glu Ser Val Leu Ser Ile Leu Gly Val Pro
 1               5                  10                  15

Arg Pro Cys Val Lys Lys Arg Ser Arg Asn Asp Ala Phe Val Leu Thr
                20                  25                  30
```

```
Val Leu Thr Cys Ser Leu Gln Ala Ile Ala Ala Pro Ala Thr Ala Pro
            35                  40                  45

Gly Thr Thr Thr Thr Arg Val Arg Gln Pro Tyr Pro His Phe Arg Val
 50                  55                  60

Ile Val Leu Asp Asp Val Asn Thr Phe Gln His Val Ala Glu Cys
65                  70                  75                  80

Leu Leu Lys Tyr Ile Pro Gly Met Thr Gly Asp Arg Ala Trp Asp Leu
                    85                  90                  95

Thr Asn Gln Val His Tyr Glu Gly Ala Ala Thr Val Trp Ser Gly Pro
                100                 105                 110

Gln Glu Gln Ala Glu Leu Tyr His Glu Gln Leu Arg Arg Glu Gly Leu
                115                 120                 125

Thr Met Ala Pro Leu Glu Ala Ala
                130                 135
```

<210> SEQ ID NO 12
<211> LENGTH: 90
<212> TYPE: PRT
<213> ORGANISM: Thermosynechococcus elongatus

<400> SEQUENCE: 12

```
Met Pro Gln Glu Arg Gln Val Thr Arg Lys His Tyr Pro Asn Tyr
1               5                   10                  15

Lys Val Ile Val Leu Asn Asp Asp Phe Asn Thr Phe Gln His Val Ala
                    20                  25                  30

Ala Cys Leu Met Lys Tyr Ile Pro Asn Met Thr Ser Asp Arg Ala Trp
                35                  40                  45

Glu Leu Thr Asn Gln Val His Tyr Glu Gly Gln Ala Ile Val Trp Val
 50                  55                  60

Gly Pro Gln Glu Gln Ala Glu Leu Tyr His Glu Gln Leu Leu Arg Ala
65                  70                  75                  80

Gly Leu Thr Met Ala Pro Leu Glu Pro Glu
                    85                  90
```

<210> SEQ ID NO 13
<211> LENGTH: 106
<212> TYPE: PRT
<213> ORGANISM: Escherichia coli

<400> SEQUENCE: 13

```
Met Gly Lys Thr Asn Asp Trp Leu Asp Phe Asp Gln Leu Ala Glu Glu
1               5                   10                  15

Lys Val Arg Asp Ala Leu Lys Pro Pro Ser Met Tyr Lys Val Ile Leu
                    20                  25                  30

Val Asn Asp Asp Tyr Thr Pro Met Glu Phe Val Ile Asp Val Leu Gln
                35                  40                  45

Lys Phe Phe Ser Tyr Asp Val Glu Arg Ala Thr Gln Leu Met Leu Ala
 50                  55                  60

Val His Tyr Gln Gly Lys Ala Ile Cys Gly Val Phe Thr Ala Glu Val
65                  70                  75                  80

Ala Glu Thr Lys Val Ala Met Val Asn Lys Tyr Ala Arg Glu Asn Glu
                    85                  90                  95

His Pro Leu Leu Cys Thr Leu Glu Lys Ala
                100                 105
```

<210> SEQ ID NO 14

```
<211> LENGTH: 106
<212> TYPE: PRT
<213> ORGANISM: Escherichia coli

<400> SEQUENCE: 14

Met Gly Lys Thr Asn Asp Trp Leu Asp Phe Asp Gln Leu Ala Glu Glu
1               5                   10                  15

Lys Val Arg Asp Ala Leu Lys Pro Pro Ser Met Tyr Lys Val Ile Leu
            20                  25                  30

Val Asn Asp Asp Tyr Thr Pro Ala Glu Phe Val Ile Asp Val Leu Gln
        35                  40                  45

Lys Phe Phe Ser Tyr Asp Val Glu Arg Ala Thr Gln Leu Met Leu Ala
50                  55                  60

Val His Tyr Gln Gly Lys Ala Ile Cys Gly Val Phe Thr Ala Glu Val
65                  70                  75                  80

Ala Glu Thr Lys Val Ala Met Val Asn Lys Tyr Ala Arg Glu Asn Glu
                85                  90                  95

His Pro Leu Leu Cys Thr Leu Glu Lys Ala
            100                 105

<210> SEQ ID NO 15
<211> LENGTH: 192
<212> TYPE: PRT
<213> ORGANISM: Plasmodium falciparum

<400> SEQUENCE: 15

Met Phe Lys Asp Leu Lys Pro Phe Phe Leu Cys Ile Ile Leu Leu Leu
1               5                   10                  15

Leu Leu Ile Tyr Lys Cys Thr His Ser Tyr Asn Ile Lys Asn Lys Asn
            20                  25                  30

Cys Pro Leu Asn Phe Met Asn Ser Cys Val Arg Ile Asn Asn Val Asn
        35                  40                  45

Lys Asn Thr Asn Ile Ser Phe Pro Lys Glu Leu Gln Lys Arg Pro Ser
50                  55                  60

Leu Val Tyr Ser Gln Lys Asn Phe Asn Leu Glu Lys Ile Lys Lys Leu
65                  70                  75                  80

Arg Asn Val Ile Lys Glu Ile Lys Lys Asp Asn Ile Lys Glu Ala Asp
                85                  90                  95

Glu His Glu Lys Lys Glu Arg Glu Lys Glu Thr Ser Ala Trp Lys Val
            100                 105                 110

Ile Leu Tyr Asn Asp Asp Ile His Asn Phe Thr Tyr Val Thr Asp Val
            115                 120                 125

Ile Val Lys Val Val Gly Gln Ile Ser Lys Ala Lys Ala His Thr Ile
        130                 135                 140

Thr Val Glu Ala His Ser Thr Gly Gln Ala Leu Ile Leu Ser Thr Trp
145                 150                 155                 160

Lys Ser Lys Ala Glu Lys Tyr Cys Gln Glu Leu Gln Gln Asn Gly Leu
                165                 170                 175

Thr Val Ser Ile Ile His Glu Ser Gln Leu Lys Asp Lys Gln Lys Lys
            180                 185                 190

<210> SEQ ID NO 16
<211> LENGTH: 236
<212> TYPE: PRT
<213> ORGANISM: Escherichia coli

<400> SEQUENCE: 16
```

```
Met Arg Leu Val Gln Leu Ser Arg His Ser Ile Ala Phe Pro Ser Pro
1               5                   10                  15

Glu Gly Ala Leu Arg Glu Pro Asn Gly Leu Leu Ala Leu Gly Gly Asp
            20                  25                  30

Leu Ser Pro Ala Arg Leu Leu Met Ala Tyr Gln Arg Gly Ile Phe Pro
        35                  40                  45

Trp Phe Ser Pro Gly Asp Pro Ile Leu Trp Trp Ser Pro Asp Pro Arg
50                  55                  60

Ala Val Leu Trp Pro Glu Ser Leu His Ile Ser Arg Ser Met Lys Arg
65                  70                  75                  80

Phe His Lys Arg Ser Pro Tyr Arg Val Thr Met Asn Tyr Ala Phe Gly
                85                  90                  95

Gln Val Ile Glu Gly Cys Ala Ser Asp Arg Glu Glu Gly Thr Trp Ile
            100                 105                 110

Thr Arg Gly Val Val Glu Ala Tyr His Arg Leu His Glu Leu Gly His
        115                 120                 125

Ala His Ser Ile Glu Val Trp Arg Glu Asp Glu Leu Val Gly Gly Met
    130                 135                 140

Tyr Gly Val Ala Gln Gly Thr Leu Phe Cys Gly Glu Ser Met Phe Ser
145                 150                 155                 160

Arg Met Glu Asn Ala Ser Lys Thr Ala Leu Leu Val Phe Cys Glu Glu
                165                 170                 175

Phe Ile Gly His Gly Gly Lys Leu Ile Asp Cys Gln Val Leu Asn Asp
            180                 185                 190

His Thr Ala Ser Leu Gly Ala Cys Glu Ile Pro Arg Arg Asp Tyr Leu
        195                 200                 205

Asn Tyr Leu Asn Gln Met Arg Leu Gly Arg Leu Pro Asn Asn Phe Trp
    210                 215                 220

Val Pro Arg Cys Leu Phe Ser Pro Gln Glu Leu Glu
225                 230                 235

<210> SEQ ID NO 17
<211> LENGTH: 231
<212> TYPE: PRT
<213> ORGANISM: Vibrio vulnificus

<400> SEQUENCE: 17

Met Ser Ser Asp Ile His Gln Ile Lys Ile Gly Leu Thr Asp Asn His
1               5                   10                  15

Pro Cys Ser Tyr Leu Pro Glu Arg Lys Glu Arg Val Ala Val Ala Leu
            20                  25                  30

Glu Ala Asp Met His Thr Ala Asp Asn Tyr Glu Val Leu Leu Ala Asn
        35                  40                  45

Gly Phe Arg Arg Ser Gly Asn Thr Ile Tyr Lys Pro His Cys Asp Ser
50                  55                  60

Cys His Ser Cys Gln Pro Ile Arg Ile Ser Val Pro Asp Ile Glu Leu
65                  70                  75                  80

Ser Arg Ser Gln Lys Arg Leu Leu Ala Lys Ala Arg Ser Leu Ser Trp
                85                  90                  95

Ser Met Lys Arg Asn Met Asp Glu Asn Trp Phe Asp Leu Tyr Ser Arg
            100                 105                 110

Tyr Ile Val Ala Arg His Arg Asn Gly Thr Met Tyr Pro Pro Lys Lys
        115                 120                 125

Asp Asp Phe Ala His Phe Ser Arg Asn Gln Trp Leu Thr Thr Gln Phe
    130                 135                 140
```

```
Leu His Ile Tyr Glu Gly Gln Arg Leu Ile Ala Val Ala Val Thr Asp
145                 150                 155                 160

Ile Met Asp His Cys Ala Ser Ala Phe Tyr Thr Phe Phe Glu Pro Glu
                165                 170                 175

His Glu Leu Ser Leu Gly Thr Leu Ala Val Leu Phe Gln Leu Glu Phe
            180                 185                 190

Cys Gln Glu Glu Lys Lys Gln Trp Leu Tyr Leu Gly Tyr Gln Ile Asp
        195                 200                 205

Glu Cys Pro Ala Met Asn Tyr Lys Val Arg Phe His Arg His Gln Lys
    210                 215                 220

Leu Val Asn Gln Arg Trp Gln
225                 230

<210> SEQ ID NO 18
<211> LENGTH: 83
<212> TYPE: PRT
<213> ORGANISM: Saccharomyces cerevisiae

<400> SEQUENCE: 18

Met Gly Ser Val His Lys His Thr Gly Arg Asn Cys Gly Arg Lys Phe
1               5                   10                  15

Lys Ile Gly Glu Pro Leu Tyr Arg Cys His Glu Cys Gly Cys Asp Asp
            20                  25                  30

Thr Cys Val Leu Cys Ile His Cys Phe Asn Pro Lys Asp His Val Asn
        35                  40                  45

His His Val Cys Thr Asp Ile Cys Thr Glu Phe Thr Ser Gly Ile Cys
    50                  55                  60

Asp Cys Gly Asp Glu Glu Ala Trp Asn Ser Pro Leu His Cys Lys Ala
65                  70                  75                  80

Glu Glu Gln

<210> SEQ ID NO 19
<211> LENGTH: 167
<212> TYPE: PRT
<213> ORGANISM: Homo sapiens

<400> SEQUENCE: 19

Met Ser Gly Ser Lys Phe Arg Gly His Gln Lys Ser Lys Gly Asn Ser
1               5                   10                  15

Tyr Asp Val Glu Val Val Leu Gln His Val Asp Thr Gly Asn Ser Tyr
            20                  25                  30

Leu Cys Gly Tyr Leu Lys Ile Lys Gly Leu Thr Glu Glu Tyr Pro Thr
        35                  40                  45

Leu Thr Thr Phe Phe Glu Gly Glu Ile Ile Ser Lys Lys His Pro Phe
    50                  55                  60

Leu Thr Arg Lys Trp Asp Ala Asp Glu Asp Val Asp Arg Lys His Trp
65                  70                  75                  80

Gly Lys Phe Leu Ala Phe Tyr Gln Tyr Ala Lys Ser Phe Asn Ser Asp
            85                  90                  95

Asp Phe Asp Tyr Glu Glu Leu Lys Asn Gly Asp Tyr Val Phe Met Arg
            100                 105                 110

Trp Lys Glu Gln Phe Leu Val Pro Asp His Thr Ile Lys Asp Ile Ser
        115                 120                 125

Gly Ala Ser Phe Ala Gly Phe Tyr Tyr Ile Cys Phe Gln Lys Ser Ala
    130                 135                 140
```

```
Ala Ser Ile Glu Gly Tyr Tyr His Arg Ser Ser Glu Trp Tyr Gln
145                 150                 155                 160

Ser Leu Asn Leu Thr His Val
                165
```

<210> SEQ ID NO 20
<211> LENGTH: 362
<212> TYPE: PRT
<213> ORGANISM: Saccharomyces cerevisiae

<400> SEQUENCE: 20

```
Met Ile Asn Asn Pro Lys Val Asp Ser Val Ala Glu Lys Pro Lys Ala
1               5                   10                  15

Val Thr Ser Lys Gln Ser Glu Gln Ala Ala Ser Pro Glu Pro Thr Pro
                20                  25                  30

Ala Pro Pro Val Ser Arg Asn Gln Tyr Pro Ile Thr Phe Asn Leu Thr
            35                  40                  45

Ser Thr Ala Pro Phe His Leu His Asp Arg His Arg Tyr Leu Gln Glu
50                  55                  60

Gln Asp Leu Tyr Lys Cys Ala Ser Arg Asp Ser Leu Ser Ser Leu Gln
65                  70                  75                  80

Gln Leu Ala His Thr Pro Asn Gly Ser Thr Arg Lys Lys Tyr Ile Val
                85                  90                  95

Glu Asp Gln Ser Pro Tyr Ser Ser Glu Asn Pro Val Ile Val Thr Ser
            100                 105                 110

Ser Tyr Asn His Thr Val Cys Thr Asn Tyr Leu Arg Pro Arg Met Gln
        115                 120                 125

Phe Thr Gly Tyr Gln Ile Ser Gly Tyr Lys Arg Tyr Gln Val Thr Val
130                 135                 140

Asn Leu Lys Thr Val Asp Leu Pro Lys Lys Asp Cys Thr Ser Leu Ser
145                 150                 155                 160

Pro His Leu Ser Gly Phe Leu Ser Ile Arg Gly Leu Thr Asn Gln His
                165                 170                 175

Pro Glu Ile Ser Thr Tyr Phe Glu Ala Tyr Ala Val Asn His Lys Glu
            180                 185                 190

Leu Gly Phe Leu Ser Ser Ser Trp Lys Asp Glu Pro Val Leu Asn Glu
        195                 200                 205

Phe Lys Ala Thr Asp Gln Thr Asp Leu Glu His Trp Ile Asn Phe Pro
210                 215                 220

Ser Phe Arg Gln Leu Phe Leu Met Ser Gln Lys Asn Gly Leu Asn Ser
225                 230                 235                 240

Thr Asp Asp Asn Gly Thr Thr Asn Ala Ala Lys Lys Leu Pro Pro Gln
                245                 250                 255

Gln Leu Pro Thr Thr Pro Ser Ala Asp Ala Gly Asn Ile Ser Arg Ile
            260                 265                 270

Phe Ser Gln Glu Lys Gln Phe Asp Asn Tyr Leu Asn Glu Arg Phe Ile
        275                 280                 285

Phe Met Lys Trp Lys Glu Lys Phe Leu Val Pro Asp Ala Leu Leu Met
290                 295                 300

Glu Gly Val Asp Gly Ala Ser Tyr Asp Gly Phe Tyr Ile Val His
305                 310                 315                 320

Asp Gln Val Thr Gly Asn Ile Gln Gly Phe Tyr Tyr His Gln Asp Ala
                325                 330                 335

Glu Lys Phe Gln Gln Leu Glu Leu Val Pro Ser Leu Lys Asn Lys Val
            340                 345                 350
```

```
Glu Ser Ser Asp Cys Ser Phe Glu Phe Ala
        355                 360
```

<210> SEQ ID NO 21
<211> LENGTH: 240
<212> TYPE: PRT
<213> ORGANISM: Unknown
<220> FEATURE:
<223> OTHER INFORMATION: Single-chain antibody variable fragment (scFv)
      against phosphotyrosine

<400> SEQUENCE: 21

```
Met Met Glu Val Gln Leu Gln Gln Ser Gly Pro Glu Leu Val Lys Pro
1               5                   10                  15

Gly Ala Ser Val Met Ile Ser Cys Arg Thr Ser Ala Tyr Thr Phe Thr
            20                  25                  30

Glu Asn Thr Val His Trp Val Lys Gln Ser His Gly Glu Ser Leu Glu
        35                  40                  45

Trp Ile Gly Gly Ile Asn Pro Tyr Tyr Gly Gly Ser Ile Phe Ser Pro
50                  55                  60

Lys Phe Lys Gly Lys Ala Thr Leu Thr Val Asp Lys Ser Ser Ser Thr
65                  70                  75                  80

Ala Tyr Met Glu Leu Arg Ser Leu Thr Ser Glu Asp Ser Ala Val Tyr
                85                  90                  95

Tyr Cys Ala Arg Arg Ala Gly Ala Tyr Tyr Phe Asp Tyr Trp Gly Gln
            100                 105                 110

Gly Thr Thr Leu Thr Val Ser Ser Gly Gly Gly Ser Gly Gly Gly Ser
        115                 120                 125

Gly Gly Gly Ser Glu Asn Val Leu Thr Gln Ser Pro Ala Ile Met Ser
    130                 135                 140

Ala Ser Pro Gly Glu Lys Val Thr Met Thr Cys Arg Ala Ser Ser Ser
145                 150                 155                 160

Val Ser Ser Ser Tyr Leu His Trp Tyr Arg Gln Lys Ser Gly Ala Ser
                165                 170                 175

Pro Lys Leu Trp Ile Tyr Ser Thr Ser Asn Leu Ala Ser Gly Val Pro
            180                 185                 190

Ala Arg Phe Ser Gly Ser Gly Ser Gly Thr Ser Tyr Ser Leu Thr Ile
        195                 200                 205

Ser Ser Val Glu Ala Glu Asp Ala Ala Thr Tyr Tyr Cys Gln Gln Tyr
    210                 215                 220

Ser Gly Tyr Arg Thr Phe Gly Gly Gly Thr Lys Leu Glu Ile Lys Arg
225                 230                 235                 240
```

<210> SEQ ID NO 22
<211> LENGTH: 111
<212> TYPE: PRT
<213> ORGANISM: Homo sapiens

<400> SEQUENCE: 22

```
Met Gly Ala Met Asp Ser Ile Gln Ala Glu Glu Trp Tyr Phe Gly Lys
1               5                   10                  15

Leu Gly Arg Lys Asp Ala Glu Arg Gln Leu Leu Ser Phe Gly Asn Pro
            20                  25                  30

Arg Gly Thr Phe Leu Ile Arg Glu Ser Glu Thr Thr Lys Gly Ala Tyr
        35                  40                  45

Ser Leu Ser Ile Arg Asp Trp Asp Asp Met Lys Gly Asp His Val Lys
50                  55                  60
```

```
His Tyr Lys Ile Arg Lys Leu Asp Asn Gly Gly Tyr Ile Thr Thr
 65                  70                  75                  80

Arg Ala Gln Phe Glu Thr Leu Gln Gln Leu Val Gln His Tyr Ser Glu
                 85                  90                  95

Arg Ala Ala Gly Leu Ser Ser Arg Leu Val Val Pro Ser His Lys
            100                 105                 110
```

<210> SEQ ID NO 23
<211> LENGTH: 111
<212> TYPE: PRT
<213> ORGANISM: Homo sapiens

<400> SEQUENCE: 23

```
Met Gly Ala Met Asp Ser Ile Gln Ala Glu Glu Trp Tyr Phe Gly Lys
 1               5                  10                  15

Leu Gly Arg Lys Asp Ala Glu Arg Gln Leu Leu Ser Phe Gly Asn Pro
                20                  25                  30

Arg Gly Thr Phe Leu Ile Arg Glu Ser Glu Thr Val Lys Gly Ala Tyr
                35                  40                  45

Ala Leu Ser Ile Arg Asp Trp Asp Asp Met Lys Gly Asp His Val Lys
 50                  55                  60

His Tyr Leu Ile Arg Lys Leu Asp Asn Gly Gly Tyr Tyr Ile Thr Thr
 65                  70                  75                  80

Arg Ala Gln Phe Glu Thr Leu Gln Gln Leu Val Gln His Tyr Ser Glu
                 85                  90                  95

Arg Ala Ala Gly Leu Ser Ser Arg Leu Val Val Pro Ser His Lys
            100                 105                 110
```

<210> SEQ ID NO 24
<211> LENGTH: 113
<212> TYPE: PRT
<213> ORGANISM: Homo sapiens

<400> SEQUENCE: 24

```
Met Gly Ala Met Asp Ser Ile Gln Ala Glu Glu Trp Tyr Phe Gly Lys
 1               5                  10                  15

Ile Thr Arg Arg Glu Ser Glu Arg Leu Leu Leu Asn Ala Glu Asn Pro
                20                  25                  30

Arg Gly Thr Phe Leu Val Arg Glu Ser Glu Thr Thr Lys Gly Ala Tyr
                35                  40                  45

Ser Leu Ser Val Ser Asp Phe Asp Asn Ala Lys Gly Leu Asn Val Lys
 50                  55                  60

His Tyr Lys Ile Arg Lys Leu Asp Ser Gly Gly Phe Tyr Ile Thr Ser
 65                  70                  75                  80

Arg Thr Gln Phe Asn Ser Leu Gln Gln Leu Val Ala Tyr Tyr Ser Lys
                 85                  90                  95

His Ala Asp Gly Leu Cys His Arg Leu Thr Thr Val Cys Pro Thr Ser
            100                 105                 110

Lys
```

<210> SEQ ID NO 25
<211> LENGTH: 113
<212> TYPE: PRT
<213> ORGANISM: Homo sapiens

<400> SEQUENCE: 25

Met Gly Ala Met Asp Ser Ile Gln Ala Glu Glu Trp Tyr Phe Gly Lys

```
              1               5                  10                 15
Ile Thr Arg Arg Glu Ser Glu Arg Leu Leu Asn Ala Glu Asn Pro
             20                 25                 30
Arg Gly Thr Phe Leu Val Arg Glu Ser Glu Val Thr Lys Gly Ala Tyr
             35                 40                 45
Ala Leu Ser Val Ser Asp Phe Asp Asn Ala Lys Gly Leu Asn Val Lys
             50                 55                 60
His Tyr Leu Ile Arg Lys Leu Asp Ser Gly Gly Phe Tyr Ile Thr Ser
65                  70                 75                 80
Arg Thr Gln Phe Asn Ser Leu Gln Gln Leu Val Ala Tyr Tyr Ser Lys
             85                 90                 95
His Ala Asp Gly Leu Cys His Arg Leu Thr Thr Val Cys Pro Thr Ser
            100                105                110
Lys

<210> SEQ ID NO 26
<211> LENGTH: 310
<212> TYPE: PRT
<213> ORGANISM: Homo sapiens

<400> SEQUENCE: 26

Met Ala Ser Leu Thr Val Lys Ala Tyr Leu Leu Gly Lys Glu Asp Ala
1               5                  10                 15
Ala Arg Glu Ile Arg Arg Phe Ser Phe Cys Cys Ser Pro Glu Pro Glu
             20                 25                 30
Ala Glu Ala Glu Ala Ala Gly Pro Gly Pro Cys Glu Arg Leu Leu
             35                 40                 45
Ser Arg Val Ala Ala Leu Phe Pro Ala Leu Arg Pro Gly Gly Phe Gln
             50                 55                 60
Ala His Tyr Arg Asp Glu Asp Gly Asp Leu Val Ala Phe Ser Ser Asp
65                  70                 75                 80
Glu Glu Leu Thr Met Ala Met Ser Tyr Val Lys Asp Asp Ile Phe Arg
             85                 90                 95
Ile Tyr Ile Lys Glu Lys Lys Glu Cys Arg Arg Asp His Arg Pro Pro
            100                105                110
Cys Ala Gln Glu Ala Pro Arg Asn Met Val His Pro Asn Val Ile Cys
            115                120                125
Asp Gly Cys Asn Gly Pro Val Val Gly Thr Arg Tyr Lys Cys Ser Val
            130                135                140
Cys Pro Asp Tyr Asp Leu Cys Ser Val Cys Glu Gly Lys Gly Leu His
145                150                155                160
Arg Gly His Thr Lys Leu Ala Phe Pro Ser Pro Phe Gly His Leu Ser
            165                170                175
Glu Gly Phe Ser His Ser Arg Trp Leu Arg Lys Val Lys His Gly His
            180                185                190
Phe Gly Trp Pro Gly Trp Glu Met Gly Pro Gly Asn Trp Ser Pro
            195                200                205
Arg Pro Pro Arg Ala Gly Glu Ala Arg Pro Gly Pro Thr Ala Glu Ser
            210                215                220
Ala Ser Gly Pro Ser Glu Asp Pro Ser Val Asn Phe Leu Lys Asn Val
225                230                235                240
Gly Glu Ser Val Ala Ala Ala Leu Ser Pro Leu Gly Ile Glu Val Asp
            245                250                255
Ile Asp Val Glu His Gly Gly Lys Arg Ser Arg Leu Thr Pro Val Ser
```

```
                260                 265                 270
Pro Glu Ser Ser Ser Thr Glu Glu Lys Ser Ser Ser Gln Pro Ser Ser
                275                 280                 285

Cys Cys Ser Asp Pro Ser Lys Pro Gly Gly Asn Val Glu Gly Ala Thr
        290                 295                 300

Gln Ser Leu Ala Glu Gln
305                 310

<210> SEQ ID NO 27
<211> LENGTH: 310
<212> TYPE: PRT
<213> ORGANISM: Homo sapiens

<400> SEQUENCE: 27

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
                20                  25                  30

Ala Glu Ala Glu Ala Ala Gly Pro Gly Pro Cys Glu Arg Leu Leu
            35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
                100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
    130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Pro Gly Asn Trp Ser Pro
    195                 200                 205

Arg Pro Pro Arg Ala Gly Glu Ala Arg Pro Gly Pro Thr Ala Glu Ser
210                 215                 220

Ala Ser Gly Pro Ser Glu Asp Pro Ser Val Asn Phe Leu Lys Asn Val
225                 230                 235                 240

Gly Glu Ser Val Ala Ala Ala Leu Ser Pro Leu Gly Ile Glu Val Asp
                245                 250                 255

Ile Asp Val Glu His Gly Gly Lys Arg Ser Arg Leu Thr Pro Val Ser
            260                 265                 270

Pro Glu Ser Ser Ser Thr Glu Glu Lys Ser Ser Ser Gln Pro Ser Ser
    275                 280                 285

Cys Cys Ser Asp Pro Ser Lys Pro Gly Gly Asn Val Glu Gly Ala Thr
        290                 295                 300

Gln Ser Leu Ala Glu Gln
305                 310
```

```
<210> SEQ ID NO 28
<211> LENGTH: 310
<212> TYPE: PRT
<213> ORGANISM: Homo sapiens

<400> SEQUENCE: 28

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
        115                 120                 125

Asp Gly Cys Asn Gly Pro Val Val Gly Thr Arg Tyr Lys Cys Ser Val
130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Glu Ala Arg Pro Gly Pro Thr Ala Glu Ser
210                 215                 220

Ala Ser Gly Pro Ser Glu Asp Pro Ser Val Asn Phe Leu Lys Asn Val
225                 230                 235                 240

Gly Glu Ser Val Ala Ala Leu Ser Pro Leu Gly Ile Glu Val Asp
                245                 250                 255

Ile Asp Val Glu His Gly Gly Lys Arg Ser Arg Leu Thr Pro Val Ser
            260                 265                 270

Pro Glu Ser Ser Ser Thr Glu Glu Lys Ser Ser Gln Pro Ser Ser
        275                 280                 285

Cys Cys Ser Asp Pro Ser Lys Pro Gly Gly Asn Val Glu Gly Ala Thr
    290                 295                 300

Gln Ser Leu Ala Glu Gln
305                 310

<210> SEQ ID NO 29
<211> LENGTH: 440
<212> TYPE: PRT
<213> ORGANISM: Homo sapiens

<400> SEQUENCE: 29

Met Ala Ser Leu Thr Val Lys Ala Tyr Leu Leu Gly Lys Glu Asp Ala
1               5                   10                  15
```

```
Ala Arg Glu Ile Arg Arg Phe Ser Phe Cys Cys Ser Pro Glu Pro Glu
             20                  25                  30

Ala Glu Ala Glu Ala Ala Ala Gly Pro Gly Pro Cys Glu Arg Leu Leu
         35                  40                  45

Ser Arg Val Ala Ala Leu Phe Pro Ala Leu Arg Pro Gly Gly Phe Gln
     50                  55                  60

Ala His Tyr Arg Asp Glu Asp Gly Asp Leu Val Ala Phe Ser Ser Asp
 65                  70                  75                  80

Glu Glu Leu Thr Met Ala Met Ser Tyr Val Lys Asp Asp Ile Phe Arg
                 85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
            130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
                180                 185                 190

Phe Gly Trp Pro Gly Trp Glu Met Gly Pro Pro Gly Asn Trp Ser Pro
            195                 200                 205

Arg Pro Pro Arg Ala Gly Glu Ala Arg Pro Gly Pro Thr Ala Glu Ser
210                 215                 220

Ala Ser Gly Pro Ser Glu Asp Pro Ser Val Asn Phe Leu Lys Asn Val
225                 230                 235                 240

Gly Glu Ser Val Ala Ala Leu Ser Pro Leu Gly Ile Glu Val Asp
                245                 250                 255

Ile Asp Val Glu His Gly Gly Lys Arg Ser Arg Leu Thr Pro Val Ser
            260                 265                 270

Pro Glu Ser Ser Ser Thr Glu Glu Lys Ser Ser Ser Gln Pro Ser Ser
            275                 280                 285

Cys Cys Ser Asp Pro Ser Lys Pro Gly Gly Asn Val Glu Gly Ala Thr
290                 295                 300

Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
                325                 330                 335

Asp Trp Thr His Leu Ser Ser Lys Glu Val Asp Pro Ser Thr Gly Glu
                340                 345                 350

Leu Gln Ser Leu Gln Met Pro Glu Ser Glu Gly Pro Ser Ser Leu Asp
                355                 360                 365

Pro Ser Gln Glu Gly Pro Thr Gly Leu Lys Glu Ala Ala Leu Tyr Pro
            370                 375                 380

His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
                405                 410                 415

Leu Gln Thr Lys Asn Tyr Asp Ile Gly Ala Ala Leu Asp Thr Ile Gln
            420                 425                 430

Tyr Ser Lys His Pro Pro Leu
```

<210> SEQ ID NO 30
<211> LENGTH: 439
<212> TYPE: PRT
<213> ORGANISM: Rattus norvegicus

<400> SEQUENCE: 30

```
Met Ala Ser Leu Thr Val Lys Ala Tyr Leu Leu Gly Lys Glu Glu Ala
1               5                   10                  15

Ala Arg Glu Ile Arg Arg Phe Ser Phe Cys Phe Ser Pro Glu Pro Glu
            20                  25                  30

Ala Glu Ala Ala Ala Gly Pro Gly Pro Cys Glu Arg Leu Leu Ser Arg
        35                  40                  45

Val Ala Val Leu Phe Pro Ala Leu Arg Pro Gly Gly Phe Gln Ala His
    50                  55                  60

Tyr Arg Asp Glu Asp Gly Asp Leu Val Ala Phe Ser Ser Asp Glu Glu
65                  70                  75                  80

Leu Thr Met Ala Met Ser Tyr Val Lys Asp Asp Ile Phe Arg Ile Tyr
                85                  90                  95

Ile Lys Glu Lys Lys Glu Cys Arg Arg Glu His Arg Pro Pro Cys Ala
            100                 105                 110

Gln Glu Ala Arg Ser Met Val His Pro Asn Val Ile Cys Asp Gly Cys
        115                 120                 125

Asn Gly Pro Val Val Gly Thr Arg Tyr Lys Cys Ser Val Cys Pro Asp
130                 135                 140

Tyr Asp Leu Cys Ser Val Cys Glu Gly Lys Gly Leu His Arg Glu His
145                 150                 155                 160

Ser Lys Leu Ile Phe Pro Asn Pro Phe Gly His Leu Ser Asp Ser Phe
                165                 170                 175

Ser His Ser Arg Trp Leu Arg Lys Leu Lys His Gly His Phe Gly Trp
            180                 185                 190

Pro Gly Trp Glu Met Gly Pro Pro Gly Asn Trp Ser Pro Arg Pro Pro
        195                 200                 205

Arg Ala Gly Asp Gly Arg Pro Cys Pro Thr Ala Glu Ser Ala Ser Ala
210                 215                 220

Pro Ser Glu Asp Pro Asn Val Asn Phe Leu Lys Asn Val Gly Glu Ser
225                 230                 235                 240

Val Ala Ala Leu Ser Pro Leu Gly Ile Glu Val Asp Ile Asp Val
                245                 250                 255

Glu His Gly Gly Lys Arg Ser Arg Leu Thr Pro Thr Ser Ala Glu Ser
            260                 265                 270

Ser Ser Thr Gly Thr Glu Asp Lys Ser Gly Thr Gln Pro Ser Ser Cys
        275                 280                 285

Ser Ser Glu Val Ser Lys Pro Asp Gly Ala Gly Glu Gly Pro Ala Gln
    290                 295                 300

Ser Leu Thr Glu Gln Met Lys Lys Ile Ala Leu Glu Ser Val Gly Gln
305                 310                 315                 320

Pro Glu Glu Leu Met Glu Ser Asp Asn Cys Ser Gly Gly Asp Asp Asp
                325                 330                 335

Trp Thr His Leu Ser Ser Lys Glu Val Asp Pro Ser Thr Gly Glu Leu
            340                 345                 350

Gln Ser Leu Gln Met Pro Glu Ser Glu Gly Pro Ser Ser Leu Asp Pro
        355                 360                 365
```

```
Ser Gln Glu Gly Pro Thr Gly Leu Lys Glu Ala Ala Leu Tyr Pro His
    370                 375                 380

Leu Pro Pro Glu Ala Asp Pro Arg Leu Ile Glu Ser Leu Ser Gln Met
385                 390                 395                 400

Leu Ser Met Gly Phe Ser Asp Glu Gly Gly Trp Leu Thr Arg Leu Leu
                405                 410                 415

Gln Thr Lys Asn Tyr Asp Ile Gly Ala Ala Leu Asp Thr Ile Gln Tyr
            420                 425                 430

Ser Lys His Pro Pro Leu
        435

<210> SEQ ID NO 31
<211> LENGTH: 292
<212> TYPE: PRT
<213> ORGANISM: Saccharomyces cerevisiae

<400> SEQUENCE: 31

Met Thr Ser Leu Asn Ile Met Gly Arg Lys Phe Ile Leu Glu Arg Ala
1               5                   10                  15

Lys Arg Asn Asp Asn Ile Glu Glu Ile Tyr Thr Ser Ala Tyr Val Ser
            20                  25                  30

Leu Pro Ser Ser Thr Asp Thr Arg Leu Pro His Phe Lys Ala Lys Glu
        35                  40                  45

Glu Asp Cys Asp Val Tyr Glu Glu Gly Thr Asn Leu Val Gly Lys Asn
    50                  55                  60

Ala Lys Tyr Thr Tyr Arg Ser Leu Gly Arg His Leu Asp Phe Leu Arg
65                  70                  75                  80

Pro Gly Leu Arg Phe Gly Gly Ser Gln Ser Ser Lys Tyr Thr Tyr Tyr
                85                  90                  95

Thr Val Glu Val Lys Ile Asp Thr Val Asn Leu Pro Leu Tyr Lys Asp
            100                 105                 110

Ser Arg Ser Leu Asp Pro His Val Thr Gly Thr Phe Thr Ile Lys Asn
        115                 120                 125

Leu Thr Pro Val Leu Asp Lys Val Val Thr Leu Phe Glu Gly Tyr Val
130                 135                 140

Ile Asn Tyr Asn Gln Phe Pro Leu Cys Ser Leu His Trp Pro Ala Glu
145                 150                 155                 160

Glu Thr Leu Asp Pro Tyr Met Ala Gln Arg Glu Ser Asp Cys Ser His
                165                 170                 175

Trp Lys Arg Phe Gly His Phe Gly Ser Asp Asn Trp Ser Leu Thr Glu
            180                 185                 190

Arg Asn Phe Gly Gln Tyr Asn His Glu Ser Ala Glu Phe Met Asn Gln
        195                 200                 205

Arg Tyr Ile Tyr Leu Lys Trp Lys Glu Arg Phe Leu Leu Asp Asp Glu
    210                 215                 220

Glu Gln Glu Asn Gln Met Leu Asp Asp Asn His His Leu Glu Gly Ala
225                 230                 235                 240

Ser Phe Glu Gly Phe Tyr Tyr Val Cys Leu Asp Gln Leu Thr Gly Ser
                245                 250                 255

Val Glu Gly Tyr Tyr His Pro Ala Cys Glu Leu Phe Gln Lys Leu
            260                 265                 270

Glu Leu Val Pro Thr Asn Cys Asp Ala Leu Asn Thr Tyr Ser Ser Gly
        275                 280                 285

Phe Glu Ile Ala
        290
```

<210> SEQ ID NO 32
<211> LENGTH: 77
<212> TYPE: PRT
<213> ORGANISM: Homo sapiens

<400> SEQUENCE: 32

Met Gly Pro Leu Gly Ser Leu Cys Gly Arg Val Phe Lys Ser Gly Glu
1               5                   10                  15

Thr Thr Tyr Ser Cys Arg Asp Cys Ala Ile Asp Pro Thr Cys Val Leu
            20                  25                  30

Cys Met Asp Cys Phe Gln Asp Ser Val His Lys Asn His Arg Tyr Lys
        35                  40                  45

Met His Thr Ser Thr Gly Gly Gly Phe Cys Cys Gly Asp Thr Glu
    50                  55                  60

Ala Trp Lys Thr Gly Pro Phe Cys Val Asn His Glu Pro
65                  70                  75

<210> SEQ ID NO 33
<211> LENGTH: 76
<212> TYPE: PRT
<213> ORGANISM: Homo sapiens

<400> SEQUENCE: 33

Met Gly Pro Leu Gly Ser Leu Cys Gly Arg Val Phe Lys Val Gly Glu
1               5                   10                  15

Pro Thr Tyr Ser Cys Arg Asp Cys Ala Val Asp Pro Thr Cys Val Leu
            20                  25                  30

Cys Met Glu Cys Phe Leu Gly Ser Ile His Arg Asp His Arg Tyr Arg
        35                  40                  45

Met Thr Thr Ser Gly Gly Gly Phe Cys Asp Cys Gly Asp Thr Glu
    50                  55                  60

Ala Trp Lys Glu Gly Pro Tyr Cys Gln Lys His Glu
65                  70                  75

<210> SEQ ID NO 34
<211> LENGTH: 421
<212> TYPE: PRT
<213> ORGANISM: Leishmania major

<400> SEQUENCE: 34

Met Ser Arg Asn Pro Ser Asn Ser Asp Ala Ala His Ala Phe Trp Ser
1               5                   10                  15

Thr Gln Pro Val Pro Gln Thr Glu Asp Glu Thr Glu Lys Ile Val Phe
            20                  25                  30

Ala Gly Pro Met Asp Glu Pro Lys Thr Val Ala Asp Ile Pro Glu Glu
        35                  40                  45

Pro Tyr Pro Ile Ala Ser Thr Phe Glu Trp Trp Thr Pro Asn Met Glu
    50                  55                  60

Ala Ala Asp Asp Ile His Ala Ile Tyr Glu Leu Leu Arg Asp Asn Tyr
65                  70                  75                  80

Val Glu Asp Asp Ser Met Phe Arg Phe Asn Tyr Ser Glu Glu Phe
                85                  90                  95

Leu Gln Trp Ala Leu Cys Pro Pro Asn Tyr Ile Pro Asp Trp His Val
            100                 105                 110

Ala Val Arg Arg Lys Ala Asp Lys Lys Leu Leu Ala Phe Ile Ala Gly
        115                 120                 125

-continued

Val Pro Val Thr Leu Arg Met Gly Thr Pro Lys Tyr Met Lys Val Lys
    130                 135                 140

Ala Gln Glu Lys Gly Glu Gly Glu Ala Ala Lys Tyr Asp Glu Pro
145                 150                 155                 160

Arg His Ile Cys Glu Ile Asn Phe Leu Cys Val His Lys Gln Leu Arg
                165                 170                 175

Glu Lys Arg Leu Ala Pro Ile Leu Ile Lys Glu Ala Thr Arg Arg Val
            180                 185                 190

Asn Arg Thr Asn Val Trp Gln Ala Val Tyr Thr Ala Gly Val Leu Leu
        195                 200                 205

Pro Thr Pro Tyr Ala Ser Gly Gln Tyr Phe His Arg Ser Leu Asn Pro
    210                 215                 220

Glu Lys Leu Val Glu Ile Arg Phe Ser Gly Ile Pro Ala Gln Tyr Gln
225                 230                 235                 240

Lys Phe Gln Asn Pro Met Ala Met Leu Lys Arg Asn Tyr Gln Leu Pro
                245                 250                 255

Ser Ala Pro Lys Asn Ser Gly Leu Arg Glu Met Lys Pro Ser Asp Val
            260                 265                 270

Pro Gln Val Arg Arg Ile Leu Met Asn Tyr Leu Asp Ser Phe Asp Val
        275                 280                 285

Gly Pro Val Phe Ser Asp Ala Glu Ile Ser His Tyr Leu Leu Pro Arg
    290                 295                 300

Asp Gly Val Val Phe Thr Tyr Val Val Glu Asn Asp Lys Lys Val Thr
305                 310                 315                 320

Asp Phe Phe Ser Phe Tyr Arg Ile Pro Ser Thr Val Ile Gly Asn Ser
                325                 330                 335

Asn Tyr Asn Leu Leu Asn Ala Ala Tyr Val His Tyr Tyr Ala Ala Thr
            340                 345                 350

Ser Ile Pro Leu His Gln Leu Ile Leu Asp Leu Leu Ile Val Ala His
        355                 360                 365

Ser Arg Gly Phe Asp Val Cys Asn Met Val Glu Ile Leu Asp Asn Arg
    370                 375                 380

Ser Phe Val Glu Gln Leu Lys Phe Gly Ala Gly Asp Gly His Leu Arg
385                 390                 395                 400

Tyr Tyr Phe Tyr Asn Trp Ala Tyr Pro Lys Ile Lys Pro Ser Gln Val
                405                 410                 415

Ala Leu Val Met Leu
            420

<210> SEQ ID NO 35
<211> LENGTH: 496
<212> TYPE: PRT
<213> ORGANISM: Homo sapiens

<400> SEQUENCE: 35

Met Ala Asp Glu Ser Glu Thr Ala Val Lys Pro Pro Ala Pro Pro Leu
1               5                   10                  15

Pro Gln Met Met Glu Gly Asn Gly Asn Gly His Glu His Cys Ser Asp
                20                  25                  30

Cys Glu Asn Glu Glu Asp Asn Ser Tyr Asn Arg Gly Gly Leu Ser Pro
            35                  40                  45

Ala Asn Asp Thr Gly Ala Lys Lys Lys Lys Lys Gln Lys Lys
    50                  55                  60

Lys Glu Lys Gly Ser Glu Thr Asp Ser Ala Gln Asp Gln Pro Val Lys
65                  70                  75                  80

```
Met Asn Ser Leu Pro Ala Glu Arg Ile Gln Glu Ile Gln Lys Ala Ile
                85                  90                  95

Glu Leu Phe Ser Val Gly Gln Gly Pro Ala Lys Thr Met Glu Glu Ala
            100                 105                 110

Ser Lys Arg Ser Tyr Gln Phe Trp Asp Thr Gln Pro Val Pro Lys Leu
            115                 120                 125

Gly Glu Val Val Asn Thr His Gly Pro Val Glu Pro Asp Lys Asp Asn
130                 135                 140

Ile Arg Gln Glu Pro Tyr Thr Leu Pro Gln Gly Phe Thr Trp Asp Ala
145                 150                 155                 160

Leu Asp Leu Gly Asp Arg Gly Val Leu Lys Glu Leu Tyr Thr Leu Leu
            165                 170                 175

Asn Glu Asn Tyr Val Glu Asp Asp Asn Met Phe Arg Phe Asp Tyr
            180                 185                 190

Ser Pro Glu Phe Leu Leu Trp Ala Leu Arg Pro Pro Gly Trp Leu Pro
            195                 200                 205

Gln Trp His Cys Gly Val Arg Val Val Ser Ser Arg Lys Leu Val Gly
    210                 215                 220

Phe Ile Ser Ala Ile Pro Ala Asn Ile His Ile Tyr Asp Thr Glu Lys
225                 230                 235                 240

Lys Met Val Glu Ile Asn Phe Leu Cys Val His Lys Lys Leu Arg Ser
                245                 250                 255

Lys Arg Val Ala Pro Val Leu Ile Arg Glu Ile Thr Arg Arg Val His
            260                 265                 270

Leu Glu Gly Ile Phe Gln Ala Val Tyr Thr Ala Gly Val Val Leu Pro
            275                 280                 285

Lys Pro Val Gly Thr Cys Arg Tyr Trp His Arg Ser Leu Asn Pro Arg
290                 295                 300

Lys Leu Ile Glu Val Lys Phe Ser His Leu Ser Arg Asn Met Thr Met
305                 310                 315                 320

Gln Arg Thr Met Lys Leu Tyr Arg Leu Pro Glu Thr Pro Lys Thr Ala
                325                 330                 335

Gly Leu Arg Pro Met Glu Thr Lys Asp Ile Pro Val Val His Gln Leu
            340                 345                 350

Leu Thr Arg Tyr Leu Lys Gln Phe His Leu Thr Pro Val Met Ser Gln
            355                 360                 365

Glu Glu Val Glu His Trp Phe Tyr Pro Gln Glu Asn Ile Ile Asp Thr
            370                 375                 380

Phe Val Val Glu Asn Ala Asn Gly Glu Val Thr Asp Phe Leu Ser Phe
385                 390                 395                 400

Tyr Thr Leu Pro Ser Thr Ile Met Asn His Pro Thr His Lys Ser Leu
                405                 410                 415

Lys Ala Ala Tyr Ser Phe Tyr Asn Val His Thr Gln Thr Pro Leu Leu
            420                 425                 430

Asp Leu Met Ser Asp Ala Leu Val Leu Ala Lys Met Lys Gly Phe Asp
            435                 440                 445

Val Phe Asn Ala Leu Asp Leu Met Glu Asn Lys Thr Phe Leu Glu Lys
450                 455                 460

Leu Lys Phe Gly Ile Gly Asp Gly Asn Leu Gln Tyr Tyr Leu Tyr Asn
465                 470                 475                 480

Trp Lys Cys Pro Ser Met Gly Ala Glu Lys Val Gly Leu Val Leu Gln
                485                 490                 495
```

<210> SEQ ID NO 36
<211> LENGTH: 127
<212> TYPE: PRT
<213> ORGANISM: Drosophila melanogaster

<400> SEQUENCE: 36

Met Gly Asp Val Gln Pro Glu Thr Cys Arg Pro Ser Ala Ala Ser Gly
1               5                   10                  15

Asn Tyr Phe Pro Gln Tyr Pro Glu Tyr Ala Ile Glu Thr Ala Arg Leu
            20                  25                  30

Arg Thr Phe Glu Ala Trp Pro Arg Asn Leu Lys Gln Lys Pro His Gln
        35                  40                  45

Leu Ala Glu Ala Gly Phe Phe Tyr Thr Gly Val Gly Asp Arg Val Arg
    50                  55                  60

Cys Phe Ser Cys Gly Gly Gly Leu Met Asp Trp Asn Asp Asn Asp Glu
65                  70                  75                  80

Pro Trp Glu Gln His Ala Leu Trp Leu Ser Gln Cys Arg Phe Val Lys
                85                  90                  95

Leu Met Lys Gly Gln Leu Tyr Ile Asp Thr Val Ala Ala Lys Pro Val
            100                 105                 110

Leu Ala Glu Glu Lys Glu Ser Thr Ser Ile Gly Gly Asp Thr
        115                 120                 125

<210> SEQ ID NO 37
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 37

Gly Gly Gly Ser Gly Gly Gly Ser Gly Gly Gly Ser Gly Leu Asn Asp
1               5                   10                  15

Phe Phe Glu Ala Gln Lys Ile Glu Trp His Glu
            20                  25

<210> SEQ ID NO 38
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 38

Gly Gly Gly Ser Gly Gly Gly Ser Gly Gly Gly Ser Gly Leu Asn Asp
1               5                   10                  15

Phe Phe Glu Ala Gln Lys Ile Glu Trp His Glu Gly Gly Ser Gly
            20                  25                  30

Gly Gly Ser Gly Gly Gly Ser Gly Leu Asn Asp Phe Phe Glu Ala Gln
        35                  40                  45

Lys Ile Glu Trp His Glu
    50

<210> SEQ ID NO 39
<211> LENGTH: 56
<212> TYPE: PRT
<213> ORGANISM: Artificial Sequence
<220> FEATURE:
<223> OTHER INFORMATION: Synthetic Polypeptide

<400> SEQUENCE: 39

```
Gly Ser Gly Gly Gly Ser Gly Gly Ser Gly Gly Ser Gly Leu
1               5                   10                  15

Asn Asp Phe Phe Glu Ala Gln Lys Ile Glu Trp His Glu Gly Gly
            20                  25                  30

Ser Gly Gly Gly Ser Gly Gly Ser Gly Leu Asn Asp Phe Phe Glu
        35                  40                  45

Ala Gln Lys Ile Glu Trp His Glu
        50                  55
```

<210> SEQ ID NO 40
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 40

```
Gly His His His His His His His His His Gly Gly Gly Ser Gly
1               5                   10                  15

Gly Gly Ser Gly Gly Gly Ser Gly Leu Asn Asp Phe Phe Glu Ala Gln
            20                  25                  30

Lys Ile Glu Trp His Glu
        35
```

<210> SEQ ID NO 41
<211> LENGTH: 65
<212> TYPE: PRT
<213> ORGANISM: Artificial Sequence
<220> FEATURE:
<223> OTHER INFORMATION: Synthetic Polypeptide

<400> SEQUENCE: 41

```
Gly His His His His His His His His His Gly Gly Gly Ser Gly
1               5                   10                  15

Gly Gly Ser Gly Gly Gly Ser Gly Leu Asn Asp Phe Phe Glu Ala Gln
            20                  25                  30

Lys Ile Glu Trp His Glu Gly Gly Gly Ser Gly Gly Gly Ser Gly Gly
        35                  40                  45

Gly Ser Gly Leu Asn Asp Phe Phe Glu Ala Gln Lys Ile Glu Trp His
        50                  55                  60

Glu
65
```

<210> SEQ ID NO 42
<211> LENGTH: 67
<212> TYPE: PRT
<213> ORGANISM: Artificial Sequence
<220> FEATURE:
<223> OTHER INFORMATION: Synthetic Polypeptide

<400> SEQUENCE: 42

```
Gly Gly Ser His His His His His His His His His Gly Gly Gly
1               5                   10                  15

Ser Gly Gly Gly Ser Gly Gly Gly Ser Gly Leu Asn Asp Phe Phe Glu
            20                  25                  30

Ala Gln Lys Ile Glu Trp His Glu Gly Gly Gly Ser Gly Gly Gly Ser
        35                  40                  45

Gly Gly Gly Ser Gly Leu Asn Asp Phe Phe Glu Ala Gln Lys Ile Glu
        50                  55                  60
```

Trp His Glu
65

<210> SEQ ID NO 43
<211> LENGTH: 66
<212> TYPE: PRT
<213> ORGANISM: Artificial Sequence
<220> FEATURE:
<223> OTHER INFORMATION: Synthetic Polypeptide

<400> SEQUENCE: 43

Gly Ser His His His His His His His His Gly Gly Gly Ser
1               5                   10                  15

Gly Gly Gly Ser Gly Gly Gly Ser Gly Leu Asn Asp Phe Phe Glu Ala
            20                  25                  30

Gln Lys Ile Glu Trp His Glu Gly Gly Ser Gly Gly Gly Ser Gly
        35                  40                  45

Gly Gly Ser Gly Leu Asn Asp Phe Phe Glu Ala Gln Lys Ile Glu Trp
    50                  55                  60

His Glu
65

<210> SEQ ID NO 44
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 44

Gly Gly Gly Ser Gly Gly Gly Ser Gly Gly Gly Ser Gly Leu Asn Asp
1               5                   10                  15

Phe Phe Glu Ala Gln Lys Ile Glu Trp His Glu Gly Gly Gly Ser Gly
            20                  25                  30

Gly Gly Ser Gly Gly Gly Ser Gly Leu Asn Asp Phe Phe Glu Ala Gln
        35                  40                  45

Lys Ile Glu Trp His Glu Gly His His His His His His
    50                  55                  60

<210> SEQ ID NO 45
<211> LENGTH: 901
<212> TYPE: PRT
<213> ORGANISM: L. pneumophila

<400> SEQUENCE: 45

Met Met Val Lys Gln Gly Val Phe Met Lys Thr Asp Gln Ser Lys Val
1               5                   10                  15

Lys Lys Leu Ser Asp Tyr Lys Ser Leu Asp Tyr Phe Val Ile His Val
20 25 30

Asp Leu Gln Ile Asp Leu Ser Lys Lys Pro Val Glu Ser Lys Ala Arg
35 40 45

Leu Thr Val Val Pro Asn Leu Asn Val Asp Ser His Ser Asn Asp Leu
50 55 60

Val Leu Asp Gly Glu Asn Met Thr Leu Val Ser Leu Gln Met Asn Asp
65 70 75 80

Asn Leu Leu Lys Glu Asn Glu Tyr Glu Leu Thr Lys Asp Ser Leu Ile
85 90 95

Ile Lys Asn Ile Pro Gln Asn Thr Pro Phe Thr Ile Glu Met Thr Ser
100 105 110

```
Leu Leu Gly Glu Asn Thr Asp Leu Phe Gly Leu Tyr Glu Thr Gly
            115                 120                 125

Val Ala Leu Val Lys Ala Glu Ser Gly Leu Arg Arg Val Phe Tyr
            130                 135                 140

Leu Pro Asp Arg Pro Asp Asn Leu Ala Thr Tyr Lys Thr Thr Ile Ile
145                 150                 155                 160

Ala Asn Gln Glu Asp Tyr Pro Val Leu Leu Ser Asn Gly Val Leu Ile
                165                 170                 175

Glu Lys Lys Glu Leu Pro Leu Gly Leu His Ser Val Thr Trp Leu Asp
                180                 185                 190

Asp Val Pro Lys Pro Ser Tyr Leu Phe Ala Leu Val Ala Gly Asn Leu
                195                 200                 205

Gln Arg Ser Val Thr Tyr Tyr Gln Thr Lys Ser Gly Arg Glu Leu Pro
            210                 215                 220

Ile Glu Phe Tyr Val Pro Pro Ser Ala Thr Ser Lys Cys Asp Phe Ala
225                 230                 235                 240

Lys Glu Val Leu Lys Glu Ala Met Ala Trp Asp Glu Arg Thr Phe Asn
                245                 250                 255

Leu Glu Cys Ala Leu Arg Gln His Met Val Ala Gly Val Asp Lys Tyr
            260                 265                 270

Ala Ser Gly Ala Ser Glu Pro Thr Gly Leu Asn Leu Phe Asn Thr Glu
            275                 280                 285

Asn Leu Phe Ala Ser Pro Glu Thr Lys Thr Asp Leu Gly Ile Leu Arg
            290                 295                 300

Val Leu Glu Val Val Ala His Glu Phe Phe His Tyr Trp Ser Gly Asp
305                 310                 315                 320

Arg Val Thr Ile Arg Asp Trp Phe Asn Leu Pro Leu Lys Glu Gly Leu
                325                 330                 335

Thr Thr Phe Arg Ala Ala Met Phe Arg Glu Glu Leu Phe Gly Thr Asp
            340                 345                 350

Leu Ile Arg Leu Leu Asp Gly Lys Asn Leu Asp Glu Arg Ala Pro Arg
            355                 360                 365

Gln Ser Ala Tyr Thr Ala Val Arg Ser Leu Tyr Thr Ala Ala Ala Tyr
        370                 375                 380

Glu Lys Ser Ala Asp Ile Phe Arg Met Met Met Leu Phe Ile Gly Lys
385                 390                 395                 400

Glu Pro Phe Ile Glu Ala Val Ala Lys Phe Phe Lys Asp Asn Asp Gly
                405                 410                 415

Gly Ala Val Thr Leu Glu Asp Phe Ile Glu Ser Ile Ser Asn Ser Ser
            420                 425                 430

Gly Lys Asp Leu Arg Ser Phe Leu Ser Trp Phe Thr Glu Ser Gly Ile
        435                 440                 445

Pro Glu Leu Ile Val Thr Asp Glu Leu Asn Pro Asp Thr Lys Gln Tyr
450                 455                 460

Phe Leu Lys Ile Lys Thr Val Asn Gly Arg Asn Arg Pro Ile Pro Ile
465                 470                 475                 480

Leu Met Gly Leu Leu Asp Ser Ser Gly Ala Glu Ile Val Ala Asp Lys
                485                 490                 495

Leu Leu Ile Val Asp Gln Glu Ile Glu Phe Gln Phe Glu Asn Ile
                500                 505                 510

Gln Thr Arg Pro Ile Pro Ser Leu Leu Arg Ser Phe Ser Ala Pro Val
            515                 520                 525

His Met Lys Tyr Glu Tyr Ser Tyr Gln Asp Leu Leu Leu Leu Met Gln
```

```
                530             535             540
Phe Asp Thr Asn Leu Tyr Asn Arg Cys Glu Ala Ala Lys Gln Leu Ile
545                 550                 555                 560

Ser Ala Leu Ile Asn Asp Phe Cys Ile Gly Lys Lys Ile Glu Leu Ser
                    565                 570                 575

Pro Gln Phe Phe Ala Val Tyr Lys Ala Leu Leu Ser Asp Asn Ser Leu
                580                 585                 590

Asn Glu Trp Met Leu Ala Glu Leu Ile Thr Leu Pro Ser Leu Glu Glu
            595                 600                 605

Leu Ile Glu Asn Gln Asp Lys Pro Asp Phe Glu Lys Leu Asn Glu Gly
        610                 615                 620

Arg Gln Leu Ile Gln Asn Ala Leu Ala Asn Glu Leu Lys Thr Asp Phe
625                 630                 635                 640

Tyr Asn Leu Leu Phe Arg Ile Gln Ile Ser Gly Asp Asp Lys Gln
                    645                 650                 655

Lys Leu Lys Gly Phe Asp Leu Lys Gln Ala Gly Leu Arg Arg Leu Lys
                660                 665                 670

Ser Val Cys Phe Ser Tyr Leu Leu Asn Val Asp Phe Glu Lys Thr Lys
                675                 680                 685

Glu Lys Leu Ile Leu Gln Phe Glu Asp Ala Leu Gly Lys Asn Met Thr
            690                 695                 700

Glu Thr Ala Leu Ala Leu Ser Met Leu Cys Glu Ile Asn Cys Glu Glu
705                 710                 715                 720

Ala Asp Val Ala Leu Glu Asp Tyr Tyr His Tyr Trp Lys Asn Asp Pro
                725                 730                 735

Gly Ala Val Asn Asn Trp Phe Ser Ile Gln Ala Leu Ala His Ser Pro
                740                 745                 750

Asp Val Ile Glu Arg Val Lys Lys Leu Met Arg His Gly Asp Phe Asp
                755                 760                 765

Leu Ser Asn Pro Asn Lys Val Tyr Ala Leu Leu Gly Ser Phe Ile Lys
            770                 775                 780

Asn Pro Phe Gly Phe His Ser Val Thr Gly Glu Gly Tyr Gln Leu Val
785                 790                 795                 800

Ala Asp Ala Ile Phe Asp Leu Asp Lys Ile Asn Pro Thr Leu Ala Ala
                805                 810                 815

Asn Leu Thr Glu Lys Phe Thr Tyr Trp Asp Lys Tyr Asp Val Asn Arg
                820                 825                 830

Gln Ala Met Met Ile Ser Thr Leu Lys Ile Ile Tyr Ser Asn Ala Thr
            835                 840                 845

Ser Ser Asp Val Arg Thr Met Ala Lys Lys Gly Leu Asp Lys Val Lys
850                 855                 860

Glu Asp Leu Pro Leu Pro Ile His Leu Thr Phe His Gly Gly Ser Thr
865                 870                 875                 880

Met Gln Asp Arg Thr Ala Gln Leu Ile Ala Asp Gly Asn Lys Glu Asn
                885                 890                 895

Ala Tyr Gln Leu His
            900

<210> SEQ ID NO 46
<211> LENGTH: 265
<212> TYPE: PRT
<213> ORGANISM: E. coli

<400> SEQUENCE: 46
```

Met Gly Thr Ala Ile Ser Ile Lys Thr Pro Glu Asp Ile Glu Lys Met
1               5                   10                  15

Arg Val Ala Gly Arg Leu Ala Ala Glu Val Leu Glu Met Ile Glu Pro
            20                  25                  30

Tyr Val Lys Pro Gly Val Ser Thr Gly Glu Leu Asp Arg Ile Cys Asn
        35                  40                  45

Asp Tyr Ile Val Asn Glu Gln His Ala Val Ser Ala Cys Leu Gly Tyr
    50                  55                  60

His Gly Tyr Pro Lys Ser Val Cys Ile Ser Ile Asn Glu Val Val Cys
65                  70                  75                  80

His Gly Ile Pro Asp Asp Ala Lys Leu Leu Lys Asp Gly Asp Ile Val
                85                  90                  95

Asn Ile Asp Val Thr Val Ile Lys Asp Gly Phe His Gly Asp Thr Ser
            100                 105                 110

Lys Met Phe Ile Val Gly Lys Pro Thr Ile Met Gly Glu Arg Leu Cys
        115                 120                 125

Arg Ile Thr Gln Glu Ser Leu Tyr Leu Ala Leu Arg Met Val Lys Pro
    130                 135                 140

Gly Ile Asn Leu Arg Glu Ile Gly Ala Ala Ile Gln Lys Phe Val Glu
145                 150                 155                 160

Ala Glu Gly Phe Ser Val Val Arg Glu Tyr Cys Gly His Gly Ile Gly
                165                 170                 175

Arg Gly Phe His Glu Glu Pro Gln Val Leu His Tyr Asp Ser Arg Glu
            180                 185                 190

Thr Asn Val Val Leu Lys Pro Gly Met Thr Phe Thr Ile Glu Pro Met
        195                 200                 205

Val Asn Ala Gly Lys Lys Glu Ile Arg Thr Met Lys Asp Gly Trp Thr
    210                 215                 220

Val Lys Thr Lys Asp Arg Ser Leu Ser Ala Gln Tyr Glu His Thr Ile
225                 230                 235                 240

Val Val Thr Asp Asn Gly Cys Glu Ile Leu Thr Leu Arg Lys Asp Asp
                245                 250                 255

Thr Ile Pro Ala Ile Ile Ser His Asp
            260                 265

<210> SEQ ID NO 47
<211> LENGTH: 322
<212> TYPE: PRT
<213> ORGANISM: M. smegmatis

<400> SEQUENCE: 47

Met Gly Thr Leu Glu Ala Asn Thr Asn Gly Pro Gly Ser Met Leu Ser
1               5                   10                  15

Arg Met Pro Val Ser Ser Arg Thr Val Pro Phe Gly Asp His Glu Thr
            20                  25                  30

Trp Val Gln Val Thr Thr Pro Glu Asn Ala Gln Pro His Ala Leu Pro
        35                  40                  45

Leu Ile Val Leu His Gly Gly Pro Gly Met Ala His Asn Tyr Val Ala
    50                  55                  60

Asn Ile Ala Ala Leu Ala Asp Glu Thr Gly Arg Thr Val Ile His Tyr
65                  70                  75                  80

Asp Gln Val Gly Cys Gly Asn Ser Thr His Leu Pro Asp Ala Pro Ala
                85                  90                  95

Asp Phe Trp Thr Pro Gln Leu Phe Val Asp Glu Phe His Ala Val Cys
            100                 105                 110

Thr Ala Leu Gly Ile Glu Arg Tyr His Val Leu Gly Gln Ser Trp Gly
115 120 125

Gly Met Leu Gly Ala Glu Ile Ala Val Arg Gln Pro Ser Gly Leu Val
130 135 140

Ser Leu Ala Ile Cys Asn Ser Pro Ala Ser Met Arg Leu Trp Ser Glu
145 150 155 160

Ala Ala Gly Asp Leu Arg Ala Gln Leu Pro Ala Glu Thr Arg Ala Ala
165 170 175

Leu Asp Arg His Glu Ala Ala Gly Thr Ile Thr His Pro Asp Tyr Leu
180 185 190

Gln Ala Ala Ala Glu Phe Tyr Arg Arg His Val Cys Arg Val Val Pro
195 200 205

Thr Pro Gln Asp Phe Ala Asp Ser Val Ala Gln Met Glu Ala Glu Pro
210 215 220

Thr Val Tyr His Thr Met Asn Gly Pro Asn Glu Phe His Val Val Gly
225 230 235 240

Thr Leu Gly Asp Trp Ser Val Ile Asp Arg Leu Pro Asp Val Thr Ala
245 250 255

Pro Val Leu Val Ile Ala Gly Glu His Asp Glu Ala Thr Pro Lys Thr
260 265 270

Trp Gln Pro Phe Val Asp His Ile Pro Asp Val Arg Ser His Val Phe
275 280 285

Pro Gly Thr Ser His Cys Thr His Leu Glu Lys Pro Glu Glu Phe Arg
290 295 300

Ala Val Val Ala Gln Phe Leu His Gln His Asp Leu Ala Ala Asp Ala
305 310 315 320

Arg Val

<210> SEQ ID NO 48
<211> LENGTH: 446
<212> TYPE: PRT
<213> ORGANISM: Y. pestis

<400> SEQUENCE: 48

Met Thr Gln Gln Glu Tyr Gln Asn Arg Arg Gln Ala Leu Leu Ala Lys
1 5 10 15

Met Ala Pro Gly Ser Ala Ala Ile Ile Phe Ala Ala Pro Glu Ala Thr
20 25 30

Arg Ser Ala Asp Ser Glu Tyr Pro Tyr Arg Gln Asn Ser Asp Phe Ser
35 40 45

Tyr Leu Thr Gly Phe Asn Glu Pro Glu Ala Val Leu Ile Leu Val Lys
50 55 60

Ser Asp Glu Thr His Asn His Ser Val Leu Phe Asn Arg Ile Arg Asp
65 70 75 80

Leu Thr Ala Glu Ile Trp Phe Gly Arg Arg Leu Gly Gln Glu Ala Ala
85 90 95

Pro Thr Lys Leu Ala Val Asp Arg Ala Leu Pro Phe Asp Glu Ile Asn
100 105 110

Glu Gln Leu Tyr Leu Leu Leu Asn Arg Leu Asp Val Ile Tyr His Ala
115 120 125

Gln Gly Gln Tyr Ala Tyr Ala Asp Asn Ile Val Phe Ala Ala Leu Glu
130 135 140

Lys Leu Arg His Gly Phe Arg Lys Asn Leu Arg Ala Pro Ala Thr Leu
145 150 155 160

```
Thr Asp Trp Arg Pro Trp Leu His Glu Met Arg Leu Phe Lys Ser Ala
            165                 170                 175

Glu Glu Ile Ala Val Leu Arg Arg Ala Gly Glu Ile Ser Ala Leu Ala
        180                 185                 190

His Thr Arg Ala Met Glu Lys Cys Arg Pro Gly Met Phe Glu Tyr Gln
        195                 200                 205

Leu Glu Gly Glu Ile Leu His Glu Phe Thr Arg His Gly Ala Arg Tyr
        210                 215                 220

Pro Ala Tyr Asn Thr Ile Val Gly Gly Glu Asn Gly Cys Ile Leu
225                 230                 235                 240

His Tyr Thr Glu Asn Glu Cys Glu Leu Arg Asp Gly Asp Leu Val Leu
                245                 250                 255

Ile Asp Ala Gly Cys Glu Tyr Arg Gly Tyr Ala Gly Asp Ile Thr Arg
                260                 265                 270

Thr Phe Pro Val Asn Gly Lys Phe Thr Pro Ala Gln Arg Ala Val Tyr
            275                 280                 285

Asp Ile Val Leu Ala Ala Ile Asn Lys Ser Leu Thr Leu Phe Arg Pro
        290                 295                 300

Gly Thr Ser Ile Arg Glu Val Thr Glu Glu Val Val Arg Ile Met Val
305                 310                 315                 320

Val Gly Leu Val Glu Leu Gly Ile Leu Lys Gly Asp Ile Glu Gln Leu
                325                 330                 335

Ile Ala Glu Gln Ala His Arg Pro Phe Phe Met His Gly Leu Ser His
                340                 345                 350

Trp Leu Gly Met Asp Val His Asp Val Gly Asp Tyr Gly Ser Ser Asp
            355                 360                 365

Arg Gly Arg Ile Leu Glu Pro Gly Met Val Leu Thr Val Glu Pro Gly
        370                 375                 380

Leu Tyr Ile Ala Pro Asp Ala Asp Val Pro Pro Gln Tyr Arg Gly Ile
385                 390                 395                 400

Gly Ile Arg Ile Glu Asp Asp Ile Val Ile Thr Ala Thr Gly Asn Glu
                405                 410                 415

Asn Leu Thr Ala Ser Val Val Lys Asp Pro Asp Ile Glu Ala Leu
                420                 425                 430

Met Ala Leu Asn His Ala Gly Glu Asn Leu Tyr Phe Gln Glu
            435                 440                 445

<210> SEQ ID NO 49
<211> LENGTH: 303
<212> TYPE: PRT
<213> ORGANISM: P. furiosus

<400> SEQUENCE: 49

Met Asp Thr Glu Lys Leu Met Lys Ala Gly Glu Ile Ala Lys Lys Val
1               5                   10                  15

Arg Glu Lys Ala Ile Lys Leu Ala Arg Pro Gly Met Leu Leu Leu Glu
            20                  25                  30

Leu Ala Glu Ser Ile Glu Lys Met Ile Met Glu Leu Gly Gly Lys Pro
        35                  40                  45

Ala Phe Pro Val Asn Leu Ser Ile Asn Glu Ile Ala Ala His Tyr Thr
    50                  55                  60

Pro Tyr Lys Gly Asp Thr Thr Val Leu Lys Glu Gly Asp Tyr Leu Lys
65                  70                  75                  80

Ile Asp Val Gly Val His Ile Asp Gly Phe Ile Ala Asp Thr Ala Val
```

```
                85                  90                  95
Thr Val Arg Val Gly Met Glu Glu Asp Glu Leu Met Glu Ala Ala Lys
                100                 105                 110

Glu Ala Leu Asn Ala Ala Ile Ser Val Ala Arg Ala Gly Val Glu Ile
                115                 120                 125

Lys Glu Leu Gly Lys Ala Ile Glu Asn Glu Ile Arg Lys Arg Gly Phe
            130                 135                 140

Lys Pro Ile Val Asn Leu Ser Gly His Lys Ile Glu Arg Tyr Lys Leu
145                 150                 155                 160

His Ala Gly Ile Ser Ile Pro Asn Ile Tyr Arg Pro His Asp Asn Tyr
                165                 170                 175

Val Leu Lys Glu Gly Asp Val Phe Ala Ile Glu Pro Phe Ala Thr Ile
                180                 185                 190

Gly Ala Gly Gln Val Ile Glu Val Pro Pro Thr Leu Ile Tyr Met Tyr
                195                 200                 205

Val Arg Asp Val Pro Val Arg Val Ala Gln Ala Arg Phe Leu Leu Ala
                210                 215                 220

Lys Ile Lys Arg Glu Tyr Gly Thr Leu Pro Phe Ala Tyr Arg Trp Leu
225                 230                 235                 240

Gln Asn Asp Met Pro Glu Gly Gln Leu Lys Leu Ala Leu Lys Thr Leu
                245                 250                 255

Glu Lys Ala Gly Ala Ile Tyr Gly Tyr Pro Val Leu Lys Glu Ile Arg
                260                 265                 270

Asn Gly Ile Val Ala Gln Phe Glu His Thr Ile Ile Val Glu Lys Asp
                275                 280                 285

Ser Val Ile Val Thr Gln Asp Met Ile Asn Lys Ser Thr Leu Glu
                290                 295                 300

<210> SEQ ID NO 50
<211> LENGTH: 428
<212> TYPE: PRT
<213> ORGANISM: Aeromonas sobria

<400> SEQUENCE: 50

His Met Ser Ser Pro Leu His Tyr Val Leu Asp Gly Ile His Cys Glu
1               5                   10                  15

Pro His Phe Phe Thr Val Pro Leu Asp His Gln Gln Pro Asp Asp Glu
                20                  25                  30

Glu Thr Ile Thr Leu Phe Gly Arg Thr Leu Cys Arg Lys Asp Arg Leu
            35                  40                  45

Asp Asp Glu Leu Pro Trp Leu Leu Tyr Leu Gln Gly Pro Gly Phe
50                  55                  60

Gly Ala Pro Arg Pro Ser Ala Asn Gly Gly Trp Ile Lys Arg Ala Leu
65                  70                  75                  80

Gln Glu Phe Arg Val Leu Leu Leu Asp Gln Arg Gly Thr Gly His Ser
                85                  90                  95

Thr Pro Ile His Ala Glu Leu Leu Ala His Leu Asn Pro Arg Gln Gln
                100                 105                 110

Ala Asp Tyr Leu Ser His Phe Arg Ala Asp Ser Ile Val Arg Asp Ala
                115                 120                 125

Glu Leu Ile Arg Glu Gln Leu Ser Pro Asp His Pro Trp Ser Leu Leu
            130                 135                 140

Gly Gln Ser Phe Gly Gly Phe Cys Ser Leu Thr Tyr Leu Ser Leu Phe
145                 150                 155                 160
```

```
Pro Asp Ser Leu His Glu Val Tyr Leu Thr Gly Gly Val Ala Pro Ile
                165                 170                 175

Gly Arg Ser Ala Asp Glu Val Tyr Arg Ala Thr Tyr Gln Arg Val Ala
            180                 185                 190

Asp Lys Asn Arg Ala Phe Phe Arg Phe Pro His Ala Gln Ala Ile
        195                 200                 205

Ala Asn Arg Leu Ala Thr His Leu Gln Arg His Asp Val Arg Leu Pro
    210                 215                 220

Asn Gly Gln Arg Leu Thr Val Glu Gln Leu Gln Gln Gly Leu Asp
225                 230                 235                 240

Leu Gly Ala Ser Gly Ala Phe Glu Glu Leu Tyr Tyr Leu Leu Glu Asp
                245                 250                 255

Ala Phe Ile Gly Glu Lys Leu Asn Pro Ala Phe Leu Tyr Gln Val Gln
                260                 265                 270

Ala Met Gln Pro Phe Asn Thr Asn Pro Val Phe Ala Ile Leu His Glu
            275                 280                 285

Leu Ile Tyr Cys Glu Gly Ala Ser His Trp Ala Ala Glu Arg Val
    290                 295                 300

Arg Gly Glu Phe Pro Ala Leu Ala Trp Ala Gln Gly Lys Asp Phe Ala
305                 310                 315                 320

Phe Thr Gly Glu Met Ile Phe Pro Trp Met Phe Glu Gln Phe Arg Glu
                325                 330                 335

Leu Ile Pro Leu Lys Glu Ala Ala His Leu Leu Ala Glu Lys Ala Asp
                340                 345                 350

Trp Gly Pro Leu Tyr Asp Pro Val Gln Leu Ala Arg Asn Lys Val Pro
            355                 360                 365

Val Ala Cys Ala Val Tyr Ala Glu Asp Met Tyr Val Glu Phe Asp Tyr
    370                 375                 380

Ser Arg Glu Thr Leu Lys Gly Leu Ser Asn Ser Arg Ala Trp Ile Thr
385                 390                 395                 400

Asn Glu Tyr Glu His Asn Gly Leu Arg Val Asp Gly Glu Gln Ile Leu
                405                 410                 415

Asp Arg Leu Ile Arg Leu Asn Arg Asp Cys Leu Glu
            420                 425

<210> SEQ ID NO 51
<211> LENGTH: 348
<212> TYPE: PRT
<213> ORGANISM: Pyrococcus furiosus

<400> SEQUENCE: 51

Met Lys Glu Arg Leu Glu Lys Leu Val Lys Phe Met Asp Glu Asn Ser
1               5                   10                  15

Ile Asp Arg Val Phe Ile Ala Lys Pro Val Asn Val Tyr Tyr Phe Ser
            20                  25                  30

Gly Thr Ser Pro Leu Gly Gly Tyr Ile Ile Val Asp Gly Asp Glu
        35                  40                  45

Ala Thr Leu Tyr Val Pro Glu Leu Glu Tyr Glu Met Ala Lys Glu Glu
    50                  55                  60

Ser Lys Leu Pro Val Val Lys Phe Lys Lys Phe Asp Glu Ile Tyr Glu
65                  70                  75                  80

Ile Leu Lys Asn Thr Glu Thr Leu Gly Ile Glu Gly Thr Leu Ser Tyr
                85                  90                  95

Ser Met Val Glu Asn Phe Lys Glu Lys Ser Asn Val Lys Glu Phe Lys
            100                 105                 110
```

```
Lys Ile Asp Asp Val Ile Lys Asp Leu Arg Ile Ile Lys Thr Lys Glu
            115                 120                 125

Glu Ile Glu Ile Ile Glu Lys Ala Cys Glu Ile Ala Asp Lys Ala Val
130                 135                 140

Met Ala Ile Glu Glu Ile Thr Gly Lys Arg Glu Arg Glu Val
145                 150                 155                 160

Ala Ala Lys Val Glu Tyr Leu Met Lys Met Asn Gly Ala Glu Lys Pro
            165                 170                 175

Ala Phe Asp Thr Ile Ile Ala Ser Gly His Arg Ser Ala Leu Pro His
            180                 185                 190

Gly Val Ala Ser Asp Lys Arg Ile Glu Arg Gly Asp Leu Val Val Ile
            195                 200                 205

Asp Leu Gly Ala Leu Tyr Asn His Tyr Asn Ser Asp Ile Thr Arg Thr
210                 215                 220

Ile Val Val Gly Ser Pro Asn Glu Lys Gln Arg Glu Ile Tyr Glu Ile
225                 230                 235                 240

Val Leu Glu Ala Gln Lys Arg Ala Val Glu Ala Ala Lys Pro Gly Met
            245                 250                 255

Thr Ala Lys Glu Leu Asp Ser Ile Ala Arg Glu Ile Ile Lys Glu Tyr
            260                 265                 270

Gly Tyr Gly Asp Tyr Phe Ile His Ser Leu Gly His Gly Val Gly Leu
            275                 280                 285

Glu Ile His Glu Trp Pro Arg Ile Ser Gln Tyr Asp Glu Thr Val Leu
            290                 295                 300

Lys Glu Gly Met Val Ile Thr Ile Glu Pro Gly Ile Tyr Ile Pro Lys
305                 310                 315                 320

Leu Gly Gly Val Arg Ile Glu Asp Thr Val Leu Ile Thr Glu Asn Gly
            325                 330                 335

Ala Lys Arg Leu Thr Lys Thr Glu Arg Glu Leu Leu
            340                 345

<210> SEQ ID NO 52
<211> LENGTH: 298
<212> TYPE: PRT
<213> ORGANISM: Elizabethkingia meningoseptica

<400> SEQUENCE: 52

Met Ile Pro Ile Thr Thr Pro Val Gly Asn Phe Lys Val Trp Thr Lys
1               5                   10                  15

Arg Phe Gly Thr Asn Pro Lys Ile Lys Val Leu Leu Leu His Gly Gly
            20                  25                  30

Pro Ala Met Thr His Glu Tyr Met Glu Cys Phe Glu Thr Phe Phe Gln
            35                  40                  45

Arg Glu Gly Phe Glu Phe Tyr Glu Tyr Asp Gln Leu Gly Ser Tyr Tyr
        50                  55                  60

Ser Asp Gln Pro Thr Asp Glu Lys Leu Trp Asn Ile Asp Arg Phe Val
65                  70                  75                  80

Asp Glu Val Glu Gln Val Arg Lys Ala Ile His Ala Asp Lys Glu Asn
                85                  90                  95

Phe Tyr Val Leu Gly Asn Ser Trp Gly Gly Ile Leu Ala Met Glu Tyr
            100                 105                 110

Ala Leu Lys Tyr Gln Gln Asn Leu Lys Gly Leu Ile Val Ala Asn Met
            115                 120                 125

Met Ala Ser Ala Pro Glu Tyr Val Lys Tyr Ala Glu Val Leu Ser Lys
```

```
        130                 135                 140
Gln Met Lys Pro Glu Val Leu Ala Glu Val Arg Ala Ile Glu Ala Lys
145                 150                 155                 160

Lys Asp Tyr Ala Asn Pro Arg Tyr Thr Glu Leu Leu Phe Pro Asn Tyr
                165                 170                 175

Tyr Ala Gln His Ile Cys Arg Leu Lys Glu Trp Pro Asp Ala Leu Asn
            180                 185                 190

Arg Ser Leu Lys His Val Asn Ser Thr Val Tyr Thr Leu Met Gln Gly
        195                 200                 205

Pro Ser Glu Leu Gly Met Ser Ser Asp Ala Arg Leu Ala Lys Trp Asp
    210                 215                 220

Ile Lys Asn Arg Leu His Glu Ile Ala Thr Pro Thr Leu Met Ile Gly
225                 230                 235                 240

Ala Arg Tyr Asp Thr Met Asp Pro Lys Ala Met Glu Glu Gln Ser Lys
                245                 250                 255

Leu Val Gln Lys Gly Arg Tyr Leu Tyr Cys Pro Asn Gly Ser His Leu
            260                 265                 270

Ala Met Trp Asp Asp Gln Lys Val Phe Met Asp Gly Val Ile Lys Phe
        275                 280                 285

Ile Lys Asp Val Asp Thr Lys Ser Phe Asn
    290                 295

<210> SEQ ID NO 53
<211> LENGTH: 310
<212> TYPE: PRT
<213> ORGANISM: N. gonorrhoeae

<400> SEQUENCE: 53

Met Tyr Glu Ile Lys Gln Pro Phe His Ser Gly Tyr Leu Gln Val Ser
1               5                   10                  15

Glu Ile His Gln Ile Tyr Trp Glu Gly Ser Gly Asn Pro Asp Gly Val
            20                  25                  30

Pro Val Ile Phe Leu His Gly Gly Pro Gly Ala Gly Ala Ser Pro Glu
        35                  40                  45

Cys Arg Gly Phe Phe Asn Pro Asp Val Phe Arg Ile Val Ile Ile Asp
    50                  55                  60

Gln Arg Gly Cys Gly Arg Ser His Pro Tyr Ala Cys Ala Glu Asp Asn
65                  70                  75                  80

Thr Thr Trp Asp Leu Val Ala Asp Ile Glu Lys Val Arg Glu Met Leu
                85                  90                  95

Gly Ile Gly Lys Trp Leu Val Phe Gly Gly Ser Trp Gly Ser Thr Leu
            100                 105                 110

Ser Leu Ala Tyr Ala Gln Thr His Pro Glu Arg Val Lys Gly Leu Val
        115                 120                 125

Leu Arg Gly Ile Phe Leu Cys Arg Pro Ser Glu Thr Ala Trp Leu Asn
    130                 135                 140

Glu Ala Gly Gly Val Ser Arg Ile Tyr Pro Glu Gln Trp Gln Lys Phe
145                 150                 155                 160

Val Ala Pro Ile Ala Glu Asn Arg Arg Asn Arg Leu Ile Glu Ala Tyr
                165                 170                 175

His Gly Leu Leu Phe His Gln Asp Glu Glu Val Cys Leu Ser Ala Ala
            180                 185                 190

Lys Ala Trp Ala Asp Trp Glu Ser Tyr Leu Ile Arg Phe Glu Pro Glu
        195                 200                 205
```

Gly Val Asp Glu Asp Ala Tyr Ala Ser Leu Ala Ile Ala Arg Leu Glu
    210                 215                 220

Asn His Tyr Phe Val Asn Gly Gly Trp Leu Gln Gly Asp Lys Ala Ile
225                 230                 235                 240

Leu Asn Asn Ile Gly Lys Ile Arg His Ile Pro Thr Val Ile Val Gln
                245                 250                 255

Gly Arg Tyr Asp Leu Cys Thr Pro Met Gln Ser Ala Trp Glu Leu Ser
                260                 265                 270

Lys Ala Phe Pro Glu Ala Glu Leu Arg Val Val Gln Ala Gly His Cys
                275                 280                 285

Ala Phe Asp Pro Pro Leu Ala Asp Ala Leu Val Gln Ala Val Glu Asp
290                 295                 300

Ile Leu Pro Arg Leu Leu
305                 310

<210> SEQ ID NO 54
<211> LENGTH: 870
<212> TYPE: PRT
<213> ORGANISM: E. coli

<400> SEQUENCE: 54

Met Thr Gln Gln Pro Gln Ala Lys Tyr Arg His Asp Tyr Arg Ala Pro
1               5                   10                  15

Asp Tyr Gln Ile Thr Asp Ile Asp Leu Thr Phe Asp Leu Asp Ala Gln
                20                  25                  30

Lys Thr Val Val Thr Ala Val Ser Gln Ala Val Arg His Gly Ala Ser
                35                  40                  45

Asp Ala Pro Leu Arg Leu Asn Gly Glu Asp Leu Lys Leu Val Ser Val
    50                  55                  60

His Ile Asn Asp Glu Pro Trp Thr Ala Trp Lys Glu Glu Gly Ala
65                  70                  75                  80

Leu Val Ile Ser Asn Leu Pro Glu Arg Phe Thr Leu Lys Ile Ile Asn
                85                  90                  95

Glu Ile Ser Pro Ala Ala Asn Thr Ala Leu Glu Gly Leu Tyr Gln Ser
                100                 105                 110

Gly Asp Ala Leu Cys Thr Gln Cys Glu Ala Glu Gly Phe Arg His Ile
            115                 120                 125

Thr Tyr Tyr Leu Asp Arg Pro Asp Val Leu Ala Arg Phe Thr Thr Lys
    130                 135                 140

Ile Ile Ala Asp Lys Ile Lys Tyr Pro Phe Leu Leu Ser Asn Gly Asn
145                 150                 155                 160

Arg Val Ala Gln Gly Glu Leu Glu Asn Gly Arg His Trp Val Gln Trp
                165                 170                 175

Gln Asp Pro Phe Pro Lys Pro Cys Tyr Leu Phe Ala Leu Val Ala Gly
            180                 185                 190

Asp Phe Asp Val Leu Arg Asp Thr Phe Thr Thr Arg Ser Gly Arg Glu
        195                 200                 205

Val Ala Leu Glu Leu Tyr Val Asp Arg Gly Asn Leu Asp Arg Ala Pro
    210                 215                 220

Trp Ala Met Thr Ser Leu Lys Asn Ser Met Lys Trp Asp Glu Glu Arg
225                 230                 235                 240

Phe Gly Leu Glu Tyr Asp Leu Asp Ile Tyr Met Ile Val Ala Val Asp
                245                 250                 255

Phe Phe Asn Met Gly Ala Met Glu Asn Lys Gly Leu Asn Ile Phe Asn
            260                 265                 270

```
Ser Lys Tyr Val Leu Ala Arg Thr Asp Thr Ala Thr Asp Lys Asp Tyr
        275                 280                 285

Leu Asp Ile Glu Arg Val Ile Gly His Glu Tyr Phe His Asn Trp Thr
    290                 295                 300

Gly Asn Arg Val Thr Cys Arg Asp Trp Phe Gln Leu Ser Leu Lys Glu
305                 310                 315                 320

Gly Leu Thr Val Phe Arg Asp Gln Glu Phe Ser Ser Asp Leu Gly Ser
                325                 330                 335

Arg Ala Val Asn Arg Ile Asn Asn Val Arg Thr Met Arg Gly Leu Gln
                340                 345                 350

Phe Ala Glu Asp Ala Ser Pro Met Ala His Pro Ile Arg Pro Asp Met
        355                 360                 365

Val Ile Glu Met Asn Asn Phe Tyr Thr Leu Thr Val Tyr Glu Lys Gly
    370                 375                 380

Ala Glu Val Ile Arg Met Ile His Thr Leu Leu Gly Glu Glu Asn Phe
385                 390                 395                 400

Gln Lys Gly Met Gln Leu Tyr Phe Glu Arg His Asp Gly Ser Ala Ala
                405                 410                 415

Thr Cys Asp Asp Phe Val Gln Ala Met Glu Asp Ala Ser Asn Val Asp
                420                 425                 430

Leu Ser His Phe Arg Arg Trp Tyr Ser Gln Ser Gly Thr Pro Ile Val
        435                 440                 445

Thr Val Lys Asp Asp Tyr Asn Pro Glu Thr Glu Gln Tyr Thr Leu Thr
    450                 455                 460

Ile Ser Gln Arg Thr Pro Ala Thr Pro Asp Gln Ala Glu Lys Gln Pro
465                 470                 475                 480

Leu His Ile Pro Phe Ala Ile Glu Leu Tyr Asp Asn Glu Gly Lys Val
                485                 490                 495

Ile Pro Leu Gln Lys Gly Gly His Pro Val Asn Ser Val Leu Asn Val
                500                 505                 510

Thr Gln Ala Glu Gln Thr Phe Val Phe Asp Asn Val Tyr Phe Gln Pro
        515                 520                 525

Val Pro Ala Leu Leu Cys Glu Phe Ser Ala Pro Val Lys Leu Glu Tyr
    530                 535                 540

Lys Trp Ser Asp Gln Gln Leu Thr Phe Leu Met Arg His Ala Arg Asn
545                 550                 555                 560

Asp Phe Ser Arg Trp Asp Ala Ala Gln Ser Leu Leu Ala Thr Tyr Ile
                565                 570                 575

Lys Leu Asn Val Ala Arg His Gln Gln Gly Gln Pro Leu Ser Leu Pro
                580                 585                 590

Val His Val Ala Asp Ala Phe Arg Ala Val Leu Leu Asp Glu Lys Ile
        595                 600                 605

Asp Pro Ala Leu Ala Ala Glu Ile Leu Thr Leu Pro Ser Val Asn Glu
    610                 615                 620

Met Ala Glu Leu Phe Asp Ile Ile Asp Pro Ile Ala Ile Ala Glu Val
625                 630                 635                 640

Arg Glu Ala Leu Thr Arg Thr Leu Ala Thr Glu Leu Ala Asp Glu Leu
                645                 650                 655

Leu Ala Ile Tyr Asn Ala Asn Tyr Gln Ser Glu Tyr Arg Val Glu His
                660                 665                 670

Glu Asp Ile Ala Lys Arg Thr Leu Arg Asn Ala Cys Leu Arg Phe Leu
        675                 680                 685
```

```
Ala Phe Gly Glu Thr His Leu Ala Asp Val Leu Val Ser Lys Gln Phe
690                 695                 700

His Glu Ala Asn Asn Met Thr Asp Ala Leu Ala Ala Leu Ser Ala Ala
705                 710                 715                 720

Val Ala Ala Gln Leu Pro Cys Arg Asp Ala Leu Met Gln Glu Tyr Asp
                725                 730                 735

Asp Lys Trp His Gln Asn Gly Leu Val Met Asp Lys Trp Phe Ile Leu
                740                 745                 750

Gln Ala Thr Ser Pro Ala Ala Asn Val Leu Glu Thr Val Arg Gly Leu
                755                 760                 765

Leu Gln His Arg Ser Phe Thr Met Ser Asn Pro Asn Arg Ile Arg Ser
770                 775                 780

Leu Ile Gly Ala Phe Ala Gly Ser Asn Pro Ala Ala Phe His Ala Glu
785                 790                 795                 800

Asp Gly Ser Gly Tyr Leu Phe Leu Val Glu Met Leu Thr Asp Leu Asn
                805                 810                 815

Ser Arg Asn Pro Gln Val Ala Ser Arg Leu Ile Glu Pro Leu Ile Arg
                820                 825                 830

Leu Lys Arg Tyr Asp Ala Lys Arg Gln Glu Lys Met Arg Ala Ala Leu
                835                 840                 845

Glu Gln Leu Lys Gly Leu Glu Asn Leu Ser Gly Asp Leu Tyr Glu Lys
850                 855                 860

Ile Thr Lys Ala Leu Ala
865                 870

<210> SEQ ID NO 55
<211> LENGTH: 889
<212> TYPE: PRT
<213> ORGANISM: P. falciparum

<400> SEQUENCE: 55

Pro Lys Ile His Tyr Arg Lys Asp Tyr Lys Pro Ser Gly Phe Ile Ile
1               5                   10                  15

Asn Gln Val Thr Leu Asn Ile Asn Ile His Asp Gln Glu Thr Ile Val
                20                  25                  30

Arg Ser Val Leu Asp Met Asp Ile Ser Lys His Asn Val Gly Glu Asp
                35                  40                  45

Leu Val Phe Asp Gly Val Gly Leu Lys Ile Asn Glu Ile Ser Ile Asn
                50                  55                  60

Asn Lys Lys Leu Val Glu Gly Glu Tyr Thr Tyr Asp Asn Glu Phe
65                  70                  75                  80

Leu Thr Ile Phe Ser Lys Phe Val Pro Lys Ser Lys Phe Ala Phe Ser
                85                  90                  95

Ser Glu Val Ile Ile His Pro Glu Thr Asn Tyr Ala Leu Thr Gly Leu
                100                 105                 110

Tyr Lys Ser Lys Asn Ile Ile Val Ser Gln Cys Glu Ala Thr Gly Phe
                115                 120                 125

Arg Arg Ile Thr Phe Phe Ile Asp Arg Pro Asp Met Met Ala Lys Tyr
130                 135                 140

Asp Val Thr Val Thr Ala Asp Lys Glu Lys Tyr Pro Val Leu Leu Ser
145                 150                 155                 160

Asn Gly Asp Lys Val Asn Glu Phe Glu Ile Pro Gly Gly Arg His Gly
                165                 170                 175

Ala Arg Phe Asn Asp Pro Pro Leu Lys Pro Cys Tyr Leu Phe Ala Val
                180                 185                 190
```

```
Val Ala Gly Asp Leu Lys His Leu Ser Ala Thr Tyr Ile Thr Lys Tyr
        195                 200                 205

Thr Lys Lys Val Glu Leu Tyr Val Phe Ser Glu Lys Tyr Val
    210                 215                 220

Ser Lys Leu Gln Trp Ala Leu Glu Cys Leu Lys Lys Ser Met Ala Phe
225                 230                 235                 240

Asp Glu Asp Tyr Phe Gly Leu Glu Tyr Asp Leu Ser Arg Leu Asn Leu
                245                 250                 255

Val Ala Val Ser Asp Phe Asn Val Gly Ala Met Glu Asn Lys Gly Leu
                260                 265                 270

Asn Ile Phe Asn Ala Asn Ser Leu Leu Ala Ser Lys Lys Asn Ser Ile
            275                 280                 285

Asp Phe Ser Tyr Ala Arg Ile Leu Thr Val Val Gly His Glu Tyr Phe
            290                 295                 300

His Gln Tyr Thr Gly Asn Arg Val Thr Leu Arg Asp Trp Phe Gln Leu
305                 310                 315                 320

Thr Leu Lys Glu Gly Leu Thr Val His Arg Glu Asn Leu Phe Ser Glu
                325                 330                 335

Glu Met Thr Lys Thr Val Thr Arg Leu Ser His Val Asp Leu Leu
                340                 345                 350

Arg Ser Val Gln Phe Leu Glu Asp Ser Ser Pro Leu Ser His Pro Ile
            355                 360                 365

Arg Pro Glu Ser Tyr Val Ser Met Glu Asn Phe Tyr Thr Thr Thr Val
    370                 375                 380

Tyr Asp Lys Gly Ser Glu Val Met Arg Met Tyr Leu Thr Ile Leu Gly
385                 390                 395                 400

Glu Glu Tyr Tyr Lys Lys Gly Phe Asp Ile Tyr Ile Lys Lys Asn Asp
                405                 410                 415

Gly Asn Thr Ala Thr Cys Glu Asp Phe Asn Tyr Ala Met Glu Gln Ala
            420                 425                 430

Tyr Lys Met Lys Lys Ala Asp Asn Ser Ala Asn Leu Asn Gln Tyr Leu
        435                 440                 445

Leu Trp Phe Ser Gln Ser Gly Thr Pro His Val Ser Phe Lys Tyr Asn
    450                 455                 460

Tyr Asp Ala Glu Lys Lys Gln Tyr Ser Ile His Val Asn Gln Tyr Thr
465                 470                 475                 480

Lys Pro Asp Glu Asn Gln Lys Glu Lys Lys Pro Leu Phe Ile Pro Ile
                485                 490                 495

Ser Val Gly Leu Ile Asn Pro Glu Asn Gly Lys Glu Met Ile Ser Gln
            500                 505                 510

Thr Thr Leu Glu Leu Thr Lys Glu Ser Asp Thr Phe Val Phe Asn Asn
        515                 520                 525

Ile Ala Val Lys Pro Ile Pro Ser Leu Phe Arg Gly Phe Ser Ala Pro
    530                 535                 540

Val Tyr Ile Glu Asp Gln Leu Thr Asp Glu Glu Arg Ile Leu Leu Leu
545                 550                 555                 560

Lys Tyr Asp Ser Asp Ala Phe Val Arg Tyr Asn Ser Cys Thr Asn Ile
                565                 570                 575

Tyr Met Lys Gln Ile Leu Met Asn Tyr Asn Glu Phe Leu Lys Ala Lys
            580                 585                 590

Asn Glu Lys Leu Glu Ser Phe Gln Leu Thr Pro Val Asn Ala Gln Phe
        595                 600                 605
```

Ile Asp Ala Ile Lys Tyr Leu Leu Glu Asp Pro His Ala Asp Ala Gly
610                 615                 620

Phe Lys Ser Tyr Ile Val Ser Leu Pro Gln Asp Arg Tyr Ile Ile Asn
625                 630                 635                 640

Phe Val Ser Asn Leu Asp Thr Asp Val Leu Ala Asp Thr Lys Glu Tyr
                645                 650                 655

Ile Tyr Lys Gln Ile Gly Asp Lys Leu Asn Asp Val Tyr Tyr Lys Met
                660                 665                 670

Phe Lys Ser Leu Glu Ala Lys Ala Asp Asp Leu Thr Tyr Phe Asn Asp
                675                 680                 685

Glu Ser His Val Asp Phe Asp Gln Met Asn Met Arg Thr Leu Arg Asn
690                 695                 700

Thr Leu Leu Ser Leu Leu Ser Lys Ala Gln Tyr Pro Asn Ile Leu Asn
705                 710                 715                 720

Glu Ile Ile Glu His Ser Lys Ser Pro Tyr Pro Ser Asn Trp Leu Thr
                725                 730                 735

Ser Leu Ser Val Ser Ala Tyr Phe Asp Lys Tyr Phe Glu Leu Tyr Asp
                740                 745                 750

Lys Thr Tyr Lys Leu Ser Lys Asp Asp Glu Leu Leu Leu Gln Glu Trp
                755                 760                 765

Leu Lys Thr Val Ser Arg Ser Asp Arg Lys Asp Ile Tyr Glu Ile Leu
770                 775                 780

Lys Lys Leu Glu Asn Glu Val Leu Lys Asp Ser Lys Asn Pro Asn Asp
785                 790                 795                 800

Ile Arg Ala Val Tyr Leu Pro Phe Thr Asn Asn Leu Arg Arg Phe His
                805                 810                 815

Asp Ile Ser Gly Lys Gly Tyr Lys Leu Ile Ala Glu Val Ile Thr Lys
                820                 825                 830

Thr Asp Lys Phe Asn Pro Met Val Ala Thr Gln Leu Cys Glu Pro Phe
                835                 840                 845

Lys Leu Trp Asn Lys Leu Asp Thr Lys Arg Gln Glu Leu Met Leu Asn
850                 855                 860

Glu Met Asn Thr Met Leu Gln Glu Pro Gln Ile Ser Asn Asn Leu Lys
865                 870                 875                 880

Glu Tyr Leu Leu Arg Leu Thr Asn Lys
                885

<210> SEQ ID NO 56
<211> LENGTH: 919
<212> TYPE: PRT
<213> ORGANISM: Unknown
<220> FEATURE:
<223> OTHER INFORMATION: Puromycin-sensitive aminopeptidase

<400> SEQUENCE: 56

Met Trp Leu Ala Ala Ala Ala Pro Ser Leu Ala Arg Arg Leu Leu Phe
1               5                   10                  15

Leu Gly Pro Pro Pro Pro Leu Leu Leu Val Phe Ser Arg Ser
                20                  25                  30

Ser Arg Arg Arg Leu His Ser Leu Gly Leu Ala Ala Met Pro Glu Lys
                35                  40                  45

Arg Pro Phe Glu Arg Leu Pro Ala Asp Val Ser Pro Ile Asn Tyr Ser
                50                  55                  60

Leu Cys Leu Lys Pro Asp Leu Asp Phe Thr Phe Glu Gly Lys Leu
65                  70                  75                  80

```
Glu Ala Ala Ala Gln Val Arg Gln Ala Thr Asn Gln Ile Val Met Asn
                85                  90                  95

Cys Ala Asp Ile Asp Ile Ile Thr Ala Ser Tyr Ala Pro Glu Gly Asp
            100                 105                 110

Glu Glu Ile His Ala Thr Gly Phe Asn Tyr Gln Asn Glu Asp Glu Lys
            115                 120                 125

Val Thr Leu Ser Phe Pro Ser Thr Leu Gln Thr Gly Thr Gly Thr Leu
130                 135                 140

Lys Ile Asp Phe Val Gly Glu Leu Asn Asp Lys Met Lys Gly Phe Tyr
145                 150                 155                 160

Arg Ser Lys Tyr Thr Thr Pro Ser Gly Glu Val Arg Tyr Ala Ala Val
                165                 170                 175

Thr Gln Phe Glu Ala Thr Asp Ala Arg Arg Ala Phe Pro Cys Trp Asp
            180                 185                 190

Glu Pro Ala Ile Lys Ala Thr Phe Asp Ile Ser Leu Val Val Pro Lys
            195                 200                 205

Asp Arg Val Ala Leu Ser Asn Met Asn Val Ile Asp Arg Lys Pro Tyr
    210                 215                 220

Pro Asp Asp Glu Asn Leu Val Glu Val Lys Phe Ala Arg Thr Pro Val
225                 230                 235                 240

Met Ser Thr Tyr Leu Val Ala Phe Val Val Gly Glu Tyr Asp Phe Val
                245                 250                 255

Glu Thr Arg Ser Lys Asp Gly Val Cys Val Arg Val Tyr Thr Pro Val
            260                 265                 270

Gly Lys Ala Glu Gln Gly Lys Phe Ala Leu Glu Val Ala Ala Lys Thr
            275                 280                 285

Leu Pro Phe Tyr Lys Asp Tyr Phe Asn Val Pro Tyr Pro Leu Pro Lys
    290                 295                 300

Ile Asp Leu Ile Ala Ile Ala Asp Phe Ala Ala Gly Ala Met Glu Asn
305                 310                 315                 320

Trp Gly Leu Val Thr Tyr Arg Glu Thr Ala Leu Leu Ile Asp Pro Lys
                325                 330                 335

Asn Ser Cys Ser Ser Ser Arg Gln Trp Val Ala Leu Val Val Gly His
            340                 345                 350

Glu Leu Ala His Gln Trp Phe Gly Asn Leu Val Thr Met Glu Trp Trp
            355                 360                 365

Thr His Leu Trp Leu Asn Glu Gly Phe Ala Ser Trp Ile Glu Tyr Leu
    370                 375                 380

Cys Val Asp His Cys Phe Pro Glu Tyr Asp Ile Trp Thr Gln Phe Val
385                 390                 395                 400

Ser Ala Asp Tyr Thr Arg Ala Gln Glu Leu Asp Ala Leu Asp Asn Ser
                405                 410                 415

His Pro Ile Glu Val Ser Val Gly His Pro Ser Glu Val Asp Glu Ile
            420                 425                 430

Phe Asp Ala Ile Ser Tyr Ser Lys Gly Ala Ser Val Ile Arg Met Leu
            435                 440                 445

His Asp Tyr Ile Gly Asp Lys Asp Phe Lys Lys Gly Met Asn Met Tyr
    450                 455                 460

Leu Thr Lys Phe Gln Gln Lys Asn Ala Ala Thr Glu Asp Leu Trp Glu
465                 470                 475                 480

Ser Leu Glu Asn Ala Ser Gly Lys Pro Ile Ala Ala Val Met Asn Thr
                485                 490                 495

Trp Thr Lys Gln Met Gly Phe Pro Leu Ile Tyr Val Glu Ala Glu Gln
```

-continued

```
                500                 505                 510
Val Glu Asp Asp Arg Leu Leu Arg Leu Ser Gln Lys Lys Phe Cys Ala
                515                 520                 525

Gly Gly Ser Tyr Val Gly Asp Cys Pro Gln Trp Met Val Pro Ile
                530                 535             540

Thr Ile Ser Thr Ser Glu Asp Pro Asn Gln Ala Lys Leu Lys Ile Leu
545                 550                 555                 560

Met Asp Lys Pro Glu Met Asn Val Val Leu Lys Asn Val Lys Pro Asp
                565                 570                 575

Gln Trp Val Lys Leu Asn Leu Gly Thr Val Gly Phe Tyr Arg Thr Gln
                580                 585                 590

Tyr Ser Ser Ala Met Leu Glu Ser Leu Leu Pro Gly Ile Arg Asp Leu
                595                 600                 605

Ser Leu Pro Pro Val Asp Arg Leu Gly Leu Gln Asn Asp Leu Phe Ser
                610                 615                 620

Leu Ala Arg Ala Gly Ile Ile Ser Thr Val Glu Val Leu Lys Val Met
625                 630                 635                 640

Glu Ala Phe Val Asn Glu Pro Asn Tyr Thr Val Trp Ser Asp Leu Ser
                645                 650                 655

Cys Asn Leu Gly Ile Leu Ser Thr Leu Leu Ser His Thr Asp Phe Tyr
                660                 665                 670

Glu Glu Ile Gln Glu Phe Val Lys Asp Val Phe Ser Pro Ile Gly Glu
                675                 680                 685

Arg Leu Gly Trp Asp Pro Lys Pro Gly Glu Gly His Leu Asp Ala Leu
                690                 695                 700

Leu Arg Gly Leu Val Leu Gly Lys Leu Gly Lys Ala Gly His Lys Ala
705                 710                 715                 720

Thr Leu Glu Glu Ala Arg Arg Phe Lys Asp His Val Glu Gly Lys
                725                 730                 735

Gln Ile Leu Ser Ala Asp Leu Arg Ser Pro Val Tyr Leu Thr Val Leu
                740                 745                 750

Lys His Gly Asp Gly Thr Thr Leu Asp Ile Met Leu Lys Leu His Lys
                755                 760                 765

Gln Ala Asp Met Gln Glu Glu Lys Asn Arg Ile Glu Arg Val Leu Gly
                770                 775             780

Ala Thr Leu Leu Pro Asp Leu Ile Gln Lys Val Leu Thr Phe Ala Leu
785                 790                 795                 800

Ser Glu Glu Val Arg Pro Gln Asp Thr Val Ser Val Ile Gly Gly Val
                805                 810                 815

Ala Gly Gly Ser Lys His Gly Arg Lys Ala Ala Trp Lys Phe Ile Lys
                820                 825                 830

Asp Asn Trp Glu Glu Leu Tyr Asn Arg Tyr Gln Gly Gly Phe Leu Ile
                835                 840                 845

Ser Arg Leu Ile Lys Leu Ser Val Gly Phe Ala Val Asp Lys Met
                850                 855                 860

Ala Gly Glu Val Lys Ala Phe Phe Glu Ser His Pro Ala Pro Ser Ala
865                 870                 875                 880

Glu Arg Thr Ile Gln Gln Cys Cys Glu Asn Ile Leu Leu Asn Ala Ala
                885                 890                 895

Trp Leu Lys Arg Asp Ala Glu Ser Ile His Gln Tyr Leu Leu Gln Arg
                900                 905                 910

Lys Ala Ser Pro Pro Thr Val
                915
```

<210> SEQ ID NO 57
<211> LENGTH: 919
<212> TYPE: PRT
<213> ORGANISM: Artificial Sequence
<220> FEATURE:
<223> OTHER INFORMATION: Synthetic Polypeptide

<400> SEQUENCE: 57

```
Met Trp Leu Ala Ala Ala Pro Ser Leu Ala Arg Arg Leu Leu Phe
1               5                   10                  15

Leu Gly Pro Pro Pro Pro Leu Leu Leu Val Phe Ser Arg Ser
                20                  25                  30

Ser Arg Arg Arg Leu His Ser Leu Gly Leu Ala Ala Met Pro Glu Lys
            35                  40                  45

Arg Pro Phe Glu Arg Leu Pro Ala Asp Val Ser Pro Ile Asn Tyr Ser
50                  55                  60

Leu Cys Leu Lys Pro Asp Leu Leu Asp Phe Thr Phe Glu Gly Lys Leu
65                  70                  75                  80

Glu Ala Ala Ala Gln Val Arg Gln Ala Thr Asn Gln Ile Val Met Asn
                85                  90                  95

Cys Ala Asp Ile Asp Ile Ile Thr Ala Ser Tyr Ala Pro Glu Gly Asp
                100                 105                 110

Glu Glu Ile His Ala Thr Gly Phe Asn Tyr Gln Asn Glu Asp Glu Lys
            115                 120                 125

Val Thr Leu Ser Phe Pro Ser Thr Leu Gln Thr Gly Thr Gly Thr Leu
130                 135                 140

Lys Ile Asp Phe Val Gly Glu Leu Asn Asp Lys Met Lys Gly Phe Tyr
145                 150                 155                 160

Arg Ser Lys Tyr Thr Thr Pro Ser Gly Glu Val Arg Tyr Ala Ala Val
                165                 170                 175

Thr Gln Phe Glu Ala Thr Asp Ala Arg Arg Ala Phe Pro Cys Trp Asp
            180                 185                 190

Glu Pro Ala Ile Lys Ala Thr Phe Asp Ile Ser Leu Val Val Pro Lys
            195                 200                 205

Asp Arg Val Ala Leu Ser Asn Met Asn Val Ile Asp Arg Lys Pro Tyr
210                 215                 220

Pro Asp Asp Glu Asn Leu Val Glu Val Lys Phe Ala Arg Thr Pro Val
225                 230                 235                 240

Met Ser Thr Tyr Leu Val Ala Phe Val Val Gly Glu Tyr Asp Phe Val
                245                 250                 255

Glu Thr Arg Ser Lys Asp Gly Val Cys Val Arg Val Tyr Thr Pro Val
            260                 265                 270

Gly Lys Ala Glu Gln Gly Lys Phe Ala Leu Glu Val Ala Lys Thr
            275                 280                 285

Leu Pro Phe Tyr Lys Asp Tyr Phe Asn Val Pro Tyr Pro Leu Pro Lys
290                 295                 300

Ile Asp Leu Ile Ala Ile Ala Asp Phe Ala Ala Gly Ala Met Glu Asn
305                 310                 315                 320

Trp Gly Leu Val Thr Tyr Arg Glu Thr Ala Leu Leu Ile Asp Pro Lys
                325                 330                 335

Asn Ser Cys Ser Ser Ser Arg Gln Trp Val Ala Leu Val Val Gly His
            340                 345                 350

Val Leu Ala His Gln Trp Phe Gly Asn Leu Val Thr Met Glu Trp Trp
            355                 360                 365
```

```
Thr His Leu Trp Leu Asn Glu Gly Phe Ala Ser Trp Ile Glu Tyr Leu
    370                 375                 380

Cys Val Asp His Cys Phe Pro Glu Tyr Asp Ile Trp Thr Gln Phe Val
385                 390                 395                 400

Ser Ala Asp Tyr Thr Arg Ala Gln Glu Leu Asp Ala Leu Asp Asn Ser
                405                 410                 415

His Pro Ile Glu Val Ser Val Gly His Pro Ser Glu Val Asp Glu Ile
            420                 425                 430

Phe Asp Ala Ile Ser Tyr Ser Lys Gly Ala Ser Val Ile Arg Met Leu
        435                 440                 445

His Asp Tyr Ile Gly Asp Lys Asp Phe Lys Lys Gly Met Asn Met Tyr
    450                 455                 460

Leu Thr Lys Phe Gln Gln Lys Asn Ala Ala Thr Glu Asp Leu Trp Glu
465                 470                 475                 480

Ser Leu Glu Asn Ala Ser Gly Lys Pro Ile Ala Ala Val Met Asn Thr
                485                 490                 495

Trp Thr Lys Gln Met Gly Phe Pro Leu Ile Tyr Val Glu Ala Glu Gln
            500                 505                 510

Val Glu Asp Asp Arg Leu Leu Arg Leu Ser Gln Lys Lys Phe Cys Ala
        515                 520                 525

Gly Gly Ser Tyr Val Gly Glu Asp Cys Pro Gln Trp Met Val Pro Ile
    530                 535                 540

Thr Ile Ser Thr Ser Glu Asp Pro Asn Gln Ala Lys Leu Lys Ile Leu
545                 550                 555                 560

Met Asp Lys Pro Glu Met Asn Val Val Leu Lys Asn Val Lys Pro Asp
                565                 570                 575

Gln Trp Val Lys Leu Asn Leu Gly Thr Val Gly Phe Tyr Arg Thr Gln
            580                 585                 590

Tyr Ser Ser Ala Met Leu Glu Ser Leu Leu Pro Gly Ile Arg Asp Leu
        595                 600                 605

Ser Leu Pro Pro Val Asp Arg Leu Gly Leu Gln Asn Asp Leu Phe Ser
    610                 615                 620

Leu Ala Arg Ala Gly Ile Ile Ser Thr Val Glu Val Leu Lys Val Met
625                 630                 635                 640

Glu Ala Phe Val Asn Glu Pro Asn Tyr Thr Val Trp Ser Asp Leu Ser
                645                 650                 655

Cys Asn Leu Gly Ile Leu Ser Thr Leu Leu Ser His Thr Asp Phe Tyr
            660                 665                 670

Glu Glu Ile Gln Glu Phe Val Lys Asp Val Phe Ser Pro Ile Gly Glu
        675                 680                 685

Arg Leu Gly Trp Asp Pro Lys Pro Gly Glu Gly His Leu Asp Ala Leu
    690                 695                 700

Leu Arg Gly Leu Val Leu Gly Lys Leu Gly Lys Ala Gly His Lys Ala
705                 710                 715                 720

Thr Leu Glu Glu Ala Arg Arg Phe Lys Asp His Val Glu Gly Lys
                725                 730                 735

Gln Ile Leu Ser Ala Asp Leu Arg Ser Pro Val Tyr Leu Thr Val Leu
            740                 745                 750

Lys His Gly Asp Gly Thr Thr Leu Asp Ile Met Leu Lys Leu His Lys
        755                 760                 765

Gln Ala Asp Met Gln Glu Glu Lys Asn Arg Ile Glu Arg Val Leu Gly
    770                 775                 780
```

```
Ala Thr Leu Leu Pro Asp Leu Ile Gln Lys Val Leu Thr Phe Ala Leu
785                 790                 795                 800

Ser Glu Glu Val Arg Pro Gln Asp Thr Val Ser Val Ile Gly Gly Val
            805                 810                 815

Ala Gly Gly Ser Lys His Gly Arg Lys Ala Ala Trp Lys Phe Ile Lys
            820                 825                 830

Asp Asn Trp Glu Glu Leu Tyr Asn Arg Tyr Gln Gly Gly Phe Leu Ile
            835                 840                 845

Ser Arg Leu Ile Lys Leu Ser Val Glu Gly Phe Ala Val Asp Lys Met
850                 855                 860

Ala Gly Glu Val Lys Ala Phe Phe Glu Ser His Pro Ala Pro Ser Ala
865                 870                 875                 880

Glu Arg Thr Ile Gln Gln Cys Cys Glu Asn Ile Leu Leu Asn Ala Ala
                885                 890                 895

Trp Leu Lys Arg Asp Ala Glu Ser Ile His Gln Tyr Leu Leu Gln Arg
            900                 905                 910

Lys Ala Ser Pro Pro Thr Val
            915

<210> SEQ ID NO 58
<211> LENGTH: 864
<212> TYPE: PRT
<213> ORGANISM: Francisella tularensis

<400> SEQUENCE: 58

Met Ile Tyr Glu Phe Val Met Thr Asp Pro Lys Ile Lys Tyr Leu Lys
1               5                   10                  15

Asp Tyr Lys Pro Ser Asn Tyr Leu Ile Asp Glu Thr His Leu Ile Phe
            20                  25                  30

Glu Leu Asp Glu Ser Lys Thr Arg Val Thr Ala Asn Leu Tyr Ile Val
        35                  40                  45

Ala Asn Arg Glu Asn Arg Glu Asn Asn Thr Leu Val Leu Asp Gly Val
    50                  55                  60

Glu Leu Lys Leu Leu Ser Ile Lys Leu Asn Asn Lys His Leu Ser Pro
65                  70                  75                  80

Ala Glu Phe Ala Val Asn Glu Asn Gln Leu Ile Ile Asn Asn Val Pro
                85                  90                  95

Glu Lys Phe Val Leu Gln Thr Val Val Glu Ile Asn Pro Ser Ala Asn
            100                 105                 110

Thr Ser Leu Glu Gly Leu Tyr Lys Ser Gly Asp Val Phe Ser Thr Gln
        115                 120                 125

Cys Glu Ala Thr Gly Phe Arg Lys Ile Thr Tyr Tyr Leu Asp Arg Pro
    130                 135                 140

Asp Val Met Ala Ala Phe Thr Val Lys Ile Ile Ala Asp Lys Lys Lys
145                 150                 155                 160

Tyr Pro Ile Ile Leu Ser Asn Gly Asp Lys Ile Asp Ser Gly Asp Ile
                165                 170                 175

Ser Asp Asn Gln His Phe Ala Val Trp Lys Asp Pro Phe Lys Lys Pro
            180                 185                 190

Cys Tyr Leu Phe Ala Leu Val Ala Gly Asp Leu Ala Ser Ile Lys Asp
        195                 200                 205

Thr Tyr Ile Thr Lys Ser Gln Arg Lys Val Ser Leu Glu Ile Tyr Ala
    210                 215                 220

Phe Lys Gln Asp Ile Asp Lys Cys His Tyr Ala Met Gln Ala Val Lys
225                 230                 235                 240
```

```
Asp Ser Met Lys Trp Asp Glu Asp Arg Phe Gly Leu Glu Tyr Asp Leu
            245                 250                 255

Asp Thr Phe Met Ile Val Ala Val Pro Asp Phe Asn Ala Gly Ala Met
        260                 265                 270

Glu Asn Lys Gly Leu Asn Ile Phe Asn Thr Lys Tyr Ile Met Ala Ser
    275                 280                 285

Asn Lys Thr Ala Thr Asp Lys Asp Phe Glu Leu Val Gln Ser Val Val
290                 295                 300

Gly His Glu Tyr Phe His Asn Trp Thr Gly Asp Arg Val Thr Cys Arg
305                 310                 315                 320

Asp Trp Phe Gln Leu Ser Leu Lys Glu Gly Leu Thr Val Phe Arg Asp
            325                 330                 335

Gln Glu Phe Thr Ser Asp Leu Asn Ser Arg Asp Val Lys Arg Ile Asp
        340                 345                 350

Asp Val Arg Ile Ile Arg Ser Ala Gln Phe Ala Glu Asp Ala Ser Pro
    355                 360                 365

Met Ser His Pro Ile Arg Pro Glu Ser Tyr Ile Glu Met Asn Asn Phe
370                 375                 380

Tyr Thr Val Thr Val Tyr Asn Lys Gly Ala Glu Ile Ile Arg Met Ile
385                 390                 395                 400

His Thr Leu Leu Gly Glu Glu Gly Phe Gln Lys Gly Met Lys Leu Tyr
            405                 410                 415

Phe Glu Arg His Asp Gly Gln Ala Val Thr Cys Asp Asp Phe Val Asn
        420                 425                 430

Ala Met Ala Asp Ala Asn Asn Arg Asp Phe Ser Leu Phe Lys Arg Trp
    435                 440                 445

Tyr Ala Gln Ser Gly Thr Pro Asn Ile Lys Val Ser Glu Asn Tyr Asp
450                 455                 460

Ala Ser Ser Gln Thr Tyr Ser Leu Thr Leu Glu Gln Thr Thr Leu Pro
465                 470                 475                 480

Thr Ala Asp Gln Lys Glu Lys Gln Ala Leu His Ile Pro Val Lys Met
            485                 490                 495

Gly Leu Ile Asn Pro Glu Gly Lys Asn Ile Ala Glu Gln Val Ile Glu
        500                 505                 510

Leu Lys Glu Gln Lys Gln Thr Tyr Thr Phe Glu Asn Ile Ala Ala Lys
    515                 520                 525

Pro Val Ala Ser Leu Phe Arg Asp Phe Ser Ala Pro Val Lys Val Glu
530                 535                 540

His Lys Arg Ser Glu Lys Asp Leu Leu His Ile Val Lys Tyr Asp Asn
545                 550                 555                 560

Asn Ala Phe Asn Arg Trp Asp Ser Leu Gln Gln Ile Ala Thr Asn Ile
            565                 570                 575

Ile Leu Asn Asn Ala Asp Leu Asn Asp Glu Phe Leu Asn Ala Phe Lys
        580                 585                 590

Ser Ile Leu His Asp Lys Asp Leu Asp Lys Ala Leu Ile Ser Asn Ala
    595                 600                 605

Leu Leu Ile Pro Ile Glu Ser Thr Ile Ala Glu Ala Met Arg Val Ile
610                 615                 620

Met Val Asp Asp Ile Val Leu Ser Arg Lys Asn Val Val Asn Gln Leu
625                 630                 635                 640

Ala Asp Lys Leu Lys Asp Asp Trp Leu Ala Val Tyr Gln Gln Cys Asn
            645                 650                 655
```

```
Asp Asn Lys Pro Tyr Ser Leu Ser Ala Glu Gln Ile Ala Lys Arg Lys
            660                 665                 670

Leu Lys Gly Val Cys Leu Ser Tyr Leu Met Asn Ala Ser Asp Gln Lys
        675                 680                 685

Val Gly Thr Asp Leu Ala Gln Gln Leu Phe Asp Asn Ala Asp Asn Met
    690                 695                 700

Thr Asp Gln Gln Thr Ala Phe Thr Glu Leu Leu Lys Ser Asn Asp Lys
705                 710                 715                 720

Gln Val Arg Asp Asn Ala Ile Asn Glu Phe Tyr Asn Arg Trp Arg His
                725                 730                 735

Glu Asp Leu Val Val Asn Lys Trp Leu Leu Ser Gln Ala Gln Ile Ser
            740                 745                 750

His Glu Ser Ala Leu Asp Ile Val Lys Gly Leu Val Asn His Pro Ala
        755                 760                 765

Tyr Asn Pro Lys Asn Pro Asn Lys Val Tyr Ser Leu Ile Gly Gly Phe
    770                 775                 780

Gly Ala Asn Phe Leu Gln Tyr His Cys Lys Asp Gly Leu Gly Tyr Ala
785                 790                 795                 800

Phe Met Ala Asp Thr Val Leu Ala Leu Asp Lys Phe Asn His Gln Val
                805                 810                 815

Ala Ala Arg Met Ala Arg Asn Leu Met Ser Trp Lys Arg Tyr Asp Ser
            820                 825                 830

Asp Arg Gln Ala Met Met Lys Asn Ala Leu Glu Lys Ile Lys Ala Ser
        835                 840                 845

Asn Pro Ser Lys Asn Val Phe Glu Ile Val Ser Lys Ser Leu Glu Ser
    850                 855                 860

<210> SEQ ID NO 59
<211> LENGTH: 353
<212> TYPE: PRT
<213> ORGANISM: Pyrococcus horikoshii

<400> SEQUENCE: 59

Met Glu Val Arg Asn Met Val Asp Tyr Glu Leu Leu Lys Lys Val Val
1               5                   10                  15

Glu Ala Pro Gly Val Ser Gly Tyr Glu Phe Leu Gly Ile Arg Asp Val
            20                  25                  30

Val Ile Glu Glu Ile Lys Asp Tyr Val Asp Glu Val Lys Val Asp Lys
        35                  40                  45

Leu Gly Asn Val Ile Ala His Lys Lys Gly Glu Gly Pro Lys Val Met
    50                  55                  60

Ile Ala Ala His Met Asp Gln Ile Gly Leu Met Val Thr His Ile Glu
65                  70                  75                  80

Lys Asn Gly Phe Leu Arg Val Ala Pro Ile Gly Gly Val Asp Pro Lys
                85                  90                  95

Thr Leu Ile Ala Gln Arg Phe Lys Val Trp Ile Asp Lys Gly Lys Phe
            100                 105                 110

Ile Tyr Gly Val Gly Ala Ser Val Pro Pro His Ile Gln Lys Pro Glu
        115                 120                 125

Asp Arg Lys Lys Ala Pro Asp Trp Asp Gln Ile Phe Ile Asp Ile Gly
    130                 135                 140

Ala Glu Ser Lys Glu Glu Ala Glu Asp Met Gly Val Lys Ile Gly Thr
145                 150                 155                 160

Val Ile Thr Trp Asp Gly Arg Leu Glu Arg Leu Gly Lys His Arg Phe
                165                 170                 175
```

```
Val Ser Ile Ala Phe Asp Asp Arg Ile Ala Val Tyr Thr Ile Leu Glu
            180                 185                 190

Val Ala Lys Gln Leu Lys Asp Ala Lys Ala Asp Val Tyr Phe Val Ala
            195                 200                 205

Thr Val Gln Glu Glu Val Gly Leu Arg Gly Ala Arg Thr Ser Ala Phe
            210                 215                 220

Gly Ile Glu Pro Asp Tyr Gly Phe Ala Ile Asp Val Thr Ile Ala Ala
225                 230                 235                 240

Asp Ile Pro Gly Thr Pro Glu His Lys Gln Val Thr His Leu Gly Lys
                    245                 250                 255

Gly Thr Ala Ile Lys Ile Met Asp Arg Ser Val Ile Cys His Pro Thr
            260                 265                 270

Ile Val Arg Trp Leu Glu Glu Leu Ala Lys Lys His Glu Ile Pro Tyr
            275                 280                 285

Gln Leu Glu Ile Leu Leu Gly Gly Thr Asp Ala Gly Ala Ile His
            290                 295                 300

Leu Thr Lys Ala Gly Val Pro Thr Gly Ala Leu Ser Val Pro Ala Arg
305                 310                 315                 320

Tyr Ile His Ser Asn Thr Glu Val Val Asp Glu Arg Asp Val Asp Ala
                325                 330                 335

Thr Val Glu Leu Met Thr Lys Ala Leu Glu Asn Ile His Glu Leu Lys
            340                 345                 350

Ile

<210> SEQ ID NO 60
<211> LENGTH: 408
<212> TYPE: PRT
<213> ORGANISM: T. aquaticus

<400> SEQUENCE: 60

Met Asp Ala Phe Thr Glu Asn Leu Asn Lys Leu Ala Glu Leu Ala Ile
1               5                   10                  15

Arg Val Gly Leu Asn Leu Glu Glu Gly Gln Glu Ile Val Ala Thr Ala
            20                  25                  30

Pro Ile Glu Ala Val Asp Phe Val Arg Leu Leu Ala Glu Lys Ala Tyr
            35                  40                  45

Glu Asn Gly Ala Ser Leu Phe Thr Val Leu Tyr Gly Asp Asn Leu Ile
        50                  55                  60

Ala Arg Lys Arg Leu Ala Leu Val Pro Glu Ala His Leu Asp Arg Ala
65                  70                  75                  80

Pro Ala Trp Leu Tyr Glu Gly Met Ala Lys Ala Phe His Glu Gly Ala
                85                  90                  95

Ala Arg Leu Ala Val Ser Gly Asn Asp Pro Lys Ala Leu Glu Gly Leu
            100                 105                 110

Pro Pro Glu Arg Val Gly Arg Ala Gln Gln Ala Gln Ser Arg Ala Tyr
            115                 120                 125

Arg Pro Thr Leu Ser Ala Ile Thr Glu Phe Val Thr Asn Trp Thr Ile
        130                 135                 140

Val Pro Phe Ala His Pro Gly Trp Ala Lys Ala Val Phe Pro Gly Leu
145                 150                 155                 160

Pro Glu Glu Glu Ala Val Gln Arg Leu Trp Gln Ala Ile Phe Gln Ala
                165                 170                 175

Thr Arg Val Asp Gln Glu Asp Pro Val Ala Ala Trp Glu Ala His Asn
            180                 185                 190
```

Arg Val Leu His Ala Lys Val Ala Phe Leu Asn Glu Lys Arg Phe His
        195                 200                 205

Ala Leu His Phe Gln Gly Pro Gly Thr Asp Leu Thr Val Gly Leu Ala
        210                 215                 220

Glu Gly His Leu Trp Gln Gly Gly Ala Thr Pro Thr Lys Lys Gly Arg
225                 230                 235                 240

Leu Cys Asn Pro Asn Leu Pro Thr Glu Glu Val Phe Thr Ala Pro His
                245                 250                 255

Arg Glu Arg Val Glu Gly Val Val Arg Ala Ser Arg Pro Leu Ala Leu
            260                 265                 270

Ser Gly Gln Leu Val Glu Gly Leu Trp Ala Arg Phe Glu Gly Gly Val
        275                 280                 285

Ala Val Glu Val Gly Ala Glu Lys Gly Glu Glu Val Leu Lys Lys Leu
    290                 295                 300

Leu Asp Thr Asp Glu Gly Ala Arg Arg Leu Gly Val Ala Leu Val
305                 310                 315                 320

Pro Ala Asp Asn Pro Ile Ala Lys Thr Gly Leu Val Phe Phe Asp Thr
                325                 330                 335

Leu Phe Asp Glu Asn Ala Ala Ser His Ile Ala Phe Gly Gln Ala Tyr
            340                 345                 350

Ala Glu Asn Leu Glu Gly Arg Pro Ser Gly Glu Glu Phe Arg Arg Arg
        355                 360                 365

Gly Gly Asn Glu Ser Met Val His Val Asp Trp Met Ile Gly Ser Glu
    370                 375                 380

Glu Val Asp Val Asp Gly Leu Leu Glu Asp Gly Thr Arg Val Pro Leu
385                 390                 395                 400

Met Arg Arg Gly Arg Trp Val Ile
                405

<210> SEQ ID NO 61
<211> LENGTH: 362
<212> TYPE: PRT
<213> ORGANISM: Bacillus stearothermophilus

<400> SEQUENCE: 61

Met Ala Lys Leu Asp Glu Thr Leu Thr Met Leu Lys Ala Leu Thr Asp
1               5                   10                  15

Ala Lys Gly Val Pro Gly Asn Glu Arg Glu Ala Arg Asp Val Met Lys
            20                  25                  30

Thr Tyr Ile Ala Pro Tyr Ala Asp Glu Val Thr Thr Asp Gly Leu Gly
        35                  40                  45

Ser Leu Ile Ala Lys Lys Glu Gly Lys Ser Gly Gly Pro Lys Val Met
    50                  55                  60

Ile Ala Gly His Leu Asp Glu Val Gly Phe Met Val Thr Gln Ile Asp
65                  70                  75                  80

Asp Lys Gly Phe Ile Arg Phe Gln Thr Leu Gly Gly Trp Trp Ser Gln
                85                  90                  95

Val Met Leu Ala Gln Arg Val Thr Ile Val Thr Lys Lys Gly Asp Ile
            100                 105                 110

Thr Gly Val Ile Gly Ser Lys Pro Pro His Ile Leu Pro Ser Glu Ala
        115                 120                 125

Arg Lys Lys Pro Val Glu Ile Lys Asp Met Phe Ile Asp Ile Gly Ala
    130                 135                 140

Thr Ser Arg Glu Glu Ala Met Glu Trp Gly Val Arg Pro Gly Asp Met

```
              145                 150                 155                 160
    Ile Val Pro Tyr Phe Glu Phe Thr Val Leu Asn Asn Glu Lys Met Leu
                    165                 170                 175

Leu Ala Lys Ala Trp Asp Asn Arg Ile Gly Cys Ala Val Ala Ile Asp
                180                 185                 190

Val Leu Lys Gln Leu Lys Gly Val Asp His Pro Asn Thr Val Tyr Gly
                    195                 200                 205

Val Gly Thr Val Gln Glu Glu Val Gly Leu Arg Gly Ala Arg Thr Ala
                210                 215                 220

Ala Gln Phe Ile Gln Pro Asp Ile Ala Phe Ala Val Asp Val Gly Ile
    225                 230                 235                 240

Ala Gly Asp Thr Pro Gly Val Ser Glu Lys Glu Ala Met Gly Lys Leu
                    245                 250                 255

Gly Ala Gly Pro His Ile Val Leu Tyr Asp Ala Thr Met Val Ser His
                    260                 265                 270

Arg Gly Leu Arg Glu Phe Val Ile Glu Val Ala Glu Glu Leu Asn Ile
                275                 280                 285

Pro His His Phe Asp Ala Met Pro Gly Val Gly Thr Asp Ala Gly Ala
                290                 295                 300

Ile His Leu Thr Gly Ile Gly Val Pro Ser Leu Thr Ile Ala Ile Pro
    305                 310                 315                 320

Thr Arg Tyr Ile His Ser His Ala Ala Ile Leu His Arg Asp Asp Tyr
                    325                 330                 335

Glu Asn Thr Val Lys Leu Leu Val Glu Val Ile Lys Arg Leu Asp Ala
                340                 345                 350

Asp Lys Val Lys Gln Leu Thr Phe Asp Glu
                355                 360

<210> SEQ ID NO 62
<211> LENGTH: 484
<212> TYPE: PRT
<213> ORGANISM: Vibrio cholera

<400> SEQUENCE: 62

Met Glu Asp Lys Val Trp Ile Ser Met Gly Ala Asp Ala Val Gly Ser
1               5                   10                  15

Leu Asn Pro Ala Leu Ser Glu Ser Leu Leu Pro His Ser Phe Ala Ser
                20                  25                  30

Gly Ser Gln Val Trp Ile Gly Glu Val Ala Ile Asp Glu Leu Ala Glu
            35                  40                  45

Leu Ser His Thr Met His Glu Gln His Asn Arg Cys Gly Gly Tyr Met
        50                  55                  60

Val His Thr Ser Ala Gln Gly Ala Met Ala Ala Leu Met Met Pro Glu
65                  70                  75                  80

Ser Ile Ala Asn Phe Thr Ile Pro Ala Pro Ser Gln Gln Asp Leu Val
                85                  90                  95

Asn Ala Trp Leu Pro Gln Val Ser Ala Asp Gln Ile Thr Asn Thr Ile
                100                 105                 110

Arg Ala Leu Ser Ser Phe Asn Asn Arg Phe Tyr Thr Thr Thr Ser Gly
            115                 120                 125

Ala Gln Ala Ser Asp Trp Leu Ala Asn Glu Trp Arg Ser Leu Ile Ser
        130                 135                 140

Ser Leu Pro Gly Ser Arg Ile Glu Gln Ile Lys His Ser Gly Tyr Asn
145                 150                 155                 160
```

```
Gln Lys Ser Val Val Leu Thr Ile Gln Gly Ser Glu Lys Pro Asp Glu
            165                 170                 175

Trp Val Ile Val Gly Gly His Leu Asp Ser Thr Leu Gly Ser His Thr
        180                 185                 190

Asn Glu Gln Ser Ile Ala Pro Gly Ala Asp Asp Ala Ser Gly Ile
            195                 200                 205

Ala Ser Leu Ser Glu Ile Ile Arg Val Leu Arg Asp Asn Asn Phe Arg
    210                 215                 220

Pro Lys Arg Ser Val Ala Leu Met Ala Tyr Ala Ala Glu Glu Val Gly
225                 230                 235                 240

Leu Arg Gly Ser Gln Asp Leu Ala Asn Gln Tyr Lys Ala Gln Gly Lys
                245                 250                 255

Lys Val Val Ser Val Leu Gln Leu Asp Met Thr Asn Tyr Arg Gly Ser
            260                 265                 270

Ala Glu Asp Ile Val Phe Ile Thr Asp Tyr Thr Asp Ser Asn Leu Thr
        275                 280                 285

Gln Phe Leu Thr Thr Leu Ile Asp Glu Tyr Leu Pro Glu Leu Thr Tyr
    290                 295                 300

Gly Tyr Asp Arg Cys Gly Tyr Ala Cys Ser Asp His Ala Ser Trp His
305                 310                 315                 320

Lys Ala Gly Phe Ser Ala Ala Met Pro Phe Glu Ser Lys Phe Lys Asp
                325                 330                 335

Tyr Asn Pro Lys Ile His Thr Ser Gln Asp Thr Leu Ala Asn Ser Asp
            340                 345                 350

Pro Thr Gly Asn His Ala Val Lys Phe Thr Lys Leu Gly Leu Ala Tyr
        355                 360                 365

Val Ile Glu Met Ala Asn Ala Gly Ser Ser Gln Val Pro Asp Asp Ser
    370                 375                 380

Val Leu Gln Asp Gly Thr Ala Lys Ile Asn Leu Ser Gly Ala Arg Gly
385                 390                 395                 400

Thr Gln Lys Arg Phe Thr Phe Glu Leu Ser Gln Ser Lys Pro Leu Thr
                405                 410                 415

Ile Gln Thr Tyr Gly Gly Ser Gly Asp Val Asp Leu Tyr Val Lys Tyr
            420                 425                 430

Gly Ser Ala Pro Ser Lys Ser Asn Trp Asp Cys Arg Pro Tyr Gln Asn
        435                 440                 445

Gly Asn Arg Glu Thr Cys Ser Phe Asn Asn Ala Gln Pro Gly Ile Tyr
    450                 455                 460

His Val Met Leu Asp Gly Tyr Thr Asn Tyr Asn Asp Val Ala Leu Lys
465                 470                 475                 480

Ala Ser Thr Gln
```

<210> SEQ ID NO 63
<211> LENGTH: 488
<212> TYPE: PRT
<213> ORGANISM: Photobacterium halotolerans

<400> SEQUENCE: 63

```
Met Glu Asp Lys Val Trp Ile Ser Ile Gly Ser Asp Ala Ser Gln Thr
1               5                   10                  15

Val Lys Ser Val Met Gln Ser Asn Ala Arg Ser Leu Leu Pro Glu Ser
            20                  25                  30

Leu Ala Ser Asn Gly Pro Val Trp Val Gly Val Asp Tyr Ser Gln
        35                  40                  45
```

Leu Ala Glu Leu Ser His His Met His Glu Asp His Gln Arg Cys Gly
 50                  55                  60

Gly Tyr Met Val His Ser Ser Pro Glu Ser Ala Ile Ala Ala Ser Asn
 65                  70                  75                  80

Met Pro Gln Ser Leu Val Ala Phe Ser Ile Pro Glu Ile Ser Gln Gln
                 85                  90                  95

Asp Thr Val Asn Ala Trp Leu Pro Gln Val Asn Ser Gln Ala Ile Thr
                100                 105                 110

Gly Thr Ile Thr Ser Leu Thr Ser Phe Ile Asn Arg Phe Tyr Thr Thr
                115                 120                 125

Thr Ser Gly Ala Gln Ala Ser Asp Trp Leu Ala Asn Glu Trp Arg Ser
130                 135                 140

Leu Ser Ala Ser Leu Pro Asn Ala Ser Val Arg Gln Val Ser His Phe
145                 150                 155                 160

Gly Tyr Asn Gln Lys Ser Val Val Leu Thr Ile Thr Gly Ser Glu Lys
                165                 170                 175

Pro Asp Glu Trp Ile Val Leu Gly Gly His Leu Asp Ser Thr Ile Gly
                180                 185                 190

Ser His Thr Asn Glu Gln Ser Val Ala Pro Gly Ala Asp Asp Asp Ala
                195                 200                 205

Ser Gly Ile Ala Ser Val Thr Glu Ile Ile Arg Val Leu Ser Glu Asn
210                 215                 220

Asn Phe Gln Pro Lys Arg Ser Ile Ala Phe Met Ala Tyr Ala Ala Glu
225                 230                 235                 240

Glu Val Gly Leu Arg Gly Ser Gln Asp Leu Ala Asn Gln Tyr Lys Ala
                245                 250                 255

Glu Gly Lys Gln Val Ile Ser Ala Leu Gln Leu Asp Met Thr Asn Tyr
                260                 265                 270

Lys Gly Ser Val Glu Asp Ile Val Phe Ile Thr Asp Tyr Thr Asp Ser
                275                 280                 285

Asn Leu Thr Thr Phe Leu Ser Gln Leu Val Asp Glu Tyr Leu Pro Ser
                290                 295                 300

Leu Thr Tyr Gly Phe Asp Thr Cys Gly Tyr Ala Cys Ser Asp His Ala
305                 310                 315                 320

Ser Trp His Lys Ala Gly Phe Ser Ala Ala Met Pro Phe Glu Ala Lys
                325                 330                 335

Phe Asn Asp Tyr Asn Pro Met Ile His Thr Pro Asn Asp Thr Leu Gln
                340                 345                 350

Asn Ser Asp Pro Thr Ala Ser His Ala Val Lys Phe Thr Lys Leu Gly
                355                 360                 365

Leu Ala Tyr Ala Ile Glu Met Ala Ser Thr Thr Gly Gly Thr Pro Pro
370                 375                 380

Pro Thr Gly Asn Val Leu Lys Asp Gly Val Pro Val Asn Gly Leu Ser
385                 390                 395                 400

Gly Ala Thr Gly Ser Gln Val His Tyr Ser Phe Glu Leu Pro Ala Gln
                405                 410                 415

Lys Asn Leu Gln Ile Ser Thr Ala Gly Gly Ser Gly Asp Val Asp Leu
                420                 425                 430

Tyr Val Ser Phe Gly Ser Glu Ala Thr Lys Gln Asn Trp Asp Cys Arg
                435                 440                 445

Pro Tyr Arg Asn Gly Asn Asn Glu Val Cys Thr Phe Ala Gly Ala Thr
450                 455                 460

Pro Gly Thr Tyr Ser Ile Met Leu Asp Gly Tyr Arg Gln Phe Ser Gly

```
                465                 470                 475                 480
Val Thr Leu Lys Ala Ser Thr Gln
                485
```

<210> SEQ ID NO 64
<211> LENGTH: 871
<212> TYPE: PRT
<213> ORGANISM: Yersinia pestis

<400> SEQUENCE: 64

```
Met Thr Gln Gln Pro Gln Ala Lys Tyr Arg His Asp Tyr Arg Ala Pro
1               5                   10                  15

Asp Tyr Thr Ile Thr Asp Ile Asp Leu Asp Phe Ala Leu Asp Ala Gln
            20                  25                  30

Lys Thr Thr Val Thr Ala Val Ser Lys Val Lys Arg Gln Gly Thr Asp
        35                  40                  45

Val Thr Pro Leu Ile Leu Asn Gly Glu Asp Leu Thr Leu Ile Ser Val
    50                  55                  60

Ser Val Asp Gly Gln Ala Trp Pro His Tyr Arg Gln Gln Asp Asn Thr
65                  70                  75                  80

Leu Val Ile Glu Gln Leu Pro Ala Asp Phe Thr Leu Thr Ile Val Asn
                85                  90                  95

Asp Ile His Pro Ala Thr Asn Ser Ala Leu Glu Gly Leu Tyr Leu Ser
            100                 105                 110

Gly Glu Ala Leu Cys Thr Gln Cys Glu Ala Glu Gly Phe Arg His Ile
        115                 120                 125

Thr Tyr Tyr Leu Asp Arg Pro Asp Val Leu Ala Arg Phe Thr Thr Arg
    130                 135                 140

Ile Val Ala Asp Lys Ser Arg Tyr Pro Tyr Leu Leu Ser Asn Gly Asn
145                 150                 155                 160

Arg Val Gly Gln Gly Glu Leu Asp Asp Gly Arg His Trp Val Lys Trp
                165                 170                 175

Glu Asp Pro Phe Pro Lys Pro Ser Tyr Leu Phe Ala Leu Val Ala Gly
            180                 185                 190

Asp Phe Asp Val Leu Gln Asp Lys Phe Ile Thr Arg Ser Gly Arg Glu
        195                 200                 205

Val Ala Leu Glu Ile Phe Val Asp Arg Gly Asn Leu Asp Arg Ala Asp
    210                 215                 220

Trp Ala Met Thr Ser Leu Lys Asn Ser Met Lys Trp Asp Glu Thr Arg
225                 230                 235                 240

Phe Gly Leu Glu Tyr Asp Leu Asp Ile Tyr Met Ile Val Ala Val Asp
                245                 250                 255

Phe Phe Asn Met Gly Ala Met Glu Asn Lys Gly Leu Asn Val Phe Asn
            260                 265                 270

Ser Lys Tyr Val Leu Ala Lys Ala Glu Thr Ala Thr Asp Lys Asp Tyr
        275                 280                 285

Leu Asn Ile Glu Ala Val Ile Gly His Glu Tyr Phe His Asn Trp Thr
    290                 295                 300

Gly Asn Arg Val Thr Cys Arg Asp Trp Phe Gln Leu Ser Leu Lys Glu
305                 310                 315                 320

Gly Leu Thr Val Phe Arg Asp Gln Glu Phe Ser Ser Asp Leu Gly Ser
                325                 330                 335

Arg Ser Val Asn Arg Ile Glu Asn Val Arg Val Met Arg Ala Ala Gln
            340                 345                 350
```

```
Phe Ala Glu Asp Ala Ser Pro Met Ala His Ala Ile Arg Pro Asp Lys
                355                 360                 365

Val Ile Glu Met Asn Asn Phe Tyr Thr Leu Thr Val Tyr Glu Lys Gly
370                 375                 380

Ser Glu Val Ile Arg Met Met His Thr Leu Leu Gly Glu Gln Gln Phe
385                 390                 395                 400

Gln Ala Gly Met Arg Leu Tyr Phe Glu Arg His Asp Gly Ser Ala Ala
                405                 410                 415

Thr Cys Asp Asp Phe Val Gln Ala Met Glu Asp Val Ser Asn Val Asp
                420                 425                 430

Leu Ser Leu Phe Arg Arg Trp Tyr Ser Gln Ser Gly Thr Pro Leu Leu
                435                 440                 445

Thr Val His Asp Asp Tyr Asp Val Glu Lys Gln Gln Tyr His Leu Phe
        450                 455                 460

Val Ser Gln Lys Thr Leu Pro Thr Ala Asp Gln Pro Glu Lys Leu Pro
465                 470                 475                 480

Leu His Ile Pro Leu Asp Ile Glu Leu Tyr Asp Ser Lys Gly Asn Val
                485                 490                 495

Ile Pro Leu Gln His Asn Gly Leu Pro Val His Val Leu Asn Val
                500                 505                 510

Thr Glu Ala Glu Gln Thr Phe Thr Phe Asp Asn Val Ala Gln Lys Pro
        515                 520                 525

Ile Pro Ser Leu Leu Arg Glu Phe Ser Ala Pro Val Lys Leu Asp Tyr
        530                 535                 540

Pro Tyr Ser Asp Gln Gln Leu Thr Phe Leu Met Gln His Ala Arg Asn
545                 550                 555                 560

Glu Phe Ser Arg Trp Asp Ala Ala Gln Ser Leu Leu Ala Thr Tyr Ile
                565                 570                 575

Lys Leu Asn Val Ala Lys Tyr Gln Gln Gln Pro Leu Ser Leu Pro
                580                 585                 590

Ala His Val Ala Asp Ala Phe Arg Ala Ile Leu Leu Asp Glu His Leu
        595                 600                 605

Asp Pro Ala Leu Ala Ala Gln Ile Leu Thr Leu Pro Ser Glu Asn Glu
610                 615                 620

Met Ala Glu Leu Phe Thr Thr Ile Asp Pro Gln Ala Ile Ser Thr Val
625                 630                 635                 640

His Glu Ala Ile Thr Arg Cys Leu Ala Gln Glu Leu Ser Asp Glu Leu
                645                 650                 655

Leu Ala Val Tyr Val Ala Asn Met Thr Pro Val Tyr Arg Ile Glu His
                660                 665                 670

Gly Asp Ile Ala Lys Arg Ala Leu Arg Asn Thr Cys Leu Asn Tyr Leu
                675                 680                 685

Ala Phe Gly Asp Glu Glu Phe Ala Asn Lys Leu Val Ser Leu Gln Tyr
        690                 695                 700

His Gln Ala Asp Asn Met Thr Asp Ser Leu Ala Ala Leu Ala Ala Ala
705                 710                 715                 720

Val Ala Ala Gln Leu Pro Cys Arg Asp Glu Leu Leu Ala Ala Phe Asp
                725                 730                 735

Val Arg Trp Asn His Asp Gly Leu Val Met Asp Lys Trp Phe Ala Leu
                740                 745                 750

Gln Ala Thr Ser Pro Ala Ala Asn Val Leu Val Gln Val Arg Thr Leu
        755                 760                 765

Leu Lys His Pro Ala Phe Ser Leu Ser Asn Pro Asn Arg Thr Arg Ser
```

```
                770            775            780
Leu Ile Gly Ser Phe Ala Ser Gly Asn Pro Ala Ala Phe His Ala Ala
785            790            795                800

Asp Gly Ser Gly Tyr Gln Phe Leu Val Glu Ile Leu Ser Asp Leu Asn
            805            810            815

Thr Arg Asn Pro Gln Val Ala Ala Arg Leu Ile Glu Pro Leu Ile Arg
            820            825            830

Leu Lys Arg Tyr Asp Ala Gly Arg Gln Ala Leu Met Arg Lys Ala Leu
            835            840            845

Glu Gln Leu Lys Thr Leu Asp Asn Leu Ser Gly Asp Leu Tyr Glu Lys
850            855            860

Ile Thr Lys Ala Leu Ala Ala
865            870

<210> SEQ ID NO 65
<211> LENGTH: 483
<212> TYPE: PRT
<213> ORGANISM: Vibrio anguillarum

<400> SEQUENCE: 65

Met Glu Glu Lys Val Trp Ile Ser Ile Gly Gly Asp Ala Thr Gln Thr
1               5                   10                  15

Ala Leu Arg Ser Gly Ala Gln Ser Leu Leu Pro Glu Asn Leu Ile Asn
            20                  25                  30

Gln Thr Ser Val Trp Val Gly Gln Val Pro Val Ser Glu Leu Ala Thr
        35                  40                  45

Leu Ser His Glu Met His Glu Asn His Gln Arg Cys Gly Gly Tyr Met
50                  55                  60

Val His Pro Ser Ala Gln Ser Ala Met Ser Val Ser Ala Met Pro Leu
65                  70                  75                  80

Asn Leu Asn Ala Phe Ser Ala Pro Glu Ile Thr Gln Gln Thr Thr Val
                85                  90                  95

Asn Ala Trp Leu Pro Ser Val Ser Ala Gln Gln Ile Thr Ser Thr Ile
            100                 105                 110

Thr Thr Leu Thr Gln Phe Lys Asn Arg Phe Tyr Thr Thr Ser Thr Gly
        115                 120                 125

Ala Gln Ala Ser Asn Trp Ile Ala Asp His Trp Arg Ser Leu Ser Ala
130                 135                 140

Ser Leu Pro Ala Ser Lys Val Glu Gln Ile Thr His Ser Gly Tyr Asn
145                 150                 155                 160

Gln Lys Ser Val Met Leu Thr Ile Thr Gly Ser Glu Lys Pro Asp Glu
                165                 170                 175

Trp Val Val Ile Gly Gly His Leu Asp Ser Thr Leu Gly Ser Arg Thr
            180                 185                 190

Asn Glu Ser Ser Ile Ala Pro Gly Ala Asp Asp Ala Ser Gly Ile
        195                 200                 205

Ala Gly Val Thr Glu Ile Ile Arg Leu Leu Ser Glu Gln Asn Phe Arg
210                 215                 220

Pro Lys Arg Ser Ile Ala Phe Met Ala Tyr Ala Ala Glu Glu Val Gly
225                 230                 235                 240

Leu Arg Gly Ser Gln Asp Leu Ala Asn Arg Phe Lys Ala Glu Gly Lys
                245                 250                 255

Lys Val Met Ser Val Met Gln Leu Asp Met Thr Asn Tyr Gln Gly Ser
            260                 265                 270
```

```
Arg Glu Asp Ile Val Phe Ile Thr Asp Tyr Thr Asp Ser Asn Phe Thr
            275                 280                 285

Gln Tyr Leu Thr Gln Leu Leu Asp Glu Tyr Leu Pro Ser Leu Thr Tyr
        290                 295                 300

Gly Phe Asp Thr Cys Gly Tyr Ala Cys Ser Asp His Ala Ser Trp His
305                 310                 315                 320

Ala Val Gly Tyr Pro Ala Ala Met Pro Phe Glu Ser Lys Phe Asn Asp
                325                 330                 335

Tyr Asn Pro Asn Ile His Ser Pro Gln Asp Thr Leu Gln Asn Ser Asp
            340                 345                 350

Pro Thr Gly Phe His Ala Val Lys Phe Thr Lys Leu Gly Leu Ala Tyr
        355                 360                 365

Val Val Glu Met Gly Asn Ala Ser Thr Pro Pro Thr Pro Ser Asn Gln
    370                 375                 380

Leu Lys Asn Gly Val Pro Val Asn Gly Leu Ser Ala Ser Arg Asn Ser
385                 390                 395                 400

Lys Thr Trp Tyr Gln Phe Glu Leu Gln Glu Ala Gly Asn Leu Ser Ile
                405                 410                 415

Val Leu Ser Gly Gly Ser Gly Asp Ala Asp Leu Tyr Val Lys Tyr Gln
            420                 425                 430

Thr Asp Ala Asp Leu Gln Gln Tyr Asp Cys Arg Pro Tyr Arg Ser Gly
        435                 440                 445

Asn Asn Glu Thr Cys Gln Phe Ser Asn Ala Gln Pro Gly Arg Tyr Ser
    450                 455                 460

Ile Leu Leu His Gly Tyr Asn Asn Tyr Ser Asn Ala Ser Leu Val Ala
465                 470                 475                 480

Asn Ala Gln

<210> SEQ ID NO 66
<211> LENGTH: 482
<212> TYPE: PRT
<213> ORGANISM: Unknown
<220> FEATURE:
<223> OTHER INFORMATION: Salinivibrio spYCSC6

<400> SEQUENCE: 66

Met Glu Asp Lys Lys Val Trp Ile Ser Ile Gly Ala Asp Ala Gln Gln
1               5                   10                  15

Thr Ala Leu Ser Ser Gly Ala Gln Pro Leu Leu Ala Gln Ser Val Ala
            20                  25                  30

His Asn Gly Gln Ala Trp Ile Gly Glu Val Ser Glu Ser Glu Leu Ala
        35                  40                  45

Ala Leu Ser His Glu Met His Glu Asn His His Arg Cys Gly Gly Tyr
    50                  55                  60

Ile Val His Ser Ser Ala Gln Ser Ala Met Ala Ala Ser Asn Met Pro
65                  70                  75                  80

Leu Ser Arg Ala Ser Phe Ile Ala Pro Ala Ile Ser Gln Gln Ala Leu
                85                  90                  95

Val Thr Pro Trp Ile Ser Gln Ile Asp Ser Ala Leu Ile Val Asn Thr
            100                 105                 110

Ile Asp Arg Leu Thr Asp Phe Pro Asn Arg Phe Tyr Thr Thr Thr Ser
        115                 120                 125

Gly Ala Gln Ala Ser Asp Trp Ile Lys Gln Arg Trp Gln Ser Leu Ser
    130                 135                 140

Ala Gly Leu Ala Gly Ala Ser Val Thr Gln Ile Ser His Ser Gly Tyr
```

```
            145                 150                 155                 160
Asn Gln Ala Ser Val Met Leu Thr Ile Glu Gly Ser Glu Ser Pro Asp
                165                 170                 175
Glu Trp Val Val Val Gly Gly His Leu Asp Ser Thr Ile Gly Ser Arg
                180                 185                 190
Thr Asn Glu Gln Ser Ile Ala Pro Gly Ala Asp Asp Ala Ser Gly
                195                 200                 205
Ile Ala Ala Val Thr Glu Val Ile Arg Val Leu Ala Gln Asn Asn Phe
210                 215                 220
Gln Pro Lys Arg Ser Ile Ala Phe Val Ala Tyr Ala Ala Glu Glu Val
225                 230                 235                 240
Gly Leu Arg Gly Ser Gln Asp Val Ala Asn Gln Phe Lys Gln Ala Gly
                245                 250                 255
Lys Asp Val Arg Gly Val Leu Gln Leu Asp Met Thr Asn Tyr Gln Gly
                260                 265                 270
Ser Ala Glu Asp Ile Val Phe Ile Thr Asp Tyr Thr Asp Asn Gln Leu
                275                 280                 285
Thr Gln Tyr Leu Thr Gln Leu Leu Asp Glu Tyr Leu Pro Thr Leu Asn
            290                 295                 300
Tyr Gly Phe Asp Thr Cys Gly Tyr Ala Cys Ser Asp His Ala Ser Trp
305                 310                 315                 320
His Gln Val Gly Tyr Pro Ala Ala Met Pro Phe Glu Ala Lys Phe Asn
                325                 330                 335
Asp Tyr Asn Pro Asn Ile His Thr Pro Gln Asp Thr Leu Ala Asn Ser
                340                 345                 350
Asp Ser Glu Gly Ala His Ala Ala Lys Phe Thr Lys Leu Gly Leu Ala
                355                 360                 365
Tyr Thr Val Glu Leu Ala Asn Ala Asp Ser Ser Pro Asn Pro Gly Asn
            370                 375                 380
Glu Leu Lys Leu Gly Glu Pro Ile Asn Gly Leu Ser Gly Ala Arg Gly
385                 390                 395                 400
Asn Glu Lys Tyr Phe Asn Tyr Arg Leu Asp Gln Ser Gly Glu Leu Val
                405                 410                 415
Ile Arg Thr Tyr Gly Gly Ser Gly Asp Val Asp Leu Tyr Val Lys Ala
                420                 425                 430
Asn Gly Asp Val Ser Thr Gly Asn Trp Asp Cys Arg Pro Tyr Arg Ser
                435                 440                 445
Gly Asn Asp Glu Val Cys Arg Phe Asp Asn Ala Thr Pro Gly Asn Tyr
            450                 455                 460
Ala Val Met Leu Arg Gly Tyr Arg Thr Tyr Asp Asn Val Ser Leu Ile
465                 470                 475                 480
Val Glu

<210> SEQ ID NO 67
<211> LENGTH: 301
<212> TYPE: PRT
<213> ORGANISM: Vibrio proteolyticus

<400> SEQUENCE: 67

Met Pro Pro Ile Thr Gln Gln Ala Thr Val Thr Ala Trp Leu Pro Gln
1               5                   10                  15

Val Asp Ala Ser Gln Ile Thr Gly Thr Ile Ser Ser Leu Glu Ser Phe
                20                  25                  30

Thr Asn Arg Phe Tyr Thr Thr Thr Ser Gly Ala Gln Ala Ser Asp Trp
```

```
            35                  40                  45
Ile Ala Ser Glu Trp Gln Ala Leu Ser Ala Ser Leu Pro Asn Ala Ser
 50                  55                  60

Val Lys Gln Val Ser His Ser Gly Tyr Asn Gln Lys Ser Val Val Met
 65                  70                  75                  80

Thr Ile Thr Gly Ser Glu Ala Pro Asp Glu Trp Ile Val Ile Gly Gly
                 85                  90                  95

His Leu Asp Ser Thr Ile Gly Ser His Thr Asn Glu Gln Ser Val Ala
                100                 105                 110

Pro Gly Ala Asp Asp Ala Ser Gly Ile Ala Ala Val Thr Glu Val
                115                 120                 125

Ile Arg Val Leu Ser Glu Asn Asn Phe Gln Pro Lys Arg Ser Ile Ala
 130                 135                 140

Phe Met Ala Tyr Ala Ala Glu Glu Val Gly Leu Arg Gly Ser Gln Asp
 145                 150                 155                 160

Leu Ala Asn Gln Tyr Lys Ser Glu Gly Lys Asn Val Val Ser Ala Leu
                165                 170                 175

Gln Leu Asp Met Thr Asn Tyr Lys Gly Ser Ala Gln Asp Val Val Phe
                180                 185                 190

Ile Thr Asp Tyr Thr Asp Ser Asn Phe Thr Gln Tyr Leu Thr Gln Leu
                195                 200                 205

Met Asp Glu Tyr Leu Pro Ser Leu Thr Tyr Gly Phe Asp Thr Cys Gly
 210                 215                 220

Tyr Ala Cys Ser Asp His Ala Ser Trp His Asn Ala Gly Tyr Pro Ala
 225                 230                 235                 240

Ala Met Pro Phe Glu Ser Lys Phe Asn Asp Tyr Asn Pro Arg Ile His
                245                 250                 255

Thr Thr Gln Asp Thr Leu Ala Asn Ser Asp Pro Thr Gly Ser His Ala
                260                 265                 270

Lys Lys Phe Thr Gln Leu Gly Leu Ala Tyr Ala Ile Glu Met Gly Ser
                275                 280                 285

Ala Thr Gly Asp Thr Pro Thr Pro Gly Asn Gln Leu Glu
 290                 295                 300

<210> SEQ ID NO 68
<211> LENGTH: 301
<212> TYPE: PRT
<213> ORGANISM: Vibrio proteolyticus

<400> SEQUENCE: 68

Met Pro Pro Ile Thr Gln Gln Ala Thr Val Thr Ala Trp Leu Pro Gln
 1               5                  10                  15

Val Asp Ala Ser Gln Ile Thr Gly Thr Ile Ser Ser Leu Glu Ser Phe
                20                  25                  30

Thr Asn Arg Phe Tyr Thr Thr Thr Ser Gly Ala Gln Ala Ser Asp Trp
                35                  40                  45

Ile Ala Ser Glu Trp Gln Phe Leu Ser Ala Ser Leu Pro Asn Ala Ser
 50                  55                  60

Val Lys Gln Val Ser His Ser Gly Tyr Asn Gln Lys Ser Val Val Met
 65                  70                  75                  80

Thr Ile Thr Gly Ser Glu Ala Pro Asp Glu Trp Ile Val Ile Gly Gly
                 85                  90                  95

His Leu Asp Ser Thr Ile Gly Ser His Thr Asn Glu Gln Ser Val Ala
                100                 105                 110
```

```
Pro Gly Ala Asp Asp Ala Ser Gly Ile Ala Ala Val Thr Glu Val
            115                 120                 125

Ile Arg Val Leu Ser Glu Asn Asn Phe Gln Pro Lys Arg Ser Ile Ala
    130                 135                 140

Phe Met Ala Tyr Ala Ala Glu Glu Val Gly Leu Arg Gly Ser Gln Asp
145                 150                 155                 160

Leu Ala Asn Gln Tyr Lys Ser Glu Gly Lys Asn Val Val Ser Ala Leu
                165                 170                 175

Gln Leu Asp Met Thr Asn Tyr Lys Gly Ser Ala Gln Asp Val Val Phe
            180                 185                 190

Ile Thr Asp Tyr Thr Asp Ser Asn Phe Thr Gln Tyr Leu Thr Gln Leu
    195                 200                 205

Met Asp Glu Tyr Leu Pro Ser Leu Thr Tyr Gly Phe Asp Thr Cys Gly
210                 215                 220

Tyr Ala Cys Ser Asp His Ala Ser Trp His Asn Ala Gly Tyr Pro Ala
225                 230                 235                 240

Ala Met Pro Phe Glu Ser Lys Phe Asn Asp Tyr Asn Pro Arg Ile His
                245                 250                 255

Thr Thr Gln Asp Thr Leu Ala Asn Ser Asp Pro Thr Gly Ser His Ala
            260                 265                 270

Lys Lys Phe Thr Gln Leu Gly Leu Ala Tyr Ala Ile Glu Met Gly Ser
    275                 280                 285

Ala Thr Gly Asp Thr Pro Thr Pro Gly Asn Gln Leu Glu
290                 295                 300

<210> SEQ ID NO 69
<211> LENGTH: 348
<212> TYPE: PRT
<213> ORGANISM: P. furiosus

<400> SEQUENCE: 69

Met Val Asp Trp Glu Leu Met Lys Lys Ile Ile Glu Ser Pro Gly Val
1               5                   10                  15

Ser Gly Tyr Glu His Leu Gly Ile Arg Asp Leu Val Val Asp Ile Leu
                20                  25                  30

Lys Asp Val Ala Asp Glu Val Lys Ile Asp Lys Leu Gly Asn Val Ile
            35                  40                  45

Ala His Phe Lys Gly Ser Ala Pro Lys Val Met Val Ala Ala His Met
        50                  55                  60

Asp Lys Ile Gly Leu Met Val Asn His Ile Asp Lys Asp Gly Tyr Leu
65                  70                  75                  80

Arg Val Val Pro Ile Gly Gly Val Leu Pro Glu Thr Leu Ile Ala Gln
                85                  90                  95

Lys Ile Arg Phe Phe Thr Glu Lys Gly Glu Arg Tyr Gly Val Val Gly
            100                 105                 110

Val Leu Pro Pro His Leu Arg Arg Glu Ala Lys Asp Gln Gly Gly Lys
        115                 120                 125

Ile Asp Trp Asp Ser Ile Ile Val Asp Val Gly Ala Ser Ser Arg Glu
    130                 135                 140

Glu Ala Glu Glu Met Gly Phe Arg Ile Gly Thr Ile Gly Glu Phe Ala
145                 150                 155                 160

Pro Asn Phe Thr Arg Leu Ser Glu His Arg Phe Ala Thr Pro Tyr Leu
                165                 170                 175

Asp Asp Arg Ile Cys Leu Tyr Ala Met Ile Glu Ala Ala Arg Gln Leu
            180                 185                 190
```

```
Gly Glu His Glu Ala Asp Ile Tyr Ile Val Ala Ser Val Gln Glu Glu
        195                 200                 205

Ile Gly Leu Arg Gly Ala Arg Val Ala Ser Phe Ala Ile Asp Pro Glu
    210                 215                 220

Val Gly Ile Ala Met Asp Val Thr Phe Ala Lys Gln Pro Asn Asp Lys
225                 230                 235                 240

Gly Lys Ile Val Pro Glu Leu Gly Lys Gly Pro Val Met Asp Val Gly
            245                 250                 255

Pro Asn Ile Asn Pro Lys Leu Arg Gln Phe Ala Asp Glu Val Ala Lys
            260                 265                 270

Lys Tyr Glu Ile Pro Leu Gln Val Glu Pro Ser Pro Arg Pro Thr Gly
        275                 280                 285

Thr Asp Ala Asn Val Met Gln Ile Asn Arg Glu Gly Val Ala Thr Ala
    290                 295                 300

Val Leu Ser Ile Pro Ile Arg Tyr Met His Ser Gln Val Glu Leu Ala
305                 310                 315                 320

Asp Ala Arg Asp Val Asp Asn Thr Ile Lys Leu Ala Lys Ala Leu Leu
            325                 330                 335

Glu Glu Leu Lys Pro Met Asp Phe Thr Pro Leu Glu
        340                 345

<210> SEQ ID NO 70
<211> LENGTH: 2
<212> TYPE: PRT
<213> ORGANISM: Artificial Sequence
<220> FEATURE:
<223> OTHER INFORMATION: Synthetic Polypeptide

<400> SEQUENCE: 70

Lys Phe
1

<210> SEQ ID NO 71
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 71

Lys Lys Met Lys Lys Met Xaa
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 72

Asp Asp Met Asp Asp Met Xaa
1               5
```

```
<210> SEQ ID NO 73
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 73

Phe Phe Met Phe Phe Met Xaa
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 74

Ala Ala Met Ala Ala Met Xaa
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 75

Phe Pro Phe Pro Phe Pro Xaa
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 76

Asp Pro Asp Pro Asp Pro Xaa
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine
```

```
<400> SEQUENCE: 77

Lys Pro Lys Pro Lys Pro Xaa
1               5

<210> SEQ ID NO 78
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 78

Tyr Ala Ala Trp Ala Ala Phe Ala Asp Asp Trp Lys
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 79

Phe Tyr Pro Leu Pro Trp Pro Asp Asp Asp Tyr
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 80

Phe Tyr Pro Leu Pro Trp Pro Asp Asp Asp Tyr Lys
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 81

Tyr Pro Leu Pro Trp Pro Asp Asp Asp Tyr Lys
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 82

Tyr Pro Tyr Pro Tyr Pro Lys
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 83
```

```
Pro Tyr Pro Tyr Pro Lys
1               5

<210> SEQ ID NO 84
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 84

Gly Pro Arg Pro
1

<210> SEQ ID NO 85
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 85

Asp Asp Pro Asp Asp Pro Xaa
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 86

Tyr Pro Tyr Pro Tyr Pro Xaa
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Azidolysine

<400> SEQUENCE: 87

Pro Tyr Pro Tyr Pro Xaa
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Azidolysine
```

```
<400> SEQUENCE: 88

Pro Phe Pro Phe Pro Xaa
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Lys-Triazole-PEG4

<400> SEQUENCE: 89

Lys Lys Met Lys Lys Met Xaa
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 90

Ala Ala Pro Ala Ala Pro Xaa
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Azidolysine

<400> SEQUENCE: 91

Ala Pro Ala Ala Pro Xaa
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 92

Tyr Tyr Pro Tyr Tyr Pro Xaa
1               5

<210> SEQ ID NO 93
<211> LENGTH: 6
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Azidolysine

<400> SEQUENCE: 93

Tyr Pro Tyr Tyr Pro Xaa
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 94

Phe Phe Pro Phe Phe Pro Xaa
1               5

<210> SEQ ID NO 95
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Azidolysine

<400> SEQUENCE: 95

Phe Pro Phe Phe Pro Xaa
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 96

Arg Arg Pro Arg Arg Pro Xaa
1               5

<210> SEQ ID NO 97
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Azidolysine

<400> SEQUENCE: 97

Arg Pro Arg Arg Pro Xaa
1               5
```

```
<210> SEQ ID NO 98
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 98

Ala Ala Pro Ala Ala Pro Xaa
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Azidolysine

<400> SEQUENCE: 99

Ala Pro Ala Ala Pro Xaa
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 100

Lys Lys Pro Lys Lys Pro Xaa
1               5

<210> SEQ ID NO 101
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Azidolysine

<400> SEQUENCE: 101

Lys Pro Lys Lys Pro Xaa
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
```

```
<223> OTHER INFORMATION: Xaa is Azidolysine

<400> SEQUENCE: 102

Lys Met Lys Lys Met Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is Azidolysine

<400> SEQUENCE: 103

Tyr Tyr Met Tyr Tyr Met Xaa
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(8)
<223> OTHER INFORMATION: Xaa is Azidolysine

<400> SEQUENCE: 104

Asp Pro Ala Ala Ala Phe Lys Xaa
1               5

<210> SEQ ID NO 105
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 105

Pro Ala Ala Ala Phe Lys
1               5

<210> SEQ ID NO 106
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (10)..(10)
<223> OTHER INFORMATION: Xaa is Azidolysine

<400> SEQUENCE: 106

Lys Ala Ala Ala Ala Ala Ala Phe Lys Xaa
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: misc_feature
<222> LOCATION: (12)..(12)
<223> OTHER INFORMATION: Xaa is Azidolysine

<400> SEQUENCE: 107

Phe Tyr Pro Leu Pro Trp Pro Asp Asp Asp Tyr Xaa
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (11)..(11)
<223> OTHER INFORMATION: Xaa is Azidolysine

<400> SEQUENCE: 108

Tyr Pro Leu Pro Trp Pro Asp Asp Asp Tyr Xaa
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (10)..(10)
<223> OTHER INFORMATION: Xaa is Azidolysine

<400> SEQUENCE: 109

Pro Leu Pro Trp Pro Asp Asp Asp Tyr Xaa
1               5                   10

<210> SEQ ID NO 110
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (9)..(9)
<223> OTHER INFORMATION: Xaa is Azidolysine

<400> SEQUENCE: 110

Leu Pro Trp Pro Asp Asp Asp Tyr Xaa
1               5

<210> SEQ ID NO 111
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 111

Phe Ala Ala Ala Trp Pro Asp Asp Asp Phe
1               5                   10

<210> SEQ ID NO 112
<211> LENGTH: 5
<212> TYPE: PRT
<213> ORGANISM: Artificial Sequence
<220> FEATURE:
```

<223> OTHER INFORMATION: Synthetic Polypeptide

<400> SEQUENCE: 112

Trp Pro Asp Asp Phe
1               5

<210> SEQ ID NO 113
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 113

Trp Ala Ala Ala Phe Pro Asp Asp Phe
1               5                   10

<210> SEQ ID NO 114
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 114

Phe Pro Asp Asp Phe
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 115

Tyr Pro Asp Asp Phe
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 116

Arg Arg Pro Phe Gln Gln
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 117

Arg Pro Phe Gln Gln
1               5

<210> SEQ ID NO 118
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 118

Ala Ala Pro Phe Gln Gln
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 119

Ala Pro Phe Gln Gln
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 120

Lys Lys Pro Phe Gln Gln
1               5

<210> SEQ ID NO 121
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 121

Lys Pro Phe Gln Gln
1               5

<210> SEQ ID NO 122
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 122

Tyr Tyr Pro Phe Gln Gln
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 123

Tyr Pro Phe Gln Gln
1               5

<210> SEQ ID NO 124
<211> LENGTH: 6
<212> TYPE: PRT
<213> ORGANISM: Artificial Sequence
<220> FEATURE:
<223> OTHER INFORMATION: Synthetic Polypeptide

```
<400> SEQUENCE: 124

Phe Phe Pro Phe Gln Gln
1               5

<210> SEQ ID NO 125
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 125

Phe Pro Phe Gln Gln
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 126

Asp Asp Pro Phe Gln Gln
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 127

Asp Pro Phe Gln Gln
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 128

Glu Glu Pro Phe Gln Gln
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 129

Glu Pro Phe Gln Gln
1               5

<210> SEQ ID NO 130
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 130
```

```
Asn Asn Pro Phe Gln Gln
1               5

<210> SEQ ID NO 131
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 131

Asn Pro Phe Gln Gln
1               5

<210> SEQ ID NO 132
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 132

Gln Gln Pro Phe Gln Gln
1               5

<210> SEQ ID NO 133
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 133

Gln Pro Phe Gln Gln
1               5

<210> SEQ ID NO 134
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 134

Val Val Pro Phe Gln Gln
1               5

<210> SEQ ID NO 135
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 135

Val Pro Phe Gln Gln
1               5

<210> SEQ ID NO 136
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 136
```

```
Ile Ile Pro Phe Gln Gln
1               5

<210> SEQ ID NO 137
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 137

Ile Pro Phe Gln Gln
1               5

<210> SEQ ID NO 138
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 138

Leu Leu Pro Phe Gln Gln
1               5

<210> SEQ ID NO 139
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 139

Leu Pro Phe Gln Gln
1               5

<210> SEQ ID NO 140
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 140

Ser Ser Pro Phe Gln Gln
1               5

<210> SEQ ID NO 141
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 141

Ser Pro Phe Gln Gln
1               5

<210> SEQ ID NO 142
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 142

Thr Thr Pro Phe Gln Gln
```

```
1               5

<210> SEQ ID NO 143
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 143

Thr Pro Phe Gln Gln
1               5

<210> SEQ ID NO 144
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 144

Cys Cys Pro Phe Gln Gln
1               5

<210> SEQ ID NO 145
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 145

Cys Pro Phe Gln Gln
1               5

<210> SEQ ID NO 146
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 146

Trp Trp Pro Phe Gln Gln
1               5

<210> SEQ ID NO 147
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 147

Trp Pro Phe Gln Gln
1               5

<210> SEQ ID NO 148
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 148

Met Met Pro Phe Gln Gln
1               5
```

```
<210> SEQ ID NO 149
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 149

Met Pro Phe Gln Gln
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 150

Pro Pro Pro Phe Gln Gln
1               5

<210> SEQ ID NO 151
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 151

Pro Pro Phe Gln Gln
1               5

<210> SEQ ID NO 152
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 152

Gly Gly Pro Phe Gln Gln
1               5

<210> SEQ ID NO 153
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 153

Gly Pro Phe Gln Gln
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 154

His His Pro Phe Gln Gln
1               5
```

```
<210> SEQ ID NO 155
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 155

His Pro Phe Gln Gln
1               5

<210> SEQ ID NO 156
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 156

Tyr Ala Ala Phe Ala Ala Trp Ala Asp Asp Asp Trp
1               5                   10

<210> SEQ ID NO 157
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 157

Ala Asp Asp Asp Trp Lys
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 158

Trp Ala Asp Asp Asp Trp Lys
1               5

<210> SEQ ID NO 159
<211> LENGTH: 6
<212> TYPE: PRT
<213> ORGANISM: Artificial Sequence
<220> FEATURE:
<223> OTHER INFORMATION: Synthetic

<400> SEQUENCE: 159

Cys Lys Val Thr His Asn
1               5

<210> SEQ ID NO 160
<211> LENGTH: 6
<212> TYPE: PRT
<213> ORGANISM: Artificial Sequence
<220> FEATURE:
<223> OTHER INFORMATION: Synthetic

<400> SEQUENCE: 160

Lys Cys Gly Ser Gly Ala
1               5
```

```
<210> SEQ ID NO 161
<211> LENGTH: 6
<212> TYPE: PRT
<213> ORGANISM: Artificial Sequence
<220> FEATURE:
<223> OTHER INFORMATION: Synthetic

<400> SEQUENCE: 161

Trp Glu Lys Thr His Cys
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic

<400> SEQUENCE: 162

Glu Ala Lys Trp Asp Asn
1               5

<210> SEQ ID NO 163
<211> LENGTH: 5
<212> TYPE: PRT
<213> ORGANISM: Artificial Sequence
<220> FEATURE:
<223> OTHER INFORMATION: Synthetic

<400> SEQUENCE: 163

Lys Val Thr His Asn
1               5

<210> SEQ ID NO 164
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is Azidolysine

<400> SEQUENCE: 164

Asp Met Asp Asp Met Xaa
1               5

<210> SEQ ID NO 165
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Azidolysine

<400> SEQUENCE: 165

Met Asp Asp Met Xaa
1               5

<210> SEQ ID NO 166
<211> LENGTH: 10
<212> TYPE: PRT
<213> ORGANISM: Artificial Sequence
<220> FEATURE:
<223> OTHER INFORMATION: Synthetic
```

```
<400> SEQUENCE: 166

Pro Gly Leu Trp Ala Ala Asp Asp Asp Trp
1               5                   10
```

METHODS AND COMPOSITIONS FOR PROTEIN SEQUENCING

CROSS-REFERENCE TO RELATED APPLICATIONS

This application is a continuation of U.S. patent application Ser. No. 16/686,028, filed Nov. 15, 2019, which claims priority under 35 U.S.C. § 119(e) to U.S. Provisional Patent Application No. 62/907,507, filed Sep. 27, 2019, and U.S. Provisional Patent Application No. 62/768,076, filed Nov. 15, 2018, each of which is hereby incorporated by reference in its entirety.

REFERENCE TO A SEQUENCE LISTING SUBMITTED AS A TEXT FILE VIA EFS-WEB

The present application contains a Sequence Listing which has been submitted in ASCII format via EFS-Web and is hereby incorporated by reference in its entirety. Said ASCII copy, created on Sep. 20, 2022, is named R070870042US05-SUBSEQ-JIB and is 197,391 bytes in size.

BACKGROUND

Proteomics has emerged as an important and necessary complement to genomics and transcriptomics in the study of biological systems. The proteomic analysis of an individual organism can provide insights into cellular processes and response patterns, which lead to improved diagnostic and therapeutic strategies. The complexity surrounding protein structure, composition, and modification present challenges in determining large-scale protein sequencing information for a biological sample.

SUMMARY

In some aspects, the application provides methods and compositions for determining amino acid sequence information from polypeptides (e.g., for sequencing one or more polypeptides). In some embodiments, amino acid sequence information can be determined for single polypeptide molecules. In some embodiments, the relative position of two or more amino acids in a polypeptide is determined, for example for a single polypeptide molecule. In some embodiments, one or more amino acids of a polypeptide are labeled (e.g., directly or indirectly) and the relative positions of the labeled amino acids in the polypeptide is determined.

In some aspects, the application provides methods comprising obtaining data during a degradation process of a polypeptide. In some embodiments, the methods further comprise analyzing the data to determine portions of the data corresponding to amino acids that are sequentially exposed at a terminus of the polypeptide during the degradation process. In some embodiments, the methods further comprise outputting an amino acid sequence representative of the polypeptide. In some embodiments, the data is indicative of amino acid identity at the terminus of the polypeptide during the degradation process. In some embodiments, the data is indicative of a signal produced by one or more amino acid recognition molecules binding to different types of terminal amino acids at the terminus during the degradation process. In some embodiments, the data is indicative of a luminescent signal generated during the degradation process. In some embodiments, the data is indicative of an electrical signal generated during the degradation process.

In some embodiments, analyzing the data further comprises detecting a series of cleavage events and determining the portions of the data between successive cleavage events. In some embodiments, analyzing the data further comprises determining a type of amino acid for each of the individual portions. In some embodiments, each of the individual portions comprises a pulse pattern (e.g., a characteristic pattern), and analyzing the data further comprises determining a type of amino acid for one or more of the portions based on its respective pulse pattern. In some embodiments, determining the type of amino acid further comprises identifying an amount of time within a portion when the data is above a threshold value and comparing the amount of time to a duration of time for the portion. In some embodiments, determining the type of amino acid further comprises identifying at least one pulse duration for each of the one or more portions. In some embodiments, determining the type of amino acid further comprises identifying at least one interpulse duration for each of the one or more portions. In some embodiments, the amino acid sequence includes a series of amino acids corresponding to the portions.

In some aspects, the application provides systems comprising at least one hardware processor, and at least one non-transitory computer-readable storage medium storing processor-executable instructions that, when executed by the at least one hardware processor, cause the at least one hardware processor to perform a method in accordance with the application. In some aspects, the application provides at least one non-transitory computer-readable storage medium storing processor-executable instructions that, when executed by at least one hardware processor, cause the at least one hardware processor to perform a method in accordance with the application.

In some aspects, the application provides methods of polypeptide sequencing. In some embodiments, the methods comprise contacting a single polypeptide molecule with one or more terminal amino acid recognition molecules. In some embodiments, the methods further comprise detecting a series of signal pulses indicative of association of the one or more terminal amino acid recognition molecules with successive amino acids exposed at a terminus of the single polypeptide molecule while it is being degraded, thereby obtaining sequence information about the single polypeptide molecule. In some embodiments, the amino acid sequence of most or all of the single polypeptide molecule is determined. In some embodiments, the series of signal pulses is a series of real-time signal pulses.

In some embodiments, association of the one or more terminal amino acid recognition molecules with each type of amino acid exposed at the terminus produces a characteristic pattern in the series of signal pulses that is different from other types of amino acids exposed at the terminus. In some embodiments, a signal pulse of the characteristic pattern corresponds to an individual association event between a terminal amino acid recognition molecule and an amino acid exposed at the terminus. In some embodiments, the characteristic pattern corresponds to a series of reversible terminal amino acid recognition molecule binding interactions with the amino acid exposed at the terminus of the single polypeptide molecule. In some embodiments, the characteristic pattern is indicative of the amino acid exposed at the terminus of the single polypeptide molecule and an amino acid at a contiguous position (e.g., amino acids of the same type or different types).

In some embodiments, the single polypeptide molecule is degraded by a cleaving reagent that removes one or more amino acids from the terminus of the single polypeptide molecule. In some embodiments, the methods further comprise detecting a signal indicative of association of the cleaving reagent with the terminus. In some embodiments, the cleaving reagent comprises a detectable label (e.g., a luminescent label, a conductivity label). In some embodiments, the single polypeptide molecule is immobilized to a surface. In some embodiments, the single polypeptide molecule is immobilized to the surface through a terminal end distal to the terminus to which the one or more terminal amino acid recognition molecules associate. In some embodiments, the single polypeptide molecule is immobilized to the surface through a linker (e.g., a solubilizing linker comprising a biomolecule).

In some aspects, the application provides methods of sequencing a polypeptide comprising contacting a single polypeptide molecule in a reaction mixture with a composition comprising one or more terminal amino acid recognition molecules and a cleaving reagent. In some embodiments, the methods further comprise detecting a series of signal pulses indicative of association of the one or more terminal amino acid recognition molecules with a terminus of the single polypeptide molecule in the presence of the cleaving reagent. In some embodiments, the series of signal pulses is indicative of a series of amino acids exposed at the terminus over time as a result of terminal amino acid cleavage by the cleaving reagent.

In some aspects, the application provides methods of sequencing a polypeptide comprising (a) identifying a first amino acid at a terminus of a single polypeptide molecule, (b) removing the first amino acid to expose a second amino acid at the terminus of the single polypeptide molecule, and (c) identifying the second amino acid at the terminus of the single polypeptide molecule. In some embodiments, (a)-(c) are performed in a single reaction mixture. In some embodiments, (a)-(c) occur sequentially. In some embodiments, (c) occurs before (a) and (b). In some embodiments, the single reaction mixture comprises one or more terminal amino acid recognition molecules. In some embodiments, the single reaction mixture comprises a cleaving reagent. In some embodiments, the first amino acid is removed by the cleaving reagent. In some embodiments, the methods further comprise repeating the steps of removing and identifying one or more amino acids at the terminus of the single polypeptide molecule, thereby determining a sequence (e.g., a partial sequence or a complete sequence) of the single polypeptide molecule.

In some aspects, the application provides methods of identifying an amino acid of a polypeptide comprising contacting a single polypeptide molecule with one or more amino acid recognition molecules that bind to the single polypeptide molecule. In some embodiments, the methods further comprise detecting a series of signal pulses indicative of association of the one or more amino acid recognition molecules with the single polypeptide molecule under polypeptide degradation conditions. In some embodiments, the methods further comprise identifying a first type of amino acid in the single polypeptide molecule based on a first characteristic pattern in the series of signal pulses.

In some aspects, the application provides methods of identifying a terminal amino acid (e.g., the N-terminal or the C-terminal amino acid) of a polypeptide. In some embodiments, the methods comprise contacting a polypeptide with one or more labeled affinity reagents (e.g., one or more amino acid recognition molecules) that selectively bind one or more types of terminal amino acids at a terminus of the polypeptide. In some embodiments, the methods further comprise identifying a terminal amino acid at the terminus of the polypeptide by detecting an interaction of the polypeptide with the one or more labeled affinity reagents.

In yet other aspects, the application provides methods of polypeptide sequencing by Edman-type degradation reactions. In some embodiments, Edman-type degradation reactions may be performed by contacting a polypeptide with different reaction mixtures for purposes of either detection or cleavage (e.g., as compared to a dynamic sequencing reaction, which can involve detection and cleavage using a single reaction mixture).

Accordingly, in some aspects, the application provides methods of determining an amino acid sequence of a polypeptide comprising (i) contacting a polypeptide with one or more labeled affinity reagents that selectively bind one or more types of terminal amino acids at a terminus of the polypeptide. In some embodiments, the methods further comprise (ii) identifying a terminal amino acid (e.g., the N-terminal or the C-terminal amino acid) at the terminus of the polypeptide by detecting an interaction of the polypeptide with the one or more labeled affinity reagents. In some embodiments, the methods further comprise (iii) removing the terminal amino acid. In some embodiments, the methods further comprise (iv) repeating (i)-(iii) one or more times at the terminus of the polypeptide to determine an amino acid sequence of the polypeptide.

In some embodiments, the methods further comprise, after (i) and before (ii), removing any of the one or more labeled affinity reagents that do not selectively bind the terminal amino acid. In some embodiments, the methods further comprise, after (ii) and before (iii), removing any of the one or more labeled affinity reagents that selectively bind the terminal amino acid.

In some embodiments, removing a terminal amino acid (e.g., (iii)) comprises modifying the terminal amino acid by contacting the terminal amino acid with an isothiocyanate (e.g., phenyl isothiocyanate), and contacting the modified terminal amino acid with a protease that specifically binds and removes the modified terminal amino acid. In some embodiments cleaving a terminal amino acid (e.g., (iii)) comprises modifying the terminal amino acid by contacting the terminal amino acid with an isothiocyanate, and subjecting the modified terminal amino acid to acidic or basic conditions sufficient to remove the modified terminal amino acid.

In some embodiments, identifying a terminal amino acid comprises identifying the terminal amino acid as being one type of the one or more types of terminal amino acids to which the one or more labeled affinity reagents bind. In some embodiments, identifying a terminal amino acid comprises identifying the terminal amino acid as being a type other than the one or more types of terminal amino acids to which the one or more labeled affinity reagents bind.

In some aspects, the application provides amino acid recognition molecules comprising a shielding element, e.g., for enhanced photostability in polypeptide sequencing reactions. In some aspects, the application provides an amino acid recognition molecule of Formula (I):

$$A\text{-}(Y)_n\text{-}D \qquad (I),$$

wherein: A is an amino acid binding component comprising at least one amino acid recognition molecule; each instance of Y is a polymer that forms a covalent or non-covalent linkage group; n is an integer from 1 to 10, inclusive; and D is a label component comprising at least one detectable label. In some embodiments, D is less than 200 Å in diameter. In some embodiments, $-(Y)_n-$ is at least 2 nm in length (e.g., at least 5 nm, at least 10 nm, at least 20 nm, at least 30 nm, at least 50 nm, or more, in length). In some embodiments, —(Y)$_n$— is between about 2 nm and about 200 nm in length (e.g., between about 2 nm and about 100 nm, between about 5 nm and about 50 nm, or between about 10 nm and about 100 nm in length). In some embodiments, each instance of Y is independently a biomolecule or a dendritic polymer (e.g., a polyol, a dendrimer). In some embodiments, the application provides a composition comprising the amino acid recognition molecule of Formula (I). In some embodiments, the amino acid recognition molecule is soluble in the composition.

In some aspects, the application provides an amino acid recognition molecule of Formula (II):

$$A\text{-}Y^1\text{-}D \qquad (II),$$

wherein: A is an amino acid binding component comprising at least one amino acid recognition molecule; $Y^1$ is a nucleic acid or a polypeptide; D is a label component comprising at least one detectable label. In some embodiments, when $Y^1$ is a nucleic acid, the nucleic acid forms a covalent or non-covalent linkage group. In some embodiments, provided that when $Y^1$ is a polypeptide, the polypeptide forms a non-covalent linkage group characterized by a dissociation constant ($K_D$) of less than $50 \times 10^{-9}$ M. In some embodiments, the $K_D$ is less than $1 \times 10^{-9}$ M, less than $1 \times 10^{-10}$ M, less than $1 \times 10^{-11}$ M, or less than $1 \times 10^{-12}$ M.

In some aspects, the application provides an amino acid recognition molecule comprising: a nucleic acid; at least one amino acid recognition molecule attached to a first attachment site on the nucleic acid; and at least one detectable label attached to a second attachment site on the nucleic acid, where the nucleic acid forms a covalent or non-covalent linkage group between the at least one amino acid recognition molecule and the at least one detectable label. In some embodiments, the nucleic acid comprises a first oligonucleotide strand.

In some embodiments, the nucleic acid further comprises a second oligonucleotide strand hybridized with the first oligonucleotide strand.

In some aspects, the application provides an amino acid recognition molecule comprising: a multivalent protein comprising at least two ligand-binding sites; at least one amino acid recognition molecule attached to the protein through a first ligand moiety bound to a first ligand-binding site on the protein; and at least one detectable label attached to the protein through a second ligand moiety bound to a second ligand-binding site on the protein. In some embodiments, the multivalent protein is an avidin protein.

In some embodiments, a shielded amino acid recognition molecule may be used in polypeptide sequencing methods in accordance with the application, or any method known in the art. Accordingly, in some aspects, the application provides methods of polypeptide sequencing (e.g., in an Edman-type degradation reaction, in a dynamic sequencing reaction, or other method known in the art) comprising contacting a polypeptide molecule with one or more shielded amino acid recognition molecules of the application. For example, in some embodiments, the methods comprise contacting a polypeptide molecule with at least one amino acid recognition molecule that comprises a shield or shielding element in accordance with the application, and detecting association of the at least one amino acid recognition molecule with the polypeptide molecule.

In some aspects, the application provides methods of identifying a protein of interest in a mixed sample. In some embodiments, the methods comprise cleaving a mixed protein sample to produce a plurality of polypeptide fragments. In some embodiments, the methods further comprise determining an amino acid sequence of at least one polypeptide fragment of the plurality in a method in accordance with the methods of the application. In some embodiments, the methods further comprise identifying a protein of interest in the mixed sample if the amino acid sequence is uniquely identifiable to the protein of interest.

In some embodiments, methods of identifying a protein of interest in a mixed sample comprise cleaving a mixed protein sample to produce a plurality of polypeptide fragments. In some embodiments, the methods further comprise labeling one or more types of amino acids in the plurality of polypeptide fragments with one or more different luminescent labels. In some embodiments, the methods further comprise measuring luminescence over time for at least one labeled polypeptide of the plurality. In some embodiments, the methods further comprise determining an amino acid sequence of the at least one labeled polypeptide based on the luminescence detected. In some embodiments, the methods further comprise identifying a protein of interest in the mixed sample if the amino acid sequence is uniquely identifiable to the protein of interest.

Accordingly, in some embodiments, a polypeptide molecule or protein of interest to be analyzed in accordance with the application can be of a mixed or purified sample. In some embodiments, the polypeptide molecule or protein of interest is obtained from a biological sample (e.g., blood, tissue, saliva, urine, or other biological source). In some embodiments, the polypeptide molecule or protein of interest is obtained from a patient sample (e.g., a human sample).

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The skilled artisan will understand that the figures, described herein, are for illustration purposes only. It is to be understood that, in some instances, various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

As is apparent from the detailed description, the examples depicted in the figures and further described for the purpose of illustration throughout the application describe non-limiting embodiments, and in some cases may simplify certain processes or omit features or steps for the purpose of clearer illustration.

Figure 1A:
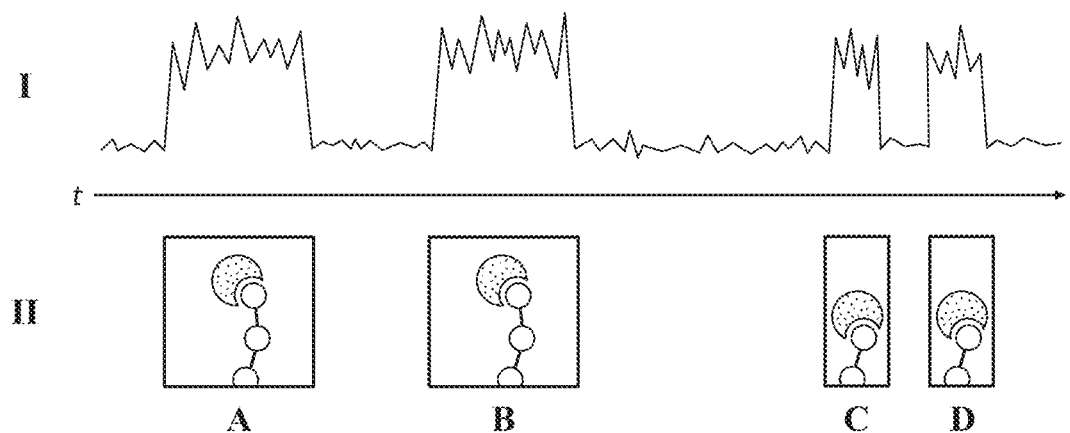
Figure 1B:
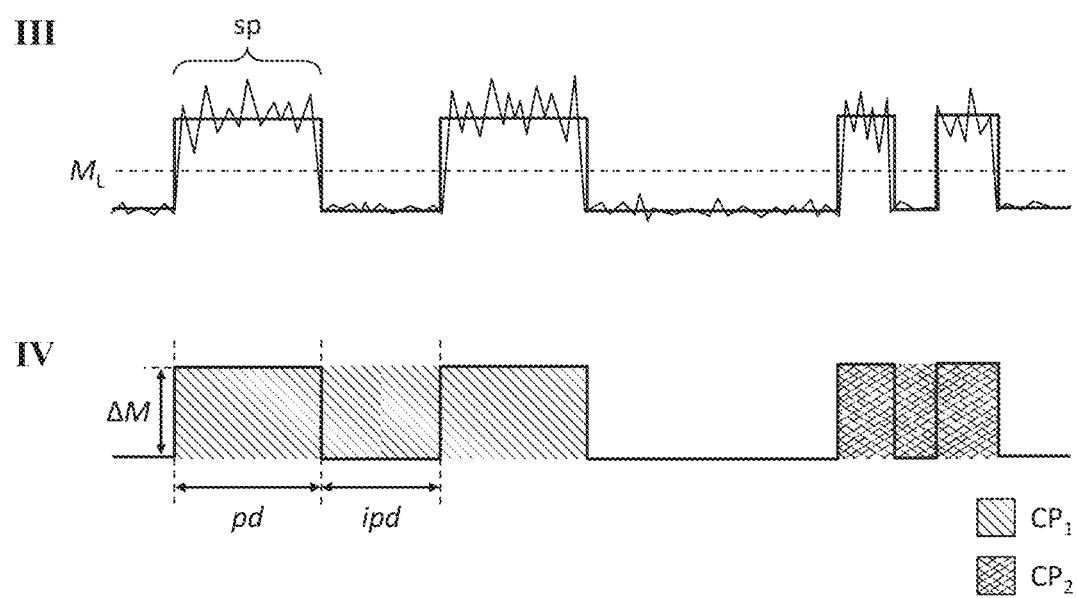

FIGS. 1A-1B show an example of polypeptide sequencing by detection (FIG. 1A) and analysis (FIG. 1B) of single molecule binding interactions.

Figure 1C:
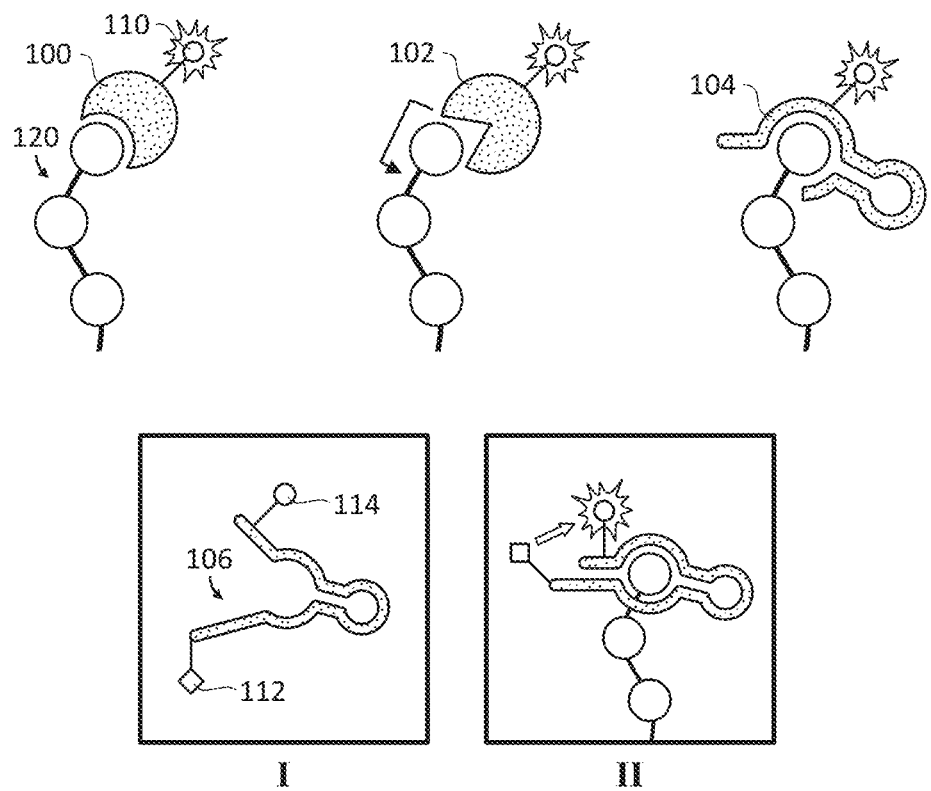
Figure 1D:
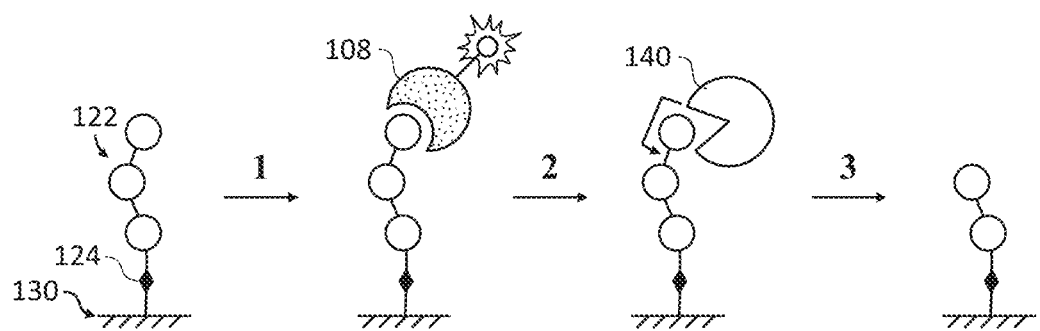
Figure 1E:
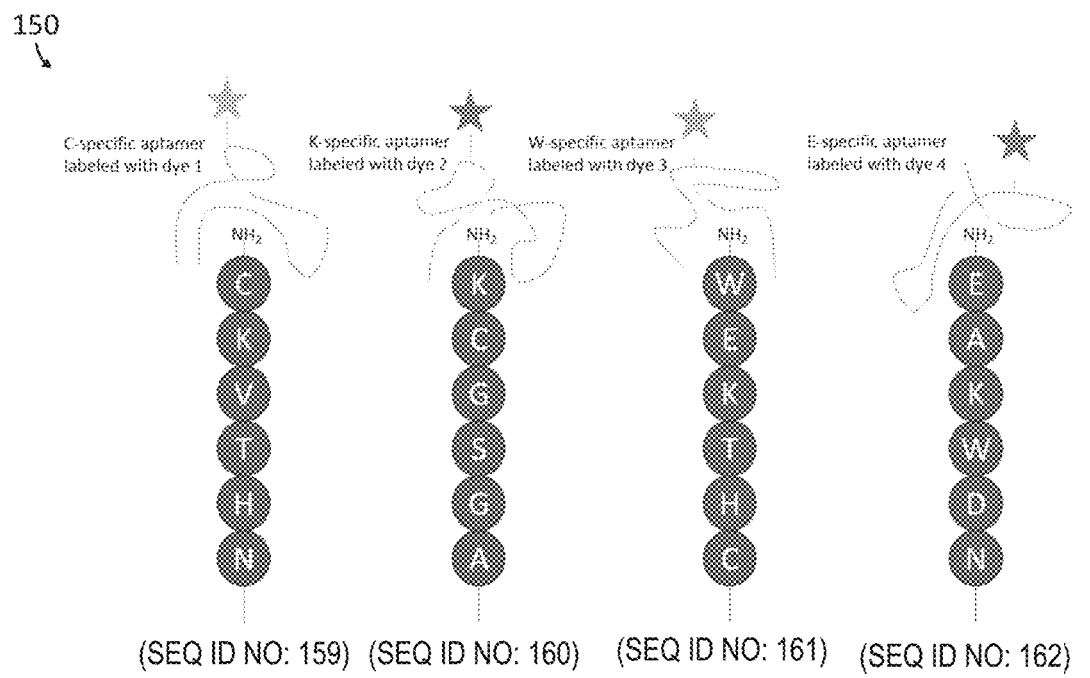
Figure 1E:
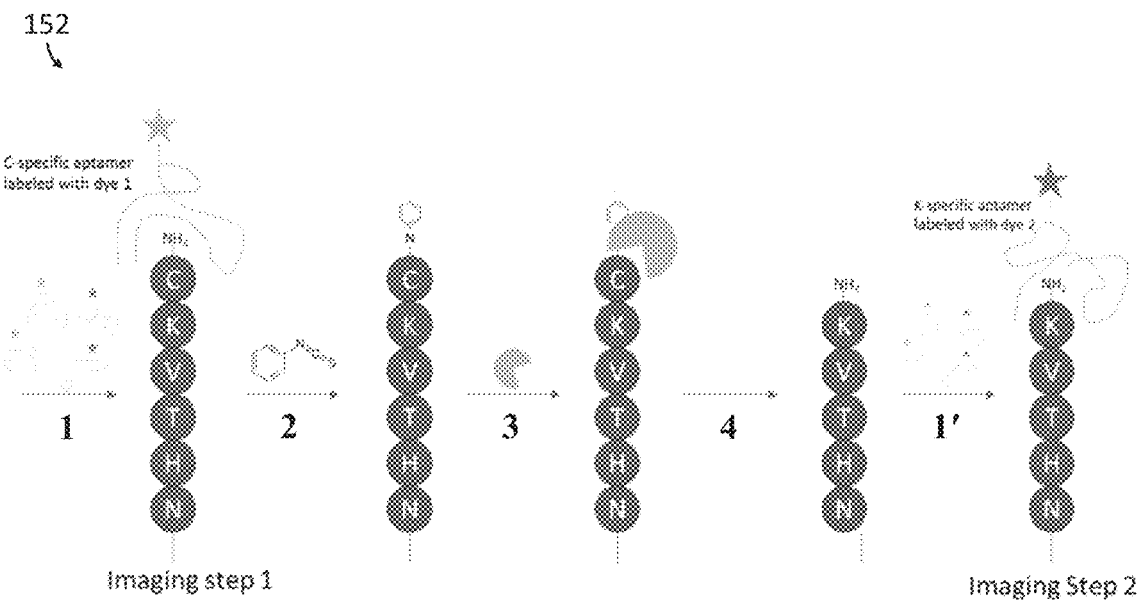

FIGS. 1C-1E show various examples of labeled affinity reagents and methods of use in accordance with the application. FIG. 1C depicts example configurations of labeled affinity reagents, including labeled enzymes and labeled aptamers which selectively bind one or more types of terminal amino acids. FIG. 1D generically depicts a degradation-based process of polypeptide sequencing using labeled affinity reagents. FIG. 1E shows an example of polypeptide sequencing using labeled aptamers by repeated cycles of terminal amino acid detection, modification, and cleavage.

Figure 2:
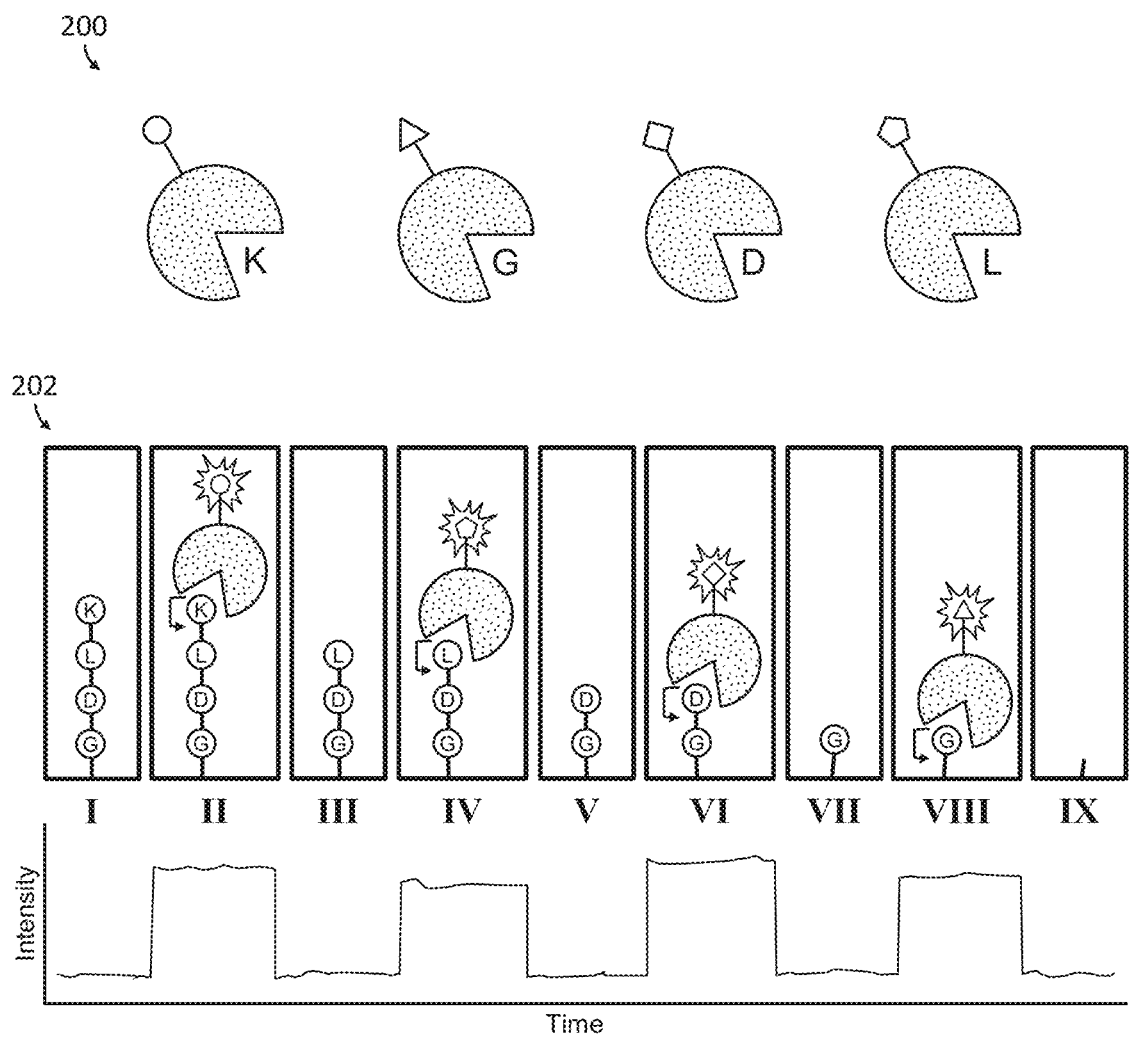

FIG. 2 shows an example of polypeptide sequencing in real-time using labeled exopeptidases that each selectively binds and cleaves a different type of terminal amino acid.

Figure 3A:
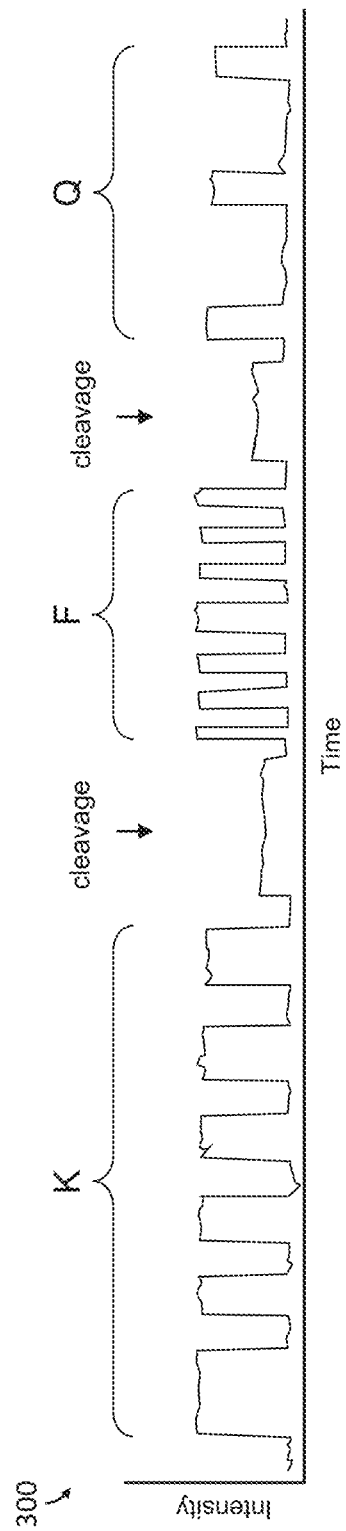
Figure 3A:
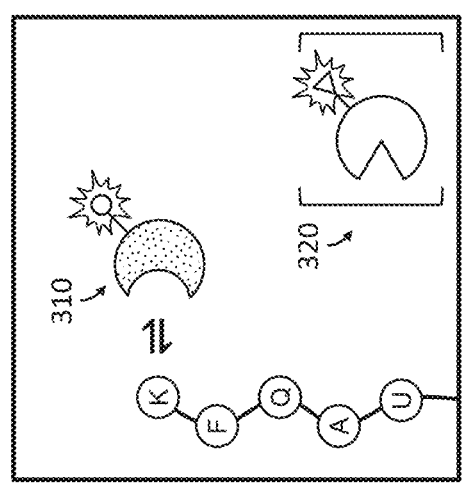
Figure 3B:
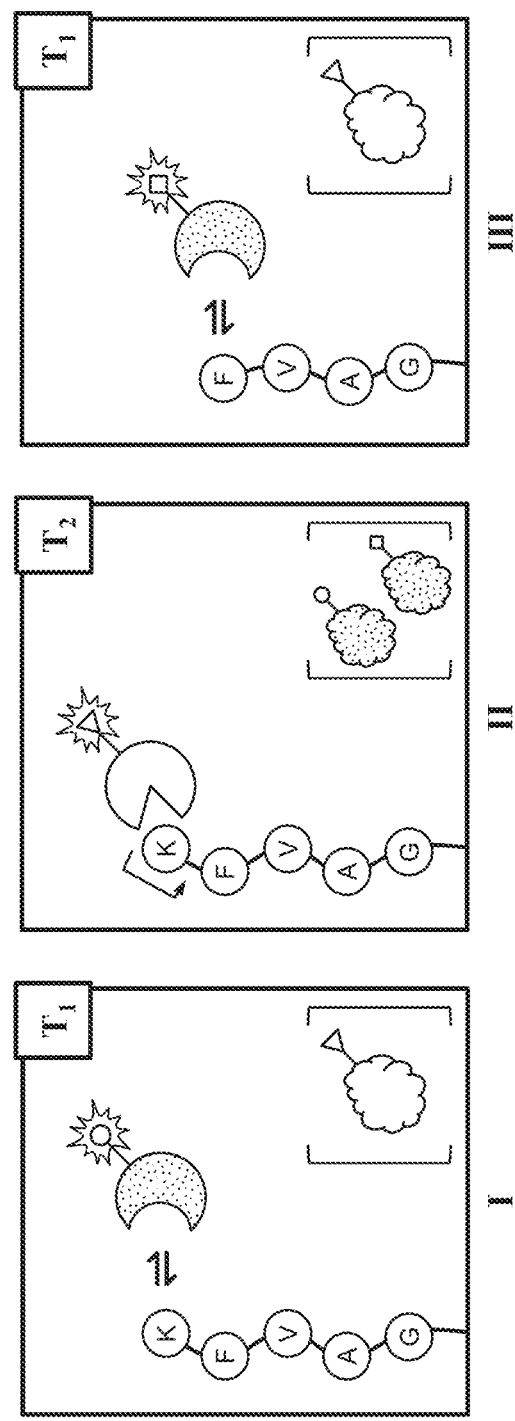

FIGS. 3A-3B show examples of polypeptide sequencing in real-time by evaluating binding interactions of terminal and/or internal amino acids with labeled affinity reagents and a labeled cleaving reagent (e.g., a labeled non-specific exopeptidase). FIG. 3A shows an example of real-time sequencing by detecting a series of pulses in a signal output. FIG. 3B schematically depicts a temperature-dependent sequencing process.

Figure 4:
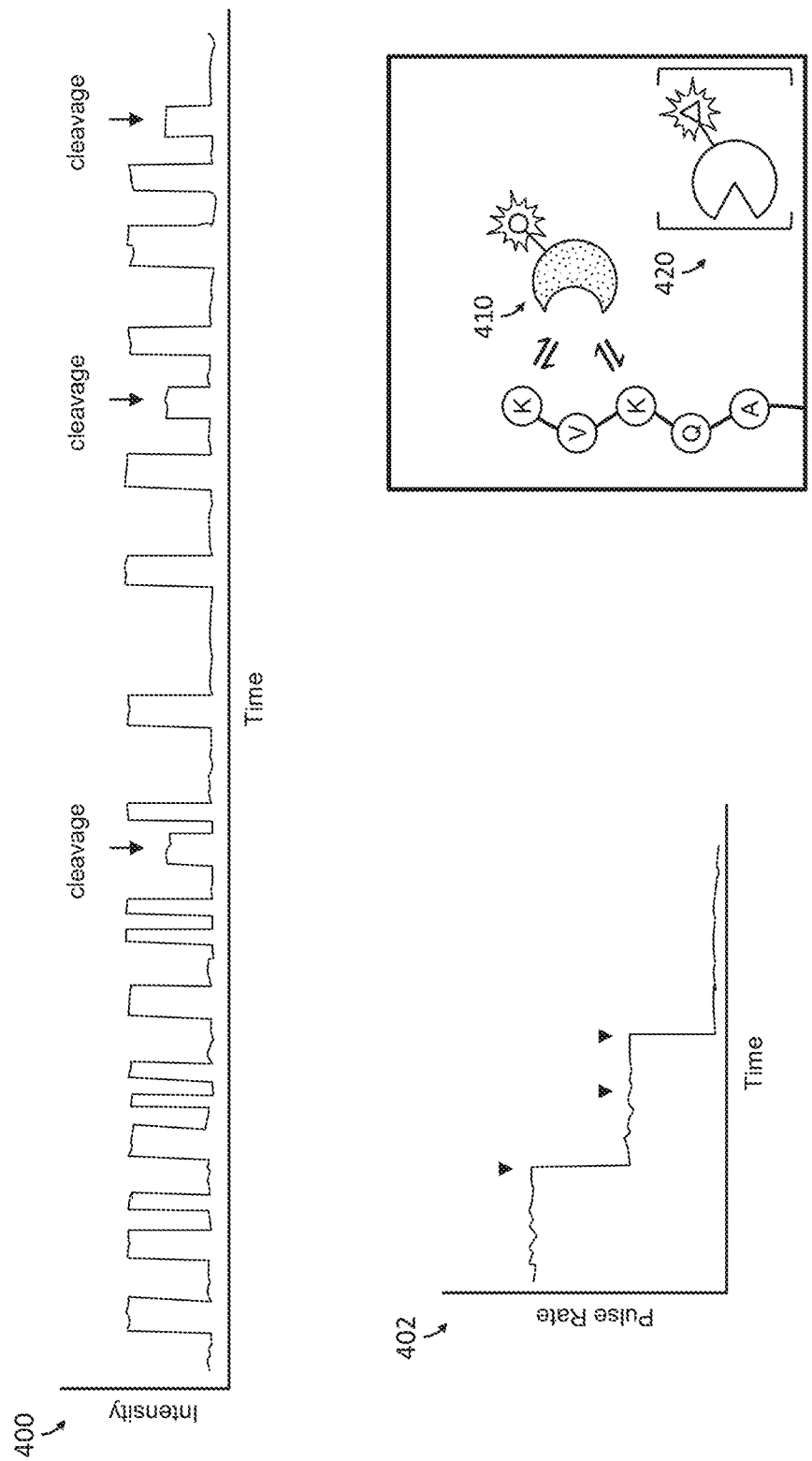

FIG. 4 shows an example of polypeptide sequencing in real-time by evaluating binding interactions of terminal and internal amino acids with labeled affinity reagents and a labeled non-specific exopeptidase.

Figure 5A:
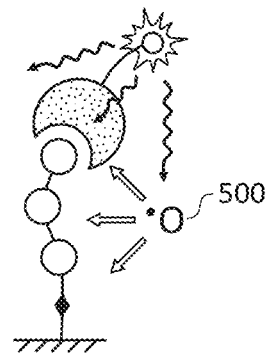
Figure 5B:
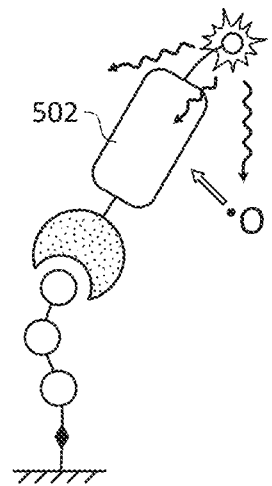
Figure 5C:
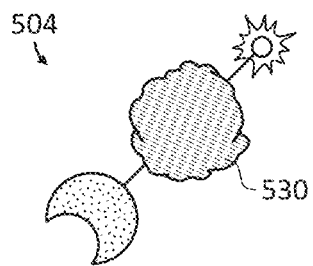
Figure 5C:
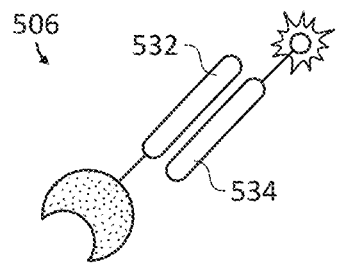
Figure 5C:
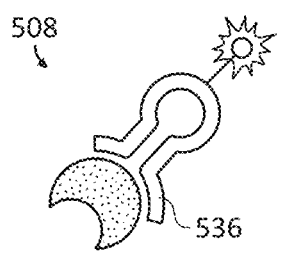
Figure 5C:
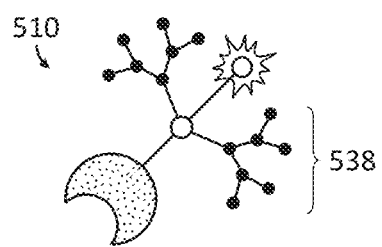
Figure 5D:
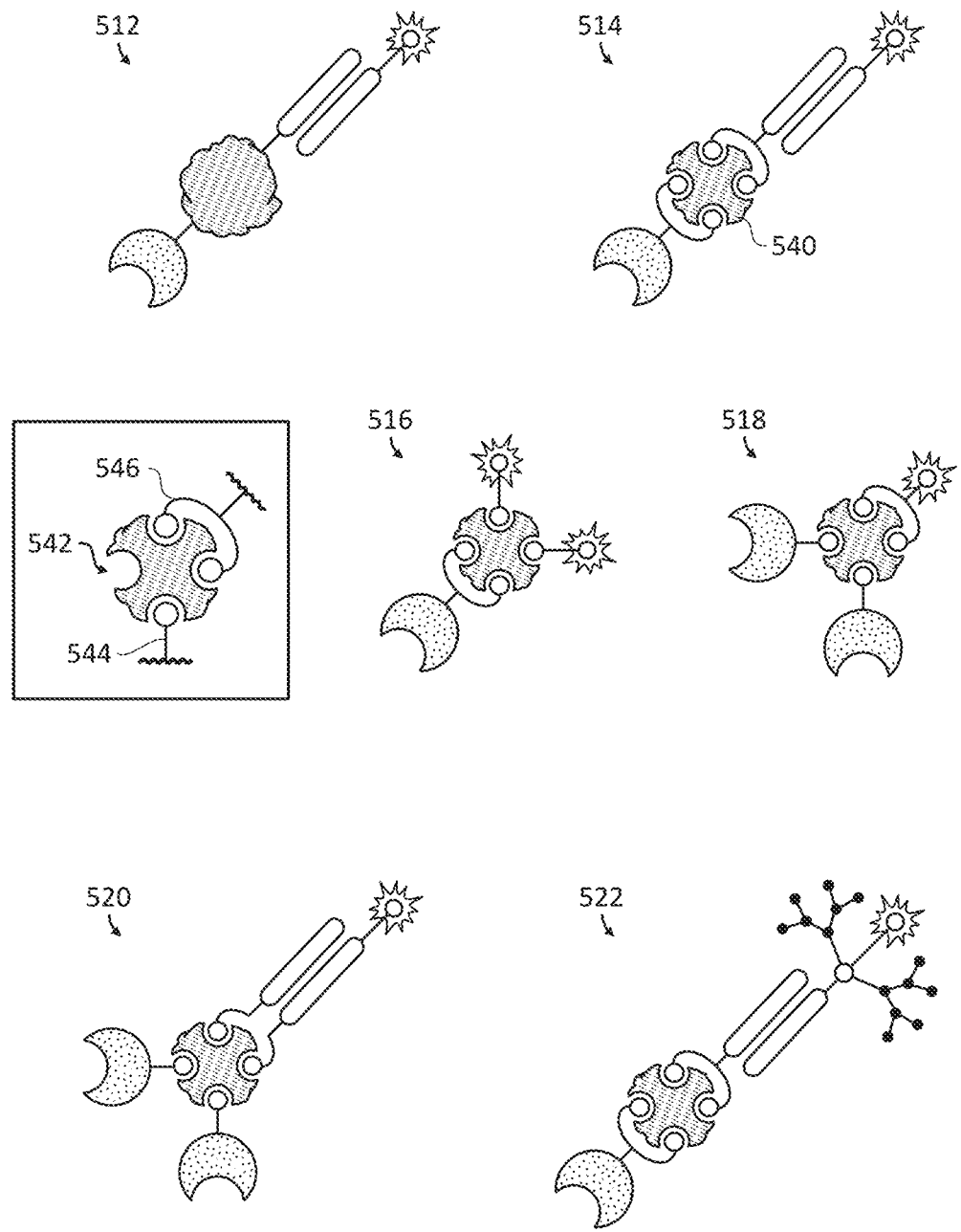
Figure 5E:
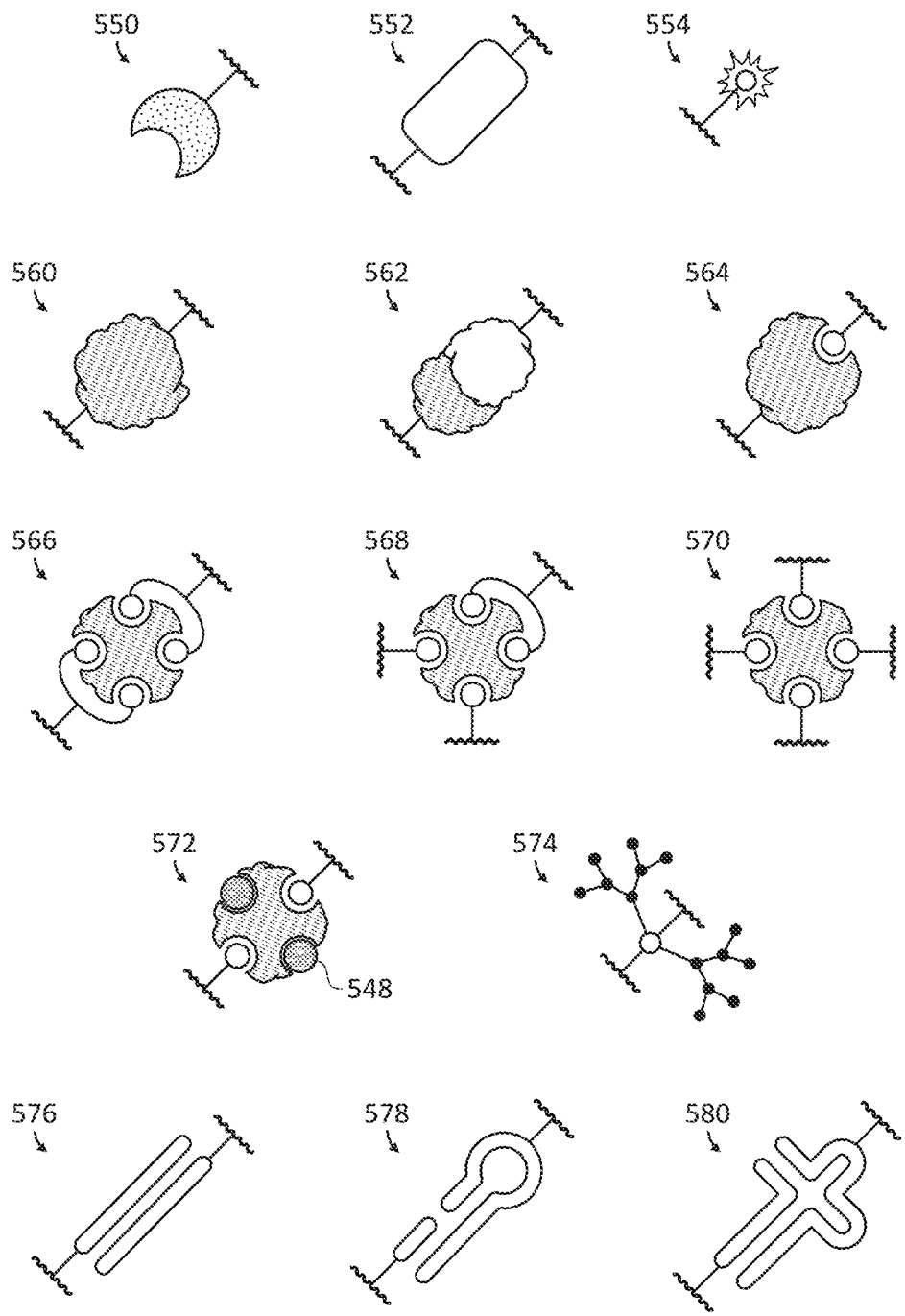

FIGS. 5A-5E show non-limiting examples of affinity reagents labeled through a shielding element. FIG. 5A illustrates single-molecule peptide sequencing with an affinity reagent labeled through a conventional covalent linkage. FIG. 5B illustrates single-molecule peptide sequencing with an affinity reagent comprising a shielding element. FIGS. 5C-5E illustrate various examples of shielding elements in accordance with the application.

Figure 6:
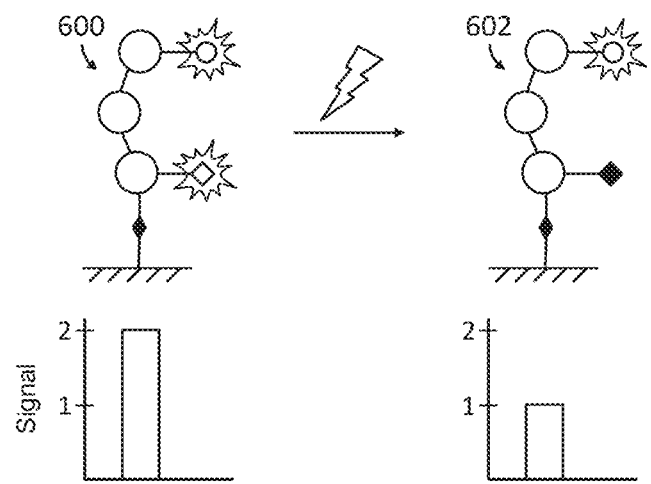

FIG. 6 shows an example of identifying polypeptides based on a unique combination of amino acids detected in a labeled polypeptide.

Figure 7:
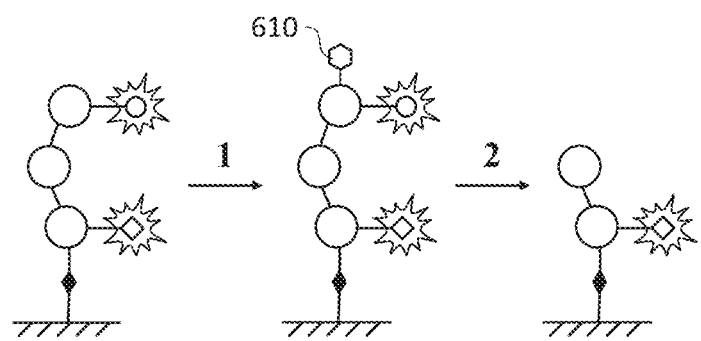

FIG. 7 shows an example of polypeptide sequencing by detecting luminescence of a labeled polypeptide which is subjected to repeated cycles of terminal amino acid modification and cleavage.

Figure 8C:
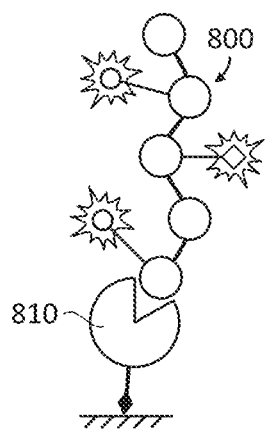
Figure 8C:
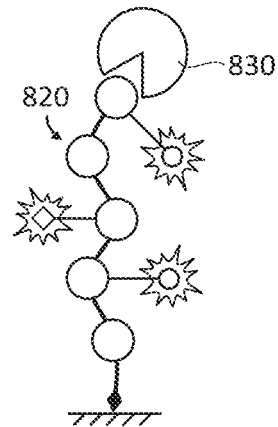
Figure 8C:
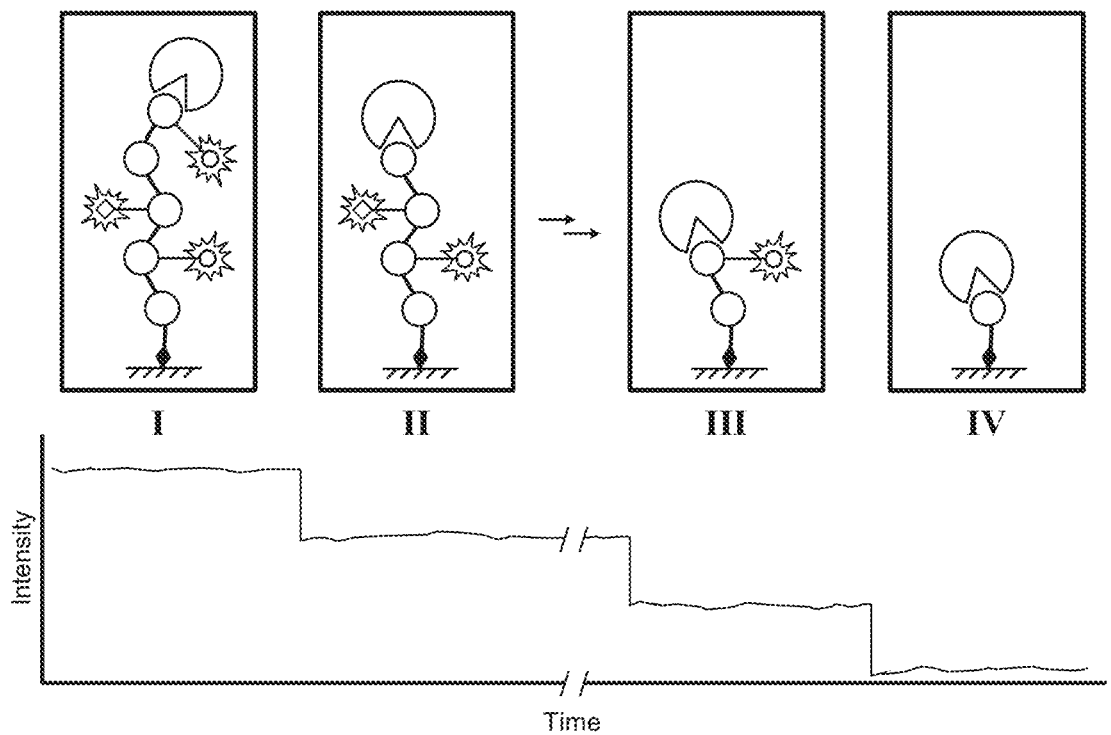

FIGS. 8A-8C show an example of polypeptide sequencing by processive enzymatic cleavage of a labeled polypeptide. FIG. 8A shows an example of sequencing by processive enzymatic cleavage of a labeled polypeptide by an immobilized terminal peptidase. FIG. 8B shows an example of sequencing by processive enzymatic cleavage of an immobilized labeled polypeptide by a terminal peptidase. FIG. 8C schematically illustrates an example of a real-time sequencing process performed in accordance with FIG. 8B.

Figure 9:
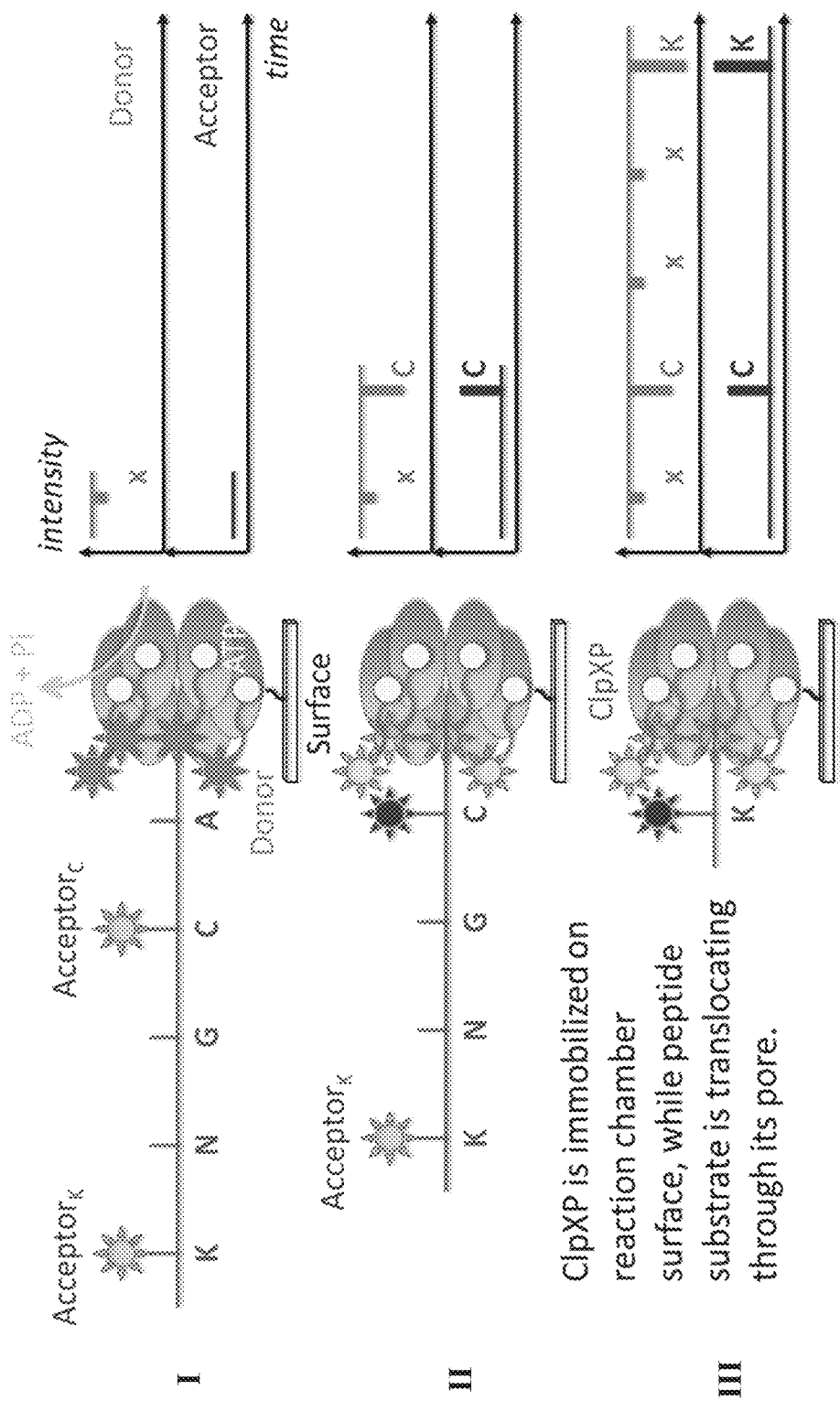

FIG. 9 schematically illustrates an example of sequencing by cofactor-based FRET using an immobilized ATP-dependent protease, donor-labeled ATP, and acceptor-labeled amino acids of a polypeptide substrate.

Figure 10A:
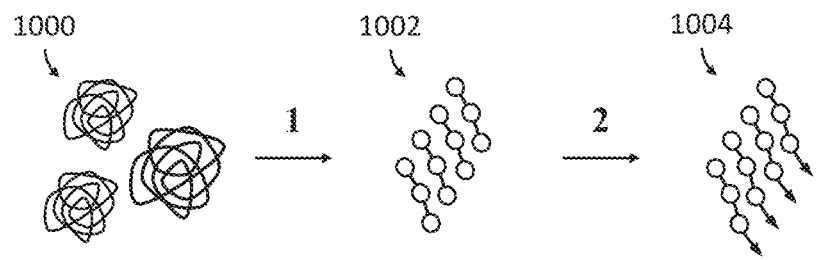
Figure 10B:
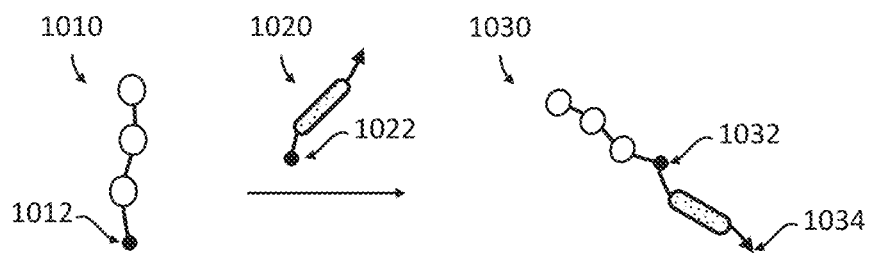
Figure 10C:
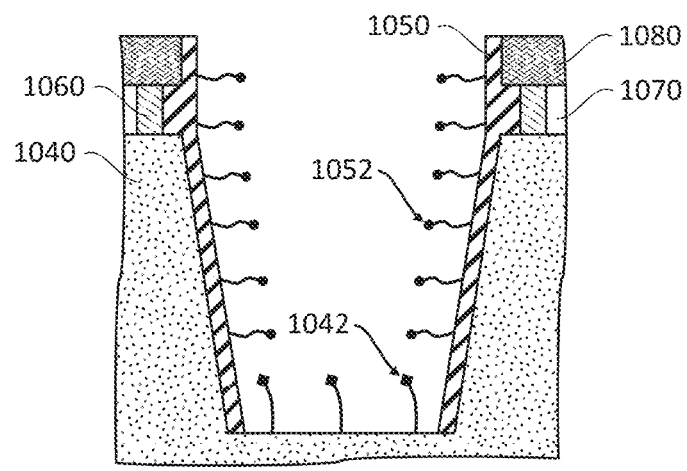

FIGS. 10A-10C show various examples of preparing samples and sample well surfaces for analysis of polypeptides and proteins in accordance with the application. FIG. 10A generically depicts an example process of preparing terminally modified polypeptides from a protein sample. FIG. 10B generically depicts an example process of conjugating a solubilizing linker to a polypeptide. FIG. 10C shows an example schematic of a sample well having modified surfaces which may be used to promote single molecule immobilization to a bottom surface.

Figure 11:
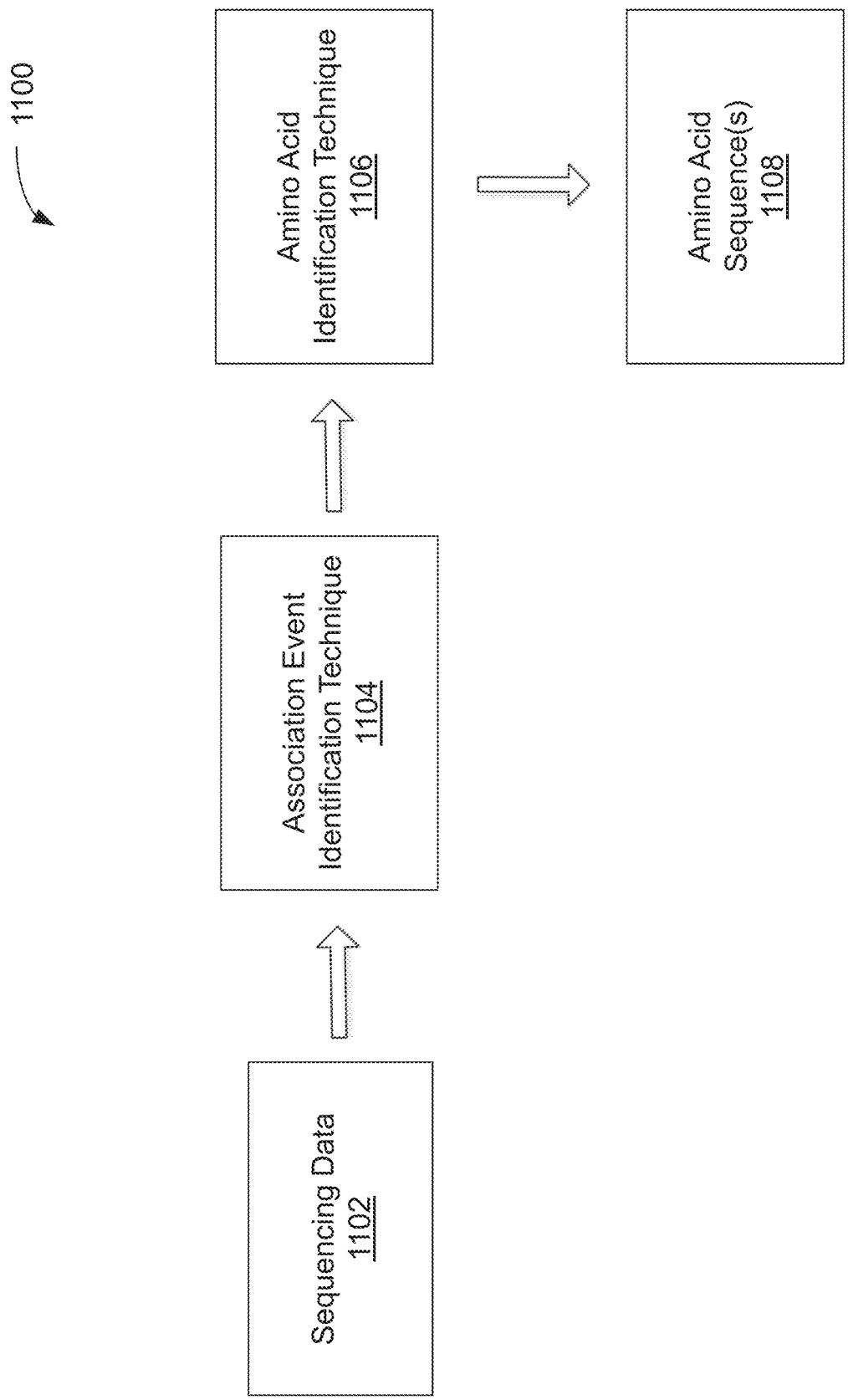

FIG. 11 is a diagram of an illustrative sequence data processing pipeline for analyzing data obtained during a polypeptide degradation process, in accordance with some embodiments of the technology described herein.

Figure 12:
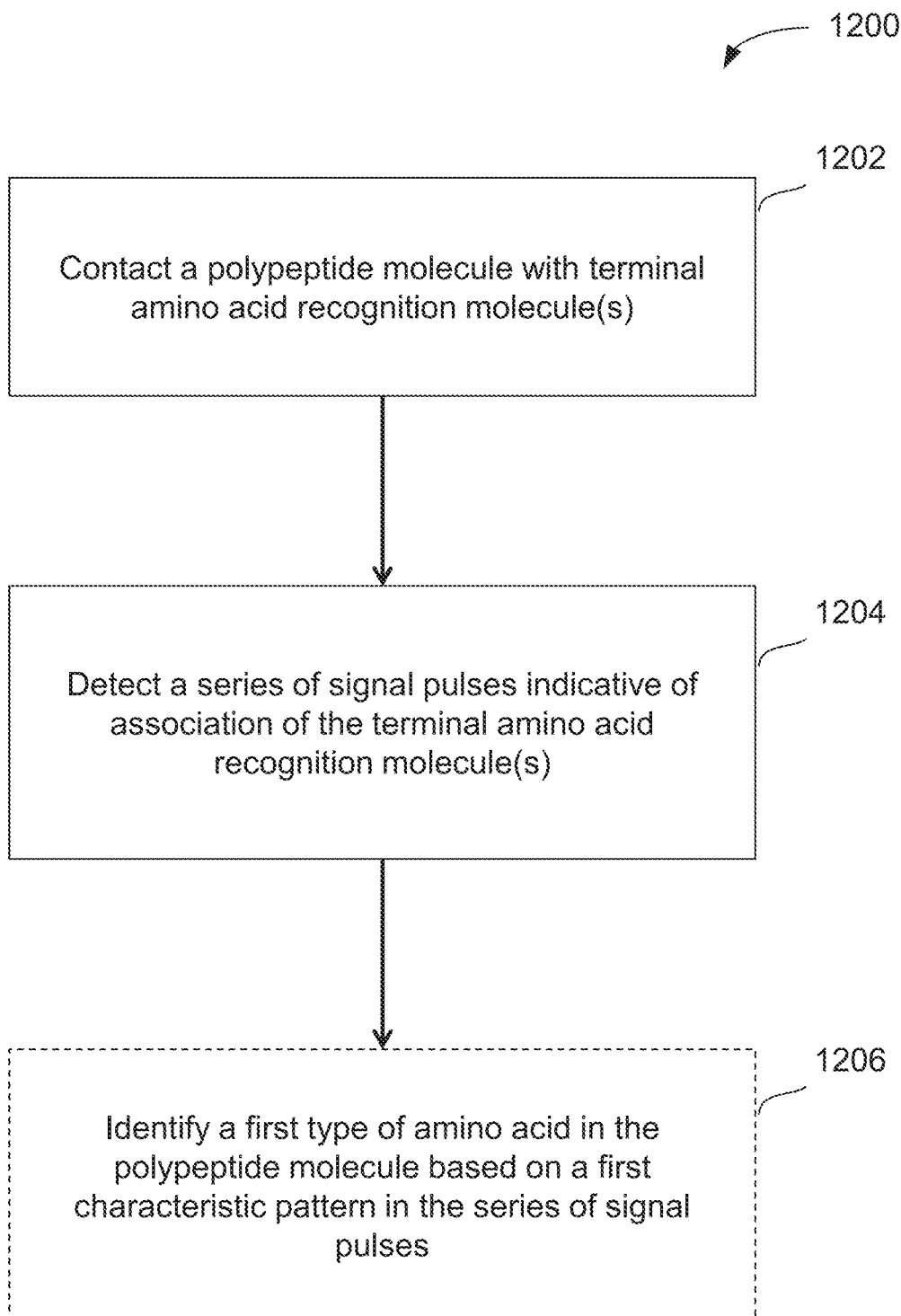

FIG. 12 is a flow chart of an illustrative process for determining an amino acid sequence of a polypeptide molecule, in accordance with some embodiments of the technology described herein.

Figure 13:
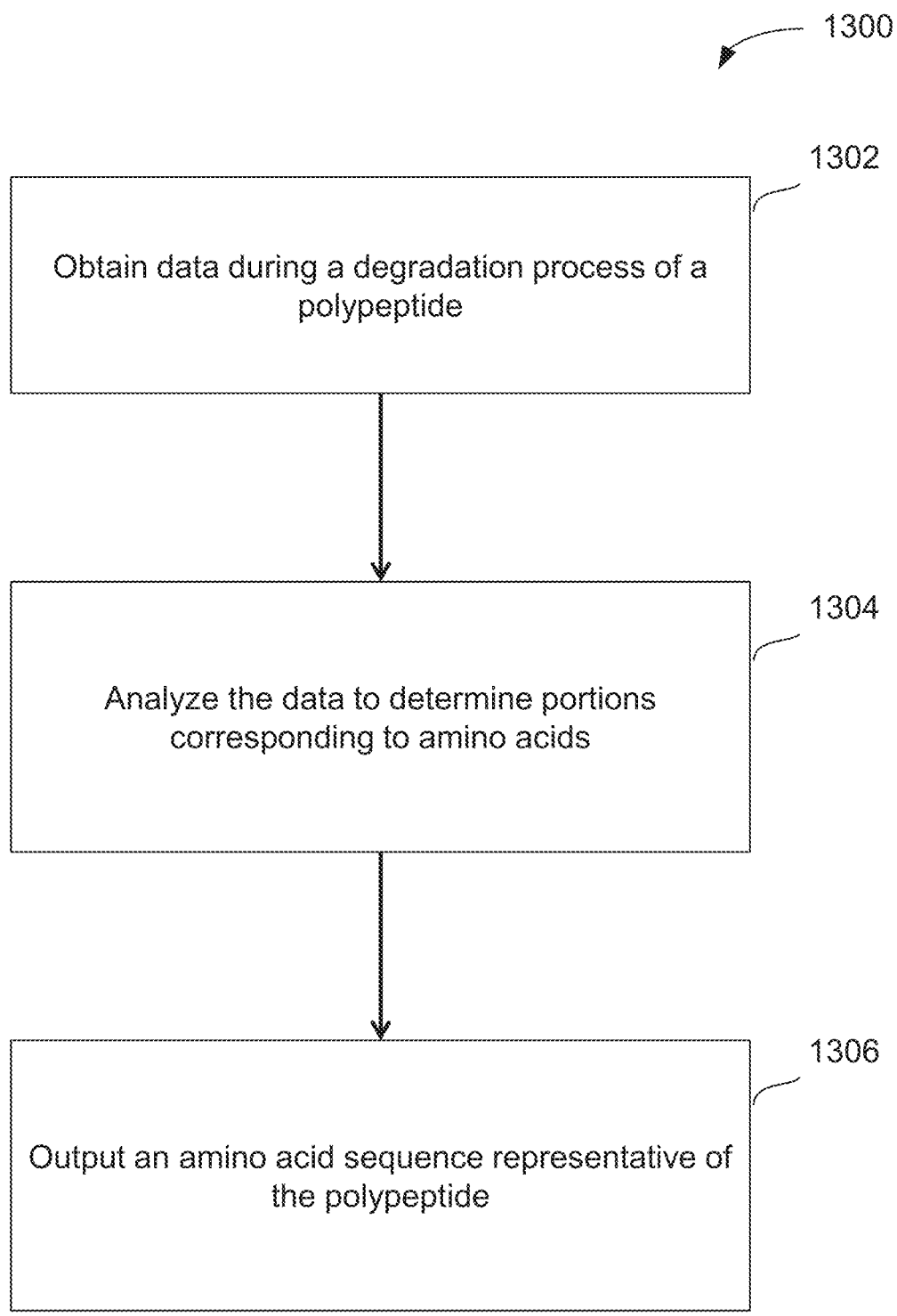

FIG. 13 is a flow chart of an illustrative process for determining an amino acid sequence representative of a polypeptide, in accordance with some embodiments of the technology described herein.

Figure 14:
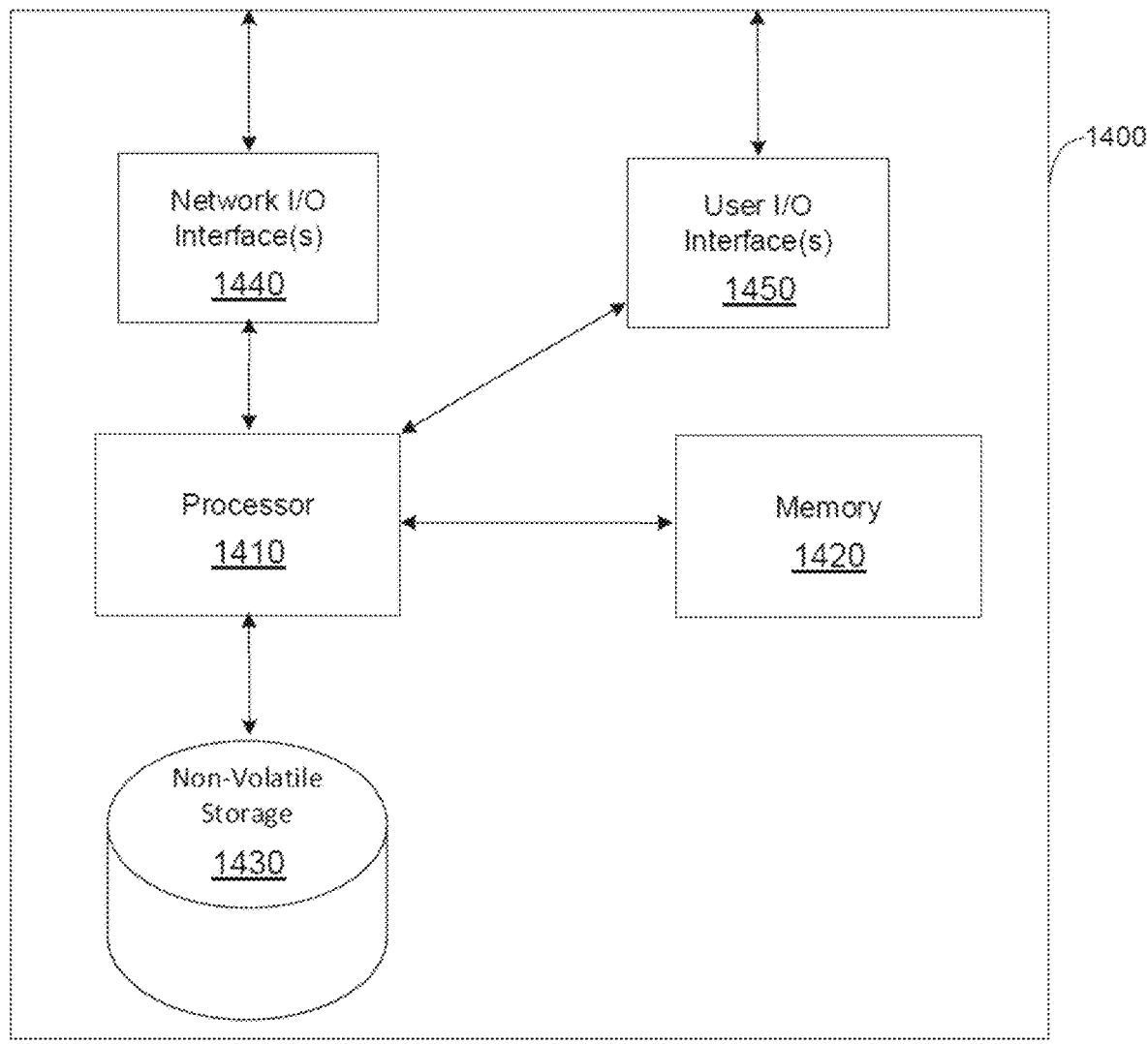

FIG. 14 is a block diagram of an illustrative computer system that may be used in implementing some embodiments of the technology described herein.

Figure 15A:
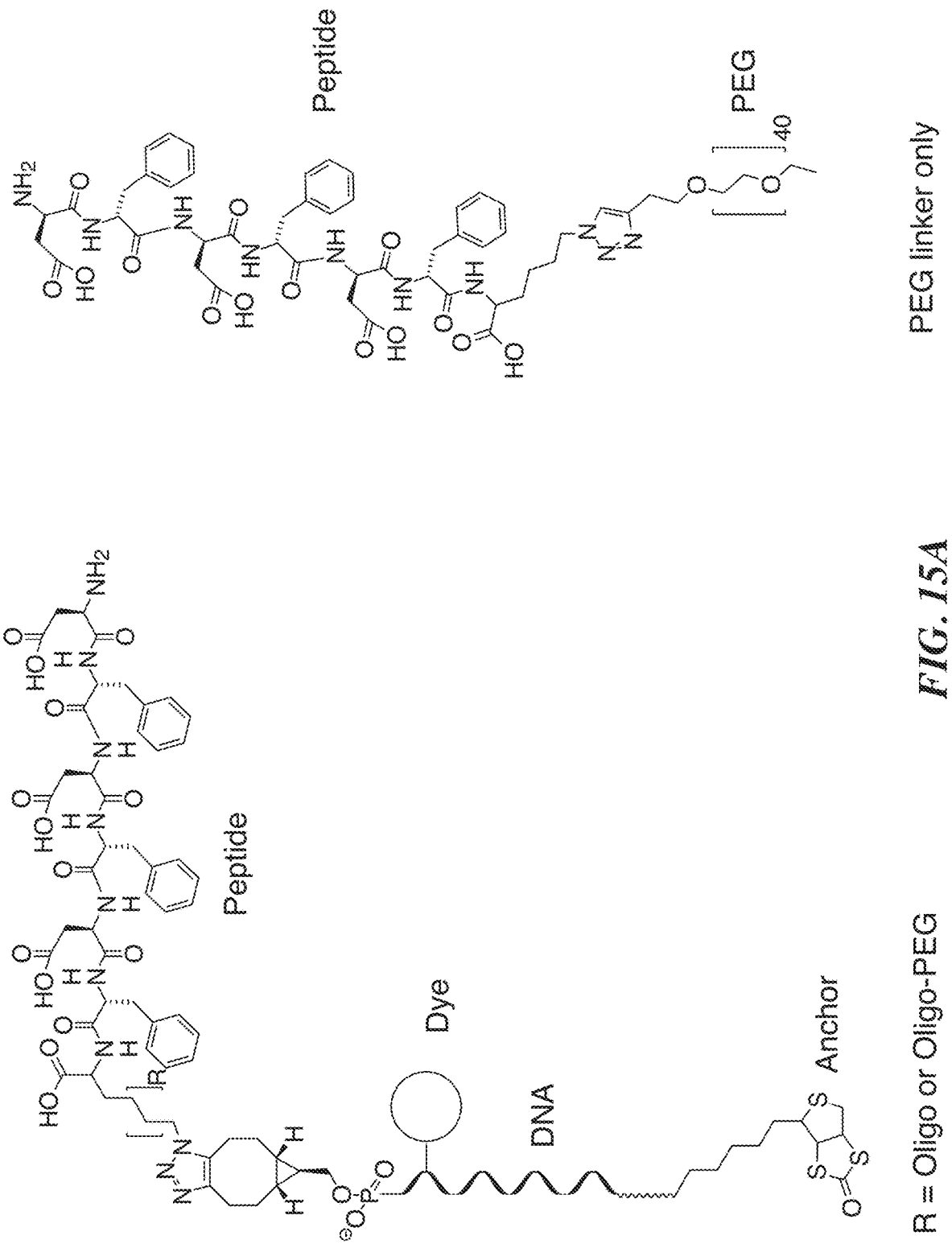
Figure 15B:
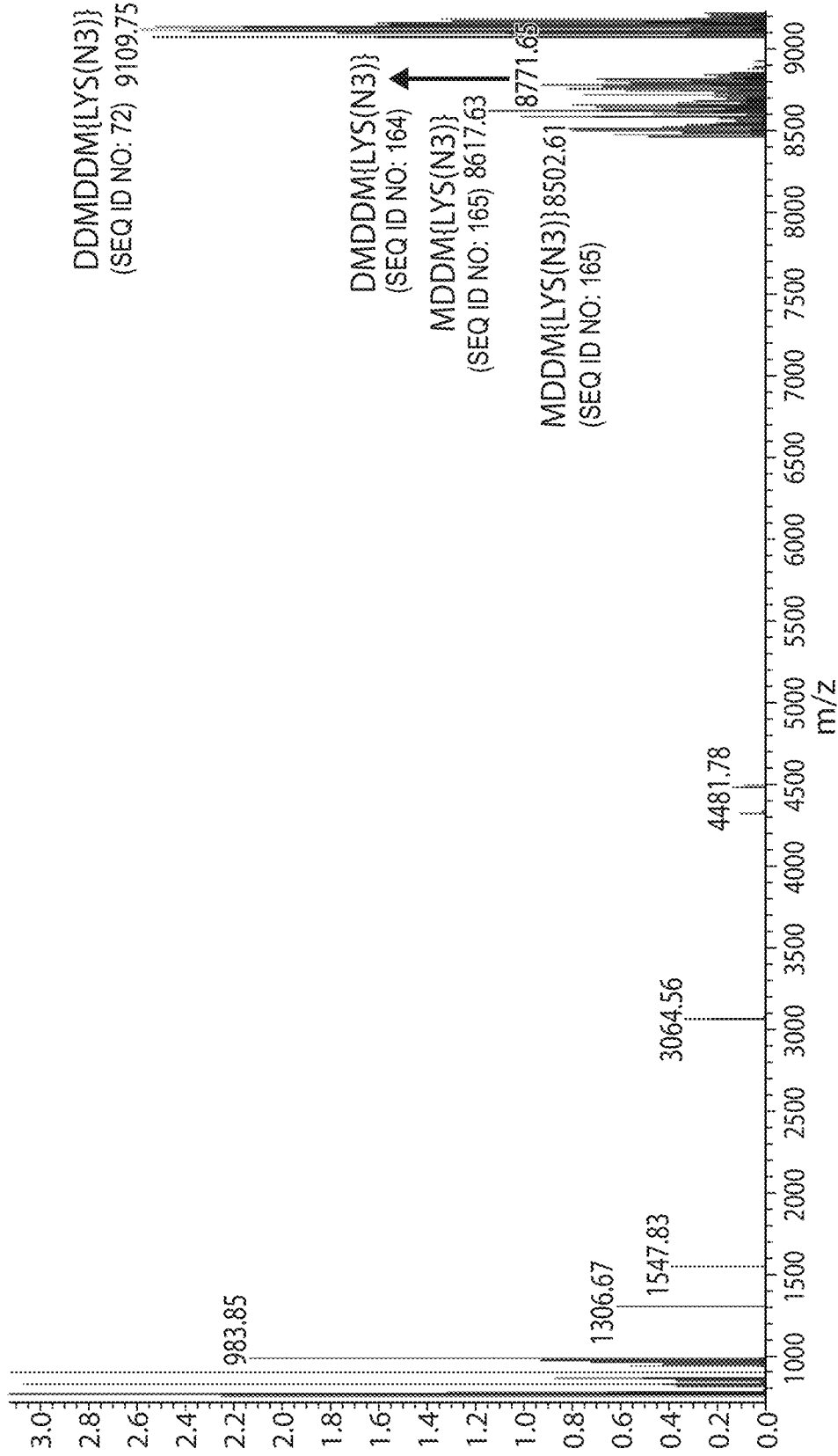
Figure 15C:
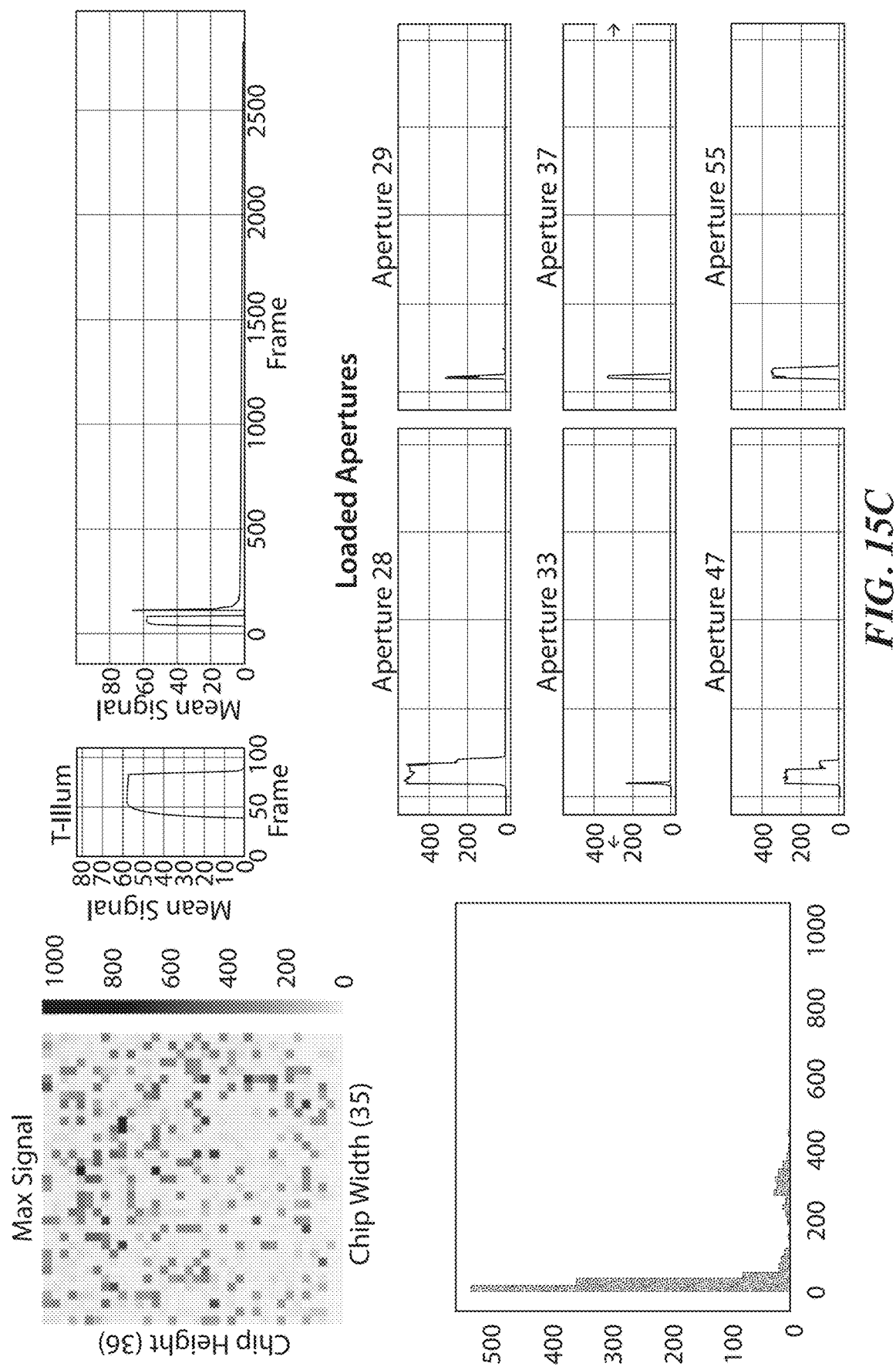

FIGS. 15A-15C show experimental data for select peptide-linker conjugates prepared and evaluated for enhanced solubility provided by different solubilizing linkers. FIG. 15A shows example structures of peptide-linker conjugates that were synthesized and evaluated. FIG. 15B shows results from LCMS which demonstrate peptide cleavage at the N-terminus. FIG. 15C shows results from a loading experiment.

Figure 16:
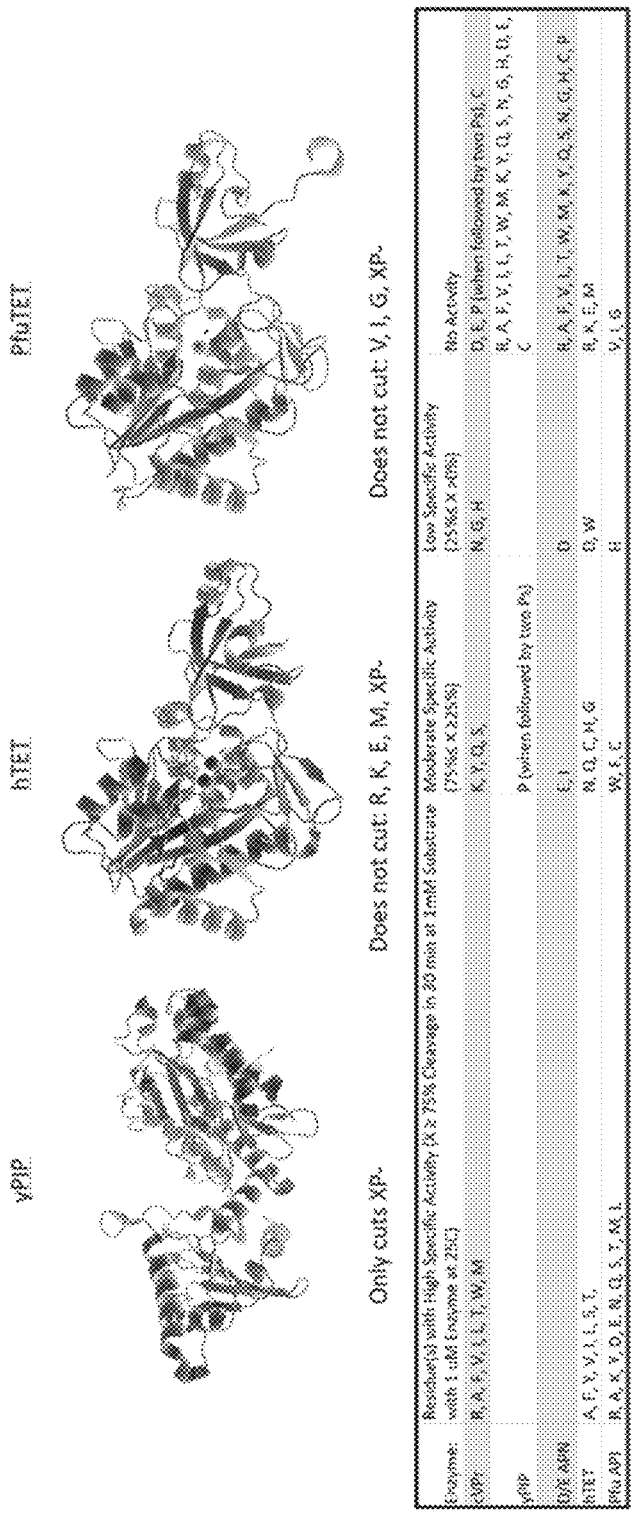

FIG. 16 shows a summary of amino acid cleavage activities for select exopeptidases based on experimental results.

Figure 17A:
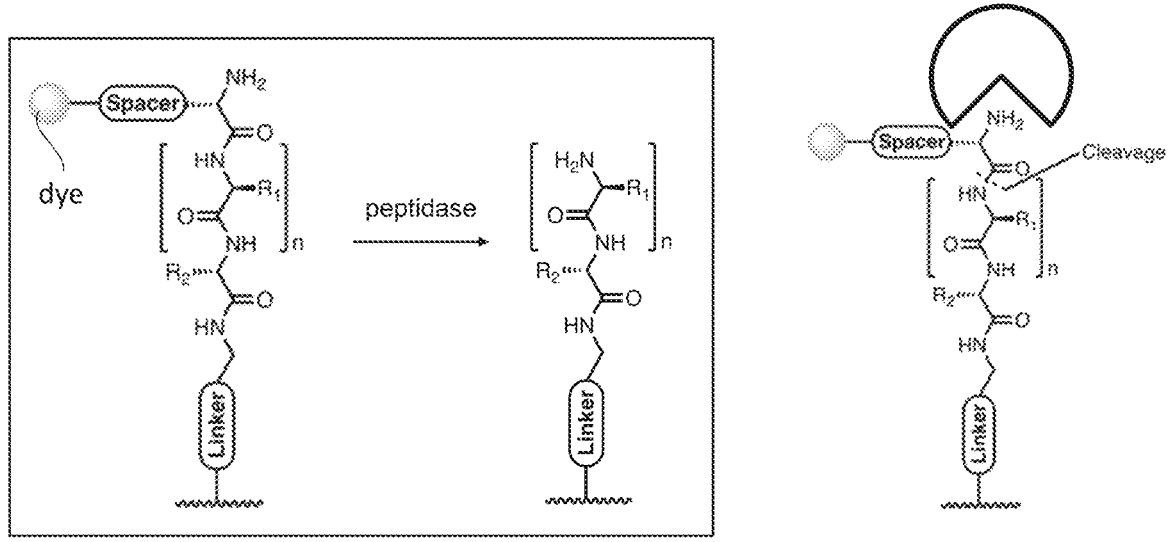
Figure 17A:
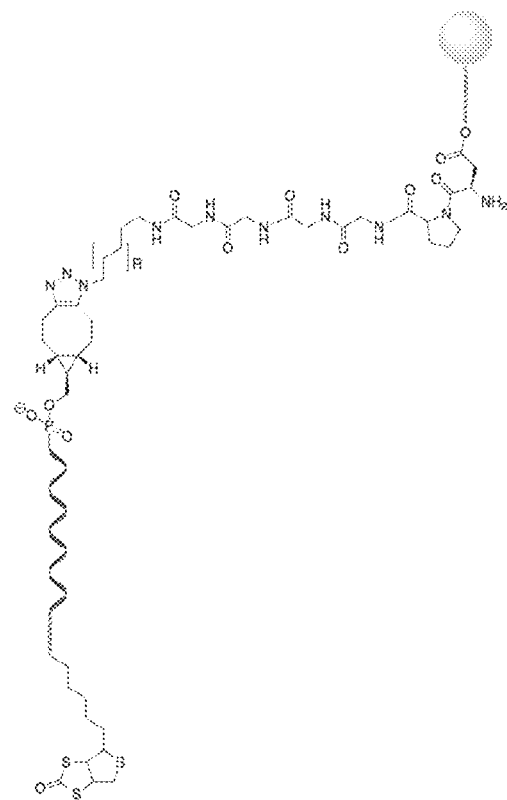
Figure 17B:
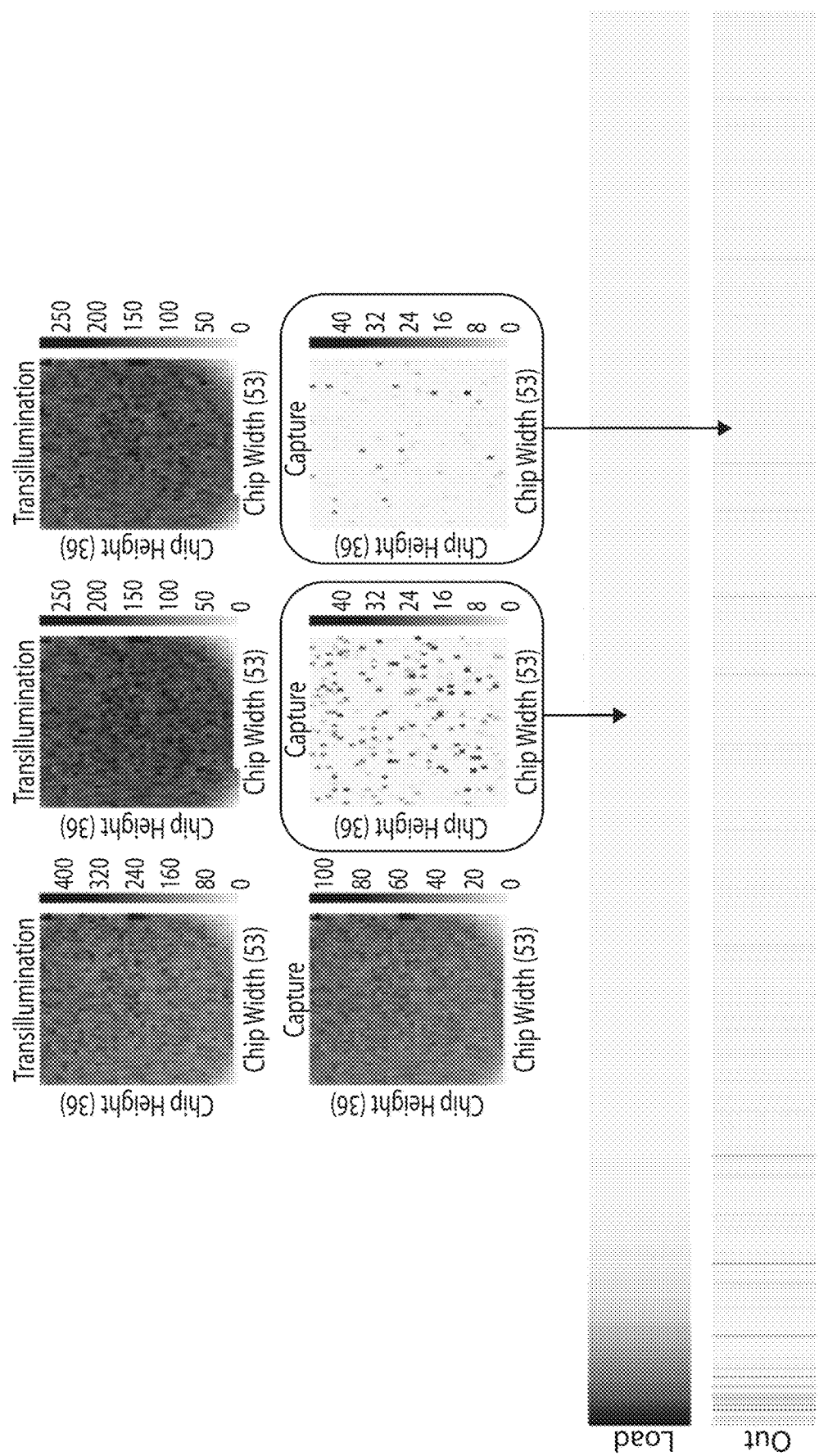
Figure 17C:
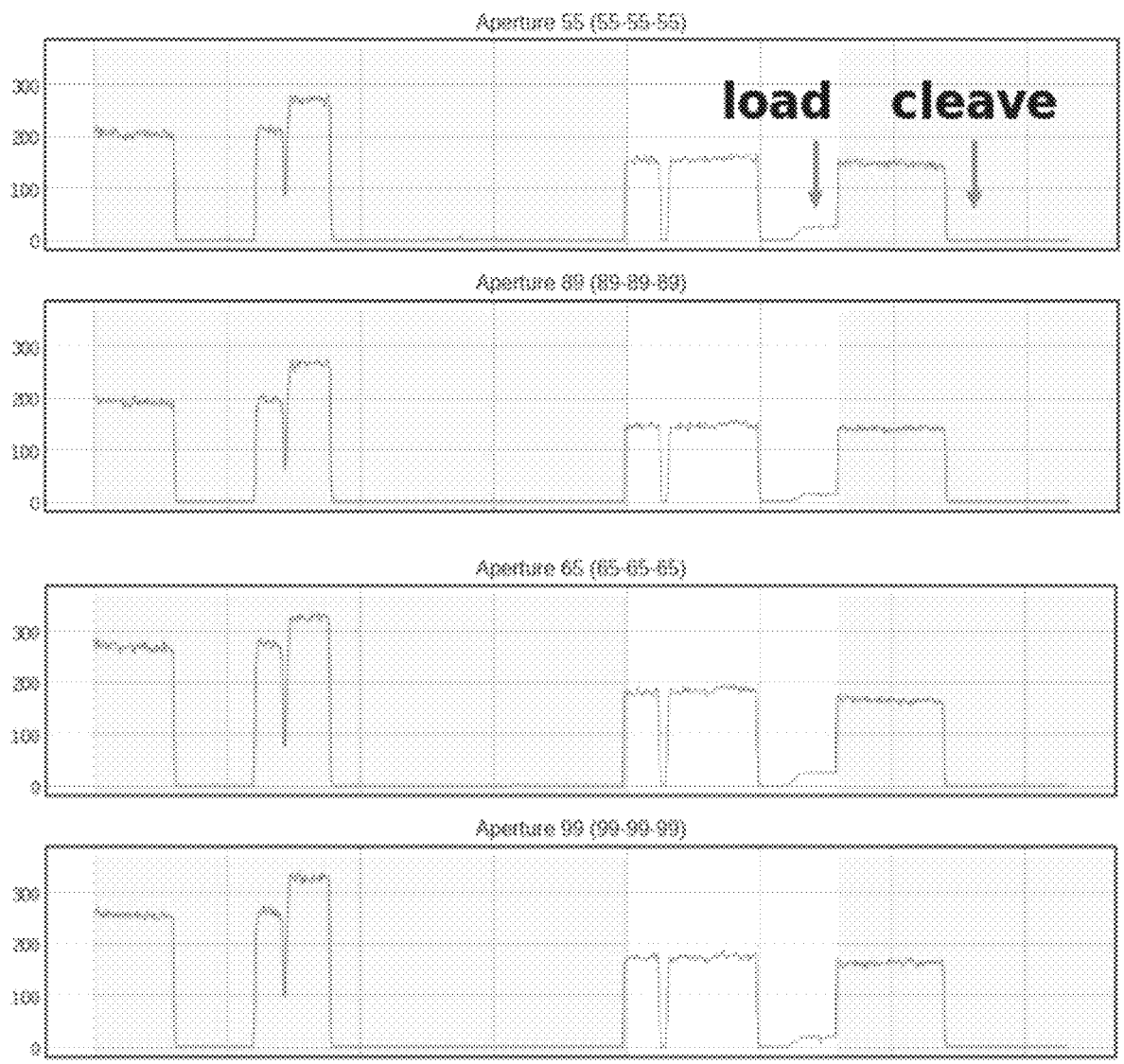

FIGS. 17A-17C show experimental data for a dye/peptide conjugate assay for detecting and cleaving terminal amino acids. FIG. 17A shows example schemes and structures used for performing a dye/peptide conjugate assay. FIG. 17B shows imaging results for peptide-linker conjugate loading into sample wells in an on-chip assay. FIG. 17C shows example signal traces which detected peptide-conjugate loading and terminal amino acid cleavage.

Figure 18A:
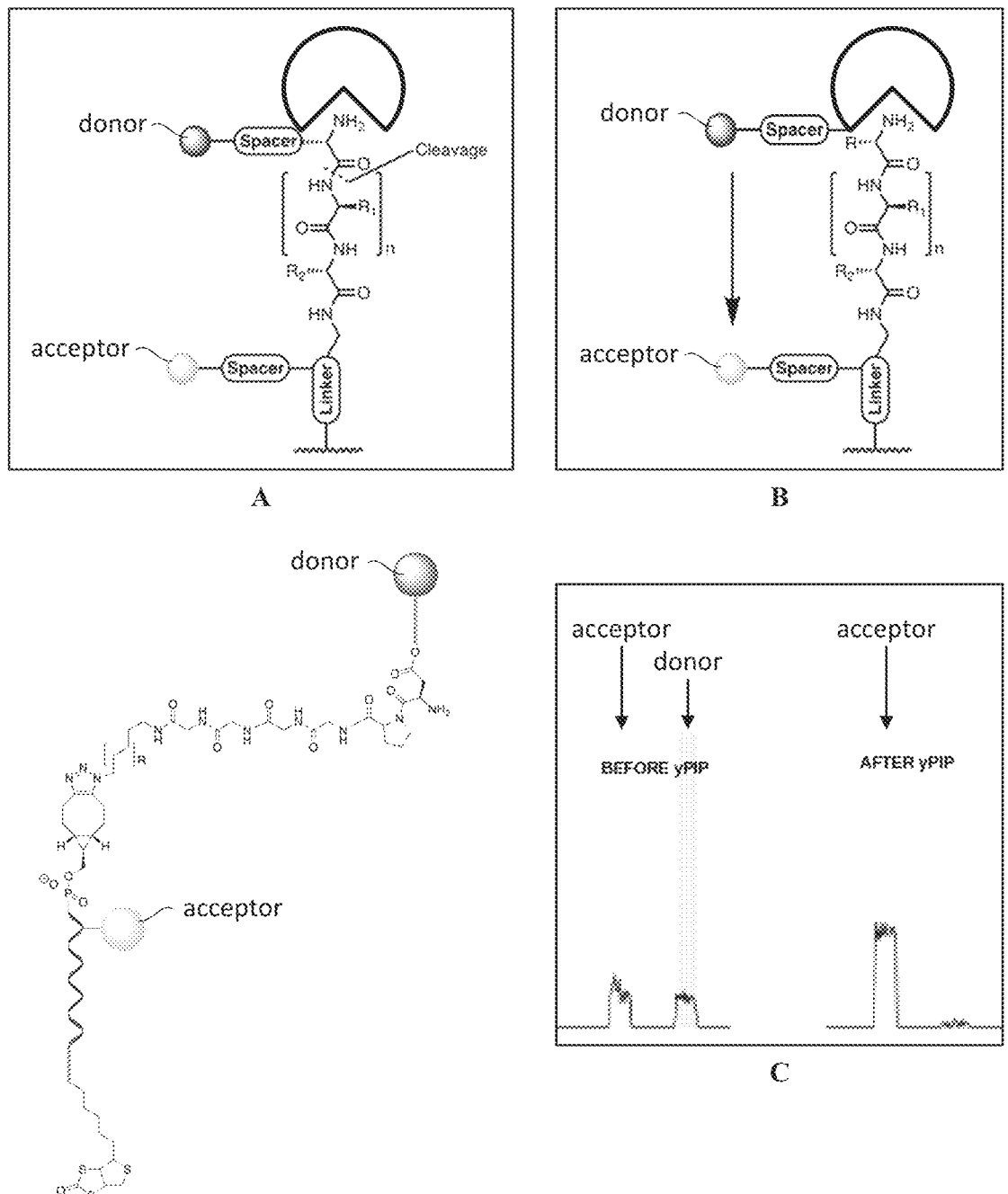
Figure 18B:
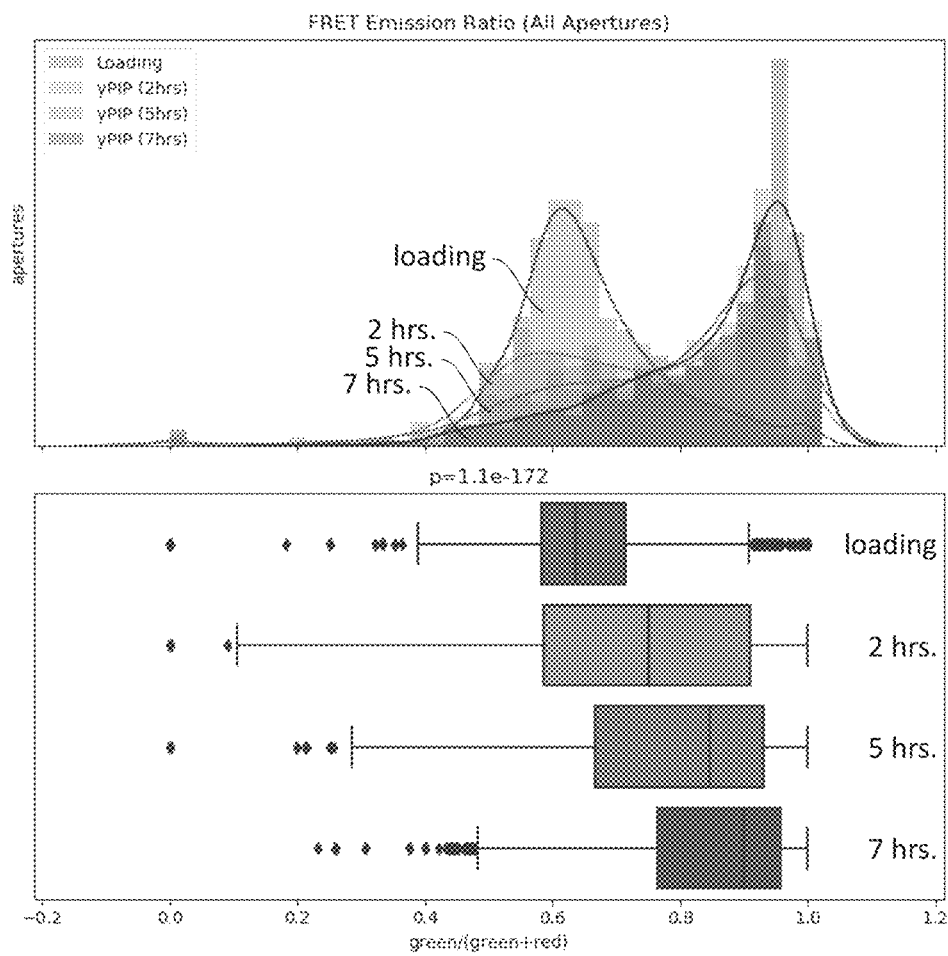
Figure 18C:
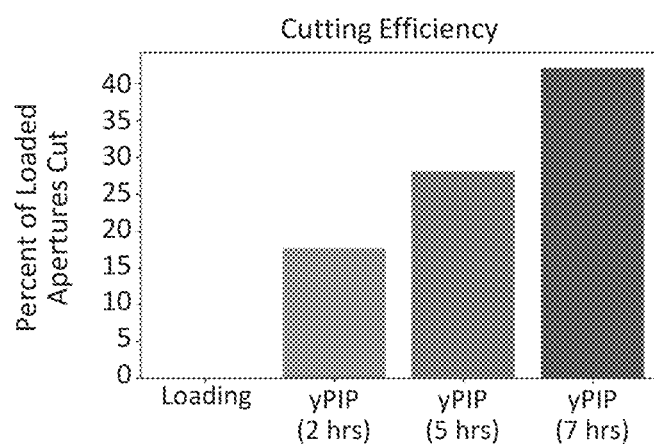

FIGS. 18A-18F show experimental data for a FRET dye/peptide conjugate assay for detecting and cleaving terminal amino acids. FIG. 18A shows example schemes and structures used for performing a FRET dye/peptide conjugate assay. FIG. 18B shows FRET imaging results for different time points. FIG. 18C shows cutting efficiency at the different time points.

Figure 18D:
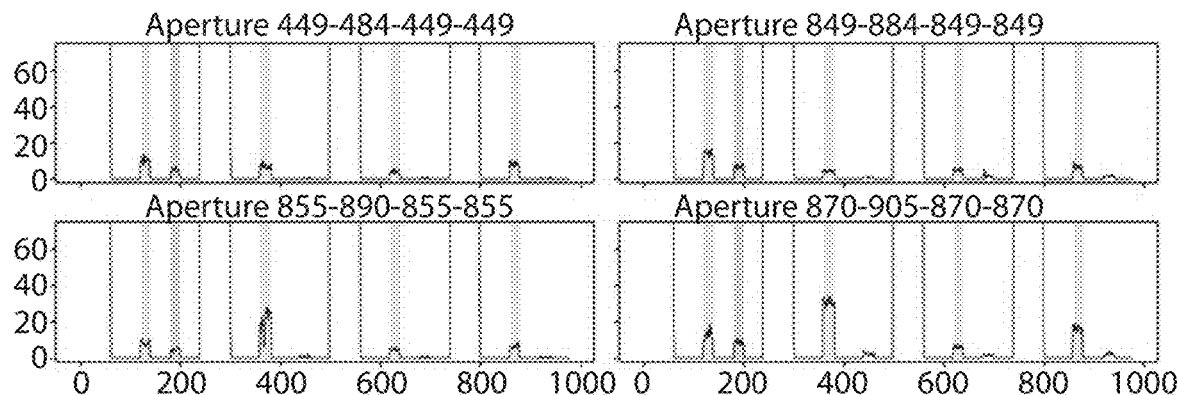
Figure 18D:
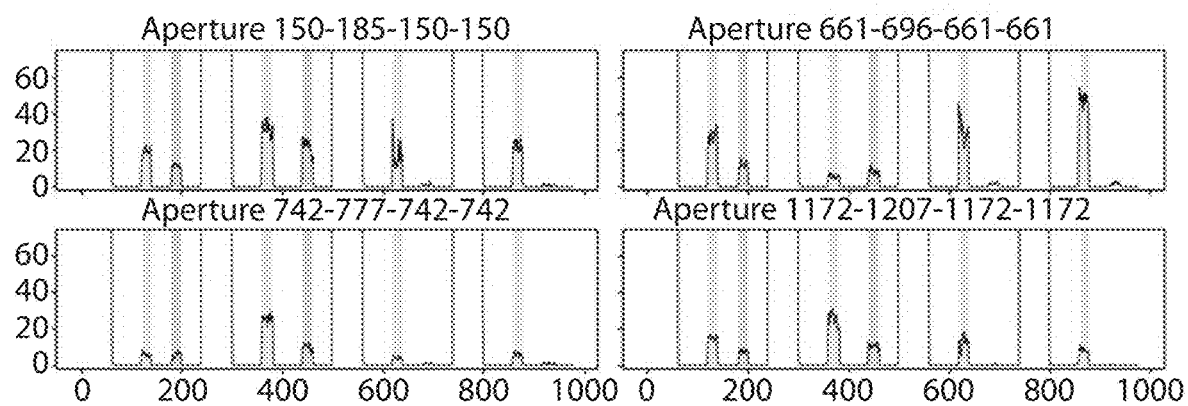
Figure 18D:
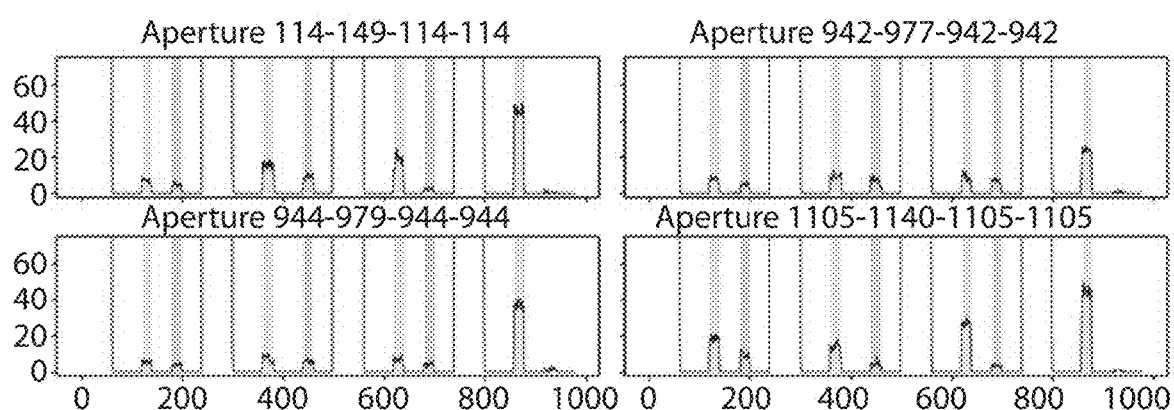
Figure 18E:
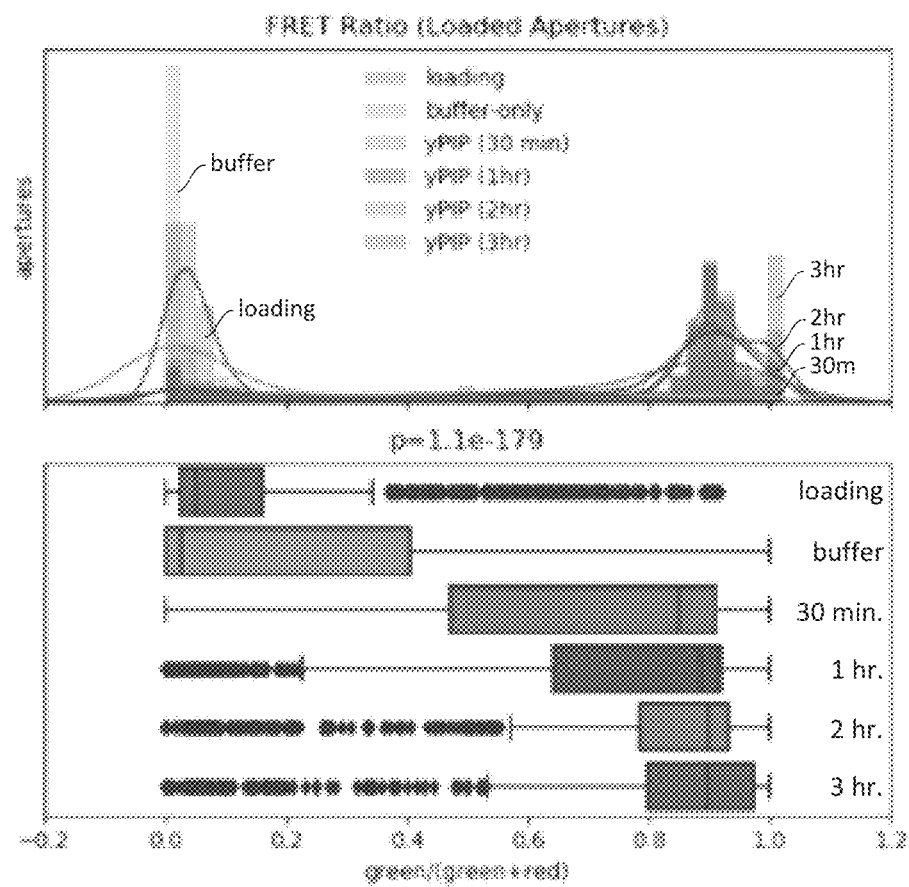
Figure 18F:
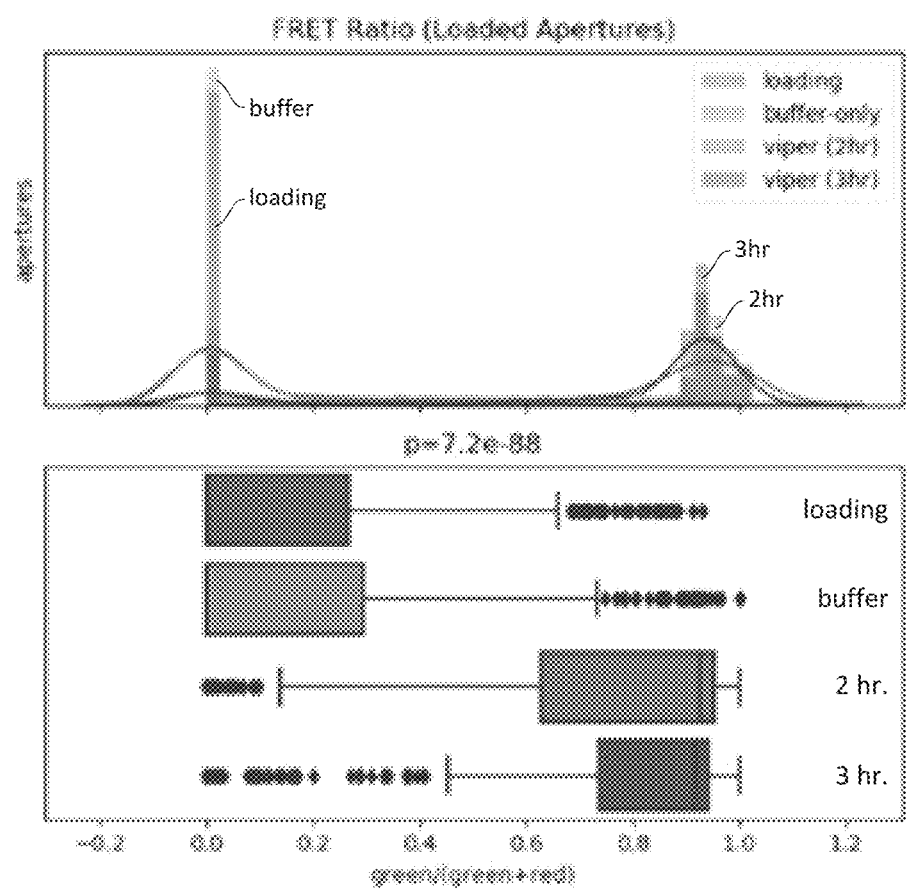

FIG. 18D shows cutting displayed at each of the different time points. FIG. 18E shows additional FRET imaging results for different time points with a proline iminopeptidase from *Yersinia pestis* (yPIP). FIG. 18F shows FRET imaging results for different time points with an aminopeptidase from *Vibrio proteolyticus* (VPr).

Figure 19A:
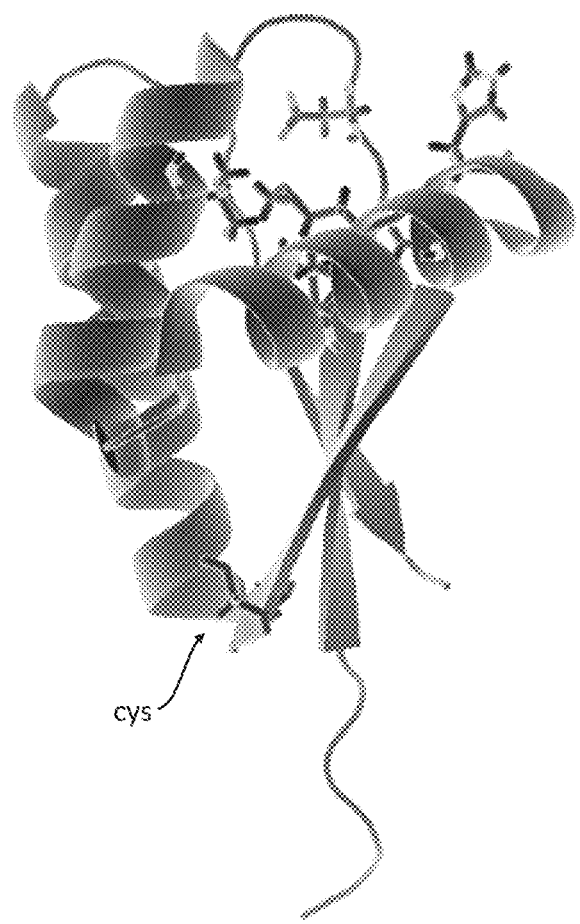
Figure 19B:
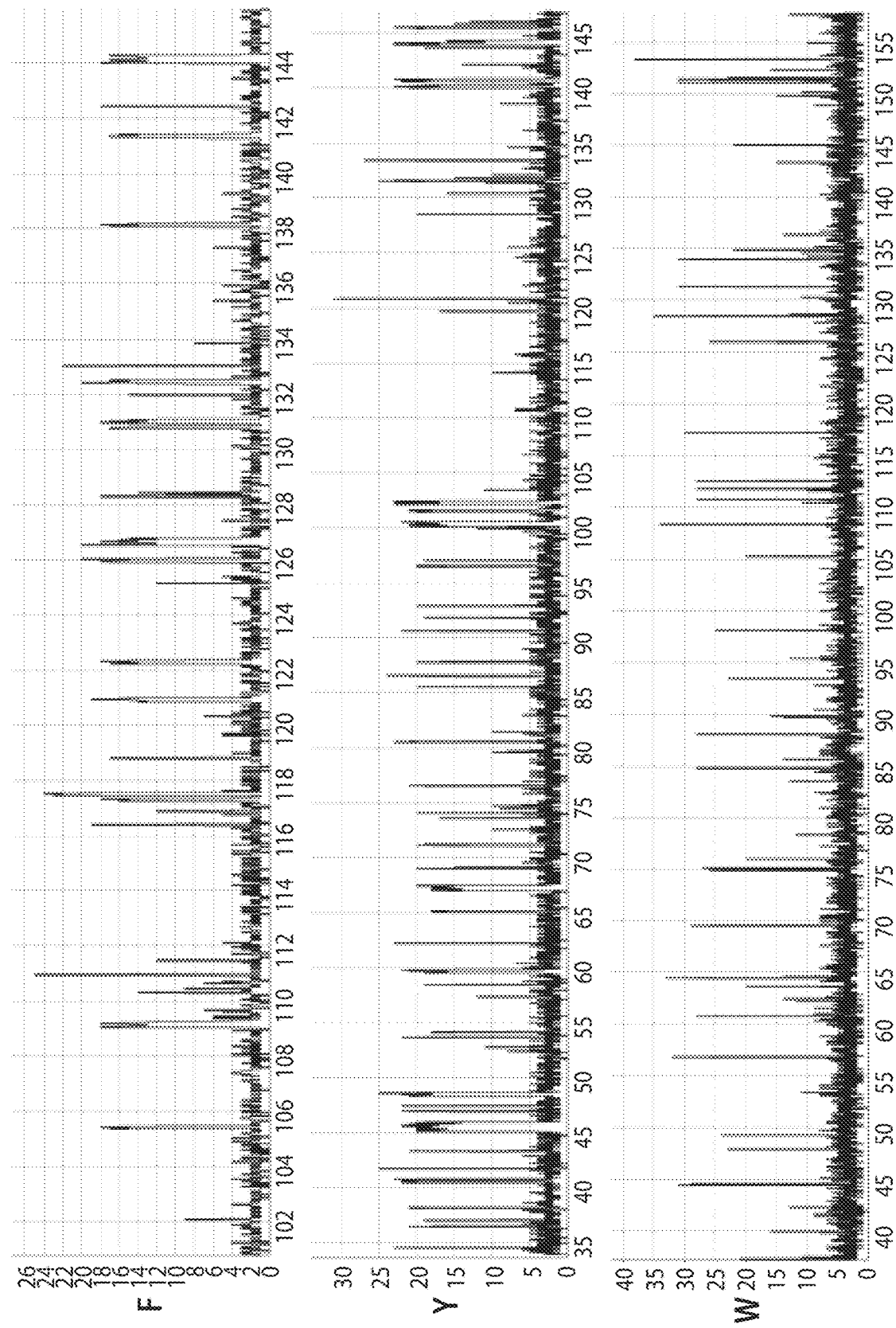
Figure 19C:
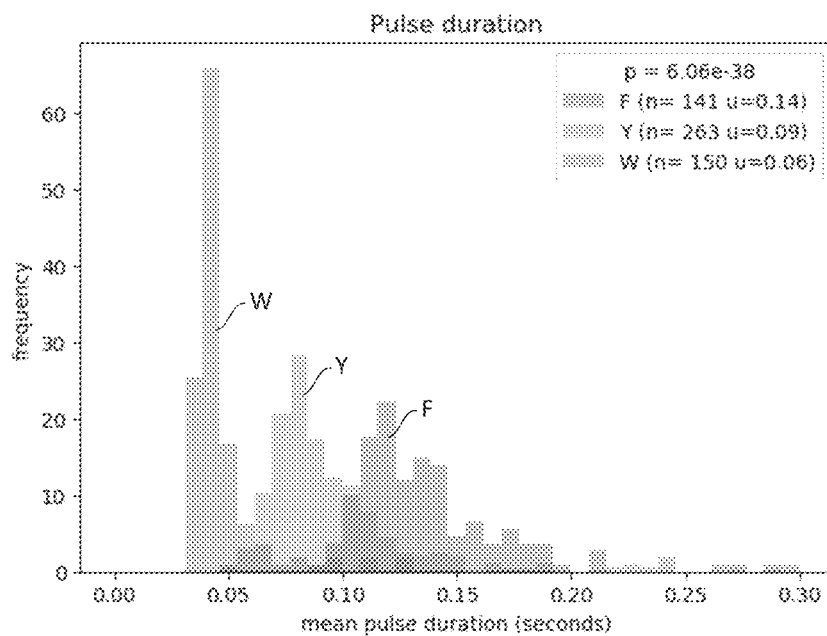
Figure 19D:
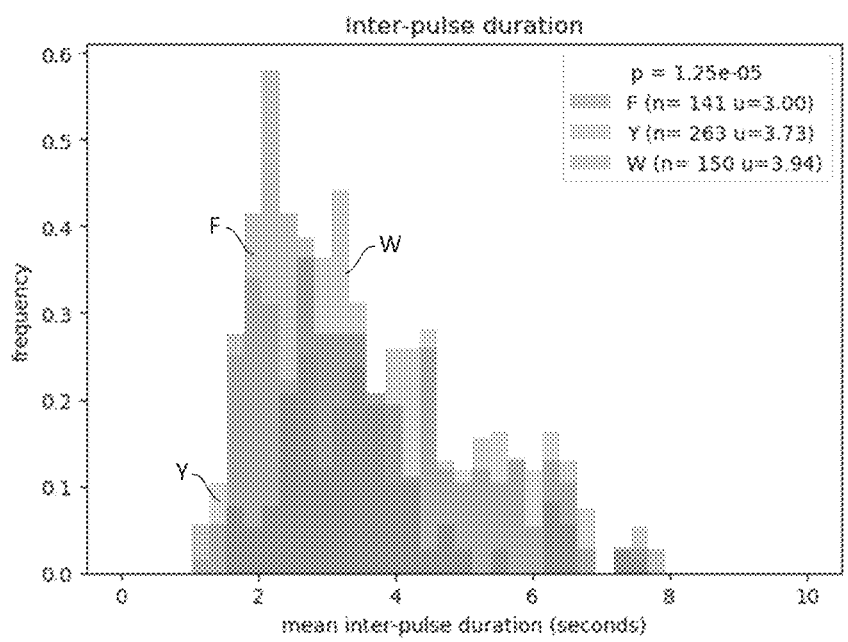
Figure 19E:
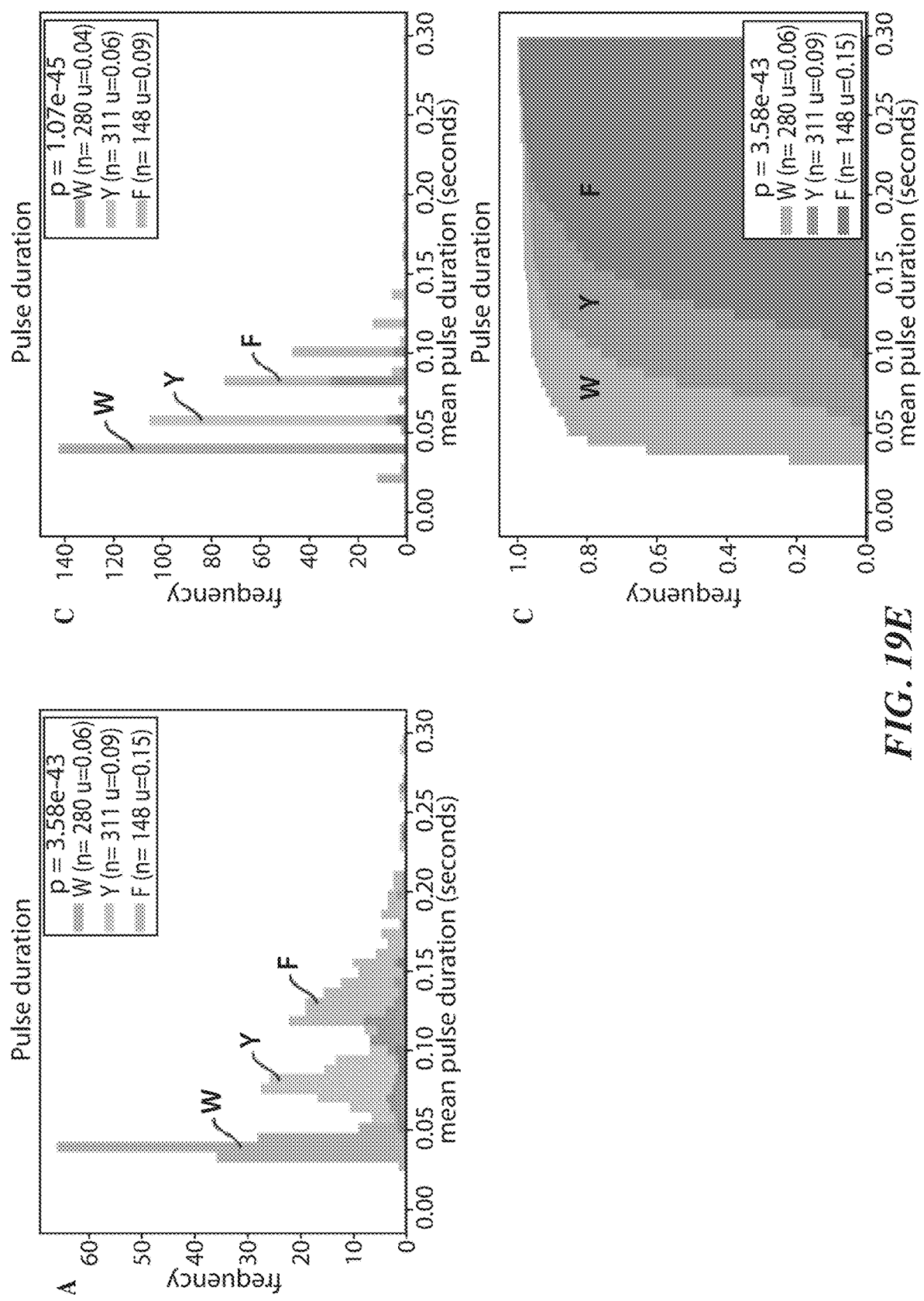
Figure 19F:
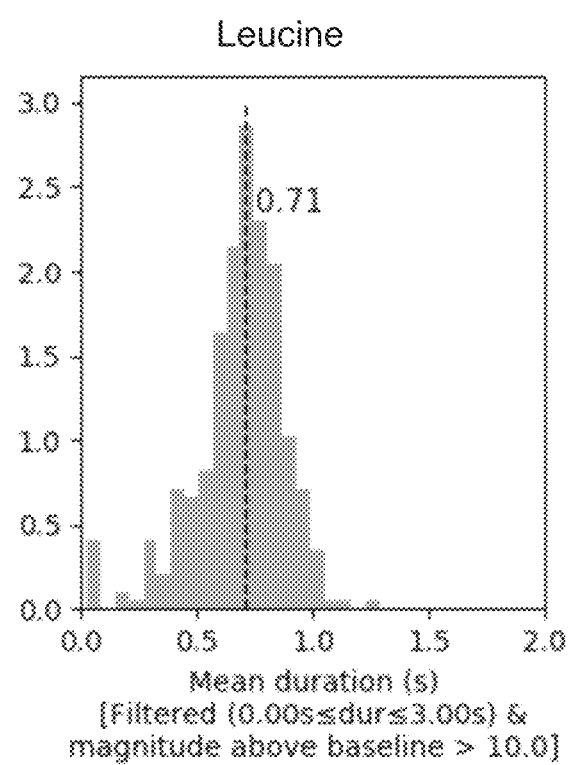
Figure 19G:
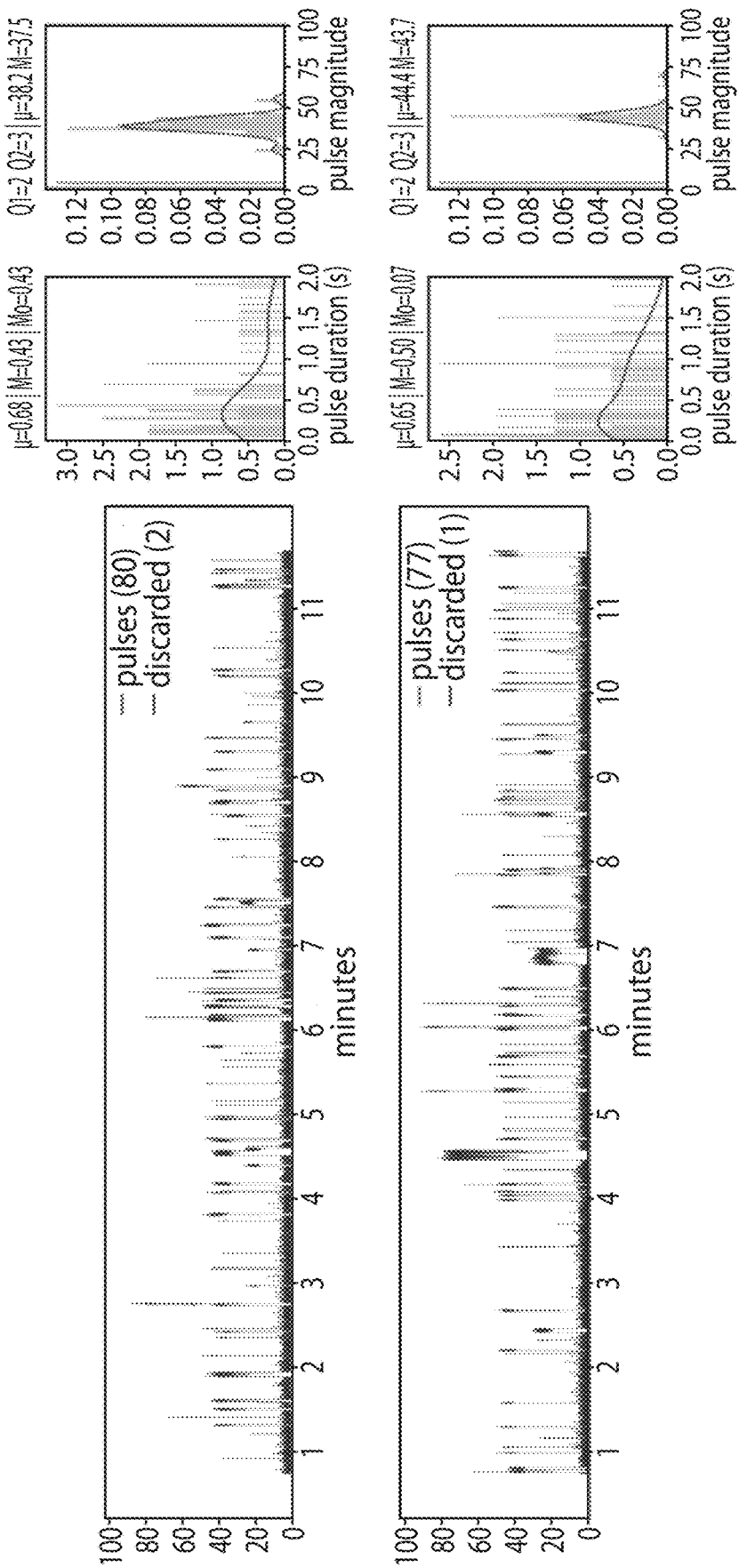
Figure 19H:
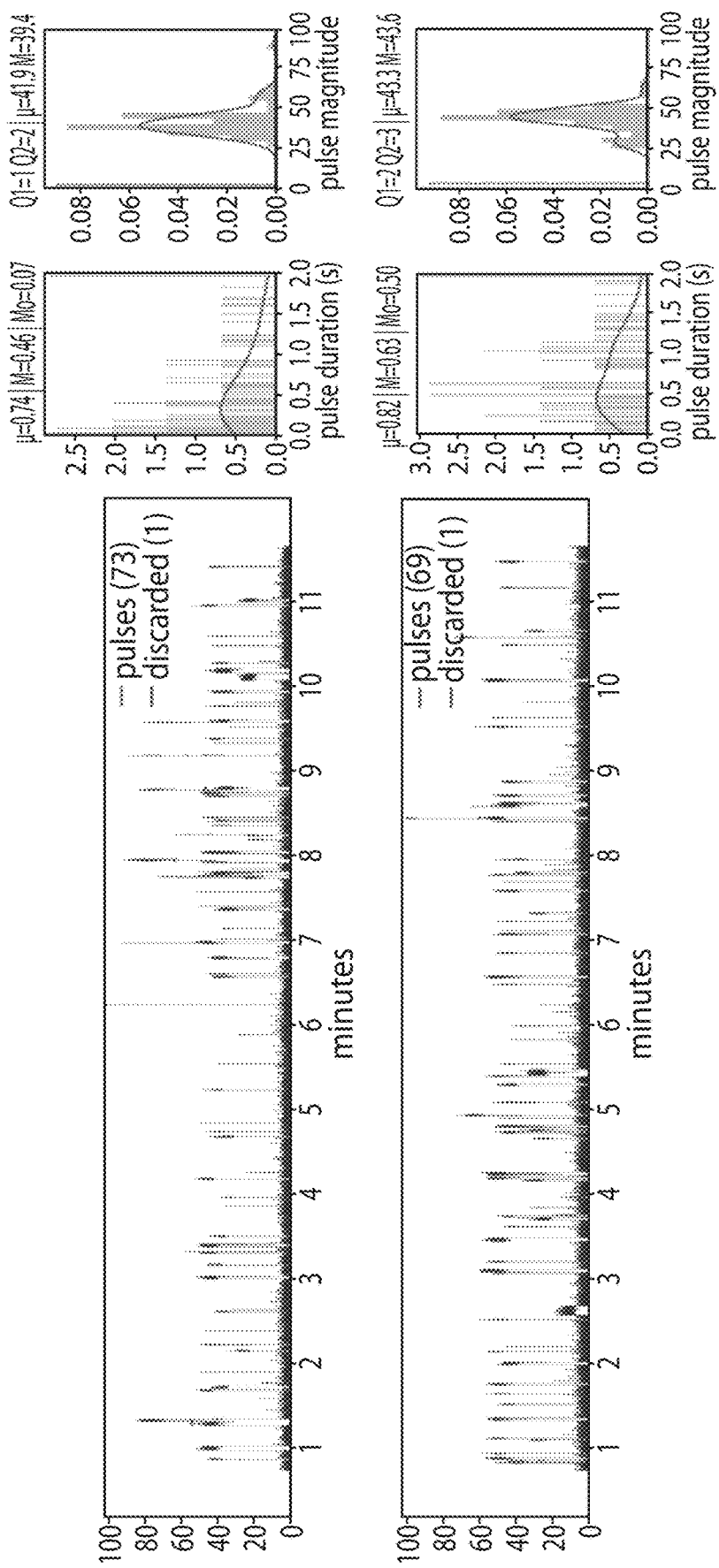
Figure 19I:
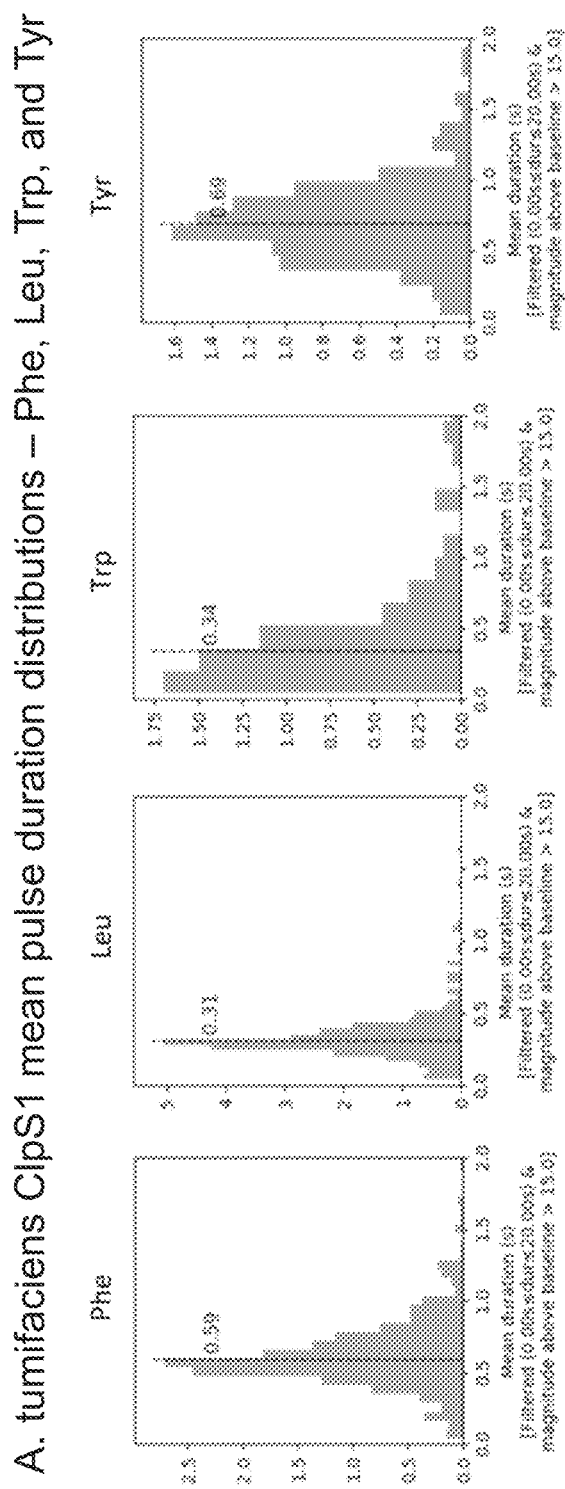
Figure 19J:
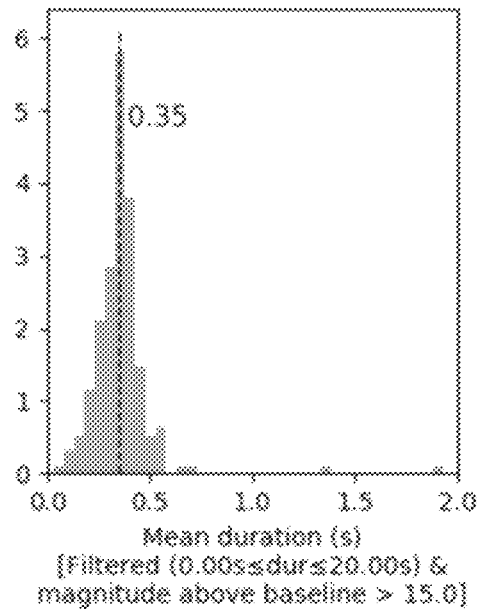
Figure 19K:
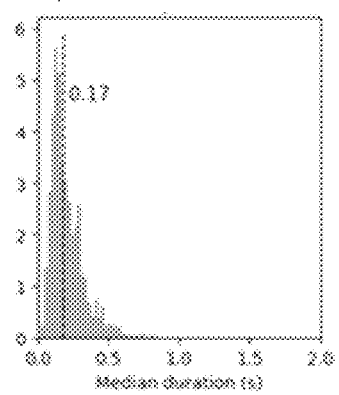
Figure 19L:
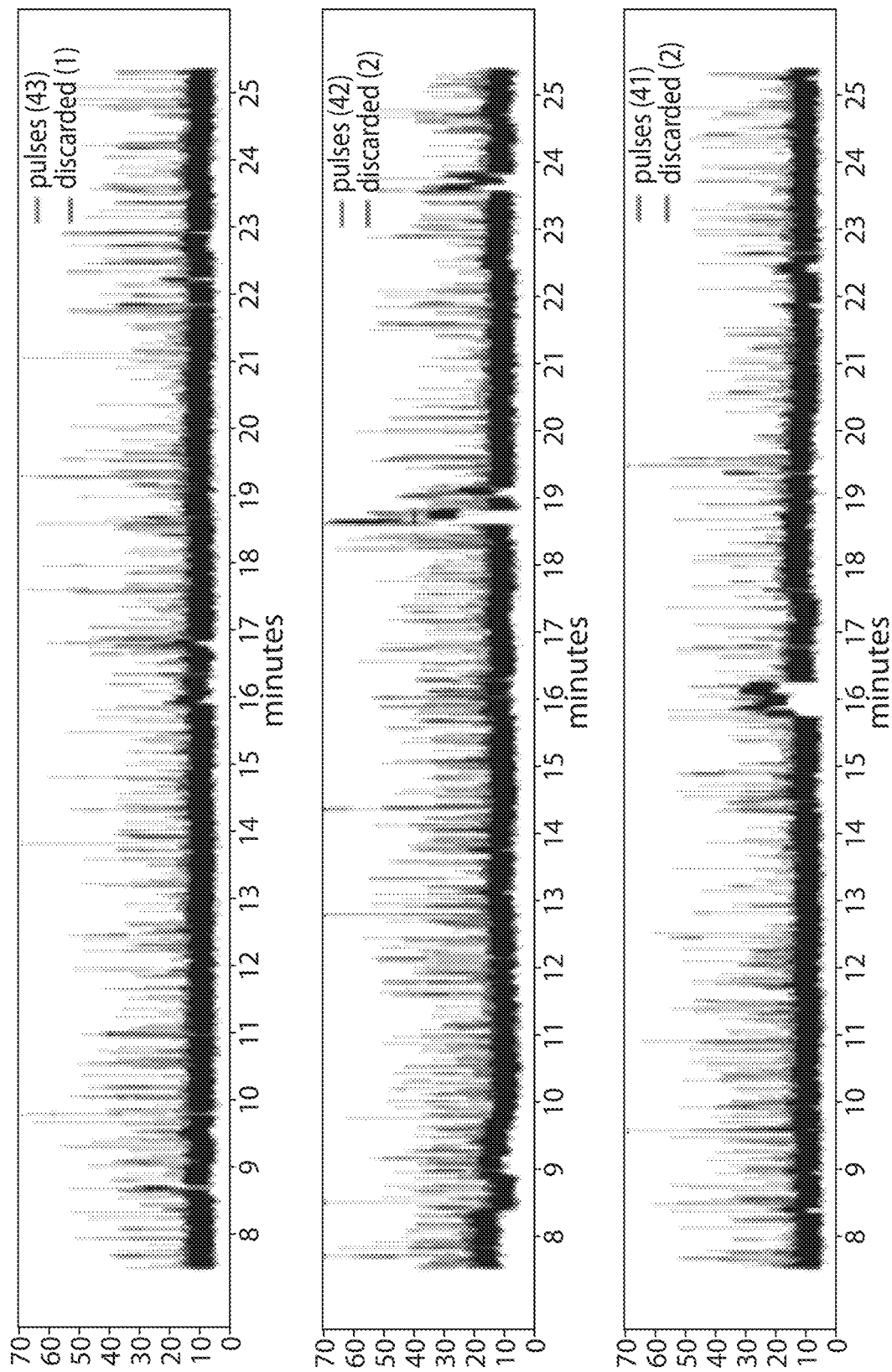

FIGS. 19A-19H show experimental data for terminal amino acid discrimination by a labeled affinity reagent. FIG. 19A shows a crystal structure of a ClpS2 protein that was labeled for these experiments. FIG. 19B shows single molecule intensity traces which illustrate N-terminal amino acid discrimination by the labeled ClpS2 protein. FIG. 19C is a plot showing mean pulse duration for different terminal amino acids. FIG. 19D is a plot showing mean interpulse duration for different terminal amino acids. FIG. 19E shows plots further illustrating discriminant pulse durations among the different terminal amino acids. FIGS. 19F, 19G, and 19H show example results from dwell time analysis demonstrating leucine recognition by a ClpS protein from *Thermosynochoccus elongatus* (teClpS). FIG. 19I shows example results from dwell time analysis demonstrating differentiable recognition of phenylalanine, leucine, tryptophan, and tyrosine by *A. tumefaciens* ClpS1. FIG. 19J shows example results from dwell time analysis demonstrating leucine recognition by *S. elongatus* ClpS2. FIGS. 19K-19L show example results from dwell time analysis demonstrating proline recognition by GID4.

Figure 20A:
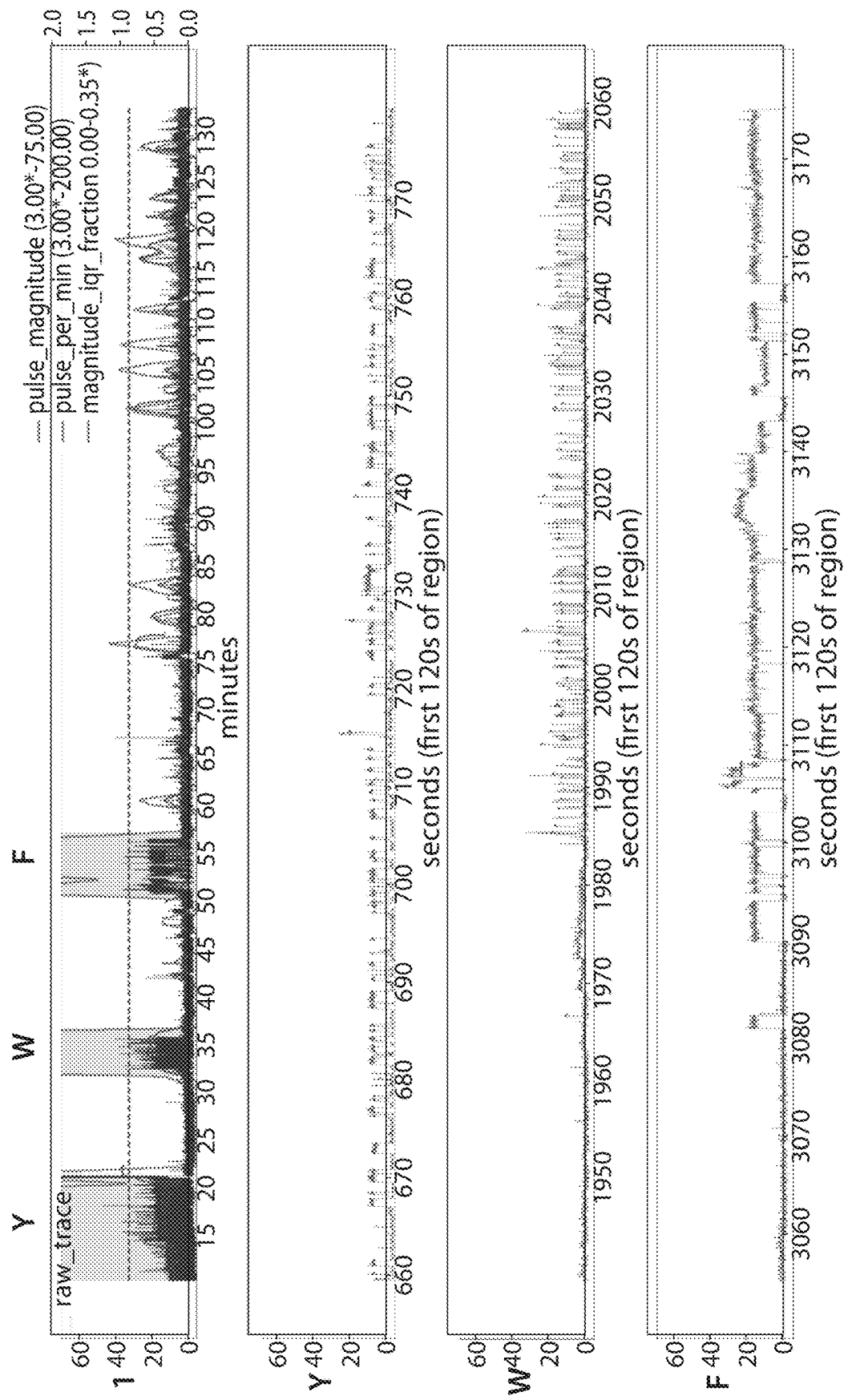

FIGS. 20A-20D show example results from polypeptide sequencing reactions conducted in real-time using a labeled ClpS2 recognition protein and an aminopeptidase cleaving reagent in the same reaction mixture. FIG. 20A shows signal trace data for a first sequencing reaction.

Figure 20B:
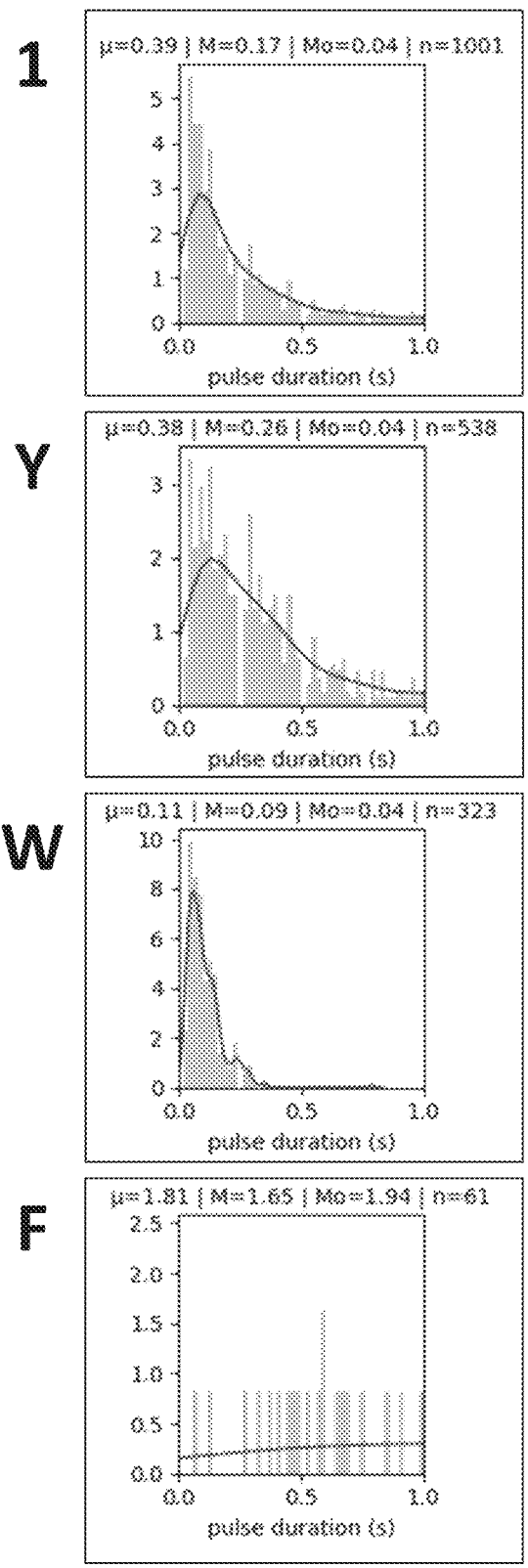
Figure 20C:
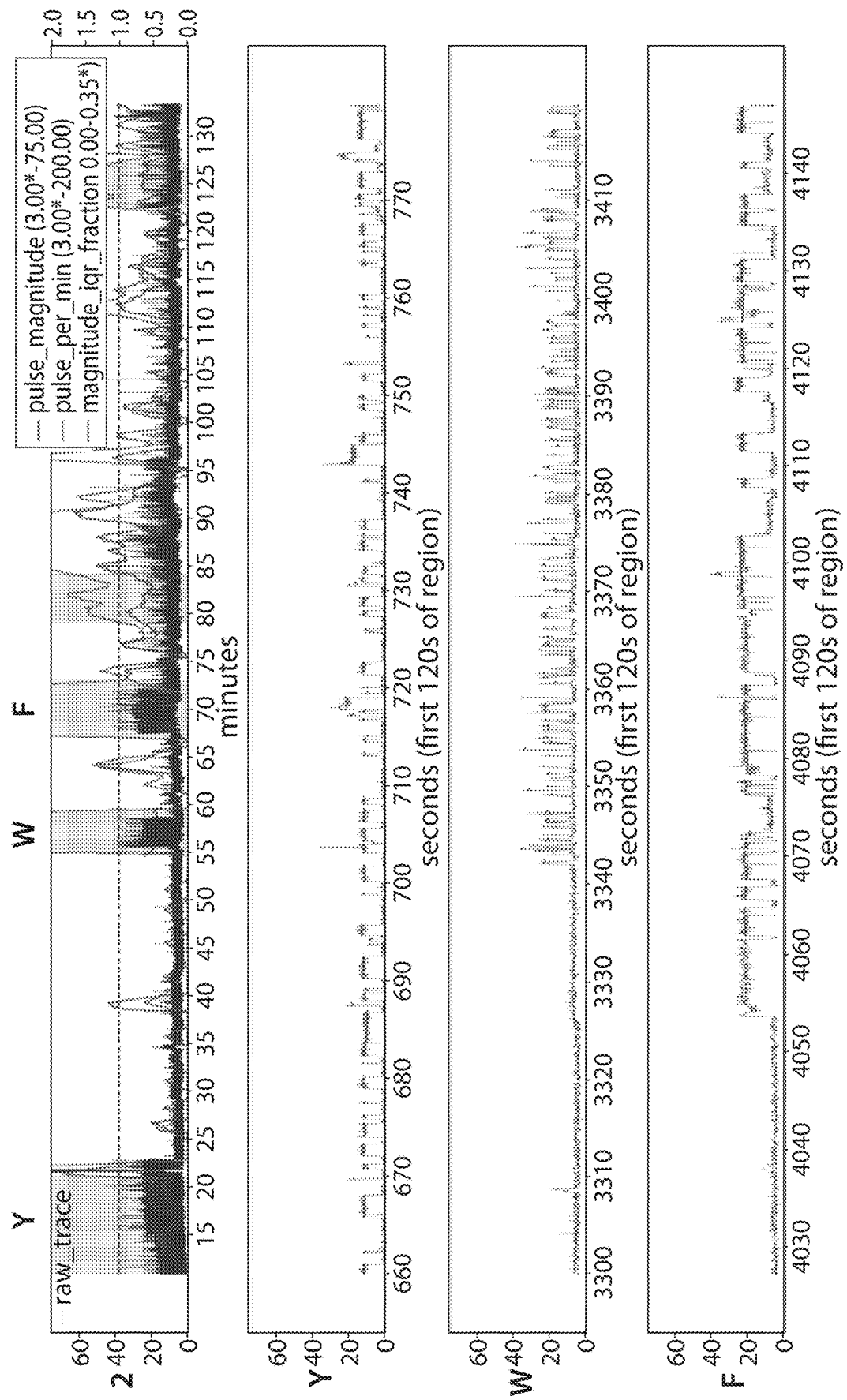
Figure 20D:
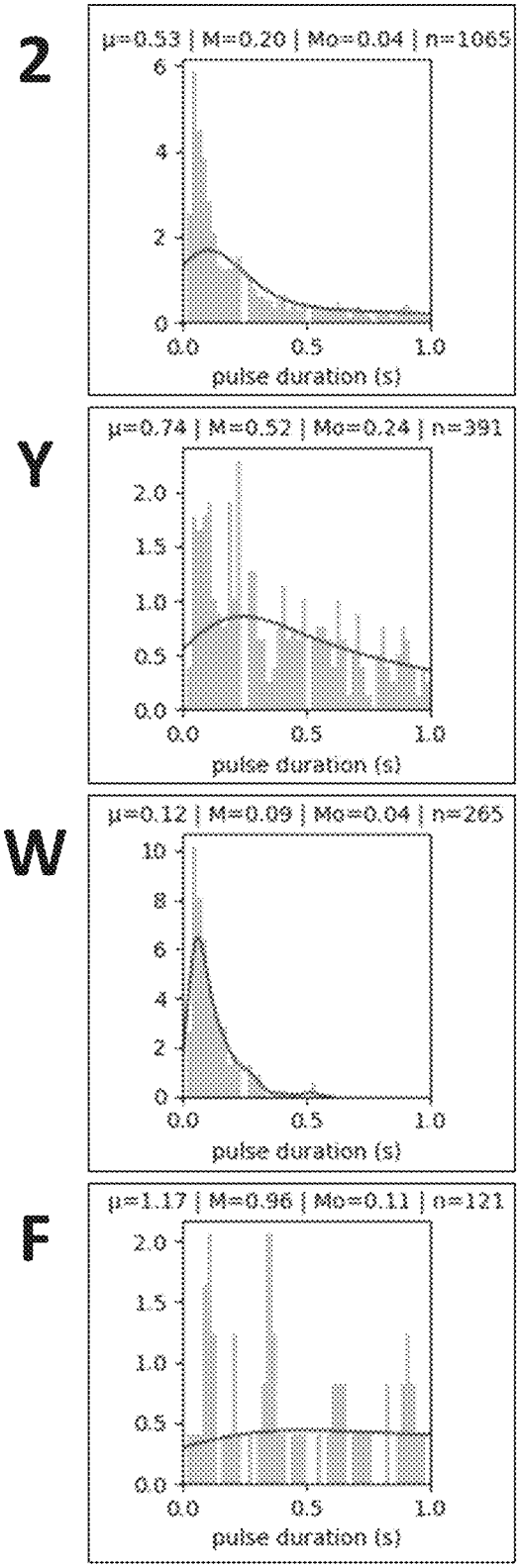

FIG. 20B shows pulse duration statistics for the signal trace data shown in FIG. 20A. FIG. 20C shows signal trace data for a second sequencing reaction. FIG. 20D shows pulse duration statistics for the signal trace data shown in FIG. 20C.

Figure 21A:
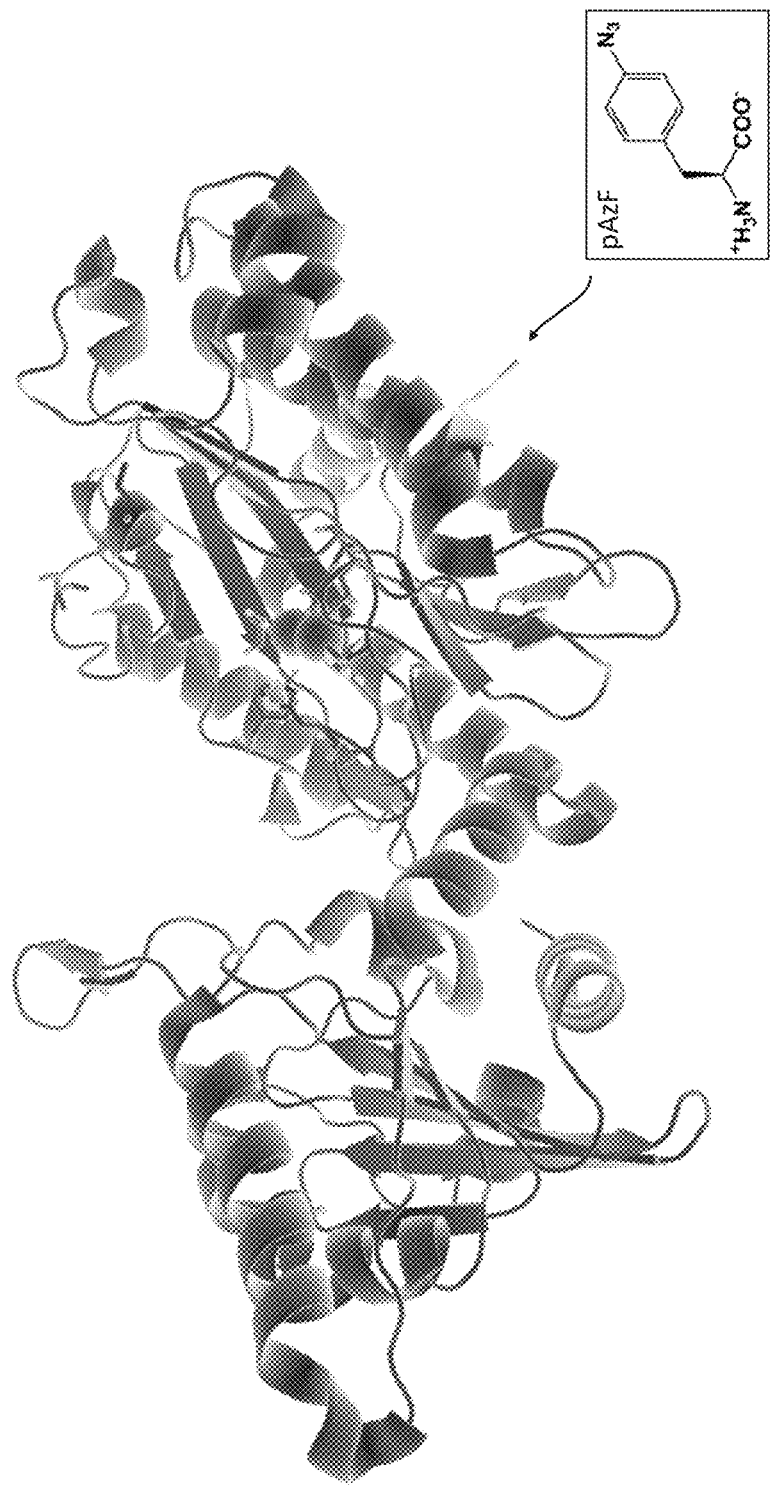
Figure 21B:
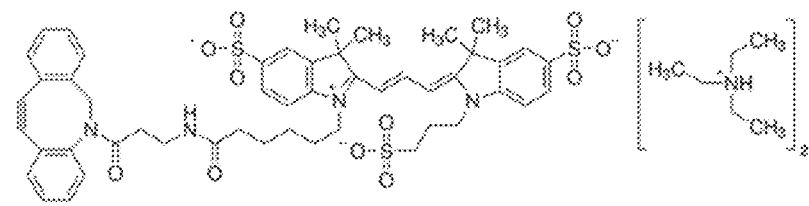
Figure 21B:
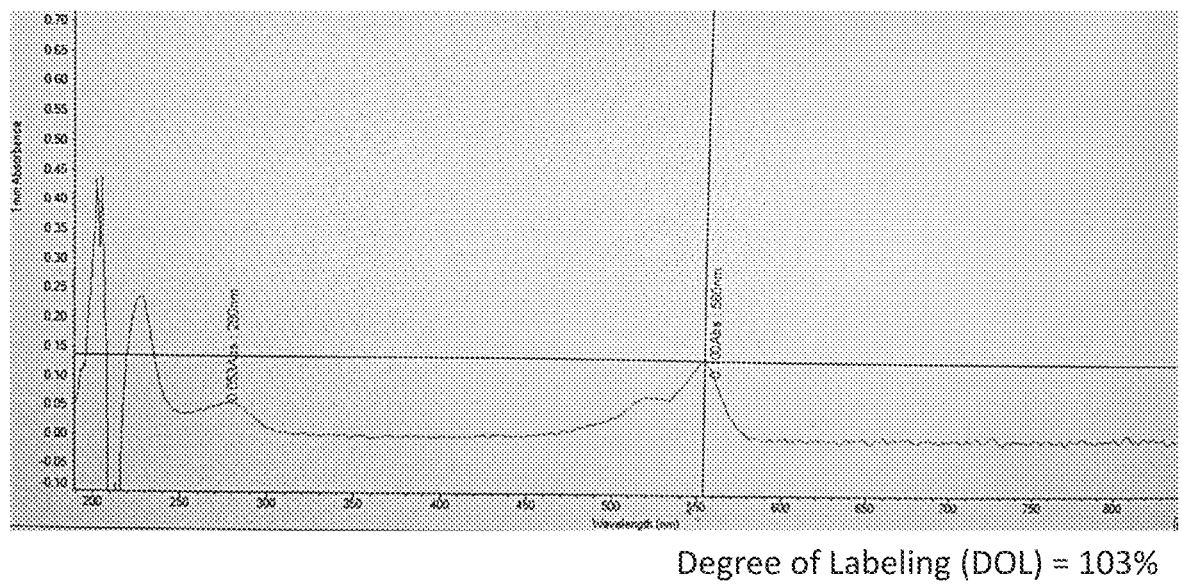
Figure 21C:
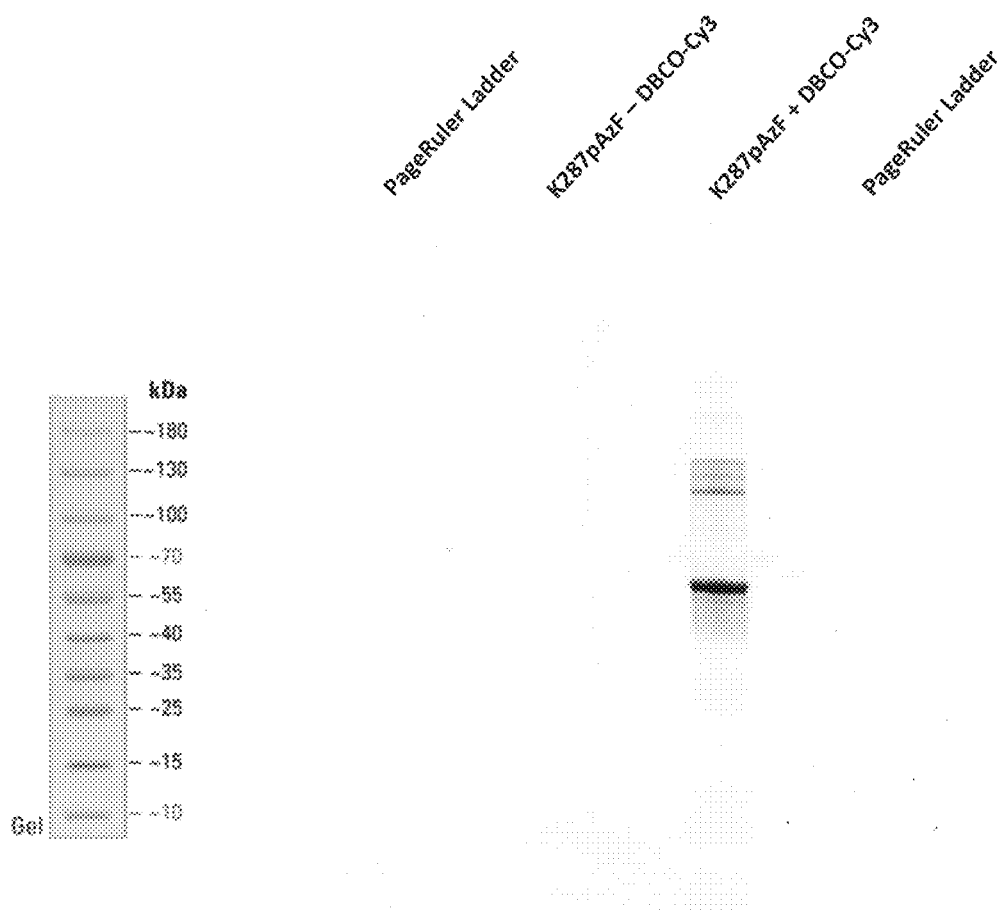
Figure 21D:
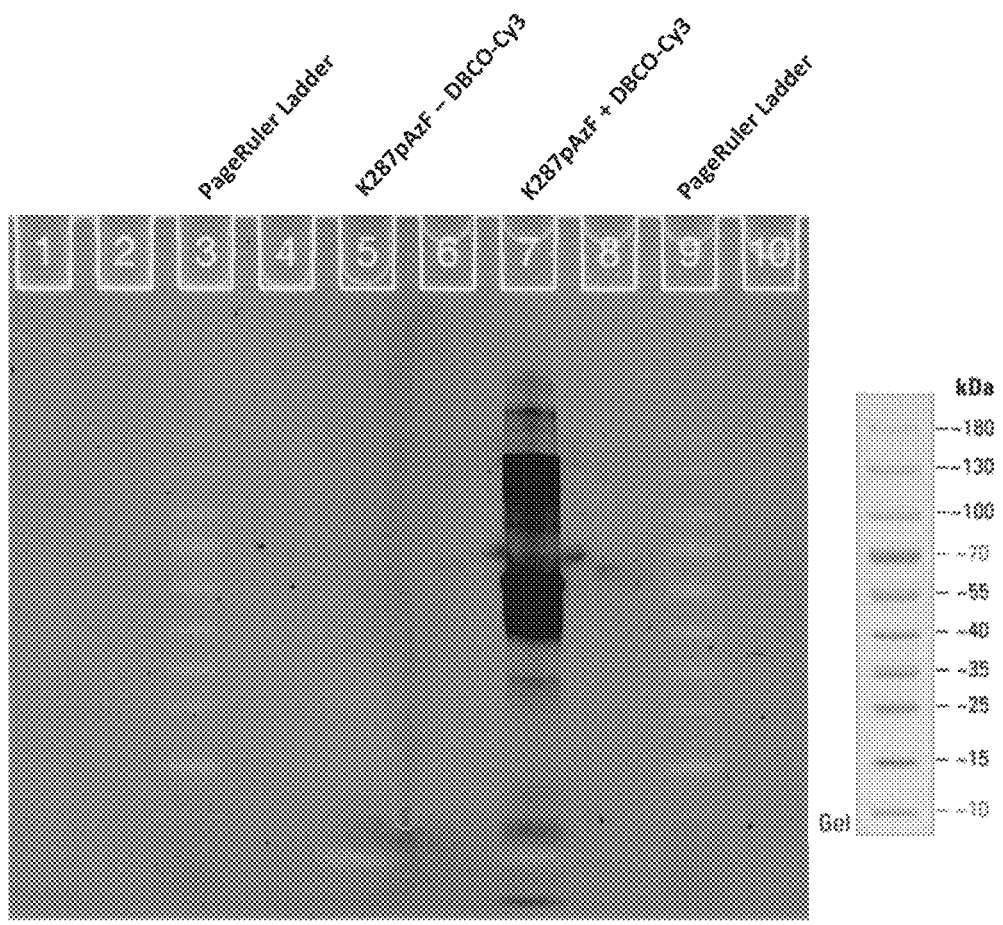
Figure 21E:
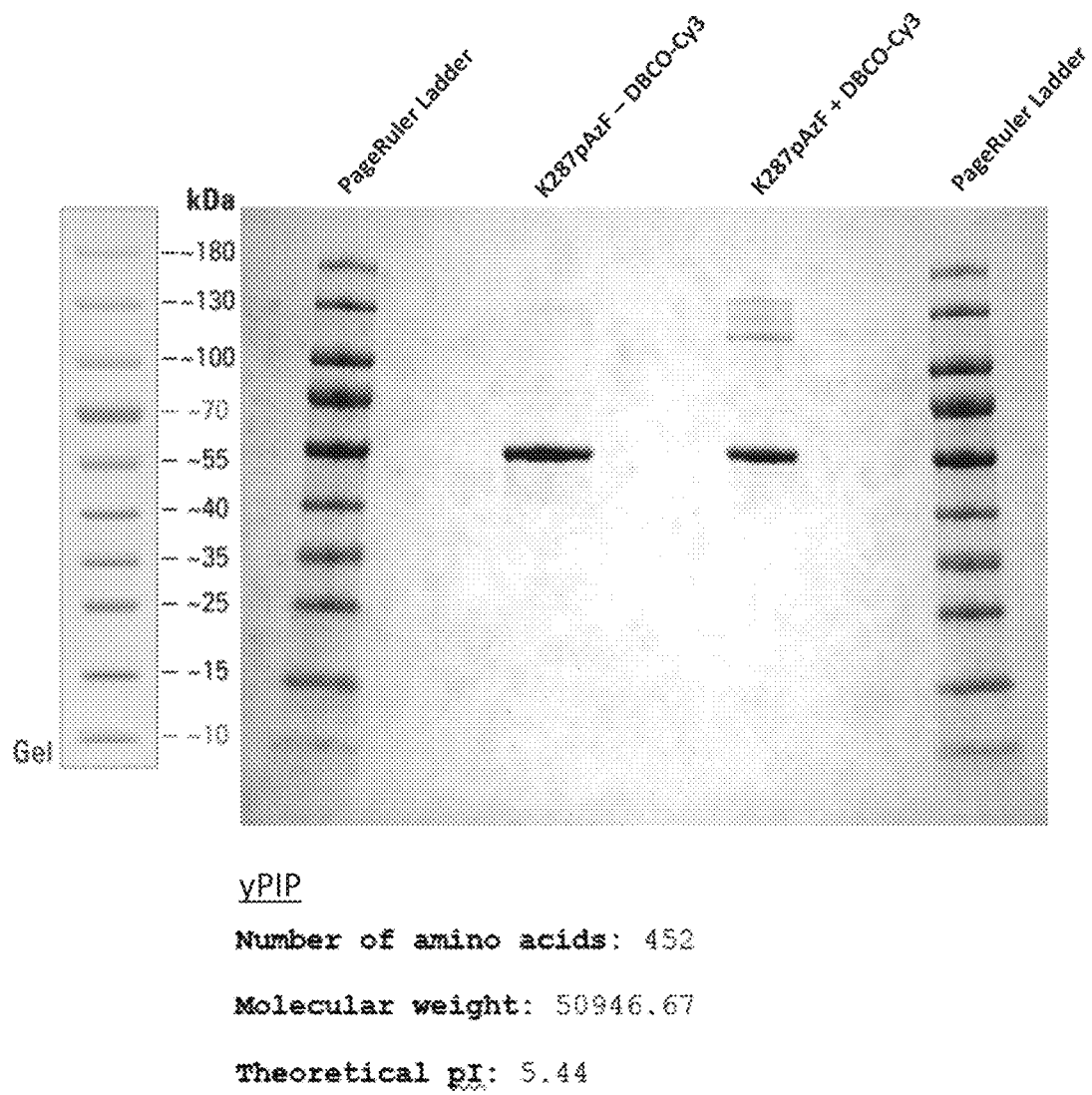
Figure 21F:
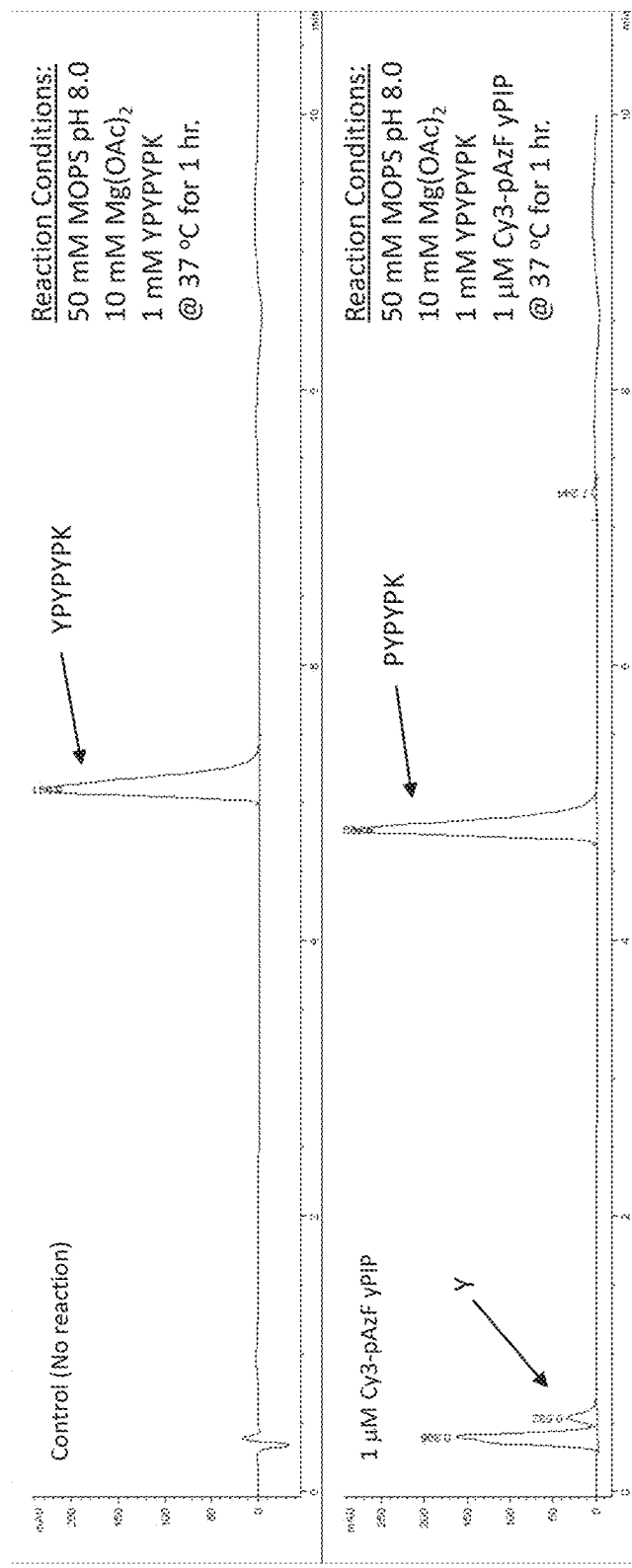

FIGS. 21A-21F show experimental data for terminal amino acid identification and cleavage by a labeled exopeptidase. FIG. 21A shows a crystal structure of a proline iminopeptidase (yPIP) that was site-specifically labeled for these experiments. FIG. 21B shows the degree of labeling for the purified protein product. FIG. 21C is an image of SDS page confirming site-specific labeling of yPIP. FIG. 21D is an overexposed image of the SDS page gel confirming site-specific labeling. FIG. 21E is an image of a Coomassie stained gel confirming purity of labeled protein product. FIG. 21F is an HPLC trace demonstrating cleavage activity of the labeled exopeptidase. The sequence YPY-PYPK corresponds to SEQ ID NO: 82. The sequence PYPYPK corresponds to SEQ ID NO: 83.

Figure 22A:
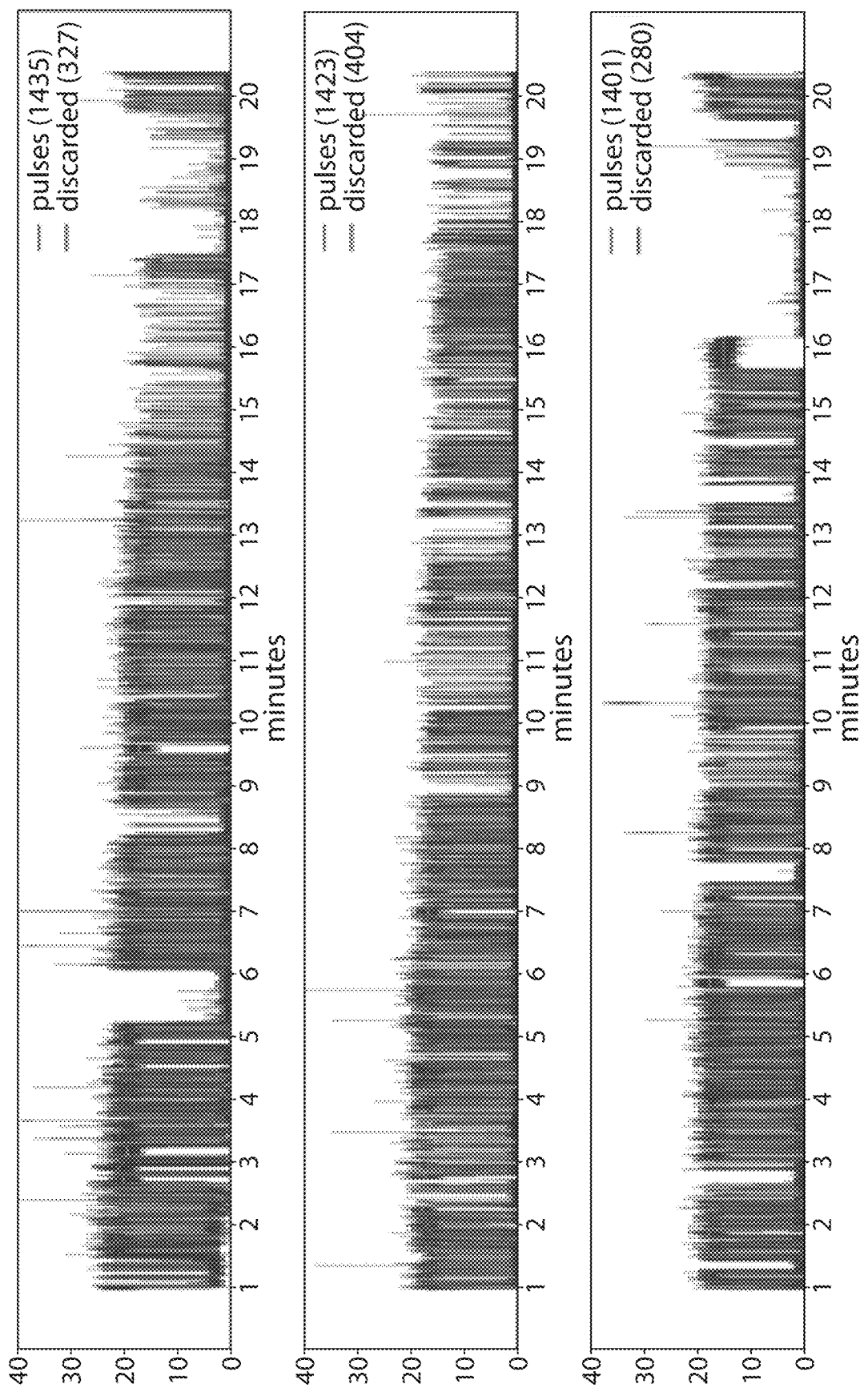
Figure 22B:
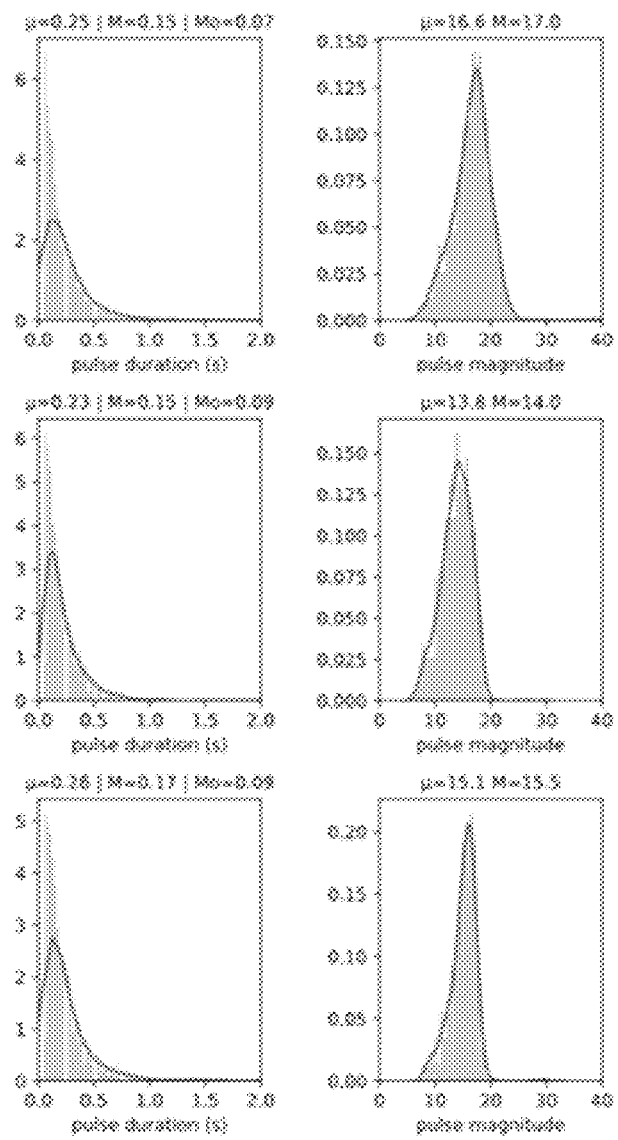
Figure 22C:
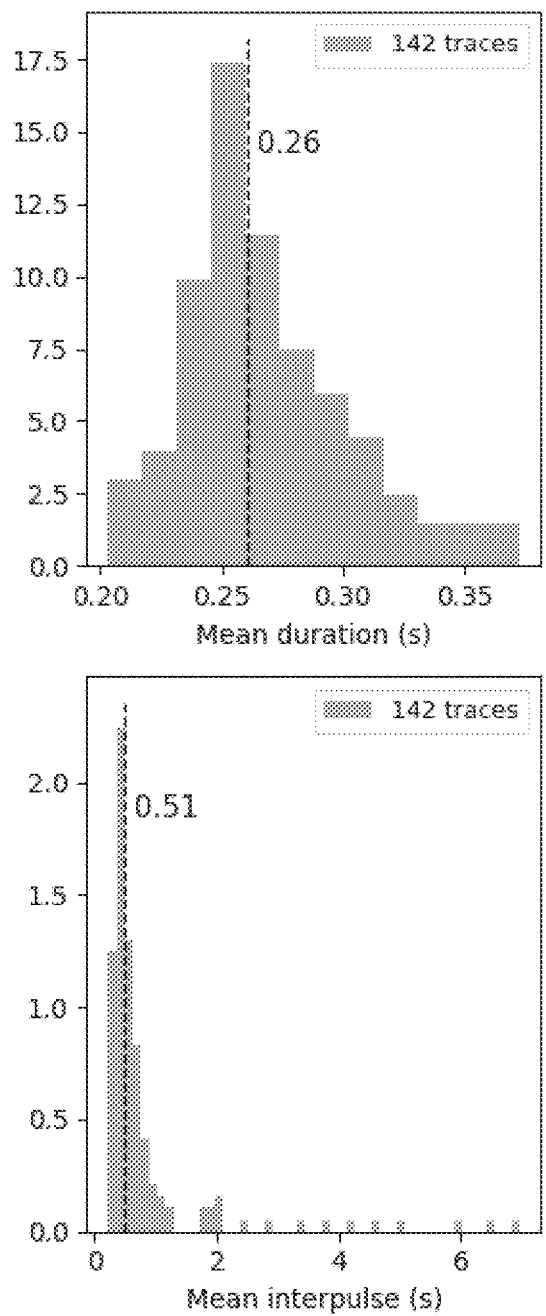
Figure 22D:
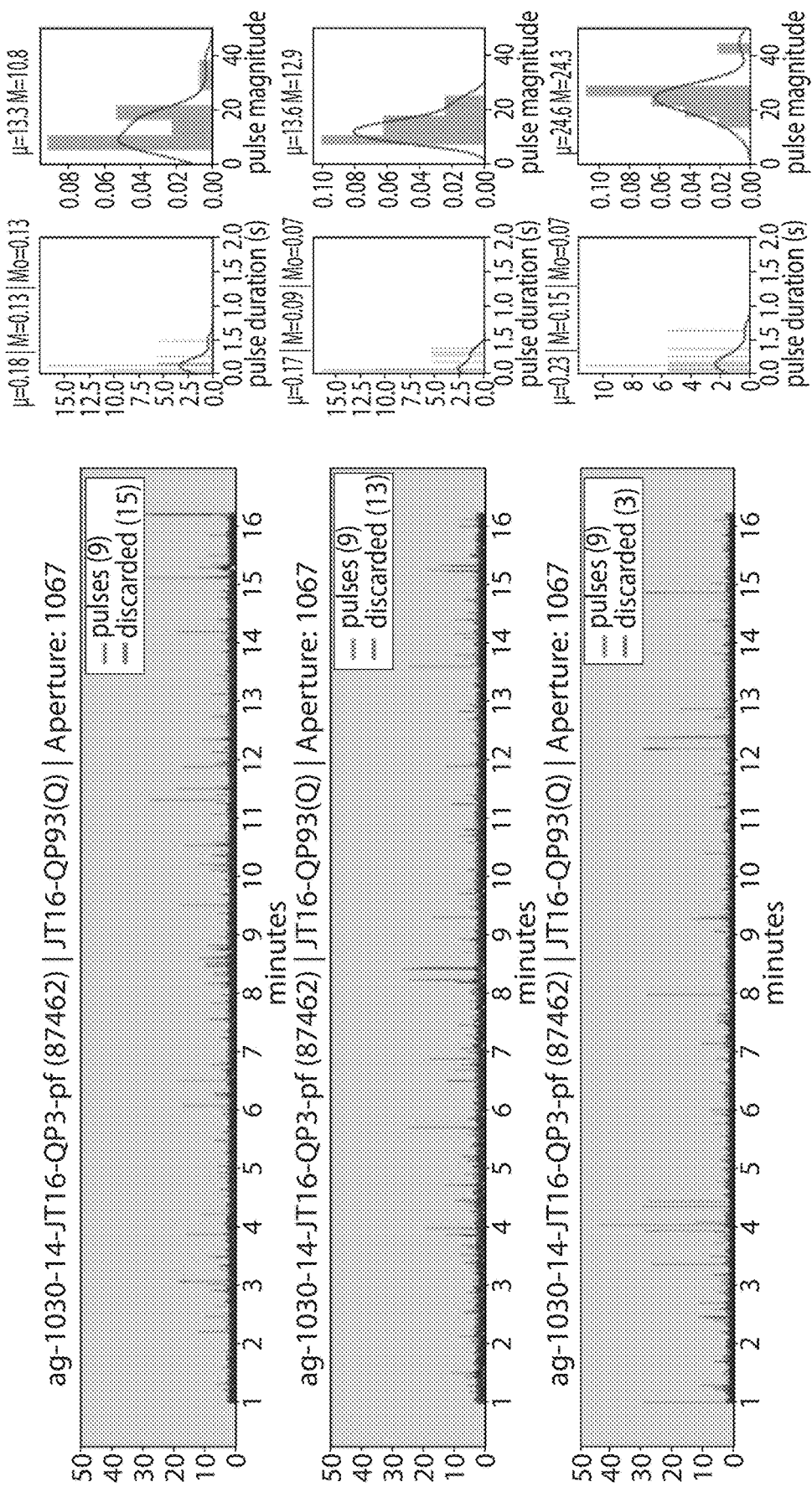
Figure 22E:
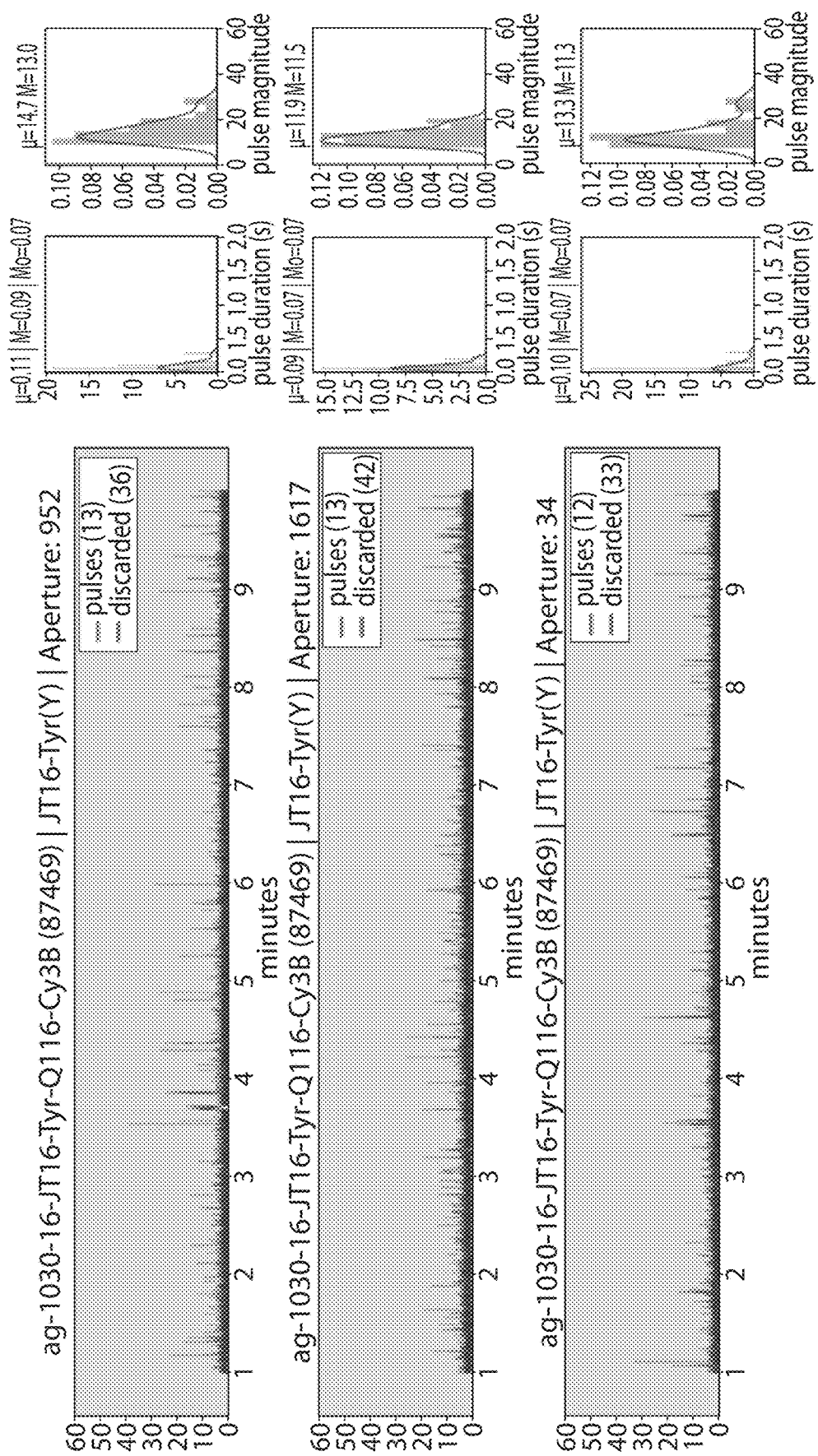
Figure 22F:
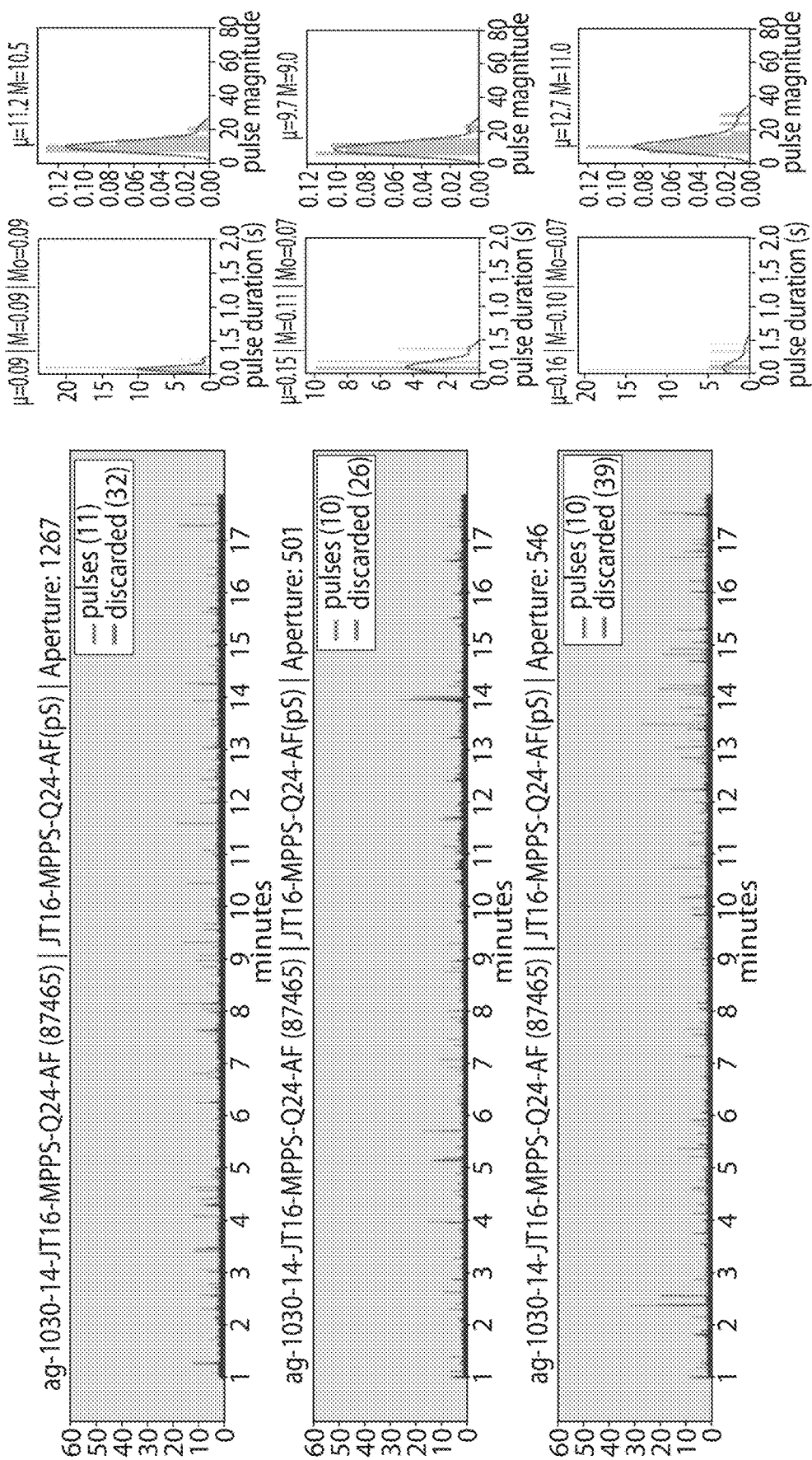

FIGS. 22A-22F show data from experiments evaluating recognition of amino acids containing specific post-translational modifications. FIG. 22A shows representative traces which demonstrated phospho-tyrosine recognition by an SH2 domain-containing protein; FIG. 22B shows pulse duration data corresponding to the traces of FIG. 22A; and FIG. 22C shows statistics determined for the traces. FIGS. 22D-22F show representative traces from negative control experiments.

Figure 23:
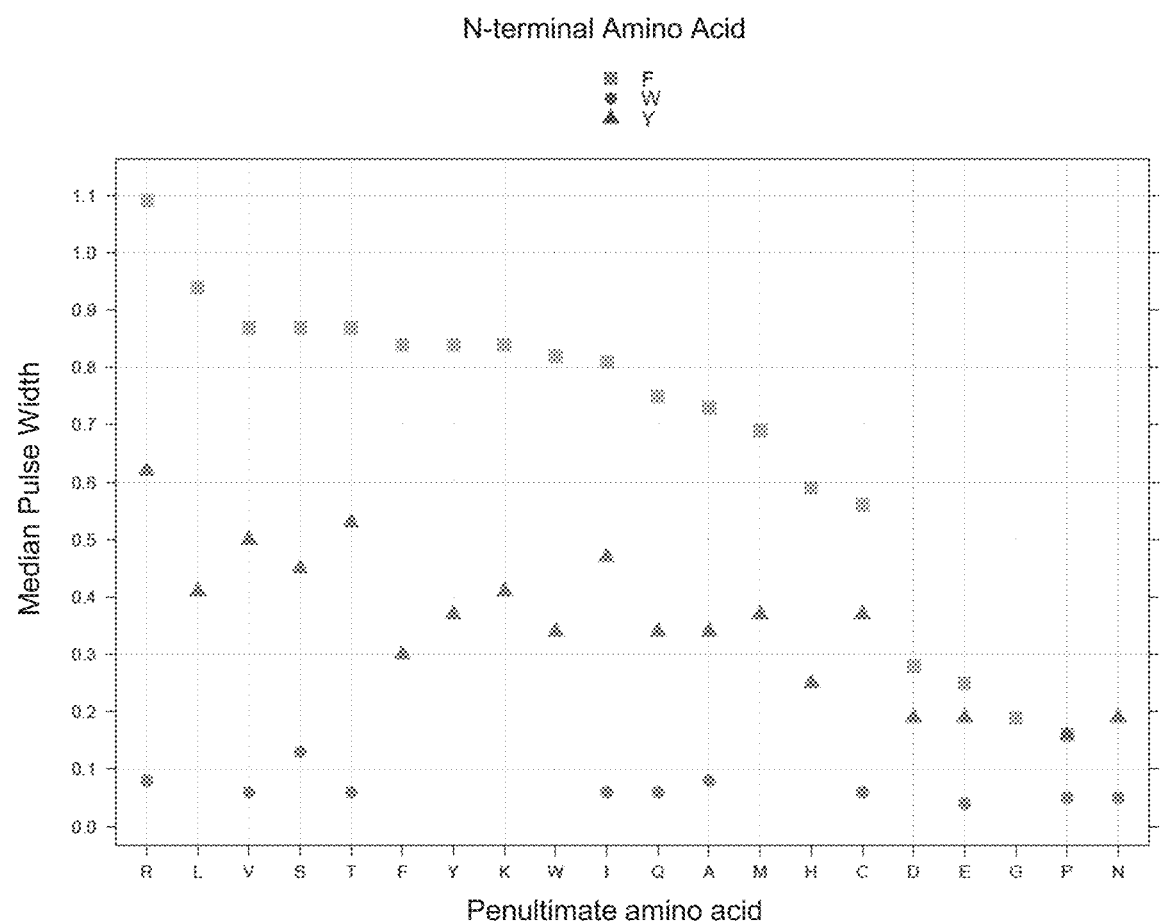

FIG. 23 is a plot showing median pulse duration from experiments evaluating the effects of penultimate amino acids on pulse duration.

Figure 24A:
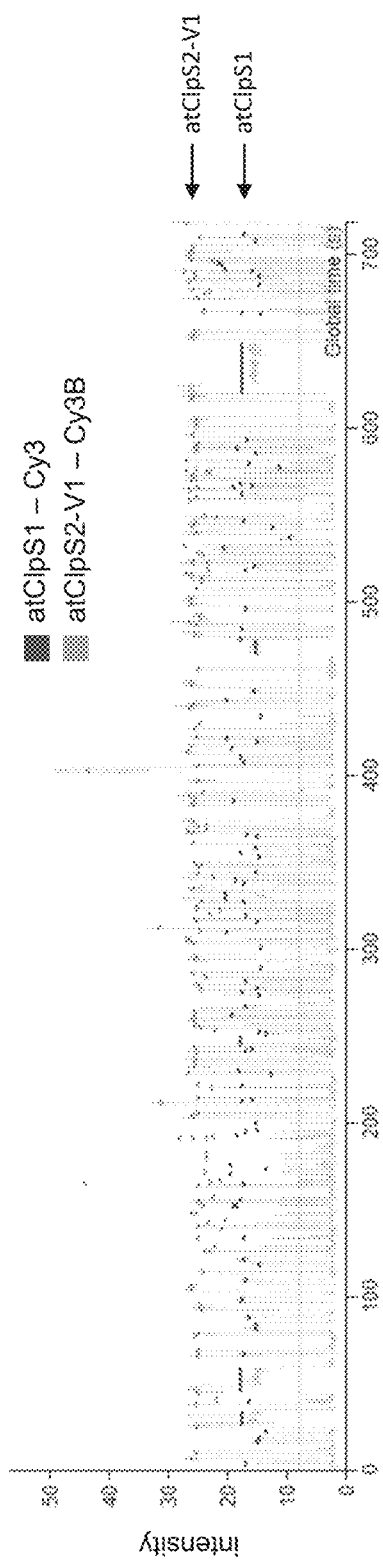
Figures 24B, 24C:
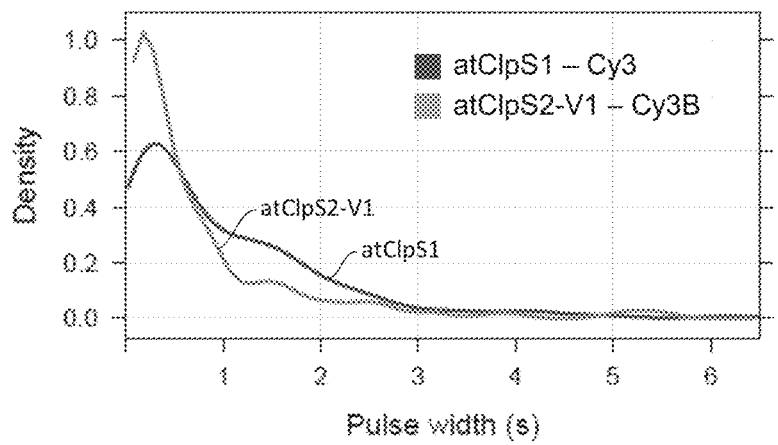

FIGS. 24A-24C show data from experiments evaluating simultaneous amino acid recognition by differentially labeled recognition molecules. FIG. 24A shows a representative trace. FIG. 24B is a plot comparing pulse duration data obtained during these experiments for each recognition molecule. FIG. 24C shows pulse duration statistics for these experiments.

Figure 25A:
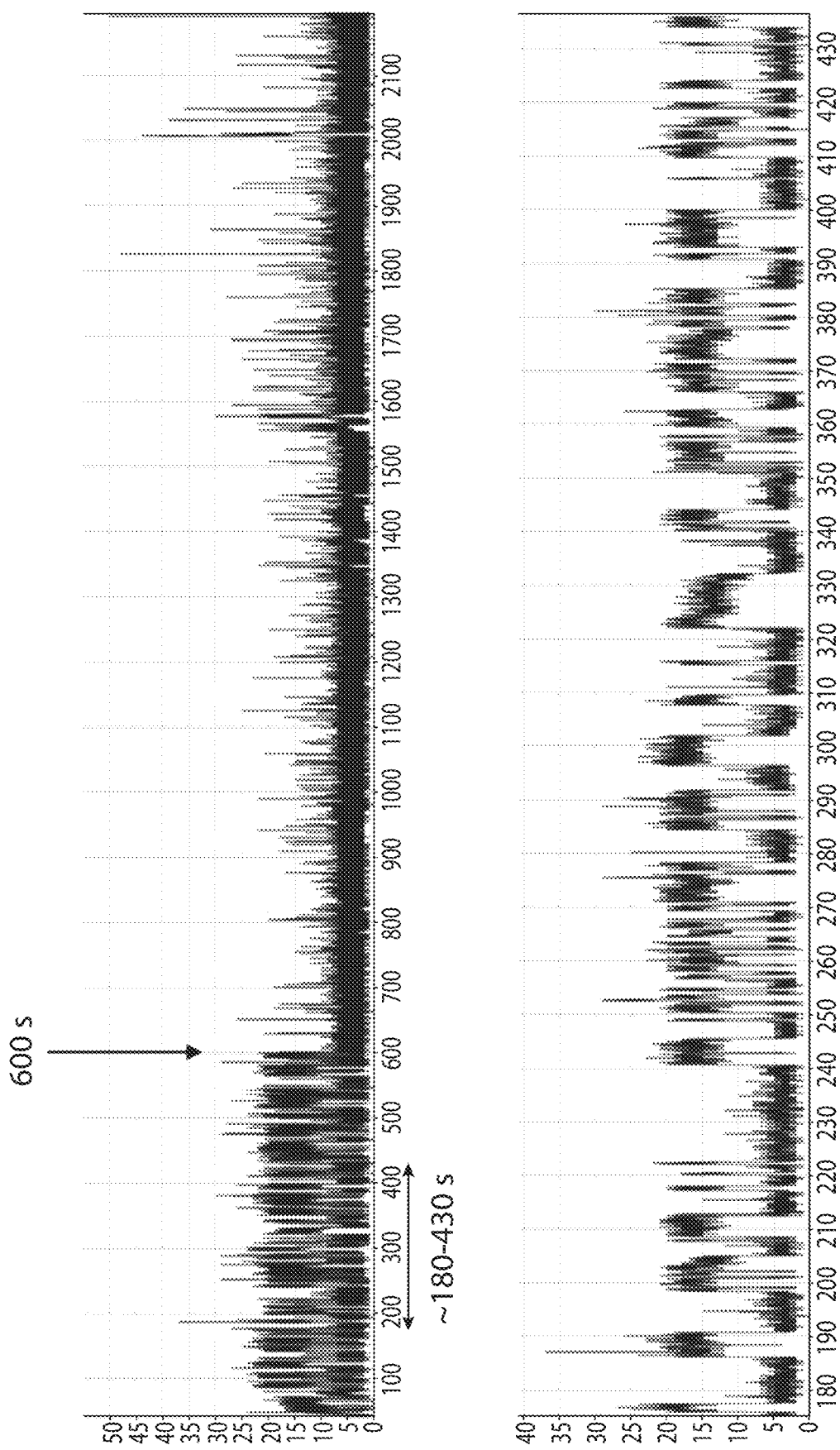
Figure 25B:
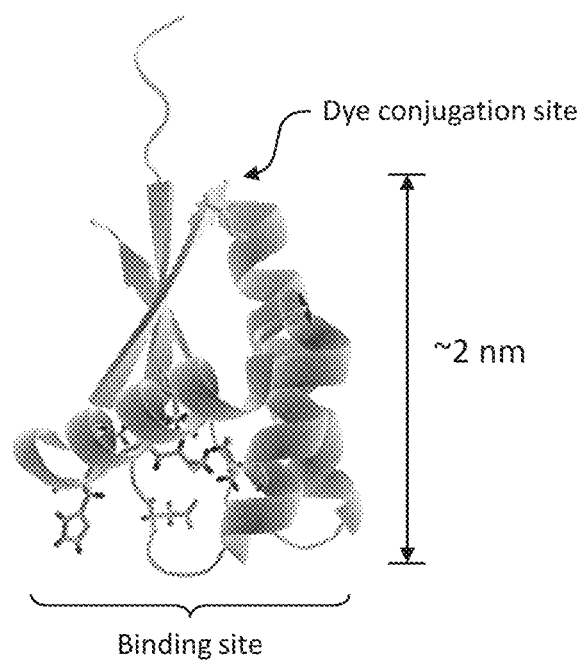
Figure 25C:
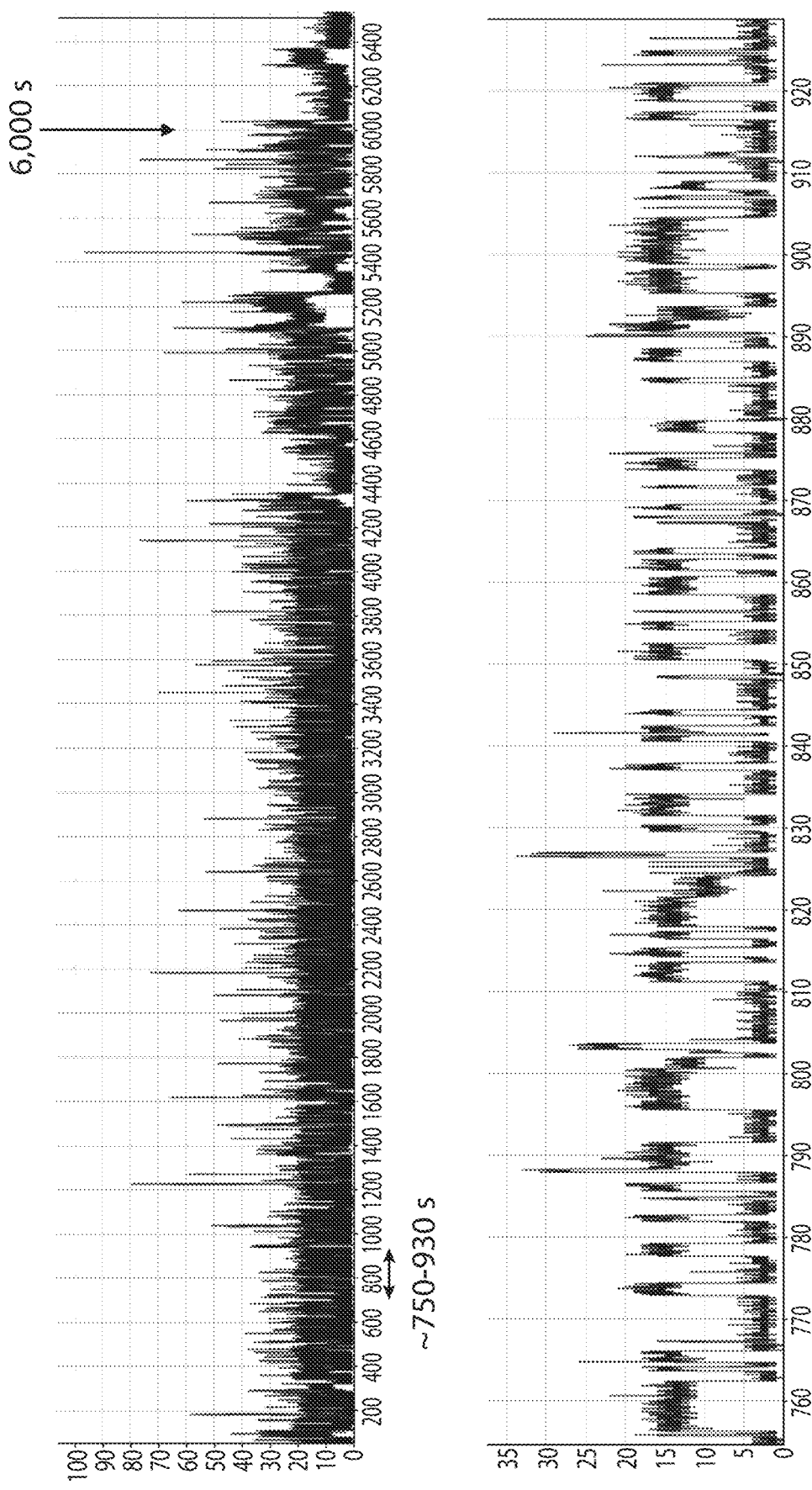
Figure 26A:
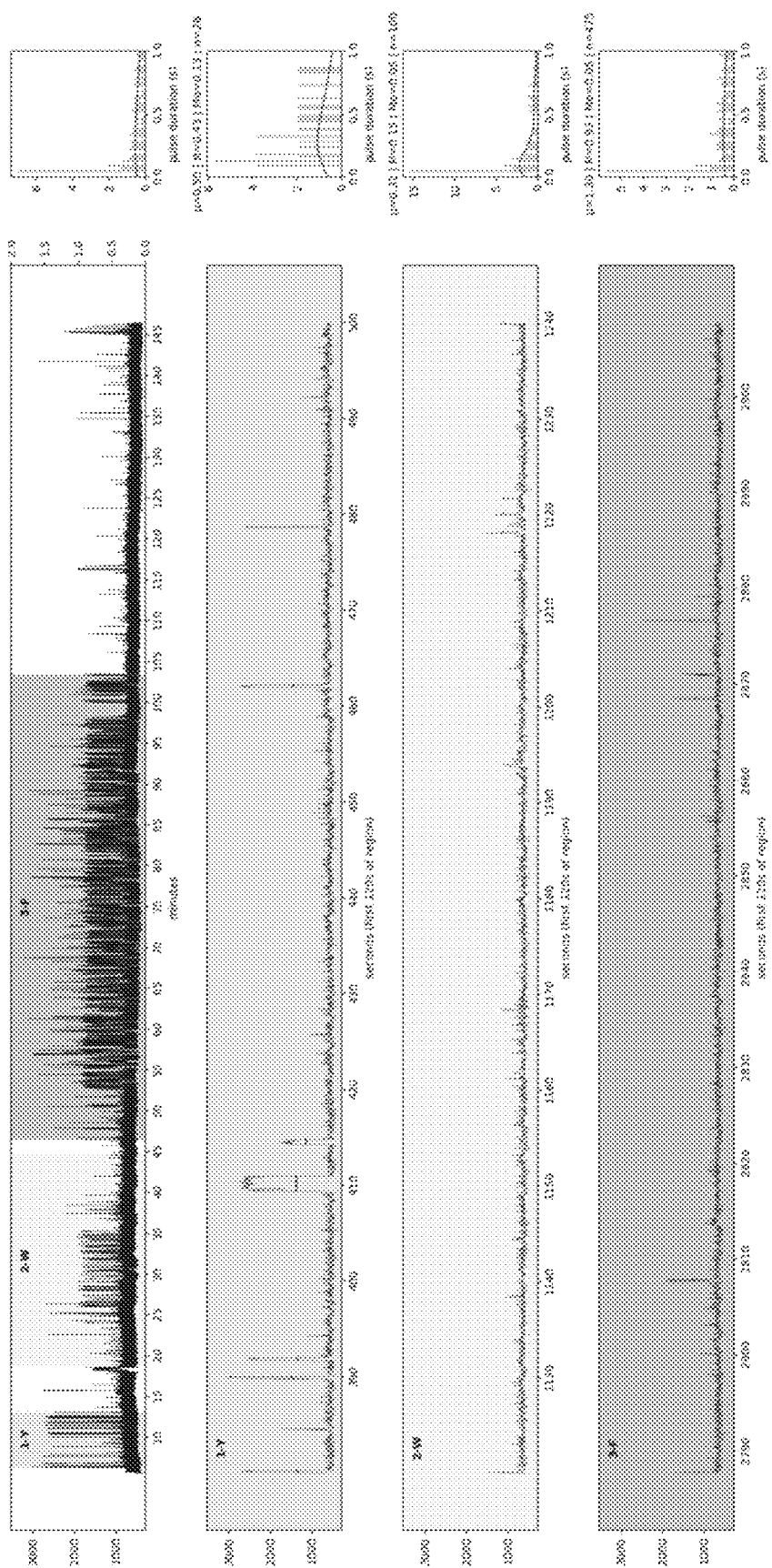
Figure 26B:
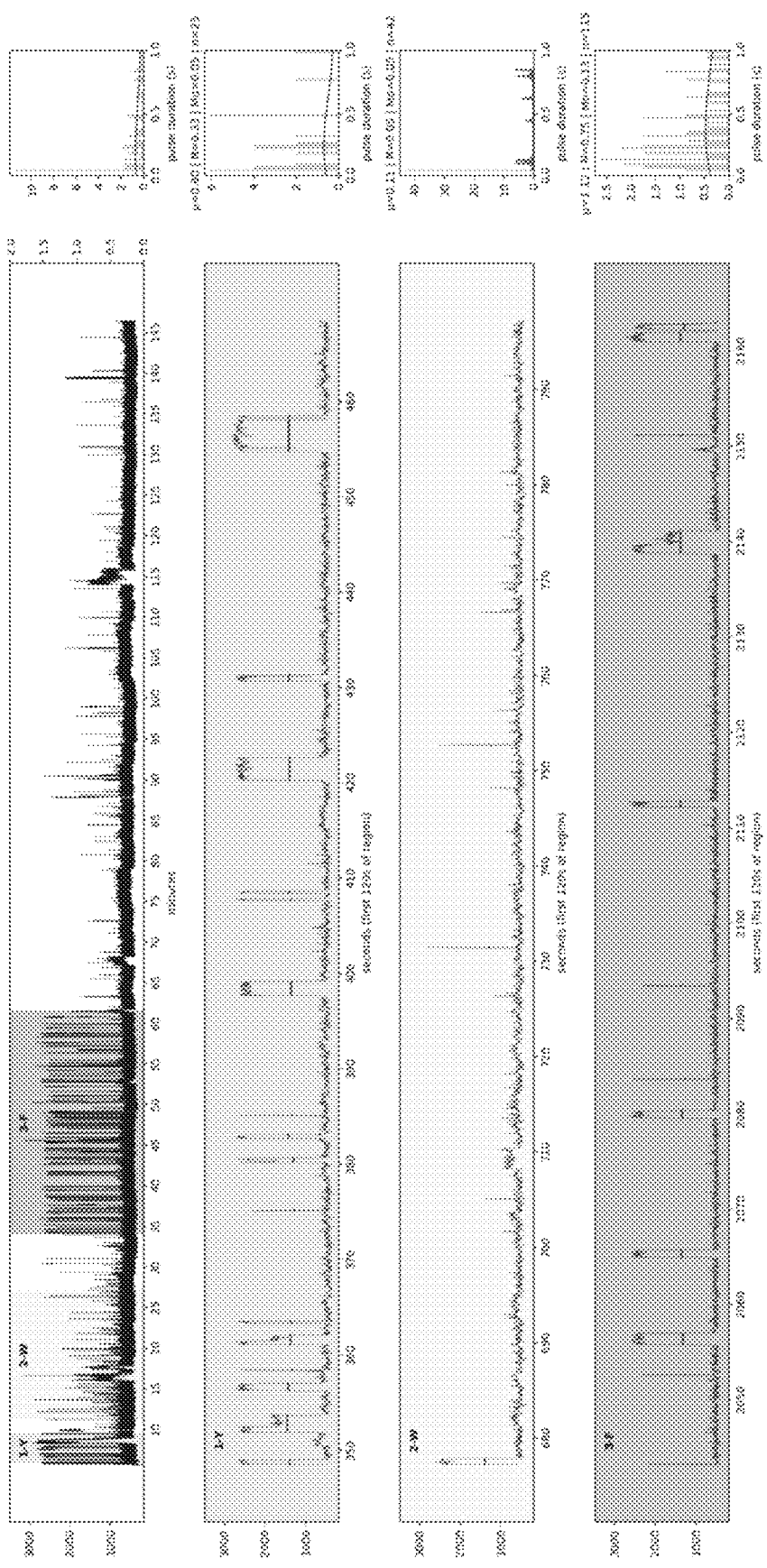
Figure 26C:
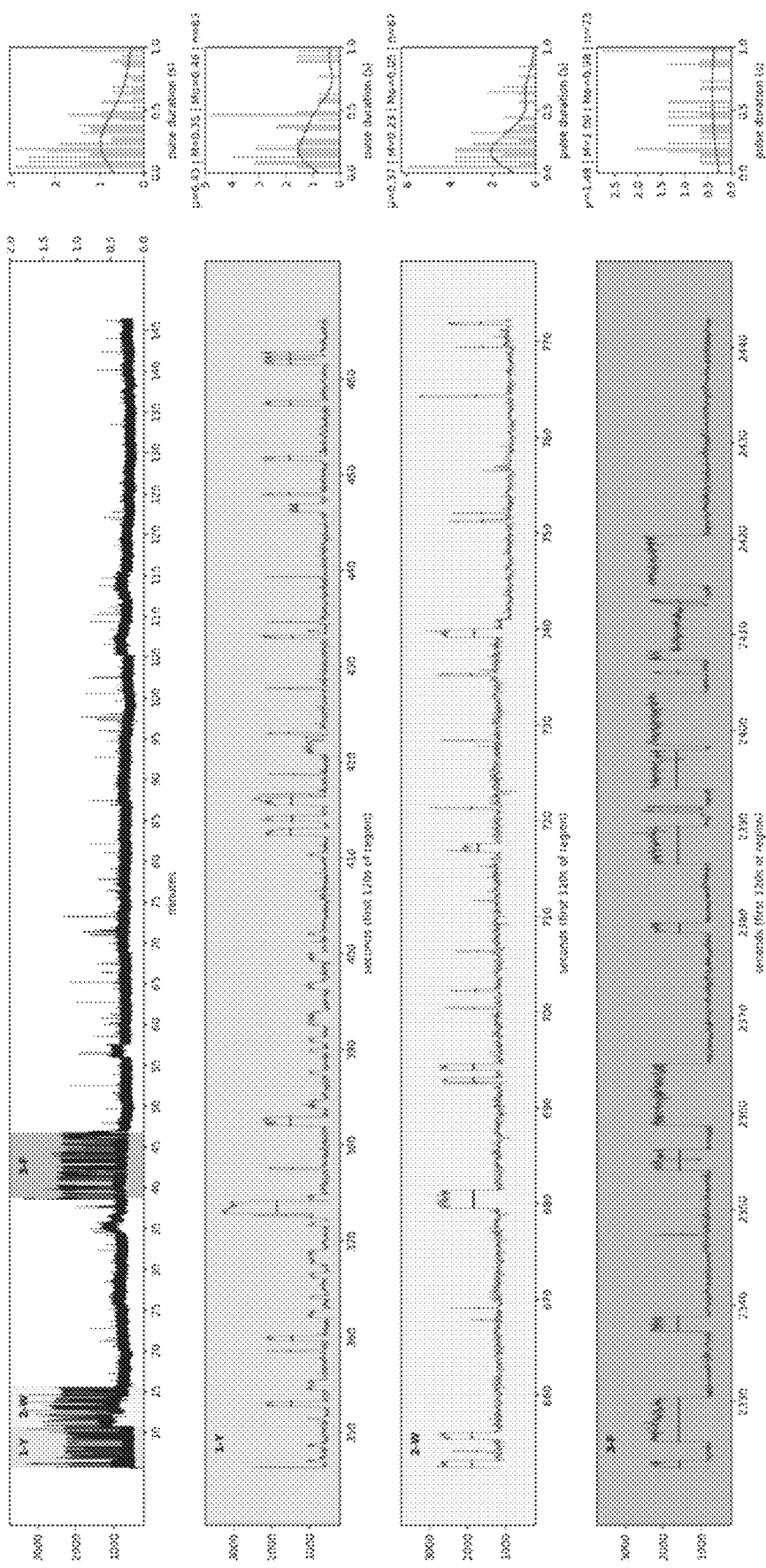
Figure 26D:
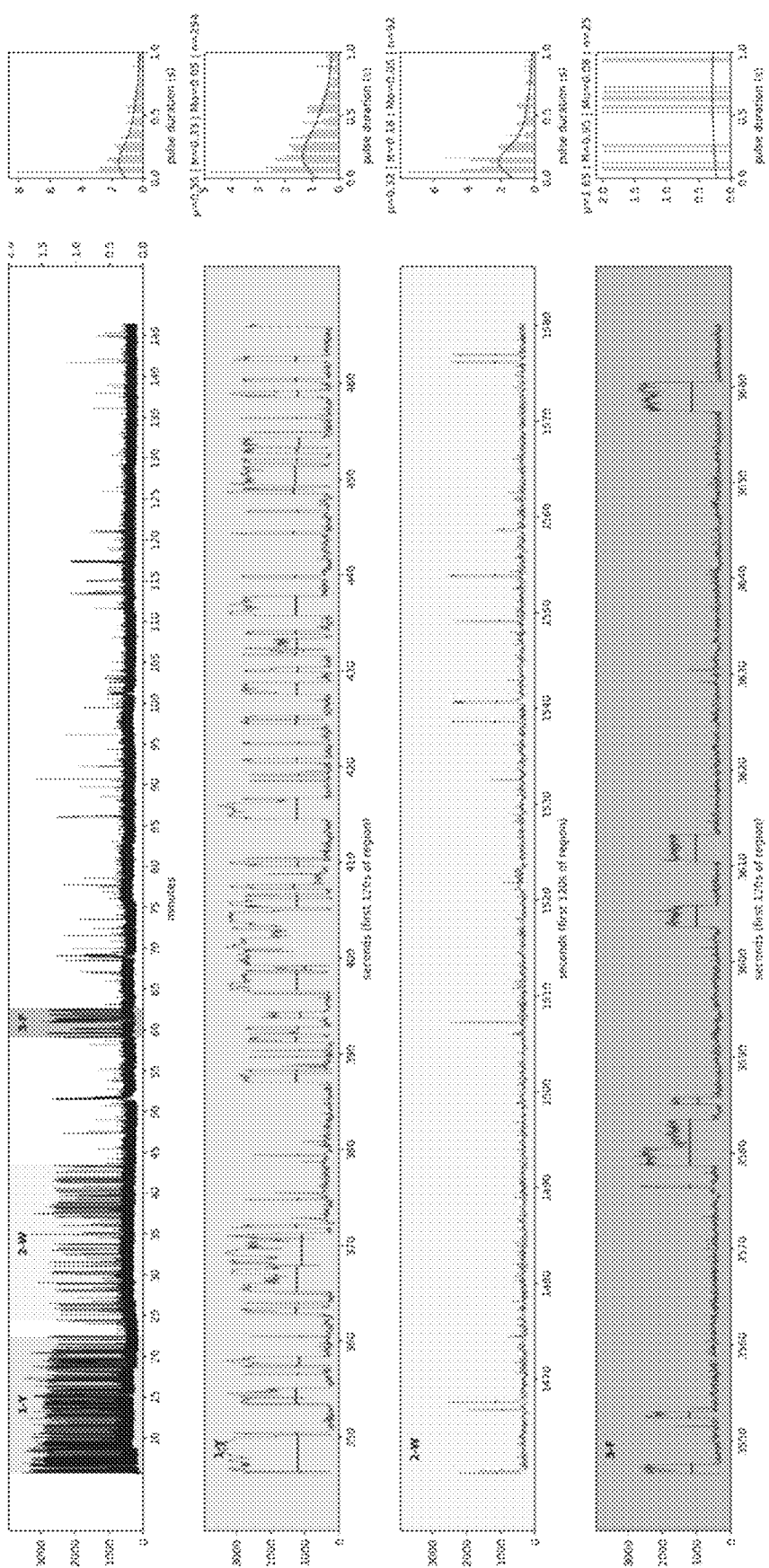

FIGS. 25A-25C show data from experiments evaluating the photostability of peptides during single-molecule recognition. FIG. 25A shows a representative trace from recognition using atClpS2-V1 labeled with a dye −2 nm from the amino acid binding site. FIG. 25B shows a visualization of the structure of the ClpS2 protein used in these experiments. FIG. 25C shows a representative trace from recognition using ClpS2 labeled with a dye >10 nm from the amino acid binding site through a DNA/protein linker.

FIGS. 26A-26D show representative traces from polypeptide sequencing reactions conducted in real-time on a complementary metal-oxide-semiconductor (CMOS) chip using a ClpS2 recognition protein labeled through a DNA/streptavidin linker in the presence of an aminopeptidase cleaving reagent.

Figure 27:
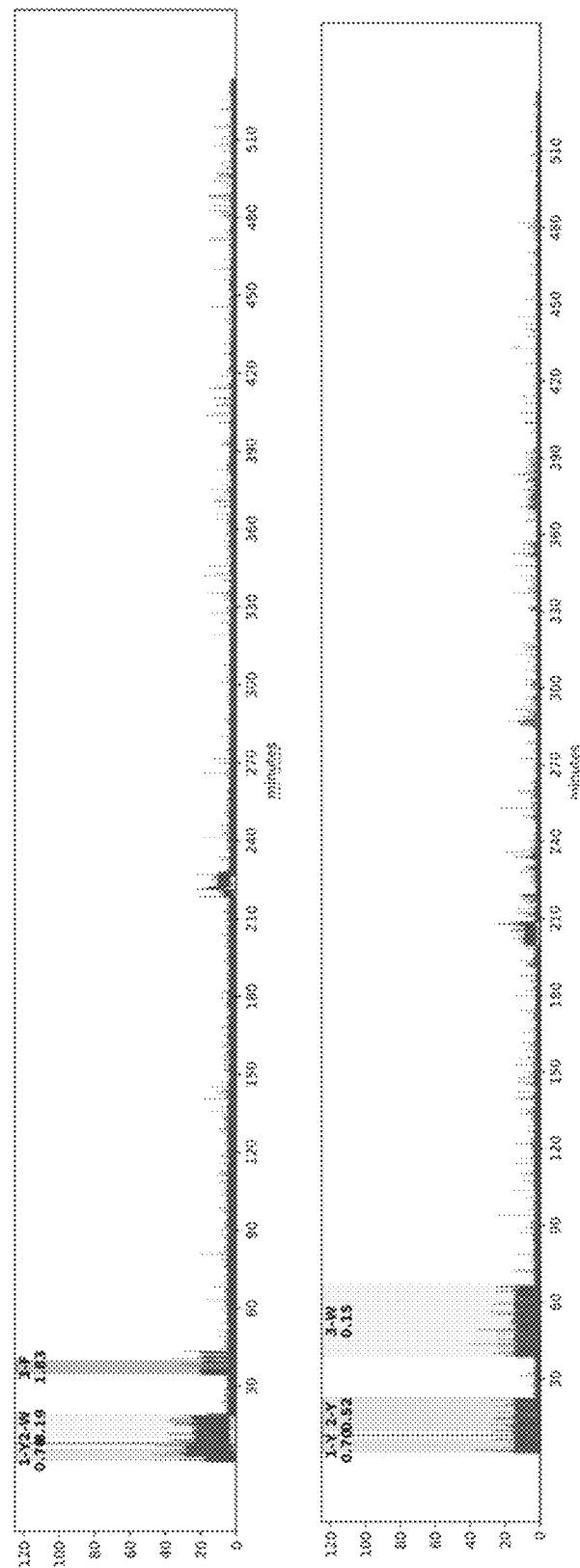

FIG. 27 shows representative traces from polypeptide sequencing reactions conducted in real-time using atClpS2-V1 recognition protein labeled through a DNA/streptavidin linker in the presence of *Pyrococcus horikoshii* TET aminopeptidase cleaving reagent.

Figure 28A:
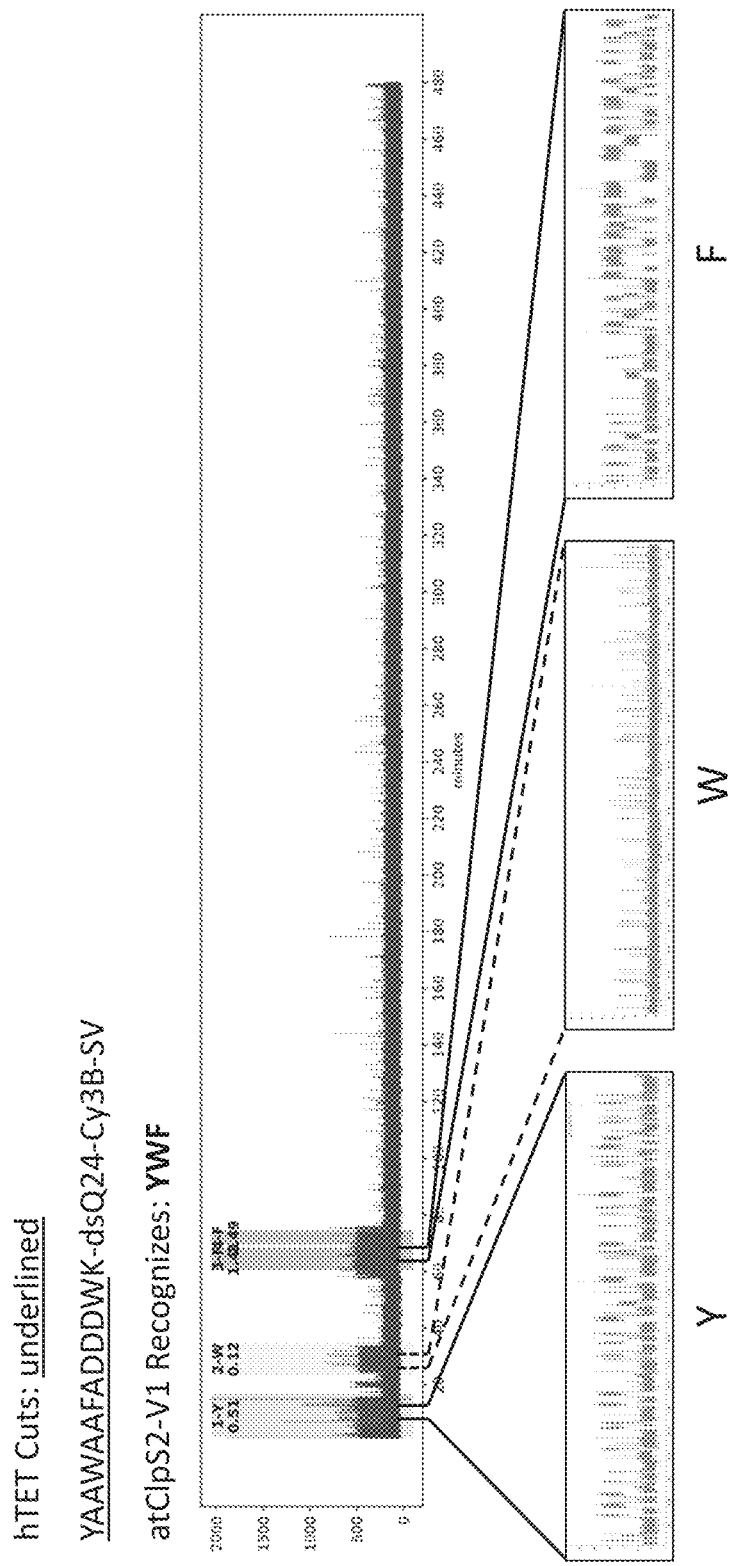
Figure 28B:
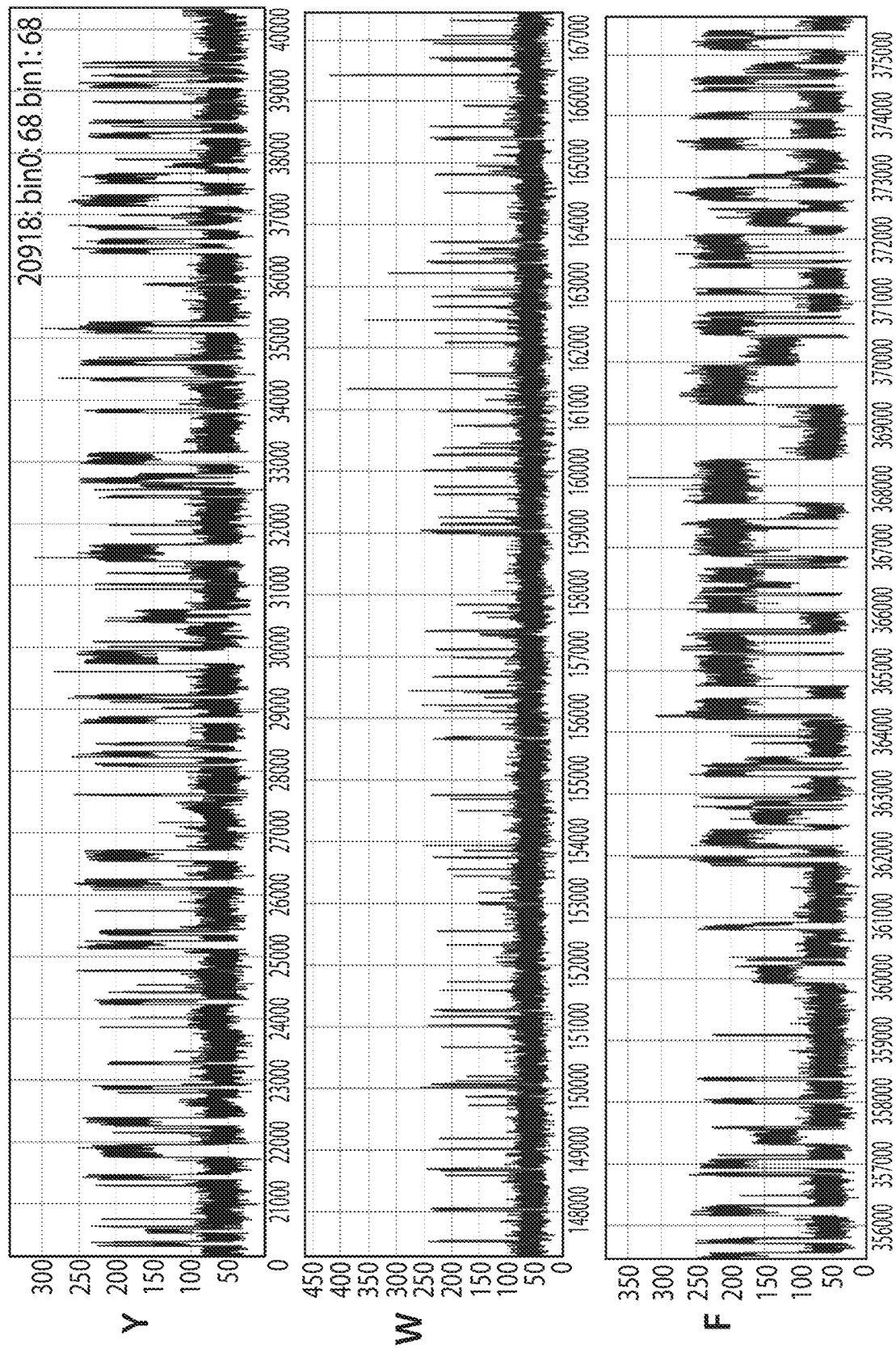
Figure 28C:
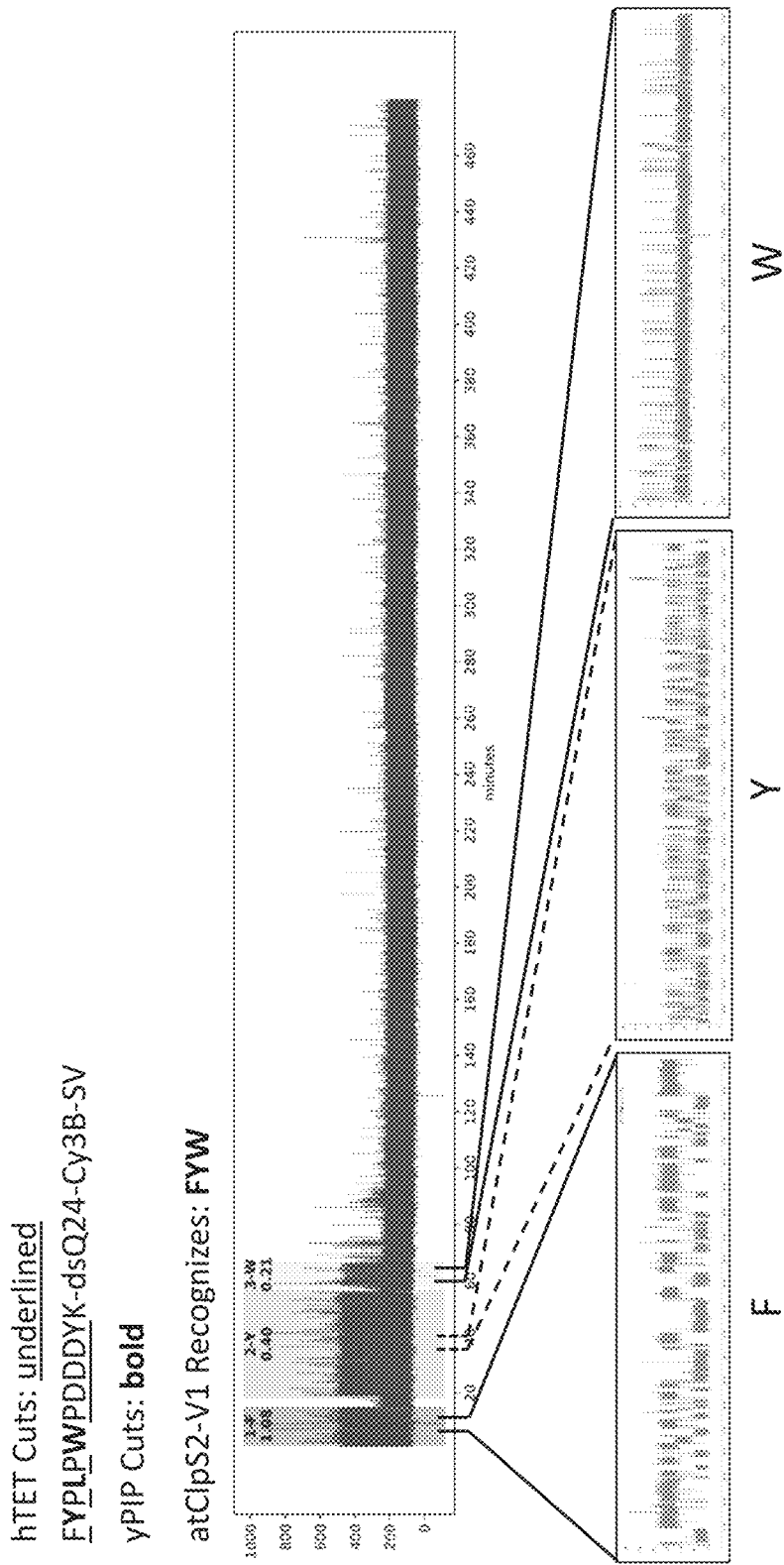
Figure 28D:
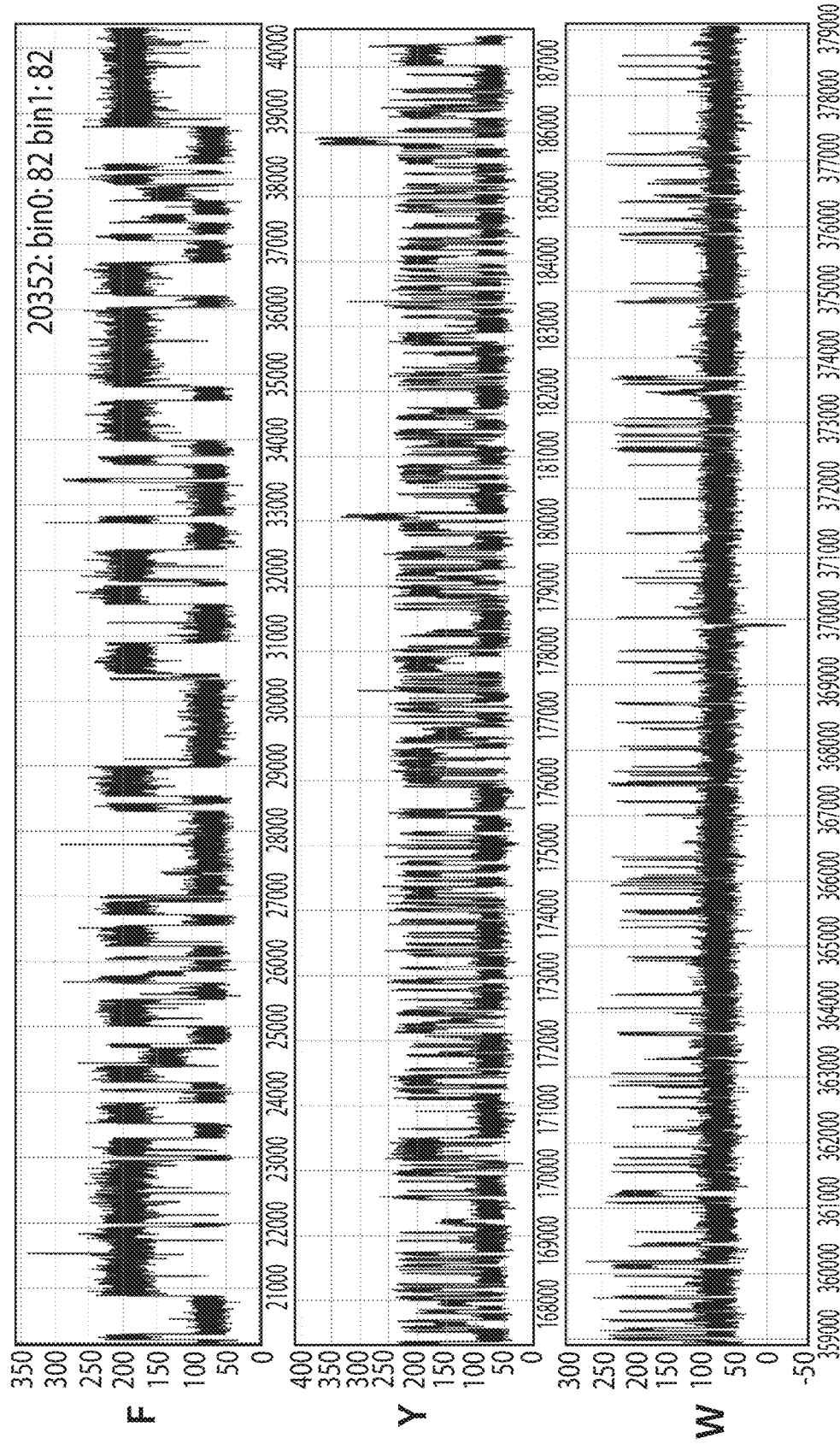
Figure 28E:
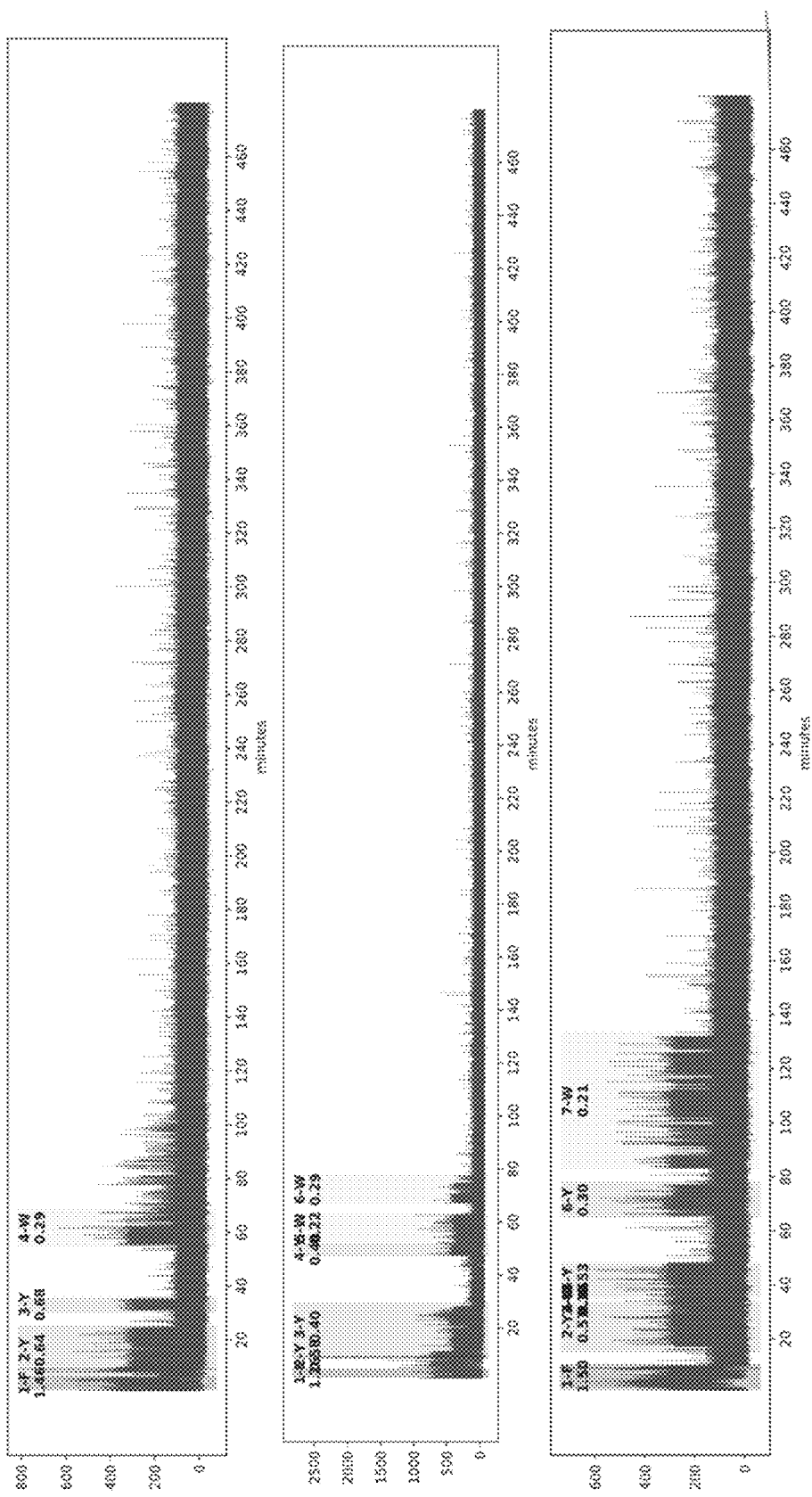
Figure 28F:
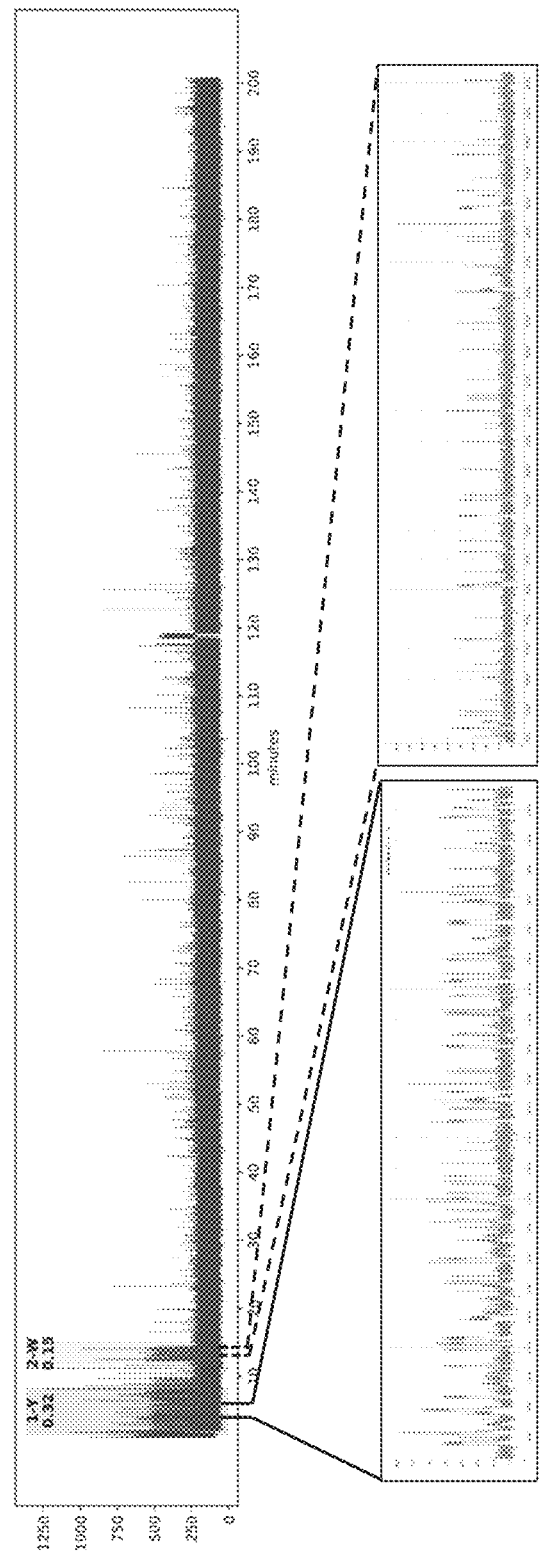
Figure 28G:
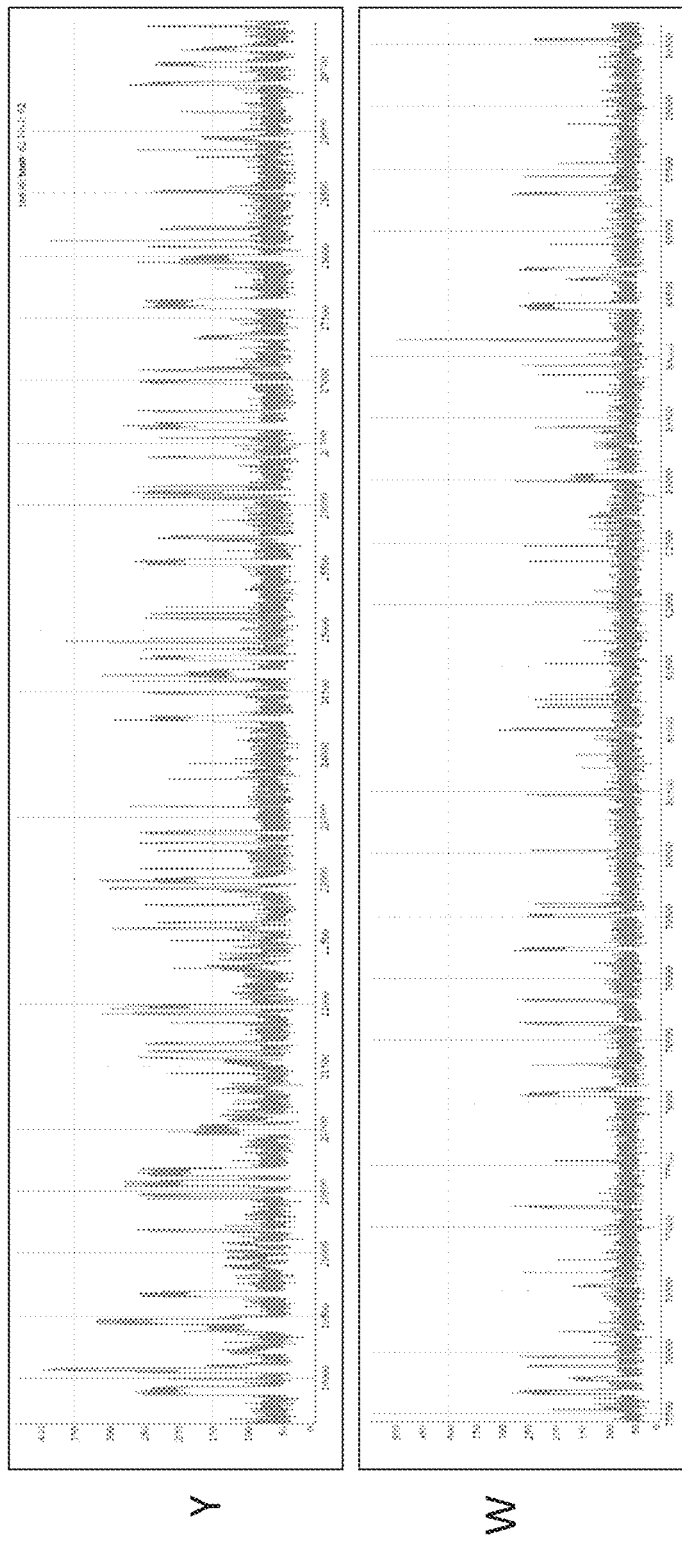
Figure 28H:
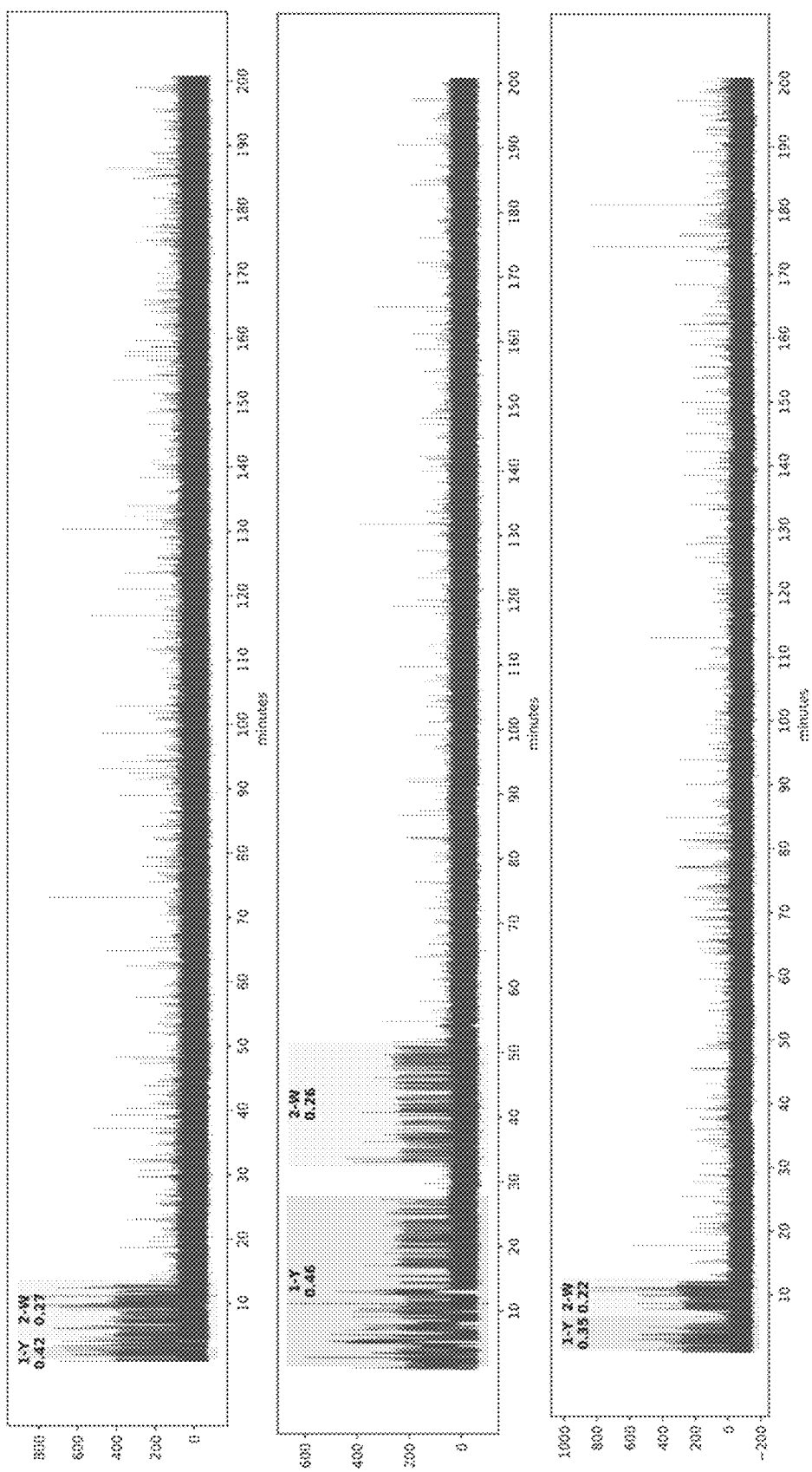
Figure 28I:
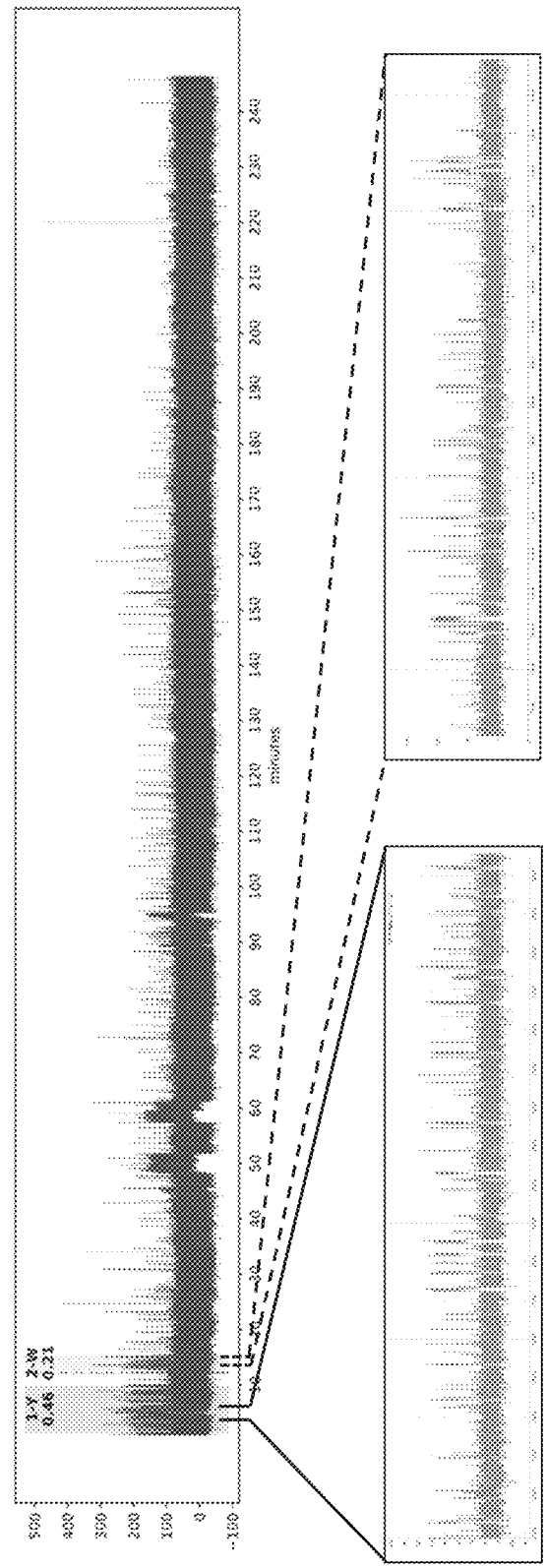
Figure 28J:
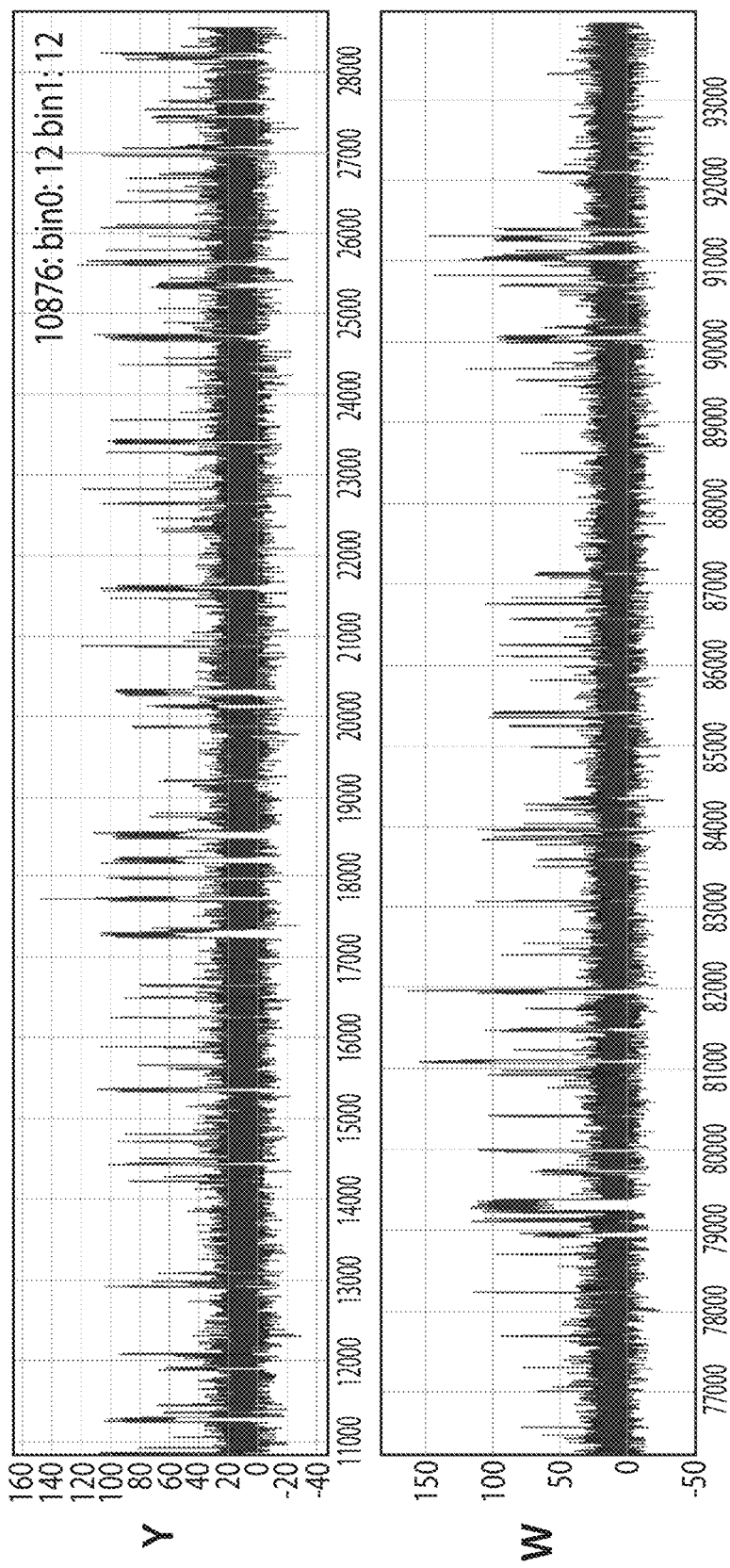

FIGS. 28A-28J show representative trace data from polypeptide sequencing reactions conducted in real-time using multiple types of exopeptidases with differential cleavage specificities. FIG. 28A shows a representative trace from a reaction performed with hTET exopeptidase, with expanded pulse pattern regions shown in FIG. 28B. The sequence YAAWAAFADDDWK in FIG. 28A corresponds to SEQ ID NO: 78. FIG. 28C shows a representative trace from a reaction performed with both hTET and yPIP exopeptidases, with expanded pulse pattern regions shown in FIG. 28D, and additional representative traces shown in FIG. 28E. The sequence FYPLPWPDDDYK in FIG. 28C corresponds to SEQ ID NO: 80. FIG. 28F shows a representative trace from a further reaction performed with both hTET and yPIP exopeptidases, with expanded pulse pattern regions shown in FIG. 28G, and additional representative traces shown in FIG. 28H. FIG. 28I shows a representative trace from a reaction performed with both PfuTET and yPIP exopeptidases, with expanded pulse pattern regions shown in FIG. 28J. The sequence YPLPWPDDDYK in FIGS. 28F and 28I corresponds to SEQ ID NO: 81.

DETAILED DESCRIPTION

Aspects of the application relate to methods of protein sequencing and identification, methods of polypeptide sequencing and identification, methods of amino acid identification, and compositions for performing such methods.

In some aspects, the application relates to the discovery of polypeptide sequencing techniques which may be implemented using existing analytic instruments with few or no device modifications. For example, previous polypeptide sequencing strategies have involved iterative cycling of different reagent mixtures through a reaction vessel containing a polypeptide being analyzed. Such strategies may require modification of an existing analytic instrument, such as a nucleic acid sequencing instrument, which may not be equipped with a flow cell or similar apparatus capable of reagent cycling. The inventors have recognized and appreciated that certain polypeptide sequencing techniques of the application do not require iterative reagent cycling, thereby permitting the use of existing instruments without significant modifications which might increase instrument size. Accordingly, in some aspects, the application provides methods of polypeptide sequencing that permit the use of smaller sequencing instruments. In some aspects, the application relates to the discovery of polypeptide sequencing techniques that allow both genomic and proteomic analyses to be performed using the same sequencing instrument.

The inventors have further recognized and appreciated that differential binding interactions can provide an additional or alternative approach to conventional labeling strategies in polypeptide sequencing. Conventional polypeptide sequencing can involve labeling each type of amino acid with a uniquely identifiable label. This process can be laborious and prone to error, as there are at least twenty different types of naturally occurring amino acids in addition to numerous post-translational variations thereof. In some aspects, the application relates to the discovery of techniques involving the use of amino acid recognition molecules which differentially associate with different types of amino acids to produce detectable characteristic signatures indicative of an amino acid sequence of a polypeptide. Accordingly, aspects of the application provide techniques that do not require polypeptide labeling and/or harsh chemical reagents used in certain conventional polypeptide sequencing approaches, thereby increasing throughput and/or accuracy of sequence information obtained from a sample.

In some aspects, the application relates to the discovery that a polypeptide sequencing reaction can be monitored in real-time using only a single reaction mixture (e.g., without requiring iterative reagent cycling through a reaction vessel). As detailed above, conventional polypeptide sequencing reactions can involve exposing a polypeptide to different reagent mixtures to cycle between steps of amino acid detection and amino acid cleavage. Accordingly, in some aspects, the application relates to an advancement in next generation sequencing that allows for the analysis of polypeptides by amino acid detection throughout an ongoing degradation reaction in real-time. Approaches for such polypeptide analysis by dynamic sequencing are described below.

As described herein, in some aspects, the application provides methods of sequencing a polypeptide by obtaining data during a polypeptide degradation process, and analyzing the data to determine portions of the data corresponding to amino acids that are sequentially exposed at a terminus of the polypeptide during the degradation process. In some embodiments, the portions of the data comprise a series of signal pulses indicative of association of one or more amino acid recognition molecules with successive amino acids exposed at the terminus of the polypeptide (e.g., during a degradation). In some embodiments, the series of signal pulses corresponds to a series of reversible single molecule binding interactions at the terminus of the polypeptide during the degradation process.

A non-limiting example of polypeptide sequencing by detecting single molecule binding interactions during a polypeptide degradation process is schematically illustrated in FIG. 1A. An example signal trace (I) is shown with a series of panels (II) that depict different association events at times corresponding to changes in the signal. As shown, an association event between an amino acid recognition molecule (stippled shape) and an amino acid at the terminus of a polypeptide (shown as beads-on-a-string) produces a change in magnitude of the signal that persists for a duration of time.

Panels (A) and (B) depict different association events between an amino acid recognition molecule and a first amino acid exposed at the terminus of the polypeptide (e.g., a first terminal amino acid). Each association event produces a change in the signal trace (I) characterized by a change in magnitude of the signal that persists for the duration of the association event.

Accordingly, the time duration between the association events of panels (A) and (B) may correspond to a duration of time within which the polypeptide is not detectably associated with an amino acid recognition molecule.

Panels (C) and (D) depict different association events between an amino acid recognition molecule and a second amino acid exposed at the terminus of the polypeptide (e.g., a second terminal amino acid). As described herein, an amino acid that is "exposed" at the terminus of a polypeptide is an amino acid that is still attached to the polypeptide and that becomes the terminal amino acid upon removal of the prior terminal amino acid during degradation (e.g., either alone or along with one or more additional amino acids). Accordingly, the first and second amino acids of the series of panels (II) provide an illustrative example of successive amino acids exposed at the terminus of the polypeptide, where the second amino acid became the terminal amino acid upon removal of the first amino acid.

As generically depicted, the association events of panels (C) and (D) produce changes in the signal trace (I) characterized by changes in magnitude that persist for time durations that are relatively shorter than that of panels (A) and (B), and the time duration between the association events of panels (C) and (D) is relatively shorter than that of panels (A) and (B). As described herein, in some embodiments, either one or both of these distinctive changes in signal may be used to determine characteristic patterns in the signal trace (I) which can discriminate between different types of amino acids. In some embodiments, a transition from one characteristic pattern to another is indicative of amino acid cleavage. As used herein, in some embodiments, amino acid cleavage refers to the removal of at least one amino acid from a terminus of a polypeptide (e.g., the removal of at least one terminal amino acid from the polypeptide). In some embodiments, amino acid cleavage is determined by inference based on a time duration between characteristic patterns. In some embodiments, amino acid cleavage is determined by detecting a change in signal produced by association of a labeled cleaving reagent with an amino acid at the terminus of the polypeptide. As amino acids are sequentially cleaved from the terminus of the polypeptide during degradation, a series of changes in magnitude, or a series of signal pulses, is detected. In some embodiments, signal pulse data can be analyzed as illustrated in FIG. 1B.

In some embodiments, signal data can be analyzed to extract signal pulse information by applying threshold levels to one or more parameters of the signal data. For example, panel (III) depicts a threshold magnitude level ("$M_L$") applied to the signal data of the example signal trace (I). In some embodiments, $M_L$ is a minimum difference between a signal detected at a point in time and a baseline determined for a given set of data. In some embodiments, a signal pulse ("sp") is assigned to each portion of the data that is indicative of a change in magnitude exceeding $M_L$ and persisting for a duration of time. In some embodiments, a threshold time duration may be applied to a portion of the data that satisfies $M_L$ to determine whether a signal pulse is assigned to that portion. For example, experimental artifacts may give rise to a change in magnitude exceeding $M_L$ that does not persist for a duration of time sufficient to assign a signal pulse with a desired confidence (e.g., transient association events which could be non-discriminatory for amino acid type, non-specific detection events such as diffusion into an observation region or reagent sticking within an observation region). Accordingly, in some embodiments, a signal pulse is extracted from signal data based on a threshold magnitude level and a threshold time duration.

Extracted signal pulse information is shown in panel (III) with the example signal trace (I) superimposed for illustrative purposes. In some embodiments, a peak in magnitude of a signal pulse is determined by averaging the magnitude detected over a duration of time that persists above $M_L$. It should be appreciated that, in some embodiments, a "signal pulse" as used herein can refer to a change in signal data that persists for a duration of time above a baseline (e.g., raw signal data, as illustrated by the example signal trace (I)), or to signal pulse information extracted therefrom (e.g., processed signal data, as illustrated in panel (IV)).

Panel (IV) shows the signal pulse information extracted from the example signal trace (I). In some embodiments, signal pulse information can be analyzed to identify different types of amino acids in a sequence based on different characteristic patterns in a series of signal pulses. For example, as shown in panel (IV), the signal pulse information is indicative of a first type of amino acid based on a first characteristic pattern ("$CP_1$") and a second type of amino acid based on a second characteristic pattern ("$CP_2$"). By way of example, the two signal pulses detected at earlier time points provide information indicative of the first amino acid at the terminus of the polypeptide based on $CP_1$, and the two signal pulses detected at later time points provide information indicative of the second amino acid at the terminus of the polypeptide based on $CP_2$.

Also as shown in panel (IV), each signal pulse comprises a pulse duration ("pd") corresponding to an association event between the amino acid recognition molecule and the amino acid of the characteristic pattern. In some embodiments, the pulse duration is characteristic of a dissociation rate of binding. Also as shown, each signal pulse of a characteristic pattern is separated from another signal pulse of the characteristic pattern by an interpulse duration ("ipd"). In some embodiments, the interpulse duration is characteristic of an association rate of binding. In some embodiments, a change in magnitude ("ΔM") can be determined for a signal pulse based on a difference between baseline and the peak of a signal pulse. In some embodiments, a characteristic pattern is determined based on pulse duration. In some embodiments, a characteristic pattern is determined based on pulse duration and interpulse duration. In some embodiments, a characteristic pattern is determined based on any one or more of pulse duration, interpulse duration, and change in magnitude.

Accordingly, as illustrated by FIGS. 1A-1B, in some embodiments, polypeptide sequencing is performed by detecting a series of signal pulses indicative of association of one or more amino acid recognition molecules with successive amino acids exposed at the terminus of a polypeptide in an ongoing degradation reaction. The series of signal pulses can be analyzed to determine characteristic patterns in the series of signal pulses, and the time course of characteristic patterns can be used to determine an amino acid sequence of the polypeptide.

In some embodiments, the series of signal pulses comprises a series of changes in magnitude of an optical signal over time. In some embodiments, the series of changes in the optical signal comprises a series of changes in luminescence produced during association events. In some embodiments, luminescence is produced by a detectable label associated with one or more reagents of a sequencing reaction. For example, in some embodiments, each of the one or more amino acid recognition molecules comprises a luminescent label. In some embodiments, a cleaving reagent comprises a luminescent label. Examples of luminescent labels and their use in accordance with the application are provided elsewhere herein.

In some embodiments, the series of signal pulses comprises a series of changes in magnitude of an electrical signal over time. In some embodiments, the series of changes in the electrical signal comprises a series of changes in conductance produced during association events. In some embodiments, conductivity is produced by a detectable label associated with one or more reagents of a sequencing reaction. For example, in some embodiments, each of the one or more amino acid recognition molecules comprises a conductivity label. Examples of conductivity labels and their use in accordance with the application are provided elsewhere herein. Methods for identifying single molecules using conductivity labels have been described (see, e.g., U.S. Patent Publication No. 2017/0037462).

In some embodiments, the series of changes in conductance comprises a series of changes in conductance through a nanopore. For example, methods of evaluating receptor-ligand interactions using nanopores have been described (see, e.g., Thakur, A. K. & Movileanu, L. (2019) *Nature Biotechnology* 37(1)). The inventors have recognized and appreciated that such nanopores may be used to monitor polypeptide sequencing reactions in accordance with the application. Accordingly, in some embodiments, the application provides methods of polypeptide sequencing comprising contacting a single polypeptide molecule with one or more amino acid recognition molecules, where the single polypeptide molecule is immobilized to a nanopore. In some embodiments, the methods further comprise detecting a series of changes in conductance through the nanopore indicative of association of the one or more terminal amino acid recognition molecules with successive amino acids exposed at a terminus of the single polypeptide while the single polypeptide is being degraded, thereby sequencing the single polypeptide molecule.

In some aspects, the application provides methods of sequencing and/or identifying an individual protein in a complex mixture of proteins by identifying one or more types of amino acids of a polypeptide from the mixture. In some embodiments, one or more amino acids (e.g., terminal amino acids and/or internal amino acids) of the polypeptide are labeled (e.g., directly or indirectly, for example using a binding agent such as an amino acid recognition molecule) and the relative positions of the labeled amino acids in the polypeptide are determined. In some embodiments, the relative positions of amino acids in a polypeptide are determined using a series of amino acid labeling and cleavage steps. However, in some embodiments, the relative position of labeled amino acids in a polypeptide can be determined without removing amino acids from the polypeptide but by translocating a labeled polypeptide through a pore (e.g., a protein channel) and detecting a signal (e.g., a FRET signal) from the labeled amino acid(s) during translocation through the pore in order to determine the relative position of the labeled amino acids in the polypeptide molecule.

In some embodiments, the identity of a terminal amino acid (e.g., an N-terminal or a C-terminal amino acid) is assessed after which the terminal amino acid is removed and the identity of the next amino acid at the terminus is assessed, and this process is repeated until a plurality of successive amino acids in the polypeptide are assessed. In some embodiments, assessing the identity of an amino acid comprises determining the type of amino acid that is present. In some embodiments, determining the type of amino acid comprises determining the actual amino acid identity, for example by determining which of the naturally-occurring 20 amino acids is the terminal amino acid is (e.g., using a binding agent that is specific for an individual terminal amino acid). In some embodiments, the type of amino acid is selected from alanine, arginine, asparagine, aspartic acid, cysteine, glutamine, glutamic acid, glycine, histidine, isoleucine, leucine, lysine, methionine, phenylalanine, proline, selenocysteine, serine, threonine, tryptophan, tyrosine, and valine.

However, in some embodiments assessing the identity of a terminal amino acid type can comprise determining a subset of potential amino acids that can be present at the terminus of the polypeptide. In some embodiments, this can be accomplished by determining that an amino acid is not one or more specific amino acids (and therefore could be any of the other amino acids). In some embodiments, this can be accomplished by determining which of a specified subset of amino acids (e.g., based on size, charge, hydrophobicity, post-translational modification, binding properties) could be at the terminus of the polypeptide (e.g., using a binding agent that binds to a specified subset of two or more terminal amino acids).

In some embodiments, assessing the identity of a terminal amino acid type comprises determining that an amino acid comprises a post-translational modification. Non-limiting examples of post-translational modifications include acetylation, ADP-ribosylation, caspase cleavage, citrullination, formylation, N-linked glycosylation, O-linked glycosylation, hydroxylation, methylation, myristoylation, neddylation, nitration, oxidation, palmitoylation, phosphorylation, prenylation, S-nitrosylation, sulfation, sumoylation, and ubiquitination.

In some embodiments, assessing the identity of a terminal amino acid type comprises determining that an amino acid comprises a side chain characterized by one or more biochemical properties. For example, an amino acid may comprise a nonpolar aliphatic side chain, a positively charged side chain, a negatively charged side chain, a nonpolar aromatic side chain, or a polar uncharged side chain. Non-limiting examples of an amino acid comprising a nonpolar aliphatic side chain include alanine, glycine, valine, leucine, methionine, and isoleucine. Non-limiting examples of an amino acid comprising a positively charged side chain includes lysine, arginine, and histidine. Non-limiting examples of an amino acid comprising a negatively charged side chain include aspartate and glutamate. Non-limiting examples of an amino acid comprising a nonpolar, aromatic side chain include phenylalanine, tyrosine, and tryptophan. Non-limiting examples of an amino acid comprising a polar uncharged side chain include serine, threonine, cysteine, proline, asparagine, and glutamine.

In some embodiments, a protein or polypeptide can be digested into a plurality of smaller polypeptides and sequence information can be obtained from one or more of these smaller polypeptides (e.g., using a method that involves sequentially assessing a terminal amino acid of a polypeptide and removing that amino acid to expose the next amino acid at the terminus).

In some embodiments, a polypeptide is sequenced from its amino (N) terminus. In some embodiments, a polypeptide is sequenced from its carboxy (C) terminus. In some embodiments, a first terminus (e.g., N or C terminus) of a polypeptide is immobilized and the other terminus (e.g., the C or N terminus) is sequenced as described herein.

As used herein, sequencing a polypeptide refers to determining sequence information for a polypeptide. In some embodiments, this can involve determining the identity of each sequential amino acid for a portion (or all) of the polypeptide. However, in some embodiments, this can involve assessing the identity of a subset of amino acids within the polypeptide (e.g., and determining the relative position of one or more amino acid types without determining the identity of each amino acid in the polypeptide). However, in some embodiments amino acid content information can be obtained from a polypeptide without directly determining the relative position of different types of amino acids in the polypeptide. The amino acid content alone may be used to infer the identity of the polypeptide that is present (e.g., by comparing the amino acid content to a database of polypeptide information and determining which polypeptide(s) have the same amino acid content).

In some embodiments, sequence information for a plurality of polypeptide products obtained from a longer polypeptide or protein (e.g., via enzymatic and/or chemical cleavage) can be analyzed to reconstruct or infer the sequence of the longer polypeptide or protein.

Accordingly, in some embodiments, the one or more types of amino acids are identified by detecting luminescence of one or more labeled affinity reagents that selectively bind the one or more types of amino acids. In some embodiments, the one or more types of amino acids are identified by detecting luminescence of a labeled polypeptide.

The inventors have further recognized and appreciated that the polypeptide sequencing techniques described herein may involve generating novel polypeptide sequencing data, particularly in contrast with conventional polypeptide sequencing techniques. Thus, conventional techniques for analyzing polypeptide sequencing data may not be sufficient when applied to the data generated using the polypeptide sequencing techniques described herein.

For example, conventional polypeptide sequencing techniques that involve iterative reagent cycling may generate data associated with individual amino acids of a polypeptide being sequenced. In such instances, analyzing the data generated may simply involve determining which amino acid is being detected at a particular time because the data being detected corresponds to only one amino acid. In contrast, the polypeptide sequencing techniques described herein may generate data during a polypeptide degradation process while multiple amino acids of the polypeptide molecule are being detected, resulting in data where it may be difficult to discern between sections of the data corresponding to different amino acids of the polypeptide. Accordingly, the inventors have developed new computational techniques for analyzing such data generated by the polypeptide sequencing techniques described herein that involve determining sections of the data that correspond to individual amino acids, such as by segmenting the data into portions that correspond to respective amino acid association events. Those sections may be then further analyzed to identify the amino acid being detected during those individual sections.

As another example, conventional sequencing techniques that involve using uniquely identifiable labels for each type of amino acid may involve simply analyzing which label is being detected at a particular time without taking into consideration any dynamics in how individual amino acids interact with other molecules. In contrast, the polypeptide sequencing techniques described herein generate data indicating how amino acids interact with recognition molecules. As discussed above, the data may include a series of characteristic patterns corresponding to association events between amino acids and their respective recognition molecules. Accordingly, the inventors have developed new computational techniques for analyzing the characteristic patterns to determine a type of amino acid corresponding to that portion of the data, allowing for an amino acid sequence of a polypeptide to be determined by analyzing a series of different characteristic patterns.

Labeled Affinity Reagents and Methods of Use

In some embodiments, methods provided herein comprise contacting a polypeptide with a labeled affinity reagent (also referred to herein as an amino acid recognition molecule, which may or may not comprise a label) that selectively binds one type of terminal amino acid. As used herein, in some embodiments, a terminal amino acid may refer to an amino-terminal amino acid of a polypeptide or a carboxy-terminal amino acid of a polypeptide. In some embodiments, a labeled affinity reagent selectively binds one type of terminal amino acid over other types of terminal amino acids. In some embodiments, a labeled affinity reagent selectively binds one type of terminal amino acid over an internal amino acid of the same type. In yet other embodiments, a labeled affinity reagent selectively binds one type of amino acid at any position of a polypeptide, e.g., the same type of amino acid as a terminal amino acid and an internal amino acid.

As used herein, in some embodiments, a type of amino acid refers to one of the twenty naturally occurring amino acids or a subset of types thereof. In some embodiments, a type of amino acid refers to a modified variant of one of the twenty naturally occurring amino acids or a subset of unmodified and/or modified variants thereof. Examples of modified amino acid variants include, without limitation, post-translationally-modified variants (e.g., acetylation, ADP-ribosylation, caspase cleavage, citrullination, formylation, N-linked glycosylation, O-linked glycosylation, hydroxylation, methylation, myristoylation, neddylation, nitration, oxidation, palmitoylation, phosphorylation, prenylation, S-nitrosylation, sulfation, sumoylation, and ubiquitination), chemically modified variants, unnatural amino acids, and proteinogenic amino acids such as selenocysteine and pyrrolysine. In some embodiments, a subset of types of amino acids includes more than one and fewer than twenty amino acids having one or more similar biochemical properties. For example, in some embodiments, a type of amino acid refers to one type selected from amino acids with charged side chains (e.g., positively and/or negatively charged side chains), amino acids with polar side chains (e.g., polar uncharged side chains), amino acids with nonpolar side chains (e.g., nonpolar aliphatic and/or aromatic side chains), and amino acids with hydrophobic side chains.

In some embodiments, methods provided herein comprise contacting a polypeptide with one or more labeled affinity reagents that selectively bind one or more types of terminal amino acids. As an illustrative and non-limiting example, where four labeled affinity reagents are used in a method of the application, any one reagent selectively binds one type of terminal amino acid that is different from another type of amino acid to which any of the other three selectively binds (e.g., a first reagent binds a first type, a second reagent binds a second type, a third reagent binds a third type, and a fourth reagent binds a fourth type of terminal amino acid). For the purposes of this discussion, one or more labeled affinity reagents in the context of a method described herein may be alternatively referred to as a set of labeled affinity reagents.

In some embodiments, a set of labeled affinity reagents comprises at least one and up to six labeled affinity reagents. For example, in some embodiments, a set of labeled affinity reagents comprises one, two, three, four, five, or six labeled affinity reagents. In some embodiments, a set of labeled affinity reagents comprises ten or fewer labeled affinity reagents. In some embodiments, a set of labeled affinity reagents comprises eight or fewer labeled affinity reagents. In some embodiments, a set of labeled affinity reagents comprises six or fewer labeled affinity reagents. In some embodiments, a set of labeled affinity reagents comprises four or fewer labeled affinity reagents. In some embodiments, a set of labeled affinity reagents comprises three or fewer labeled affinity reagents. In some embodiments, a set of labeled affinity reagents comprises two or fewer labeled affinity reagents. In some embodiments, a set of labeled affinity reagents comprises four labeled affinity reagents. In some embodiments, a set of labeled affinity reagents comprises at least two and up to twenty (e.g., at least two and up to ten, at least two and up to eight, at least four and up to twenty, at least four and up to ten) labeled affinity reagents. In some embodiments, a set of labeled affinity reagents comprises more than twenty (e.g., 20 to 25, 20 to 30) affinity reagents. It should be appreciated, however, that any number of affinity reagents may be used in accordance with a method of the application to accommodate a desired use.

In accordance with the application, in some embodiments, one or more types of amino acids are identified by detecting luminescence of a labeled affinity reagent (e.g., an amino acid recognition molecule comprising a luminescent label). In some embodiments, a labeled affinity reagent comprises an affinity reagent that selectively binds one type of amino acid and a luminescent label having a luminescence that is associated with the affinity reagent. In this way, the luminescence (e.g., luminescence lifetime, luminescence intensity, and other luminescence properties described elsewhere herein) may be associated with the selective binding of the affinity reagent to identify an amino acid of a polypeptide. In some embodiments, a plurality of types of labeled affinity reagents may be used in a method according to the application, wherein each type comprises a luminescent label having a luminescence that is uniquely identifiable from among the plurality. Suitable luminescent labels may include luminescent molecules, such as fluorophore dyes, and are described elsewhere herein.

In some embodiments, one or more types of amino acids are identified by detecting one or more electrical characteristics of a labeled affinity reagent. In some embodiments, a labeled affinity reagent comprises an affinity reagent that selectively binds one type of amino acid and a conductivity label that is associated with the affinity reagent. In this way, the one or more electrical characteristics (e.g., charge, current oscillation color, and other electrical characteristics) may be associated with the selective binding of the affinity reagent to identify an amino acid of a polypeptide. In some embodiments, a plurality of types of labeled affinity reagents may be used in a method according to the application, wherein each type comprises a conductivity label that produces a change in an electrical signal (e.g., a change in conductance, such as a change in amplitude of conductivity and conductivity transitions of a characteristic pattern) that is uniquely identifiable from among the plurality. In some embodiments, the plurality of types of labeled affinity reagents each comprises a conductivity label having a different number of charged groups (e.g., a different number of negatively and/or positively charged groups). Accordingly, in some embodiments, a conductivity label is a charge label. Examples of charge labels include dendrimers, nanoparticles, nucleic acids and other polymers having multiple charged groups. In some embodiments, a conductivity label is uniquely identifiable by its net charge (e.g., a net positive charge or a net negative charge), by its charge density, and/or by its number of charged groups.

In some embodiments, an affinity reagent (e.g., an amino acid recognition molecule) may be engineered by one skilled in the art using conventionally known techniques. In some embodiments, desirable properties may include an ability to bind selectively and with high affinity to one type of amino acid only when it is located at a terminus (e.g., an N-terminus or a C-terminus) of a polypeptide. In yet other embodiments, desirable properties may include an ability to bind selectively and with high affinity to one type of amino acid when it is located at a terminus (e.g., an N-terminus or a C-terminus) of a polypeptide and when it is located at an internal position of the polypeptide. In some embodiments, desirable properties include an ability to bind selectively and with low affinity (e.g., with a $K_D$ of about 50 nM or higher, for example, between about 50 nM and about 50 µM, between about 100 nM and about 10 µM, between about 500 nM and about 50 µM) to more than one type of amino acid. For example, in some aspects, the application provides methods of sequencing by detecting reversible binding interactions during a polypeptide degradation process. Advantageously, such methods may be performed using an affinity reagent that reversibly binds with low affinity to more than one type of amino acid (e.g., a subset of amino acid types).

As used herein, in some embodiments, the terms "selective" and "specific" (and variations thereof, e.g., selectively, specifically, selectivity, specificity) refer to a preferential binding interaction. For example, in some embodiments, a labeled affinity reagent that selectively binds one type of amino acid preferentially binds the one type over another type of amino acid. A selective binding interaction will discriminate between one type of amino acid (e.g., one type of terminal amino acid) and other types of amino acids (e.g., other types of terminal amino acids), typically more than about 10- to 100-fold or more (e.g., more than about 1,000- or 10,000-fold). Accordingly, it should be appreciated that a selective binding interaction can refer to any binding interaction that is uniquely identifiable to one type of amino acid over other types of amino acids. For example, in some aspects, the application provides methods of polypeptide sequencing by obtaining data indicative of association of one or more amino acid recognition molecules with a polypeptide molecule. In some embodiments, the data comprises a series of signal pulses corresponding to a series of reversible amino acid recognition molecule binding interactions with an amino acid of the polypeptide molecule, and the data may be used to determine the identity of the amino acid. As such, in some embodiments, a "selective" or "specific" binding interaction refers to a detected binding interaction that discriminates between one type of amino acid and other types of amino acids.

In some embodiments, a labeled affinity reagent (e.g., an amino acid recognition molecule) selectively binds one type of amino acid with a dissociation constant ($K_D$) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to as low as $10^{-16}$ M) without significantly binding to other types of amino acids. In some embodiments, a labeled affinity reagent selectively binds one type of amino acid (e.g., one type of terminal amino acid) with a $K_D$ of less than about 100 nM, less than about 50 nM, less than about 25 nM, less than about 10 nM, or less than about 1 nM. In some embodiments, a labeled affinity reagent selectively binds one type of amino acid with a $K_D$ of between about 50 nM and about 50 M (e.g., between about 50 nM and about 500 nM, between about 50 nM and about 5 µM, between about 500 nM and about 50 µM, between about 5 µM and about 50 µM, or between about 10 µM and about 50 µM). In some embodiments, a labeled affinity reagent selectively binds one type of amino acid with a $K_D$ of about 50 nM.

In some embodiments, a labeled affinity reagent (e.g., an amino acid recognition molecule) selectively binds two or more types of amino acids with a dissociation constant ($K_D$) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to as low as $10^{-16}$ M). In some embodiments, a labeled affinity reagent selectively binds two or more types of amino acids with a $K_D$ of less than about 100 nM, less than about 50 nM, less than about 25 nM, less than about 10 nM, or less than about 1 nM. In some embodiments, a labeled affinity reagent selectively binds two or more types of amino acids with a $K_D$ of between about 50 nM and about 50 M (e.g., between about 50 nM and about 500 nM, between about 50 nM and about 5 µM, between about 500 nM and about 50 µM, between about 5 µM and about 50 µM, or between about 10 µM and about 50 µM). In some embodiments, a labeled affinity reagent selectively binds two or more types of amino acids with a $K_D$ of about 50 nM.

In accordance with the methods and compositions provided herein, FIG. 1C shows various example configurations and uses of labeled affinity reagents. In some embodiments, a labeled affinity reagent 100 comprises a luminescent label 110 (e.g., a label) and an affinity reagent (shown as stippled shapes) that selectively binds one or more types of terminal amino acids of a polypeptide 120. In some embodiments, an affinity reagent is selective for one type of amino acid or a subset (e.g., fewer than the twenty common types of amino acids) of types of amino acids at a terminal position or at both terminal and internal positions.

As described herein, an affinity reagent (also known as a "recognition molecule") may be any biomolecule capable of selectively or specifically binding one molecule over another molecule (e.g., one type of amino acid over another type of amino acid, as with an "amino acid recognition molecule" referred to herein). In some embodiments, an affinity reagent is not a peptidase or does not have peptidase activity. For example, in some embodiments, methods of polypeptide sequencing of the application involve contacting a polypeptide molecule with one or more affinity reagents and a cleaving reagent. In such embodiments, the one or more affinity reagents do not have peptidase activity, and removal of one or more amino acids from the polypeptide molecule (e.g., amino acid removal from a terminus of the polypeptide molecule) is performed by the cleaving reagent.

Affinity reagents (e.g., recognition molecules) include, for example, proteins and nucleic acids, which may be synthetic or recombinant. In some embodiments, an affinity reagent or recognition molecule may be an antibody or an antigen-binding portion of an antibody, an SH2 domain-containing protein or fragment thereof, or an enzymatic biomolecule, such as a peptidase, an aminotransferase, a ribozyme, an aptazyme, or a tRNA synthetase, including aminoacyl-tRNA synthetases and related molecules described in U.S. patent application Ser. No. 15/255,433, filed Sep. 2, 2016, titled "MOLECULES AND METHODS FOR ITERATIVE POLYPEPTIDE ANALYSIS AND PROCESSING."

In some embodiments, an affinity reagent or recognition molecule of the application is a degradation pathway protein. Examples of degradation pathway proteins suitable for use as recognition molecules include, without limitation, N-end rule pathway proteins, such as Arg/N-end rule pathway proteins, Ac/N-end rule pathway proteins, and Pro/N-end rule pathway proteins. In some embodiments, a recognition molecule is an N-end rule pathway protein selected from a Gid protein (e.g., Gid4 or Gid10 protein), a UBR box protein (e.g., UBR1, UBR2) or UBR box domain-containing protein fragment thereof, a p62 protein or ZZ domain-containing fragment thereof, and a ClpS protein (e.g., ClpS1, ClpS2).

In some embodiments, an affinity reagent or recognition molecule of the application is a ClpS protein, such as *Agrobacterium tumifaciens* ClpS1, *Agrobacterium tumifaciens* ClpS2, *Synechococcus elongatus* ClpS 1, *Synechococcus elongatus* ClpS2, *Thermosynechococcus elongatus* ClpS, *Escherichia coli* ClpS, or *Plasmodium falciparum* ClpS. In some embodiments, the recognition molecule is an L/F transferase, such as *Escherichia coli* leucyl/phenylalanyl-tRNA-protein transferase. In some embodiments, the recognition molecule is a D/E leucyltransferase, such as *Vibrio vulnificus* Aspartate/glutamate leucyltransferase Bpt. In some embodiments, the recognition molecule is a UBR protein or UBR-box domain, such as the UBR protein or UBR-box domain of human UBR1 and UBR2 or *Saccharomyces cerevisiae* UBR1. In some embodiments, the recognition molecule is a p62 protein, such as *H. sapiens* p62 protein or *Rattus norvegicus* p62 protein, or truncation variants thereof that minimally include a ZZ domain. In some embodiments, the recognition molecule is a Gid4 protein, such as *H. sapiens* GID4 or *Saccharomyces cerevisiae* GID4. In some embodiments, the recognition molecule is a Gid10 protein, such as *Saccharomyces cerevisiae* GID10. In some embodiments, the recognition molecule is an N-meristoyltransferase, such as *Leishmania major* N-meristoyltransferase or *H. sapiens* N-meristoyltransferase NMT1. In some embodiments, the recognition molecule is a BIR2 protein, such as *Drosophila melanogaster* BIR2. In some embodiments, the recognition molecule is a tyrosine kinase or SH2 domain of a tyrosine kinase, such as *H. sapiens* Fyn SH2 domain, *H. sapiens* Src tyrosine kinase SH2 domain, or variants thereof, such as *H. sapiens* Fyn SH2 domain triple mutant superbinder. In some embodiments, the recognition molecule is an antibody or antibody fragment, such as a single-chain antibody variable fragment (scFv) against phosphotyrosine or another post-translationally modified amino acid variant described herein.

Table 1 provides a list of example sequences of amino acid recognition molecules. Also shown are the amino acid binding preferences of each molecule with respect to amino acid identity at a terminal position of a polypeptide unless otherwise specified in Table 1. It should be appreciated that these sequences and other examples described herein are meant to be non-limiting, and recognition molecules in accordance with the application can include any homologs, variants thereof, or fragments thereof minimally containing domains or subdomains responsible for peptide recognition.

TABLE 1

Non-limiting examples of amino acid recognition proteins.

| Name | Binding Pref.* | SEQ ID NO: | Sequence |
|---|---|---|---|
| *Agrobacterium tumifaciens* ClpS2 variant 1 | F, W, Y | 1 | MSDSPVDLKPKPKVKPKLERPKLYKVMLLNDDYTPMSFV TVVLKAVFRMSEDTGRRVMMTAHRFGSAVVVVCERDIAE TKAKEATDLGKEAGFPLMFTTEPEE |
| *Agrobacterium tumifaciens* ClpS2 | F, W, Y | 2 | MSDSPVDLKPKPKVKPKLERPKLYKVMLLNDDYTPREFV TVVLKAVFRMSEDTGRRVMMTAHRFGSAVVVVCERDIAE TKAKEATDLGKEAGFPLMFTTEPEE |
| *Agrobacterium tumifaciens* ClpS2 C71S | F, W, Y | 3 | MSDSPVDLKPKPKVKPKLERPKLYKVMLLNDDYTPREFV TVVLKAVFRMSEDTGRRVMMTAHRFGSAVVVVSERDIAE TKAKEATDLGKEAGFPLMFTTEPEE |
| *Agrobacterium tumifaciens* ClpS1 | F, W, Y, L | 4 | MIAEPICMQGEGDGEDGGTNRGTSVITRVKPKTKRPNLY RVLLLNDDYTPMEFVIHILERFFQKDREAATRIMLHVHQ HGVGECGVFTYEVAETKVSQVMDFARQHQHPLQCVMEKK |
| *Agrobacterium tumifaciens* ClpS2 variant 1 C72S | F, W, Y | 5 | MSDSPVDLKPKPKVKPKLERPKLYKVMLLNDDYTPMSFV TVVLKAVFRMSEDTGRRVMMTAHRFGSAVVVVSERDIAE TKAKEATDLGKEAGFPLMFTTEPEE |
| *Agrobacterium tumifaciens* ClpS1 C7S | F, W, Y, L | 6 | MIAEPISMQGEGDGEDGGTNRGTSVITRVKPKTKRPNLY RVLLLNDDYTPMEFVIHILERFFQKDREAATRIMLHVHQ HGVGECGVFTYEVAETKVSQVMDFARQHQHPLQCVMEKK |
| *Agrobacterium tumifaciens* ClpS1 C7S C84S C112S | F, W, Y, L | 7 | MIAEPISMQGEGDGEDGGTNRGTSVITRVKPKTKRPNLY RVLLLNDDYTPMEFVIHILERFFQKDREAATRIMLHVHQ HGVGESGVFTYEVAETKVSQVMDFARQHQHPLQSVMEKK |
| *Agrobacterium tumifaciens* ClpS2 thermostable variant | F, W, Y | 8 | MSDSPVDLKPKPKVKPKLERPKLYKVILLNDDYTPMEFV VEVLKRVFNMSEEQARRVMMTAHKKGKAVVGVCPRDIAE TKAKQATDLAREAGFPLMFTTEPEE |
| *Agrobacterium tumifaciens* ClpS2 thermostable variant C72S | F, W, Y | 9 | MSDSPVDLKPKPKVKPKLERPKLYKVILLNDDYTPMEFV VEVLKRVFNMSEEQARRVMMTAHKKGKAVVGVSPRDIAE TKAKQATDLAREAGFPLMFTTEPEE |
| *Synechococcus elongatus* ClpS1 | F, W, Y | 10 | MAVETIQKPETTTKRKIAPRYRVLLHNDDFNPMEYVVMV LMQTVPSLTQPQAVDIMMEAHTNGTGLVITCDIEPAEFY CEQLKSHGLSSSIEPDD |
| *Synechococcus elongatus* ClpS2 | F, W, Y, L, V, I | 11 | MSPQPDESVLSILGVPRPCVKKRSRNDAFVLTVLTCSLQ AIAAPATAPGTTTTRVRQPYPHFRVIVLDDDVNTFQHVA ECLLKYIPGMTGDRAWDLTNQVHYEGAATVWSGPQEQAE LYHEQLRREGLTMAPLEAA |
| *Thermosynechococcus elongatus* ClpS | F, W, Y, L | 12 | MPQERQQVTRKHYPNYKVIVLNDDFNTFQHVAACLMKYI PNMTSDRAWELTNQVHYEGQAIVWVGPQEQAELYHEQLL RAGLTMAPLEPE |
| *Escherichia coli* ClpS | F, W, Y, L | 13 | MGKTNDWLDFDQLAEEKVRDALKPPSMYKVILVNDDYTP MEFVIDVLQKFFSYDVERATQLMLAVHYQGKAICGVFTA EVAETKVAMVNKYARENEHPLLCTLEKA |

TABLE 1-continued

Non-limiting examples of amino acid recognition proteins.

| Name | Binding Pref.* | SEQ ID NO: | Sequence |
|---|---|---|---|
| *Escherichia coli* ClpS M40A | F, W, Y, L | 14 | MGKTNDWLDFDQLAEEKVRDALKPPSMYKVILVNDDYTP AEFVIDVLQKFFSYDVERATQLMLAVHYQGKAICGVFTA EVAETKVAMVNKYARENEHPLLCTLEKA |
| *Plasmodium falciparum* ClpS | F, W, Y, L, I | 15 | MEKDLKPFFLCIILLLLLIYKCTHSYNIKNKNCPLNFMN SCVRINNVNKNTNISFPKELQKRPSLVYSQKNFNLEKIK KLRNVIKEIKKDNIKEADEHEKKEREKETSAWKVILYND DIHNFTYVTDVIVKVVGQISKAKAHTITVEAHSTGQALI LSTWKSKAEKYCQELQQNGLTVSIIHESQLKDKQKK |
| *Escherichia coli* leucyl/phenylalanyl-tRNA-protein transferase | K, R | 16 | MRLVQLSRHSIAFPSPEGALREPNGLLALGGDLSPARLL MAYQRGIFPWFSPGDPILWWSPDPRAVLWPESLHISRSM KRFHKRSPYRVTMNYAFGQVIEGCASDREEGTWITRGVV EAYHRLHELGHAHSIEVWREDELVGGMYGVAQGTLFCGE SMFSRMENASKTALLVFCEEFIGHGGKLIDCQVLNDHTA SLGACEIPRRDYLNYLNQMRLGRLPNNFWVPRCLFSPQE LE |
| *Vibrio vulnificus* Aspartate/glutamate leucyltransferase Bpt | D, E | 17 | MSSDIHQIKIGLTDNHPCSYLPERKERVAVALEADMHTA DNYEVLLANGFRRSGNTIYKPHCDSCHSCQPIRISVPDI ELSRSQKRLLAKARSLSWSMKRNMDENWFDLYSRYIVAR HRNGTMYPPKKDDFAHFSRNQWLTTQFLHIYEGQRLIAV AVTDIMDHCASAFYTFFEPEHELSLGTLAVLFQLEFCQE EKKQWLYLGYQIDECPAMNYKVRFHRHQKLVNQRWQ |
| *Saccharomyces cerevisiae* UBR1 | K, R, H | 18 | MGSVHKHTGRNCGRKFKIGEPLYRCHECGCDDTCVLCIH CFNPKDHVNHHVCTDICTEFTSGICDCGDEEAWNSPLHC KAEEQ |
| *H. sapiens* GID4 | P | 19 | MSGSKFRGHQKSKGNSYDVEVVLQHVDTGNSYLCGYLKI KGLTEEYPTLTTFFEGEIISKKHPFLTRKWDADEDVDRK HWGKFLAFYQYAKSFNSDDFDYEELKNGDYVFMRWKEQF LVPDHTIKDISGASFAGFYYICFQKSAASIEGYYYHRSS EWYQSLNLTHV |
| *Saccharomyces cerevisiae* GID4 | P | 20 | MINNPKVDSVAEKPKAVTSKQSEQAASPEPTPAPPVSRN QYPITFNLTSTAPFHLHDRHRYLQEQDLYKCASRDSLSS LQQLAHTPNGSTRKKYIVEDQSPYSSENPVIVTSSYNHT VCTNYLRPRMQFTGYQISGYKRYQVTVNLKTVDLPKKDC TSLSPHLSGFLSIRGLTNQHPEISTYFEAYAVNHKELGF LSSSWKDEPVLNEFKATDQTDLEHWINFPSFRQLFLMSQ KNGLNSTDDNGTTNAAKKLPPQQLPTTPSADAGNISRIF SQEKQEDNYLNERFIFMKWKEKFLVPDALLMEGVDGASY DGFYYIVHDQVTGNIQGFYYHQDAEKFQQLELVPSLKNK VESSDCSFEFA |
| Single-chain antibody variable fragment (scFv) against phosphotyrosine** | phospho-Y | 21 | MMEVQLQQSGPELVKPGASVMISCRTSAYTFTENTVHWV KQSHGESLEWIGGINPYYGGSIFSPKFKGKATLTVDKSS STAYMELRSLTSEDSAVYYCARRAGAYYFDYWGQGTTLT VSSGGGSGGGSGGGSENVLTQSPAIMSASPGEKVTMTCR ASSSVSSSYLHWYRQKSGASPKLWIYSTSNLASGVPARF SGSGSGTSYSLTISSVEAEDAATYYCQQYSGYRTFGGGT KLEIKR |
| *H. sapiens* Fyn SH2 domain** | phospho-Y | 22 | MGAMDSIQAEEWYFGKLGRKDAERQLLSFGNPRGTFLIR ESETTKGAYSLSIRDWDDMKGDHVKHYKIRKLDNGGYYI TTRAQFETLQQLVQHYSERAAGLSSRLVVPSHK |
| *H. sapiens* Fyn SH2 domain triple mutant superbinder** | phospho-Y | 23 | MGAMDSIQAEEWYFGKLGRKDAERQLLSFGNPRGTFLIR ESETVKGAYALSIRDWDDMKGDHVKHYLIRKLDNGGYYI TTRAQFETLQQLVQHYSERAAGLSSRLVVPSHK |
| *H. sapiens* Src tyrosine kinase SH2 domain** | phospho-Y | 24 | MGAMDSIQAEEWYFGKITRRESERLLLNAENPRGTFLVR ESETTKGAYSLSVSDFDNAKGLNVKHYKIRKLDSGGFYI TSRTQFNSLQQLVAYYSKHADGLCHRLTTVCPTSK |
| *H. sapiens* Src tyrosine kinase SH2 domain triple mutant** | phospho-Y | 25 | MGAMDSIQAEEWYFGKITRRESERLLLNAENPRGTFLVR ESEVTKGAYALSVSDFDNAKGLNVKHYLIRKLDSGGFYI TSRTQFNSLQQLVAYYSKHADGLCHRLTTVCPTSK |
| *H. sapiens* p62 fragment 1-310 | K, R, H, W, F, Y | 26 | MASLTVKAYLLGKEDAAREIRRFSFCCSPEPEAEAEAAA GPGPCERLLSRVAALFPALRPGGFQAHYRDEDGDLVAFS SDEELTMAMSYVKDDIFRIYIKEKKECRRDHRPPCAQEA |

TABLE 1-continued

Non-limiting examples of amino acid recognition proteins.

| Name | Binding Pref.* | SEQ ID NO: | Sequence |
|---|---|---|---|
| | | | PRNMVHPNVICDGCNGPVVGTRYKCSVCPDYDLCSVCEG KGLHRGHTKLAFPSPFGHLSEGFSHSRWLRKVKHGHFGW PGWEMGPPGNWSPRPPRAGEARPGPTAESASGPSEDPSV NFLKNVGESVAAALSPLGIEVDIDVEHGGKRSRLTPVSP ESSSTEEKSSSQPSSCCSDPSKPGGNVEGATQSLAEQ |
| H. sapiens p62 fragment 1-180 | K, R, H, W, F, Y | 27 | MASLTVKAYLLGKEDAAREIRRFSFCCSPEPEAEAEAAA GPGPCERLLSRVAALFPALRPGGFQAHYRDEDGDLVAFS SDEELTMAMSYVKDDIFRIYIKEKKECRRDHRPPCAQEA PRNMVHPNVICDGCNGPVVGTRYKCSVCPDYDLCSVCEG KGLHRGHTKLAFPSPFGHLSEGFSHSRWLRKVKHGHFGW PGWEMGPPGNWSPRPPRAGEARPGPTAESASGPSEDPSV NFLKNVGESVAAALSPLGIEVDIDVEHGGKRSRLTPVSP ESSSTEEKSSSQPSSCCSDPSKPGGNVEGATQSLAEQ |
| H. sapiens p62 fragment 126-180 | K, R, H, W, F, Y | 28 | MASLTVKAYLLGKEDAAREIRRFSFCCSPEPEAEAEAAA GPGPCERLLSRVAALFPALRPGGFQAHYRDEDGDLVAFS SDEELTMAMSYVKDDIFRIYIKEKKECRRDHRPPCAQEA PRNMVHPNVICDGCNGPVVGTRYKCSVCPDYDLCSVCEG KGLHRGHTKLAFPSPFGHLSEGFSHSRWLRKVKHGHFGW PGWEMGPPGNWSPRPPRAGEARPGPTAESASGPSEDPSV NFLKNVGESVAAALSPLGIEVDIDVEHGGKRSRLTPVSP ESSSTEEKSSSQPSSCCSDPSKPGGNVEGATQSLAEQ |
| H. sapiens p62 protein | K, R, H, W, F, Y | 29 | MASLTVKAYLLGKEDAAREIRRFSFCCSPEPEAEAEAAA GPGPCERLLSRVAALFPALRPGGFQAHYRDEDGDLVAFS SDEELTMAMSYVKDDIFRIYIKEKKECRRDHRPPCAQEA PRNMVHPNVICDGCNGPVVGTRYKCSVCPDYDLCSVCEG KGLHRGHTKLAFPSPFGHLSEGFSHSRWLRKVKHGHFGW PGWEMGPPGNWSPRPPRAGEARPGPTAESASGPSEDPSV NFLKNVGESVAAALSPLGIEVDIDVEHGGKRSRLTPVSP ESSSTEEKSSSQPSSCCSDPSKPGGNVEGATQSLAEQMR KIALESEGRPEEQMESDNCSGGDDDWTHLSSKEVDPSTG ELQSLQMPESEGPSSLDPSQEGPTGLKEAALYPHLPPEA DPRLIESLSQMLSMGFSDEGGWLTRLLQTKNYDIGAALD TIQYSKHPPPL |
| Rattus norvegicus p62 protein | K, R, H, W, F, Y | 30 | MASLTVKAYLLGKEEAAREIRRFSFCFSPEPEAEAAAGP GPCERLLSRVAVLFPALRPGGFQAHYRDEDGDLVAFSSD EELTMAMSYVKDDIFRIYIKEKKECRREHRPPCAQEARS MVHPNVICDGCNGPVVGTRYKCSVCPDYDLCSVCEGKGL HREHSKLIFPNPFGHLSDSFSHSRWRLKLKHGHFGWPGW EMGPPGNWSPRPPRAGDGRPCPTAESASAPSEDPNVNFL KNVGESVAAALSPLGIEVDIDVEHGGKRSRLTPTSAESS STGTEDKSGTQPSSCSSEVSKPDGAGEGPAQSLTEQMKK IALESVGQPEELMESDNCSGGDDDWTHLSSKEVDPSTGE LQSLQMPESEGPSSLDPSQEGPTGLKEAALYPHLPPEAD PRLIESLSQMLSMGFSDEGGWLTRLLQTKNYDIGAALDT IQYSKHPPPL |
| Saccharomyces cerevisiae GID10 | P, M, V | 31 | MTSLNIMGRKFILERAKRNDNIEEIYTSAYVSLPSSTDT RLPHFKAKEEDCDVYEEGTNLVGKNAKYTYRSLGRHLDF LRPGLRFGGSQSSKYTYYTVEVKIDTVNLPLYKDSRSLD PHVTGTFTIKNLTPVLDKVVTLFEGYVINYNQFPLCSLH WPAEETLDPYMAQRESDCSHWKRFGHFGSDNWSLTERNF GQYNHESAEFMNQRYTYLKWKERFLLDDEEQENQMLDDN HHLEGASFEGFYYVCLDQLTGSVEGYYYHPACELFQKLE LVPTNCDALNTYSSGFEIA |
| UBR-box domain from Homo sapiens UBR1 | K, R, H | 32 | MGPLGSLCGRVFKSGETTYSCRDCAIDPTCVLCMDCFQD SVHKNHRYKMHTSTGGGFCDCGDTEAWKTGPFCVNHEP |
| UBR-box domain from Homo sapiens UBR2 | K, R, H | 33 | MGPLGSLCGRVFKVGEPTYSCRDCAVDPTCVLCMECFLG SIHRDHRYRMTTSGGGGFCDCGDTEAWKEGPYCQKHE |
| Leishmania major G N-meristoyltransferase | | 34 | MSRNPSNSDAAHAFWSTQPVPQTEDETEKIVFAGPMDEP KTVADIPEEPYPIASTFEWWTPNMEAADDIHAIYELLRD NYVEDDDSMFRFNYSEEFLQWALCAPPNYIPDWHVAVRRK ADKKLLAFIAGVPVTLRMGTPKYMKVKAQEKGEGEEAAK YDEPRHICEINFLCVHKQLREKRLAPILIKEATRRVNRT NVWQAVYTAGVLLPTPYASGQYFHRSLNPEKLVEIRFSG IPAQYQKFQNPMAMLKRNYQLPSAPKNSGLREMKPSDVP QVRRILMNYLDSFDVGPVFSDAEISHYLLPRDGVVFTYV |

TABLE 1-continued

Non-limiting examples of amino acid recognition proteins.

| Name | Binding Pref.* | SEQ ID NO: | Sequence |
|---|---|---|---|
| | | | VENDKKVTDFFSFYRIPSTVIGNSNYNLLNAAYVHYYAA TSIPLHQLILDLLIVAHSRGFDVCNMVEILDNRSFVEQL KFGAGDGHLRYYFYNWAYPKIKPSQVALVML |
| H. sapiens N-meristoyltransferase NMT1 | G | 35 | MADESETAVKPPAPPLPQMMEGNGNGHEHCSDCENEEDN SYNRGGLSPANDTGAKKKKKKQKKKKEKGSETDSAQDQP VKMNSLPAERIQEIQKAIELFSVGQGPAKTMEEASKRSY QFWDTQPVPKLGEVVNTHGPVEPDKDNIRQEPYTLPQGF TWDALDLGDRGVLKELYTLLNENYVEDDDNMFRFDYSPE FLLWALRPPGWLPQWHCGVRVVSSRKLVGFISAIPANTH IYDTEKKMVEINFLCVHKKLRSKRVAPVLIREITRRVHL EGIFQAVYTAGVVLPKPVGTCRYWHRSLNPRKLIEVKFS HLSRNMTMQRTMKLYRLPETPKTAGLRPMETKDIPVVHQ LLTRYLKQFHLTPVMSQEEVEHWFYPQENIIDTFVVENA NGEVTDFLSFYTLPSTIMNHPTHKSLKAAYSFYNVHTQT PLLDLMSDALVLAKMKGFDVFNALDLMENKTFLEKLKFG IGDGNLQYYLYNWKCPSMGAEKVGLVLQ |
| Drosophila melanogaster BIR2 | A | 36 | MGDVQPETCRPSAASGNYFPQYPEYAIETARLRTFEAWP RNLKQKPHQLAEAGFFYTGVGDRVRCFSCGGGLMDWNDN DEPWEQHALWLSQCRFVKLMKGQLYIDTVAAKPVLAEEK EESTSIGGDT |

*Binding preferences are inferred from published scientific literature and/or further demonstrated by the inventors in single-molecule experiments, as described herein.
**Binding to phosphotyrosine may occur at a peptide terminus or at an internal position.

Accordingly, in some embodiments, the application provides an amino acid recognition molecule having an amino acid sequence selected from Table 1 (or having an amino acid sequence that has at least 50%, at least 60%, at least 70%, at least 80%, 80-90%, 90-95%, 95-99%, or higher, amino acid sequence identity to an amino acid sequence selected from Table 1). In some embodiments, an amino acid recognition molecule has 25-50%, 50-60%, 60-70%, 70-80%, 80-90%, 90-95%, or 95-99%, or higher, amino acid sequence identity to an amino acid recognition molecule listed in Table 1. In some embodiments, an amino acid recognition molecule is a modified amino acid recognition molecule and includes one or more amino acid mutations relative to a sequence set forth in Table 1.

In some embodiments, an amino acid recognition molecule comprises a tag sequence that provides one or more functions other than amino acid binding. For example, in some embodiments, a tag sequence comprises a biotin ligase recognition sequence that permits biotinylation of the recognition molecule (e.g., incorporation of one or more biotin molecules, including biotin and bis-biotin moieties). Additional examples of functional sequences in a tag sequence include purification tags, cleavage sites, and other moieties useful for purification and/or modification of recognition molecules. Table 2 provides a list of non-limiting sequences of terminal tag sequences, any one or more of which may be used in combination with any one of the amino acid recognition molecules of the application (e.g., in combination with a sequence set forth in Table 1). It should be appreciated that the tag sequences shown in Table 2 are meant to be non-limiting, and recognition molecules in accordance with the application can include any one or more of the tag sequences (e.g., His-tags and/or biotinylation tags) at the N- or C-terminus of a recognition molecule polypeptide, split between the N- and C-terminus, or otherwise rearranged as practiced in the art.

TABLE 2

Non-limiting examples of terminal tag sequences.

| Name | SEQ ID NO: | Sequence |
|---|---|---|
| Biotinylation tag | 37 | GGGSGGGSGGGSGLNDFFEAQKIEWHE |
| Bis-biotinylation tag | 38 | GGGSGGGSGGGSGLNDFFEAQKIEWHEGGGSGGGSGGGSGLNDFFE AQKIEWHE |
| Bis-biotinylation tag | 39 | GSGGGSGGGSGGGSGLNDFFEAQKIEWHEGGGSGGGSGGGSGLNDF FEAQKIEWHE |
| His/biotinylation tag | 40 | GHHHHHHHHHGGGSGGGSGGGSGLNDFFEAQKIEWHE |
| His/bis-biotinylation tag | 41 | GHHHHHHHHHGGGSGGGSGGGSGLNDFFEAQKIEWHEGGGSGGGS GGGSGLNDFFEAQKIEWHE |
| His/bis-biotinylation tag | 42 | GGSHHHHHHHHHGGGSGGGSGGGSGLNDFFEAQKIEWHEGGGSGG GSGGGSGLNDFFEAQKIEWHE |

TABLE 2-continued

Non-limiting examples of terminal tag sequences.

| Name | SEQ ID NO: | Sequence |
|---|---|---|
| His/bis-biotinylation tag | 43 | GSHHHHHHHHHGGGSGGGSGGGSGLNDFFEAQKIEWHEGGGSGGG SGGGSGLNDFFEAQKIEWHE |
| Bis-biotinylation/His tag | 44 | GGGSGGGSGGGSGLNDFFEAQKIEWHEGGGSGGGSGGGSGLNDFFE AQKIEWHEGHHHHHH |

In some embodiments, a recognition molecule or affinity reagent of the application is a peptidase. A peptidase, also referred to as a protease or proteinase, is an enzyme that catalyzes the hydrolysis of a peptide bond. Peptidases digest polypeptides into shorter fragments and may be generally classified into endopeptidases and exopeptidases, which cleave a polypeptide chain internally and terminally, respectively. In some embodiments, labeled affinity reagent 100 comprises a peptidase that has been modified to inactivate exopeptidase or endopeptidase activity. In this way, labeled affinity reagent 100 selectively binds without also cleaving the amino acid from a polypeptide. In yet other embodiments, a peptidase that has not been modified to inactivate exopeptidase or endopeptidase activity may be used. For example, in some embodiments, a labeled affinity reagent comprises a labeled exopeptidase 102.

In accordance with certain embodiments of the application, protein sequencing methods may comprise iterative detection and cleavage at a terminal end of a polypeptide. In some embodiments, labeled exopeptidase 102 may be used as a single reagent that performs both steps of detection and cleavage of an amino acid. As generically depicted, in some embodiments, labeled exopeptidase 102 has aminopeptidase or carboxypeptidase activity such that it selectively binds and cleaves an N-terminal or C-terminal amino acid, respectively, from a polypeptide. It should be appreciated that, in certain embodiments, labeled exopeptidase 102 may be catalytically inactivated by one skilled in the art such that labeled exopeptidase 102 retains selective binding properties for use as a non-cleaving labeled affinity reagent 100, as described herein.

An exopeptidase generally requires a polypeptide substrate to comprise at least one of a free amino group at its amino-terminus or a free carboxyl group at its carboxy-terminus. In some embodiments, an exopeptidase in accordance with the application hydrolyses a bond at or near a terminus of a polypeptide. In some embodiments, an exopeptidase hydrolyses a bond not more than three residues from a polypeptide terminus. For example, in some embodiments, a single hydrolysis reaction catalyzed by an exopeptidase cleaves a single amino acid, a dipeptide, or a tripeptide from a polypeptide terminal end.

In some embodiments, an exopeptidase in accordance with the application is an aminopeptidase or a carboxypeptidase, which cleaves a single amino acid from an amino- or a carboxy-terminus, respectively. In some embodiments, an exopeptidase in accordance with the application is a dipeptidyl-peptidase or a peptidyl-dipeptidase, which cleave a dipeptide from an amino- or a carboxy-terminus, respectively. In yet other embodiments, an exopeptidase in accordance with the application is a tripeptidyl-peptidase, which cleaves a tripeptide from an amino-terminus. Peptidase classification and activities of each class or subclass thereof is well known and described in the literature (see, e.g., Gurupriya, V. S. & Roy, S. C. Proteases and Protease Inhibitors in Male Reproduction. Proteases in Physiology and Pathology 195-216 (2017); and Brix, K. & Stöcker, W. Proteases: Structure and Function. Chapter 1). In some embodiments, a peptidase in accordance with the application removes more than three amino acids from a polypeptide terminus. Accordingly, in some embodiments, the peptidase is an endopeptidase, e.g., that cleaves preferentially at particular positions (e.g., before or after a particular amino acid). In some embodiments, the size of a polypeptide cleavage product of endopeptidase activity will will depend on the distribution of cleavage sites (e.g., amino acids) within the polypeptide being analyzed.

An exopeptidase in accordance with the application may be selected or engineered based on the directionality of a sequencing reaction. For example, in embodiments of sequencing from an amino-terminus to a carboxy-terminus of a polypeptide, an exopeptidase comprises aminopeptidase activity. Conversely, in embodiments of sequencing from a carboxy-terminus to an amino-terminus of a polypeptide, an exopeptidase comprises carboxypeptidase activity. Examples of carboxypeptidases that recognize specific carboxy-terminal amino acids, which may be used as labeled exopeptidases or inactivated to be used as non-cleaving labeled affinity reagents described herein, have been described in the literature (see, e.g., Garcia-Guerrero, M. C., et al. (2018) *PNAS* 115(17)).

Suitable peptidases for use as cleaving reagents and/or affinity reagents (e.g., recognition molecules) include aminopeptidases that selectively bind one or more types of amino acids. In some embodiments, an aminopeptidase recognition molecule is modified to inactivate aminopeptidase activity. In some embodiments, an aminopeptidase cleaving reagent is non-specific such that it cleaves most or all types of amino acids from a terminal end of a polypeptide. In some embodiments, an aminopeptidase cleaving reagent is more efficient at cleaving one or more types of amino acids from a terminal end of a polypeptide as compared to other types of amino acids at the terminal end of the polypeptide. For example, an aminopeptidase in accordance with the application specifically cleaves alanine, arginine, asparagine, aspartic acid, cysteine, glutamine, glutamic acid, glycine, histidine, isoleucine, leucine, lysine, methionine, phenylalanine, proline, selenocysteine, serine, threonine, tryptophan, tyrosine, and/or valine. In some embodiments, an aminopeptidase is a proline aminopeptidase. In some embodiments, an aminopeptidase is a proline iminopeptidase. In some embodiments, an aminopeptidase is a glutamate/aspartate-specific aminopeptidase. In some embodiments, an aminopeptidase is a methionine-specific aminopeptidase. In some embodiments, an aminopeptidase is an aminopeptidase set forth in Table 3. In some embodiments, an aminopeptidase cleaving reagent cleaves a peptide substrate as set forth in Table 3.

In some embodiments, an aminopeptidase is a non-specific aminopeptidase. In some embodiments, a non-specific aminopeptidase is a zinc metalloprotease. In some embodiments, a non-specific aminopeptidase is an aminopeptidase set forth in Table 4. In some embodiments, a non-specific aminopeptidase cleaves a peptide substrate as set forth in Table 4.

Accordingly, in some embodiments, the application provides an aminopeptidase (e.g., an aminopeptidase recognition molecule, an aminopeptidase cleaving reagent) having an amino acid sequence selected from Table 3 or Table 4 (or having an amino acid sequence that has at least 50%, at least 60%, at least 70%, at least 80%, 80-90%, 90-95%, 95-99%, or higher, amino acid sequence identity to an amino acid sequence selected from Table 3 or Table 4). In some embodiments, an aminopeptidase has 25-50%, 50-60%, 60-70%, 70-80%, 80-90%, 90-95%, or 95-99%, or higher, amino acid sequence identity to an aminopeptidase listed in Table 3 or Table 4. In some embodiments, an aminopeptidase is a modified aminopeptidase and includes one or more amino acid mutations relative to a sequence set forth in Table 3 or Table 4.

TABLE 3

Non-limiting examples of aminopeptidases.

| Name | SEQ ID NO: | Sequence |
|---|---|---|
| *L. pneumophila* M1 Aminopeptidase (Glu/Asp Specific) | 45 | MMVKQGVFMKTDQSKVKKLSDYKSLDYFVIHVDLQIDLSKKPVESK ARLTVVPNLNVDSHSNDLVLDGENMTLVSLQMNDNLLKENEYELTK DSLIIKNIPQNTPFTIEMTSLLGENTDLFGLYETEGVALVKAESEG LRRVFYLPDRPDNLATYKTTIIANQEDYPVLLSNGVLIEKKELPLG LHSVTWLDDVPKPSYLFALVAGNLQRSVTYYQTKSGRELPIEFYVP PSATSKCDFAKEVLKEAMAWDERTFNLECALRQHMVAGVDKYASGA SEPTGLNLFNTENLFASPETKTDLGILRVLEVVAHEFFHYWSGDRV TIRDWFNLPLKEGLITFRAAMFREELFGTDLIRLLDGKNLDERAPR QSAYTAVRSLYTAAAYEKSADIFRMMMLFIGKEPFIEAVAKFFKDN DGGAVTLEDFIESISNSSGKDLRSFLSWFTESGIPELIVTDELNPD TKQYFLKIKTVNGRNRPIPILMGLLDSSGAEIVADKLLIVDQEEIE FQFENIQTRPIPSLLRSFSAPVHMKYEYSYQDLLLLMQFDTNLYNR CEAAKQLISALINDFCIGKKIELSPQFFAVYKALLSDNSLNEWMLA ELITLPSLEELIENQDKPDFEKLNEGRQLIQNALANELKTDFYNLL FRIQISGDDDKQKLKGFDLKQAGLRRLKSVCFSYLLNVDFEKTKEK LILQFEDALGKNMTETALALSMLCEINCEEADVALEDYYHYWKNDP GAVNNWFSIQALAHSPDVIERVKKLMRHGDFDLSNPNKVYALLGSF IKNPFGFHSVTGEGYQLVADAIFDLDKINPTLAANLTEKFTYWDKY DVNRQAMMISTLKIIYSNATSSDVRTMAKKGLDKVKEDLPLPIHLT FHGGSTMQDRTAQLIADGNKENAYQLH |
| *E. coli* methionine aminopeptidase (Met specific) | 46 | MGTAISIKTPEDIEKMRVAGRLAAEVLEMIEPYVKPGVSTGELDRI CNDYIVNEQHAVSACLGYHGYPKSVCISINEVVCHGIPDDAKLLKD GDIVNIDVIVIKDGFHGDTSKMFIVGKPTIMGERLCRITQESLYLA LRMVKPGINLREIGAAIQKFVEAEGFSVVREYCGHGIGRGEHEEPQ VLHYDSRETNVVLKPGMTFTIEPMVNAGKKEIRTMKDGWTVKTKDR SLSAQYEHTIVVTDNGCEILTLRKDDTIPAIISHD |
| *M. smegmatis* Proline iminopeptidase (Pro specific) | 47 | MGTLEANTNGPGSMLSRMPVSSRTVPFGDHETWVQVTTPENAQPHA LPLIVLHGGPGMAHNYVANIAALADETGRTVIHYDQVGCGNSTHLP DAPADFWTPQLFVDEFHAVCTALGIERYHVLGQSWGGMLGAEIAVR QPSGLVSLAICNSPASMRLWSEAAGDLRAQLPAETRAALDRHEAAG TITHPDYLQAAAEFYRRHVCRVVPTPQDFADSVAQMEAEPTVYHTM NGPNEFHVVGTLGDWSVIDRLPDVTAPVLVIAGEHDEATPKTWQPF VDHIPDVRSHVFPGTSHCTHLEKPEEFRAVVAQFLHQHDLAADARV |
| *Y. pestis* Proline iminopeptidase (Pro Specific) | 48 | MTQQEYQNRRQALLAKMAPGSAAIIFAAPEATRSADSEYPYRQNSD FSYLTGFNEPEAVLILVKSDETHNHSVLFNRIRDLTAEIWFGRRLG QEAAPTKLAVDRALPFDEINEQLYLLLNRLDVIYHAQGQYAYADNI VFAALEKLRHGFRKNLRAPATLIDWRPWLHEMRLEKSAEEIAVLRR AGEISALAHTRAMEKCRPGMFEYQLEGEILHEFTRHGARYPAYNTI VGGGENGCILHYTENECELRDGDLVLIDAGCEYRGYAGDITRTFPV NGKFTPAQRAVYDIVLAAINKSLTLFRPGTSIREVTEEVVRIMVVG LVELGILKGDIEQLIAEQAHRPFFMHGLSHWLGMDVHDVGDYGSSD RGRILEPGMVLTVEPGLYIAPDADVPPQYRGIGIRIEDDIVITATG NENLTASVVKDPDDIEALMALNHAGENLYFQE |
| *P. furiosus* methionine aminopeptidase | 49 | MDTEKLMKAGEIAKKVREKAIKLARPGMLLLELAESIEKMIMELGG KPAFPVNLSINEIAAHYTPYKGDTTVLKEGDYLKIDVGVHIDGFIA DTAVTVRVGMEEDELMEAAKEALNAAISVARAGVEIKELGKAIENE IRKRGFKPIVNLSGHKIERYKLHAGISIPNIYRPHDNYVLKEGDVF AIEPFATIGAGQVIEVPPTLIYMYVRDVPVRVAQARFLLAKIKREY GTLPFAYRWLQNDMPEGQLKLALKTLEKAGAIYGYPVLKEIRNGIV AQFEHTIIVEKDSVIVTQDMINKSTLE |
| *Aeromonas sobria* Proline aminopeptidase | 50 | HMSSPLHYVLDGIHCEPHFFTVPLDHQQPDDEETITLFGRTLCRKD RLDDELPWLLYLQGGPGFGAPRPSANGGWIKRALQEFRVLLLDQRG TGHSTPIHAELLAHLNPRQQADYLSHFRADSIVRDAELIREQLSPD HPWSLLGQSFGGFCSLTYLSLFPDSLHEVYLTGGVAPIGRSADEVY RATYQRVADKNRAFFARFPHAQAIANRLATHLQRHDVRLPNGQRLT VEQLQQQGLDLGASGAFEELYYLLEDAFIGEKLNPAFLYQVQAMQP |

TABLE 3-continued

Non-limiting examples of aminopeptidases.

| Name | SEQ ID NO: | Sequence |
|---|---|---|
| | | FNTNPVFAILHELIYCEGAASHWAAERVRGEFPALAWAQGKDFAFT GEMIFPWMFEQFRELIPLKEAAHLLAEKADWGPLYDPVQLARNKVP VACAVYAEDMYVEFDYSRETLKGLSNSRAWITNEYEHNGLRVDGEQ ILDRLIRLNRDCLE |
| Pyrococcus furiosus Proline Aminopeptidase (X-/-Pro) | 51 | MKERLEKLVKFMDENSIDRVFIAKPVNVYYFSGTSPLGGGYIIVDG DEATLYVPELEYEMAKEESKLPVVKFKKFDEIYEILKNTETLGIEG TLSYSMVENFKEKSNVKEFKKIDDVIKDLRIIKTKEEIEIIEKACE IADKAVMAAIEEITEGKREREVAAKVEYLMKMNGAEKPAFDTIIAS GHRSALPHGVASDKRIERGDLVVIDLGALYNHYNSDITRTIVVGSP NEKQREIYEIVLEAQKRAVEAAKPGMTAKELDSIAREIIKEYGYGD YFIHSLGHGVGLEIHEWPRISQYDETVLKEGMVITIEPGIYIPKLG GVRIEDTVLITENGAKRLTKTERELL |
| Elizabethkingia meningoseptica Proline aminopeptidase | 52 | MIPITTPVGNFKVWTKRFGTNPKIKVLLLHGGPAMTHEYMECFETF FQREGFEFYEYDQLGSYYSDQPTDEKLWNIDRFVDEVEQVRKAIHA DKENFYVLGNSWGGILAMEYALKYQQNLKGLIVANMMASAPEYVKY AEVLSKQMKPEVLAEVRAIEAKKDYANPRYTELLFPNYYAQHICRL KEWPDALNRSLKHVNSTVYTLMQGPSELGMSSDARLAKWDIKNRLH EIATPTLMIGARYDTMDPKAMEEQSKLVQKGRYLYCPNGSHLAMWD DQKVFMDGVIKFIKDVDTKSFN |
| N. gonorrhoeae Proline Iminopeptidase | 53 | MYEIKQPFHSGYLQVSEIHQIYWEESGNPDGVPVIFLHGGPGAGAS PECRGFFNPDVFRIVIIDQRGCGRSHPYACAEDNTTWDLVADIEKV REMLGIGKWLVFGGSWGSTLSLAYAQTHPERVKGLVLRGIFLCRPS ETAWLNEAGGVSRIYPEQWQKFVAPIAENRRNRLIEAYHGLLFHQD EEVCLSAAKAWADWESYLIRFEPEGVDEDAYASLAIARLENHYFVN GGWLQGDKAILNNIGKIRHIPTVIVQGRYDLCTPMQSAWELSKAFP EAELRVVQAGHCAFDPPLADALVQAVEDILPRLL |

TABLE 4

Non-limiting examples of non-specific aminopeptidases.

| Name | SEQ ID NO: | Sequence |
|---|---|---|
| E. coli Aminopeptidase N* (Zinc Metalloprotease) | 54 | MTQQPQAKYRHDYRAPDYQITDIDLTFDLDAQKTVVTAVSQAVRHG ASDAPLRLNGEDLKLVSVHINDEPWTAWKEEEGALVISNLPERFTL KIINEISPAANTALEGLYQSGDALCTQCEAEGFRHITYYLDRPDVL ARFTTKIIADKIKYPFLLSNGNRVAQGELENGRHWVQWQDPFPKPC YLFALVAGDFDVLRDTFTTRSGREVALELYVDRGNLDRAPWAMTSL KNSMKWDEERFGLEYDLDIYMIVAVDFFNMGAMENKGLNIFNSKYV LARTDTATDKDYLDIERVIGHEYFHNWTGNRVTCRDWFQLSLKEGL TVFRDQEFSSDLGSRAVNRINNVRTMRGLQFAEDASPMAHPIRPDM VIEMNNFYTLTVYEKGAEVIRMIHTLLGEENFQKGMQLYFERHDGS AATCDDFVQAMEDASNVDLSHFRRWYSQSGTPIVTVKDDYNPETEQ YTLTISQRTPATPDQAEKQPLHIPFAIELYDNEGKVIPLQKGGHPV NSVLNVTQAEQTFVFDNVYFQPVPALLCEFSAPVKLEYKWSDQQLT FLMRHARNDFSRWDAAQSLLATYIKLNVARHQQGQPLSLPVHVADA FRAVLLDEKIDPALAAEILTLPSVNEMAELFDIIDPTAIAEVREAL TRTLATELADELLAIYNANYQSEYRVEHEDIAKRTLRNACLRFLAF GETHLADVLVSKQFHEANNMTDALAALSAAVAAQLPCRDALMQEYD DKWHQNGLVMDKWFILQATSPAANVLETVRGLLQHRSFTMSNPNRI RSLIGAFAGSNPAAFHAEDGSGYLFLVEMLTDLNSRNPQVASRLIE PLIRLKRYDAKRQEKMRAALEQLKGLENLSGDLYEKITKALA |
| P. falciparum M1 aminopeptidase** | 55 | PKIHYRKDYKPSGFIINQVTLNINIHDQETIVRSVLDMDISKHNVG EDLVFDGVGLKINEISINNKKLVEGEEYTYDNEFLTIFSKFVPKSK FAFSSEVIIHPETNYALTGLYKSKNIIVSQCEATGFRRITFFIDRP DMMAKYDVTVTADKEKYPVLLSNGDKVNEFEIPGGRHGARFNDPPL KPCYLFAVVAGDLKHLSATYITKYTKKKVELYVFSEEKYVSKLQWA LECLKKSMAFDEDYFGLEYDLSRLNLVAVSDFNVGAMENKGLNIFN ANSLLASKKNSIDFSYARILTVVGHEYFHQYTGNRVTLRDWFQLTL KEGLTVHRENLFSEEMTKTVTTRLSHVDLLRSVQFLEDSSPLSHPI RPESYVSMENFYTTTVYDKGSEVMRMYLTILGEEYYKKGFDIYIKK NDGNTATCEDFNYAMEQAYKMKKADNSANLNQYLLWFSQSGTPHVS FKYNYDAEKKQYSIHVNQYTKPDENQKEKKPLFIPISVGLINPENG KEMISQTTLELTKESDTFVFNNIAVKPIPSLFRGFSAPVYIEDQLT DEERILLLKYDSDAFVRYNSCTNIYMKQILMNYNEFLKAKNEKLES FQLTPVNAQFIDAIKYLLEDPHADAGKSYIVSLPQDRYIINFVSN LDTDVLADTKEYIYKQIGDKLNDVYYKMFKSLEAKADDLTYFNDES HVDFDQMNMRTLRNTLLSLLSKAQYPNILNEIIEHSKSPYPSNWLT SLSVSAYFDKYFELYDKTYKLSKDDELLLQEWLKTVSRSDRKDIYE |

TABLE 4-continued

Non-limiting examples of non-specific aminopeptidases.

| Name | SEQ ID NO: | Sequence |
|---|---|---|
| | | ILKKLENEVLKDSKNPNDIRAVYLPFTNNLRRFHDISGKGYKLIAE VITKTDKFNPMVATQLCEPFKLWNKLDTKRQELMLNEMNTMLQEPQ ISNNLKEYLLRLTNK |
| Puromycin-sensitive aminopeptidase ("NPEPPS") | 56 | MWLAAAAPSLARRLLFLGPPPPPLLLLVFSRSSRRRLHSLGLAAMP EKRPFERLPADVSPINYSLCLCKPDLLDFTFEGKLEAAAQVRQATNQ IVMNCADIDIITASYAPEGDEEIHATGFNYQNEDEKVTLSFPSTLQ TGTGTLKIDFVGELNDKMKGFYRSKYTTPSGEVRYAAVTQFEATDA RRAFPCWDEPAIKATFDISLVVPKDRVALSNMNVIDRKPYPDDENL VEVKFARTPVMSTYLVAFVVGEYDFVETRSKDGVCVRVYTPVGKAE QGKFALEVAAKTLPFYKDYFNVPYPLPKIDLIAIADPAAGAMENWG LVTYRETALLIDPKNSCSSSRQWVALVVGHELAHQWFGNLVTMEWW THLWLNEGFASWIEYLCVDHCFPEYDIWTQFVSADYTRAQELDALD NSHPIEVSVGHPSEVDEIFDAISYSKGASVIRMLHDYIGDKDFKKG MNMYLTKFQQKNAATEDLWESLENASGKPIAAVMNTWTKQMGFPLI YVEAEQVEDDRLLRLSQKKFCAGGSYVGEDCPQWMVPITISTSEDP NQAKLKILMDKPEMNVVLKNVKPDQWVKLNLGTVGFYRTQYSSAML ESLLPGIRDLSLPPVDRLGLQNDLFSLARAGIISTVEVLKVMEAFV NEPNYTVWSDLSCNLGILSTLLSHTDFYEEIQEFVKDVFSPIGERL GWDPKPGEGHLDALLRGLVLGKLGKAGHKATLEEARRRFKDHVEGK QILSADLRSPVYLTVLKHGDGTTLDIMLKLHKQADMQEEKNRIERV LGATLLPDLIQKVLTFALSEEVRPQDTVSVIGGVAGGSKHGRKAAW KFIKDNWEELYNRYQGGFLISRLIKLSVEGFAVDKMAGEVKAFFES HPAPSAERTIQQCCENILLNAAWLKRDAESIHQYLLQRKASPPTV |
| NPEPPS E366V | 57 | MWLAAAAPSLARRLLFLGPPPPPLLLLVFSRSSRRRLHSLGLAAMP EKRPFERLPADVSPINYSLCLCKPDLLDFTFEGKLEAAAQVRQATNQ IVMNCADIDIITASYAPEGDEEIHATGFNYQNEDEKVTLSFPSTLQ TGTGTLKIDFVGELNDKMKGFYRSKYTTPSGEVRYAAVTQFEATDA RRAFPCWDEPAIKATFDISLVVPKDRVALSNMNVIDRKPYPDDENL VEVKFARTPVMSTYLVAFVVGEYDFVETRSKDGVCVRVYTPVGKAE QGKFALEVAAKTLPFYKDYFNVPYPLPKIDLIAIADPAAGAMENWG LVTYRETALLIDPKNSCSSSRQWVALVVGHVLAHQWFGNLVTMEWW THLWLNEGFASWIEYLCVDHCFPEYDIWTQFVSADYTRAQELDALD NSHPIEVSVGHPSEVDEIFDAISYSKGASVIRMLHDYIGDKDFKKG MNMYLTKFQQKNAATEDLWESLENASGKPIAAVMNTWTKQMGFPLI YVEAEQVEDDRLLRLSQKKFCAGGSYVGEDCPQWMVPITISTSEDP NQAKLKILMDKPEMNVVLKNVKPDQWVKLNLGTVGFYRTQYSSAML ESLLPGIRDLSLPPVDRLGLQNDLFSLARAGIISTVEVLKVMEAFV NEPNYTVWSDLSCNLGILSTLLSHTDFYEEIQEFVKDVFSPIGERL GWDPKPGEGHLDALLRGLVLGKLGKAGHKATLEEARRRFKDHVEGK QILSADLRSPVYLTVLKHGDGTTLDIMLKLHKQADMQEEKNRIERV LGATLLPDLIQKVLTFALSEEVRPQDTVSVIGGVAGGSKHGRKAAW KFIKDNWEELYNRYQGGFLISRLIKLSVEGFAVDKMAGEVKAFFES HPAPSAERTIQQCCENILLNAAWLKRDAESIHQYLLQRKASPPTV |
| *Francisella tularensis* Aminopeptidase N TABLE 4-continued Non-limiting examples of non-specific aminopeptidases.

| Name | SEQ ID NO: | Sequence |
|---|---|---|
| *T. aquaticus* Aminopeptidase T | 60 | MDAFTENLNKLAELAIRVGLNLEEGQEIVATAPIEAVDFVRLLAEK AYENGASLFTVLYGDNLIARKRLALVPEAHLDRAPAWLYEGMAKAF HEGAARLAVSGNDPKALEGLPPERVGRAQQAQSRAYRPTLSAITEF VTNWTIVPFAHPGWAKAVFPGLPEEEAVQRLWQAIFQATRVDQEDP VAAWEAHNRVLHAKVAFLNEKRFHALHFQGPGTDLTVGLAEGHLWQ GGATPTKKGRLCNPNLPTEEVFTAPHRERVEGVVRASRPLALSGQL VEGLWARFEGGVAVEVGAEKGEEVLKKLLDTDEGARRLGEVALVPA DNPIAKTGLVFFDTLFDENAASHIAFGQAYAENLEGRPSGEEFRRR GGNESMVHVDWMIGSEEVDVDGLLEDGTRVPLMRRGRWVI |
| *Bacillus stearothermophilus* Peptidase M28 | 61 | MAKLDETLTMLKALTDAKGVPGNEREARDVMKTYIAPYADEVTTDG LGSLIAKKEGKSGGPKVMIAGHLDEVGFMVTQIDDKGFIRFQTLGG WWSQVMLAQRVTIVTKKGDITGVIGSKPPHILPSEARKKPVEIKDM FIDIGATSREEAMEWGVRPGDMIVPYFEFTVLNNEKMLLAKAWDNR IGCAVAIDVLKQLKGVDHPNTVYGVGTVQEEVGLRGARTAAQFIQP DIAFAVDVGIAGDTPGVSEKEAMGKLGAGPHIVLYDATMVSHRGLR EFVIEVAEELNIPHHFDAMPGVGTDAGAIHLTGIGVPSLTIAIPTR YIHSHAAILHRDDYENTVKLLVEVIKRLDADKVKQLTFDE |
| *Vibrio cholera* Aminopeptidase | 62 | MEDKVWISMGADAVGSLNPALSESLLPHSFASGSQVWIGEVAIDEL AELSHTMHEQHNRCGGYMVHTSAQGAMAALMMPESIANFTIPAPSQ QDLVNAWLPQVSADQITNTIRALSSFNNRFYTTTSGAQASDWLANE WRSLISSLPGSRIEQIKHSGYNQKSVVLTIQGSEKPDEWVIVGGHL DSTLGSHTNEQSIAPGADDDASGIASLSEIIRVLRDNNFRPKRSVA LMAYAAEEVGLRGSQDLANQYKAQGKKVVSVLQLDMTNYRGSAEDI VPITDYTDSNLTQFLTTLIDEYLPELTYGYDRCGYACSDHASWHKA GFSAAMPFESKFKDYNPKIHTSQDTLANSDPTGNHAVKFTKLGLAY VIEMANAGSSQVPDDSVLQDGTAKINLSGARGTQKRFTFELSQSKP LTIQTYGGSGDVDLYVKYGSAPSKSNWDCRPYQNGNRETCSFNNAQ PGIYHVMLDGYTNYNDVALKASTQ |
| *Photobacterium halotolerans* Aminopeptidase | 63 | MEDKVWISIGSDASQTVKSVMQSNARSLLPESLASNGPVWVGQVDY SQLAELSHHMHEDHQRCGGYMVHSSPESAIAASNMPQSLVAFSIPE ISQQDTVNAWLPQVNSQAITGTITSLTSFINRFYTTTSGAQASDWL ANEWRSLSASLPNASVRQVSHFGYNQKSVVLTITGSEKPDEWIVLG GHLDSTIGSHTNEQSVAPGADDDASGIASVTEIIRVLSENNFQPKR SIAFMAYAAEEVGLRGSQDLANQYKAEGKQVISALQLDMTNYKGSV EDIVFITDYTDSNLTTFLSQLVDEYLPSLTYGFDTCGYACSDHASW HKAGESAAMPFEAKFNDYNPMIHTPNDTLQNSDPTASHAVKFTKLG LAYAIEMASTTGGTPPPTGNVLKDGVPVNGLSGATGSQVHYSFELP AQKNLQISTAGGSGDVDLYVSFGSEATKQNWDCRPYRNGNNEVCTF AGATPGTYSIMLDGYRQFSGVTLKASTQ |
| *Yersinia pestis* AminopeptidaseN | 64 | MTQQPQAKYRHDYRAPDYTITDIDLDFALDAQKTTVTAVSKVKRQG TDVTPLILNGEDLTLISVSVDGQAWPHYRQQDNTLVIEQLPADFTL TIVNDIHPATNSALEGLYLSGEALCTQCEAEGFRHITYYLDRPDVL ARFTTRIVADKSRYPYLLSNGNRVGQGELDDGRHWVKWEDPFPKPS YLFALVAGDFDVLQDKFITRSGREVALEIFVDRGNLDRADWAMTSL KNSMKWDETRFGLEYDLDIYMIVAVDFFNMGAMENKGLNVFNSKYV LAKAETATDKDYLNIEAVIGHEYFHNWTGNRVTCRDWFQLSLKEGL TVFRDQEFSSDLGSRSVNRIENVRVMRAAQFAEDASPMAHAIRPDK VIEMNNFYTLTVYEKGSEVIRMMHTLLGEQQFQAGMRLYFERHDGS AATCDDFVQAMEDVSNVDLSLFRRWYSQSGTPLLTVHDDYDVEKQQ YHLFVSQKTLPTADQPEKLPLHIPLDIELYDSKGNVIPLQHNGLPV HHVLNVTEAEQTFTFDNVAQKPIPSLLREFSAPVKLDYPYSDQQLT FLMQHARNEFSRWDAAQSLLATYIKLNVAKYQQQQPLSLPAHVADA FRAILLDEHLDPALAAQILTLPSENEMAELFTTIDPQAISTVHEAI TRCLAQELSDELLAVYVANMTPVYRIEHGDIAKRALRNTCLNYLAF GDEEFANKLVSLQYHQADNMTDSLAALAAAVAAQLPCRDELLAAFD VRWNHDGLVMDKWFALQATSPAANVLVQVRTLLKHPAFSLSNPNRT RSLIGSFASGNPAAFHAADGSGYQFLVEILSDLNTRNPQVAARLIE PLIRLKRYDAGRQALMRKALEQLKTLDNLSGDLYEKITKALAA |
| *Vibrio anguillarum* Aminopeptidase | 65 | MEEKVWISIGGDATQTALRSGAQSLLPENLINQTSVWVGQVPVSEL ATLSHEMHENHQRCGGYMVHPSAQSAMSVSAMPLNLNAFSAPEITQ QTTVNAWLPSVSAQQITSTITTLTQFKNRFYTTSTGAQASNWIADH WRSLSASLPASKVEQITHSGYNQKSVMLTITGSEKPDEWVVIGGHL DSTLGSRTNESSIAPGADDDASGIAGVTEIIRLLSEQNFRPKRSIA FMAYAAEEVGLRGSQDLANRFKAEGKKVMSVMQLDMTNYQGSREDI VPITDYTDSNFTQYLTQLLDEYLPSLTYGFDTCGYACSDHASWHAV GYPAAMPFESKFNDYNPNIHSPQDTLQNSDPTGFHAVKFTKLGLAY VVEMGNASTPPTPSNQLKNGVPVNGLSASRNSKTWYQFELQEAGNL SIVLSGGSGDADLYVKYQTDADLQQYDCRPYRSGNNETCQFSNAQP GRYSILLHGYNNYSNASLVANAQ |

TABLE 4-continued

Non-limiting examples of non-specific aminopeptidases.

| Name | SEQ ID NO: | Sequence |
|---|---|---|
| *Salinivibrio* spYCSC6 Aminopeptidase | 66 | MEDKKVWISIGADAQQTALSSGAQPLLAQSVAHNGQAWIGEVSESE LAALSHEMHENHHRCGGYIVHSSAQSAMAASNMPLSRASFIAPAIS QQALVTPWISQIDSALIVNTIDRLTDFPNRFYTTTSGAQASDWIKQ RWQSLSAGLAGASVTQISHSGYNQASVMLTIEGSESPDEWVVVGGH LDSTIGSRTNEQSIAPGADDDASGIAAVTEVIRVLAQNNFQPKRSI AFVAYAAEEVGLRGSQDVANQFKQAGKDVRGVLQLDMTNYQGSAED IVFITDYTDNQLTQYLTQLLDEYLPTLNYGFDTCGYACSDHASWHQ VGYPAAMPFEAKFNDYNPNIHTPQDTLANSDSEGAHAAKFTKLGLA YTVELANADSSPNPGNELKLGEPINGLSGARGNEKYFNYRLDQSGE LVIRTYGGSGDVDLYVKANGDVSTGNWDCRPYRSGNDEVCRFDNAT PGNYAVMLRGYRTYDNVSLIVE |
| *Vibrio proteolyticus* Aminopeptidase I | 67 | MPPITQQATVTAWLPQVDASQITGTISSLESFTNRFYTTTSGAQAS DWIASEWQALSASLPNASVKQVSHSGYNQKSVVMTITGSEAPDEWI VIGGHLDSTIGSHTNEQSVAPGADDDASGIAAVTEVIRVLSENNFQ PKRSIAFMAYAAEEVGLRGSQDLANQYKSEGKNVVSALQLDMTNYK GSAQDVVFITDYTDSNFTQYLTQLMDEYLPSLTYGFDTCGYACSDH ASWHNAGYPAAMPFESKFNDYNPRIHTTQDTLANSDPTGSHAKKFT QLGLAYAIEMGSATGDTPTPGNQLE |
| *Vibrio proteolyticus* Aminopeptidase I (A55F) | 68 | MPPITQQATVTAWLPQVDASQITGTISSLESFTNRFYTTTSGAQAS DWIASEWQFLSASLPNASVKQVSHSGYNQKSVVMTITGSEAPDEWI VIGGHLDSTIGSHTNEQSVAPGADDDASGIAAVTEVIRVLSENNFQ PKRSIAFMAYAAEEVGLRGSQDLANQYKSEGKNVVSALQLDMTNYK GSAQDVVFITDYTDSNFTQYLTQLMDEYLPSLTYGFDTCGYACSDH ASWHNAGYPAAMPFESKFNDYNPRIHTTQDTLANSDPTGSHAKKFT QLGLAYAIEMGSATGDTPTPGNQLE |
| *P. furiosus* Aminopeptidase I | 69 | MVDWELMKKIIESPGVSGYEHLGIRDLVVDILKDVADEVKIDKLGN VIAHFKGSAPKVMVAAHMDKIGLMVNHIDKDGYLRVVPIGGVLPET LIAQKIRFFTEKGERYGVVGVLPPHLRREAKDQGGKIDWDSIIVDV GASSREEAEEMGFRIGTIGEFAPNFTRLSEHRFATPYLDDRICLYA MIEAARQLGEHEADIYIVASVQEEIGLRGARVASFAIDPEVGIAMD VTFAKQPNDKGKIVPELGKGPVMDVGPNINPKLRQFADEVAKKYEI PLQVEPSPRPTGTDANVMQINREGVATAVLSIPIRYMHSQVELADA RDVDNTIKLAKALLEELKPMDFTPLE |

*Cleavage efficiency (from most to least): arginine > lysine > hydrophobic residues (including alanine, leucine, methionine, and phenylalanine) > proline (see, e.g., Matthews Biochemistry 47, 2008, 5303-5311).
**Cleavage efficiency (from most to least): leucine > alanine > arginine > phenylalanine > proline; does not cleave after glutamate and aspartate.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100], in which each deletion, insertion, substitution or addition of an amino acid residue in the second amino acid sequence compared to the first amino acid sequence is considered as a difference at a single amino acid residue (position). Alternatively, the degree of sequence identity between two amino acid sequences may be calculated using a known computer algorithm (e.g., by the local homology algorithm of Smith and Waterman (1970) Adv. Appl. Math. 2:482c, by the homology alignment algorithm of Needleman and Wunsch, J. Mol. Biol. (1970) 48:443, by the search for similarity method of Pearson and Lipman. Proc. Natl. Acad. Sci. USA (1998) 85:2444, or by computerized implementations of algorithms available as Blast, Clustal Omega, or other sequence alignment algorithms) and, for example, using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8%, or 99.9% identical) over a specified region or over the entire sequence, when compared and aligned for maximum correspondence over a comparison window, or designated region as measured using one of the above sequence comparison algorithms or by manual alignment and visual inspection. Optionally, the identity exists over a region that is at least about 25, 50, 75, or 100 amino acids in length, or over a region that is 100 to 150, 150 to 200, 100 to 200, or 200 or more, amino acids in length.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the above sequence comparison algorithms or by manual alignment and visual inspection. Optionally, the alignment exists over a region that is at least about 25, 50, 75, or 100 amino acids in length, or over a region that is 100 to 150, 150 to 200, 100 to 200, or 200 or more amino acids in length.

In addition to protein molecules, nucleic acid molecules possess a variety of advantageous properties for use as affinity reagents (e.g., amino acid recognition molecules) in accordance with the application.

Nucleic acid aptamers are nucleic acid molecules that have been engineered to bind desired targets with high affinity and selectivity. Accordingly, nucleic acid aptamers may be engineered to selectively bind a desired type of amino acid using selection and/or enrichment techniques known in the art. Thus, in some embodiments, an affinity reagent comprises a nucleic acid aptamer (e.g., a DNA aptamer, an RNA aptamer). As shown in FIG. 1C, in some embodiments, a labeled affinity reagent is a labeled aptamer 104 that selectively binds one type of terminal amino acid. For example, in some embodiments, labeled aptamer 104 selectively binds one type of amino acid (e.g., a single type of amino acid or a subset of types of amino acids) at a terminus of a polypeptide, as described herein. Although not shown, it should be appreciated that labeled aptamer 104 may be engineered to selectively bind one type of amino acid at any position of a polypeptide (e.g., at a terminal position or at terminal and internal positions of a polypeptide) in accordance with a method of the application.

In some embodiments, a labeled affinity reagent comprises a label having binding-induced luminescence. For example, in some embodiments, a labeled aptamer 106 comprises a donor label 112 and an acceptor label 114 and functions as illustrated in panels (I) and (II) of FIG. 1C. As depicted in panel (I), labeled aptamer 106 as a free molecule adopts a conformation in which donor label 112 and acceptor label 114 are separated by a distance that limits detectable FRET between the labels (e.g., about 10 nm or more). As depicted in panel (II), labeled aptamer 106 as a selectively bound molecule adopts a conformation in which donor label 112 and acceptor label 114 are within a distance that promotes detectable FRET between the labels (e.g., about 10 nm or less). In yet other embodiments, labeled aptamer 106 comprises a quenching moiety and functions analogously to a molecular beacon, wherein luminescence of labeled aptamer 106 is internally quenched as a free molecule and restored as a selectively bound molecule (see, e.g., Hamaguchi, et al. (2001) Analytical Biochemistry 294, 126-131). Without wishing to be bound by theory, it is thought that these and other types of mechanisms for binding-induced luminescence may advantageously reduce or eliminate background luminescence to increase overall sensitivity and accuracy of the methods described herein.

In addition to methods of identifying a terminal amino acid of a polypeptide, the application provides methods of sequencing polypeptides using labeled affinity reagents. In some embodiments, methods of sequencing may involve subjecting a polypeptide terminus to repeated cycles of terminal amino acid detection and terminal amino acid cleavage. For example, in some embodiments, the application provides a method of determining an amino acid sequence of a polypeptide comprising contacting a polypeptide with one or more labeled affinity reagents described herein and subjecting the polypeptide to Edman degradation.

Conventional Edman degradation involves repeated cycles of modifying and cleaving the terminal amino acid of a polypeptide, wherein each successively cleaved amino acid is identified to determine an amino acid sequence of the polypeptide. As an illustrative example of a conventional Edman degradation, the N-terminal amino acid of a polypeptide is modified using phenyl isothiocyanate (PITC) to form a PITC-derivatized N-terminal amino acid. The PITC-derivatized N-terminal amino acid is then cleaved using acidic conditions, basic conditions, and/or elevated temperatures. It has also been shown that the step of cleaving the PITC-derivatized N-terminal amino acid may be accomplished enzymatically using a modified cysteine protease from the protozoa *Trypanosoma cruzi*, which involves relatively milder cleavage conditions at a neutral or near-neutral pH. Non-limiting examples of useful enzymes are described in U.S. patent application Ser. No. 15/255,433, filed Sep. 2, 2016, titled "MOLECULES AND METHODS FOR ITERATIVE POLYPEPTIDE ANALYSIS AND PROCESSING."

An example of sequencing by Edman degradation using labeled affinity reagents in accordance with the application is depicted in FIG. 1D. In some embodiments, sequencing by Edman degradation comprises providing a polypeptide 122 that is immobilized to a surface 130 of a solid support (e.g., immobilized to a bottom or sidewall surface of a sample well) through a linker 124. In some embodiments, as described herein, polypeptide 122 is immobilized at one terminus (e.g., an amino-terminal amino acid or a carboxy-terminal amino acid) such that the other terminus is free for detecting and cleaving of a terminal amino acid. Accordingly, in some embodiments, the reagents used in Edman degradation methods described herein preferentially interact with terminal amino acids at the non-immobilized (e.g., free) terminus of polypeptide 122. In this way, polypeptide 122 remains immobilized over repeated cycles of detecting and cleaving. To this end, in some embodiments, linker 124 may be designed according to a desired set of conditions used for detecting and cleaving, e.g., to limit detachment of polypeptide 122 from surface 130 under chemical cleavage conditions. Suitable linker compositions and techniques for immobilizing a polypeptide to a surface are described in detail elsewhere herein.

In accordance with the application, in some embodiments, a method of sequencing by Edman degradation comprises a step (1) of contacting polypeptide 122 with one or more labeled affinity reagents that selectively bind one or more types of terminal amino acids. As shown, in some embodiments, a labeled affinity reagent 108 interacts with polypeptide 122 by selectively binding the terminal amino acid. In some embodiments, step (1) further comprises removing any of the one or more labeled affinity reagents that do not selectively bind the terminal amino acid (e.g., the free terminal amino acid) of polypeptide 122.

In some embodiments, the method further comprises identifying the terminal amino acid of polypeptide 122 by detecting labeled affinity reagent 108. In some embodiments, detecting comprises detecting a luminescence from labeled affinity reagent 108. As described herein, in some embodiments, the luminescence is uniquely associated with labeled affinity reagent 108, and the luminescence is thereby associated with the type of amino acid to which labeled affinity reagent 108 selectively binds. As such, in some embodiments, the type of amino acid is identified by determining one or more luminescence properties of labeled affinity reagent 108.

In some embodiments, a method of sequencing by Edman degradation comprises a step (2) of removing the terminal amino acid of polypeptide 122. In some embodiments, step (2) comprises removing labeled affinity reagent 108 (e.g., any of the one or more labeled affinity reagents that selectively bind the terminal amino acid) from polypeptide 122. In some embodiments, step (2) comprises modifying the terminal amino acid (e.g., the free terminal amino acid) of polypeptide 122 by contacting the terminal amino acid with an isothiocyanate (e.g., PITC) to form an isothiocyanate-modified terminal amino acid. In some embodiments, an isothiocyanate-modified terminal amino acid is more susceptible to removal by a cleaving reagent (e.g., a chemical or enzymatic cleaving reagent) than an unmodified terminal amino acid.

In some embodiments, step (2) comprises removing the terminal amino acid by contacting polypeptide 122 with a protease 140 that specifically binds and cleaves the isothiocyanate-modified terminal amino acid. In some embodiments, protease 140 comprises a modified cysteine protease. In some embodiments, protease 140 comprises a modified cysteine protease, such as a cysteine protease from *Trypanosoma cruzi* (see, e.g., Borgo, et al. (2015) Protein Science 24:571-579). In yet other embodiments, step (2) comprises removing the terminal amino acid by subjecting polypeptide 122 to chemical (e.g., acidic, basic) conditions sufficient to cleave the isothiocyanate-modified terminal amino acid.

In some embodiments, a method of sequencing by Edman degradation comprises a step (3) of washing polypeptide 122 following terminal amino acid cleavage. In some embodiments, washing comprises removing protease 140. In some embodiments, washing comprises restoring polypeptide 122 to neutral pH conditions (e.g., following chemical cleavage by acidic or basic conditions). In some embodiments, a method of sequencing by Edman degradation comprises repeating steps (1) through (3) for a plurality of cycles.

An example method of sequencing by Edman degradation is shown in FIG. 1E. In some embodiments, a sample containing a complex mixture of polypeptides (e.g., a mixture of proteins) can be degraded using common enzymes into short polypeptide fragments of approximately 6 to 40 amino acids. In some embodiments, sequencing of this polypeptide library in accordance with methods of the application would reveal the identity and abundance of each of the polypeptides present in the original complex mixture. As described herein and in the literature, most polypeptides in the size range of 6 to 40 amino acids can be uniquely identified by determining the number and location of just four amino acids within a polypeptide chain.

Accordingly, in some embodiments, a method of sequencing by Edman degradation may be performed using a set of labeled aptamers 150 comprising four DNA aptamer types, each type recognizing a different N-terminal amino acid. Each aptamer type may be labeled with a different luminescent label, such that the different aptamer types can be distinguished based on one or more luminescence properties. For illustrative purposes, the example set of labeled aptamers 150 includes: a cysteine-specific aptamer labeled with a first luminescent label ("dye 1"); a lysine-specific aptamer labeled with a second luminescent label ("dye 2"); a tryptophan-specific aptamer labeled with a third luminescent label ("dye 3"); and a glutamate-specific aptamer labeled with a fourth luminescent label ("dye 4").

In some embodiments, a method of sequencing by Edman degradation in accordance with the application proceeds according to a process 152 shown in FIG. 1E. In some embodiments, prior to step (1), single polypeptide molecules from a polypeptide library are immobilized to a surface of a solid support, e.g., at a bottom or sidewall surface of a sample well of an array of sample wells. In some embodiments, as described elsewhere herein, moieties that enable surface immobilization (e.g., biotin) or improve solubility (e.g., oligonucleotides) may be chemically or enzymatically attached to the C-terminus of the polypeptides. To determine the sequence of each polypeptide, in some embodiments, immobilized polypeptides are subjected to repeated cycles of N-terminal amino acid detection and N-terminal amino acid cleavage, as illustrated by process 152. In some embodiments, process 152 comprises reagent addition and wash steps which are performed by injection into a flowcell above the detection surface using an automated fluidic system. In some embodiments, steps (1) through (4) illustrate one cycle of detection and cleavage using labeled aptamers 150.

In some embodiments, a method of sequencing by Edman degradation according to process 152 comprises a step (1) of flowing in a mixture of four orthogonally labeled DNA aptamers and incubating to allow the aptamers to bind to any immobilized polypeptides (e.g., polypeptides immobilized within a sample well of an array) that contain one of the four correct amino acids at the N-terminus. In some embodiments, the method further comprises washing the immobilized polypeptides to remove unbound aptamers. In some embodiments, the method further comprises imaging the immobilized polypeptides ("Imaging step 1"). In some embodiments, the acquired images contain enough information to determine the location of aptamer-bound polypeptides (e.g., location within an array of sample wells) and which of the four aptamers is bound at each location. In some embodiments, the method further comprises washing the immobilized polypeptides using an appropriate buffer to remove the aptamers from the immobilized polypeptides.

In some embodiments, a method of sequencing according to process 152 comprises a step (2) of flowing in a solution containing a reactive molecule (e.g., PITC, as shown) that specifically modifies the N-terminal amine group. An isothiocyanate molecule such as PITC, in some embodiments, modifies the N-terminal amino acid into a substrate for cleavage by a modified protease such as the cysteine protease cruzain from *Trypanosoma Cruzi*.

In some embodiments, a method of sequencing according to process 152 comprises a step (3) of washing the immobilized polypeptides before flowing in a suitable modified protease that recognizes and cleaves the modified N-terminal amino acid from the immobilized polypeptide.

In some embodiments, the method comprises a step (4) of washing the immobilized polypeptides after enzymatic cleavage. In some embodiments, steps (1) through (4) depict one cycle of Edman degradation. Accordingly, step (1') as shown is the start of the next reaction cycle which proceeds as steps (1') through (4') performed as described above for steps (1) through (4). In some embodiments, steps (1) through (4) are repeated for approximately 20-40 cycles.

In some embodiments, a labeled isothiocyanate (e.g., a dye-labeled PITC) may be used to monitor sample loading. For example, in some embodiments, prior to subjecting a polypeptide sample to a method of sequencing as shown in process 152, the polypeptide sample is pre-conjugated with a luminescent label at a terminal end by modification of the terminal end using a dye-labeled PITC. In this way, loading of the polypeptide sample into an array of sample wells may be monitored by detecting luminescence from the labels prior to initiating process 152. In some embodiments, the luminescence is used to determine single occupancy of sample wells in the array (e.g., a fraction of sample wells containing a single polypeptide molecule), which may advantageously increase the amount of information reliably obtained for a given sample. Once a desired sample loading status is determined by luminescence, process 152 may be initiated by chemical or enzymatic cleavage, as described, before proceeding with step (1).

In some embodiments, a labeled isothiocyanate (e.g., a dye-labeled PITC) may be used to monitor reaction progress for a polypeptide sample in an array. For example, in some embodiments, step (2) comprises flowing in a solution containing a dye-labeled PITC that specifically modifies and labels N-terminal amine groups of polypeptides in the sample. In some embodiments, luminescence from the labels may be detected during or after step (2) to evaluate N-terminal PITC modification of polypeptides in the sample. Accordingly, in some embodiments, luminescence is used to determine whether or when to proceed from step (2) to step (3). In some embodiments, luminescence from the labels may be detected during or after step (3) to evaluate N-terminal amino acid cleavage of polypeptides in the sample— e.g., to determine whether or when to proceed from step (3) to step (4).

A method of sequencing according to process 152 utilizes separate reagents for detecting and cleaving a terminal amino acid of a polypeptide. Nonetheless, in some aspects, the application provides a method of sequencing in which a single reagent comprising a peptidase may be used for detecting and cleaving a terminal amino acid of a polypeptide. FIG. 2 shows an example of polypeptide sequencing using a set of labeled exopeptidases 200, wherein each labeled exopeptidase selectively binds and cleaves a different type of terminal amino acid.

As generically illustrated in the example of FIG. 2, labeled exopeptidases 200 include a lysine-specific exopeptidase comprising a first luminescent label, a glycine-specific exopeptidase comprising a second luminescent label, an aspartate-specific exopeptidase comprising a third luminescent label, and a leucine-specific exopeptidase comprising a fourth luminescent label. In accordance with certain embodiments described herein, each of labeled exopeptidases 200 selectively binds and cleaves its respective amino acid only when that amino acid is at an amino- or carboxy-terminus of a polypeptide. Accordingly, as sequencing by this approach proceeds from one terminus of a peptide toward the other, labeled exopeptidases 200 are engineered or selected such that all reagents of the set will possess either aminopeptidase or carboxypeptidase activity.

As further shown in FIG. 2, process 202 schematically illustrates a real-time sequencing reaction using labeled exopeptidases 200. Panels (I) through (IX) illustrate a progression of events involving iterative detection and cleavage at a terminal end of a polypeptide in relation to a signal output shown below, and corresponding to, the event depicted in each panel. For illustrative purposes, a polypeptide is shown having an arbitrarily selected amino acid sequence of "KLDG . . . " (proceeding from one terminus toward the other).

Panel (I) depicts the start of a sequencing reaction, wherein a polypeptide is immobilized to a surface of a solid support, such as a bottom or sidewall surface of a sample well. In some embodiments, sequencing methods in accordance with the application comprise single molecule sequencing in real-time. In some embodiments, a plurality of single molecule sequencing reactions are performed simultaneously in an array of sample wells. In such embodiments, polypeptide immobilization prevents diffusion of a polypeptide out of a sample well by anchoring the polypeptide within the sample well for single molecule analysis.

Panel (II) depicts a detection event, wherein the lysine-specific exopeptidase from the set of labeled affinity reagents 200 selectively binds the terminal lysine residue of the polypeptide. As shown in the signal trace below panels (I) and (II), signal output reports on this binding event by displaying an increase in signal intensity, which may be used to identify the luminescent label of the lysine-specific exopeptidase to thereby identify the terminal amino acid. Panel (III) illustrates that, after selectively binding a terminal amino acid, a labeled peptidase cleaves the terminal amino acid. As a result, these components are free to diffuse away from an observation region for luminescence detection, which is reported in the signal output by a drop in signal intensity, as shown in the trace below panel (III). Panels (IV) through (IX) proceed analogously to the process as described for panels (I) through (III). That is, a labeled exopeptidase binds and cleaves a corresponding terminal amino acid to produce a corresponding increase and decrease, respectively, in signal output.

In some aspects, the application provides methods of polypeptide sequencing in real-time by evaluating binding interactions of terminal amino acids with labeled amino acid recognition molecules (e.g., labeled affinity reagents) and a labeled cleaving reagent (e.g., a labeled non-specific exopeptidase). FIG. 3A shows an example of a method of sequencing in which discrete binding events give rise to signal pulses of a signal output 300. The inset panel of FIG. 3A illustrates a general scheme of real-time sequencing by this approach. As shown, a labeled affinity reagent 310 selectively associates with (e.g., binds to) and dissociates from a terminal amino acid (shown here as lysine), which gives rise to a series of pulses in signal output 300 which may be used to identify the terminal amino acid. In some embodiments, the series of pulses provide a pulsing pattern (e.g., a characteristic pattern) which may be diagnostic of the identity of the corresponding terminal amino acid.

Without wishing to be bound by theory, labeled affinity reagent 310 selectively binds according to a binding affinity ($K_D$) defined by an association rate, or an "on" rate, of binding ($k_{on}$) and a dissociation rate, or an "off" rate, of binding ($k_{off}$). The rate constants $k_{off}$ and $k_{on}$ are the critical determinants of pulse duration (e.g., the time corresponding to a detectable binding event) and interpulse duration (e.g., the time between detectable binding events), respectively. In some embodiments, these rates can be engineered to achieve pulse durations and pulse rates (e.g., the frequency of signal pulses) that give the best sequencing accuracy.

As shown in the inset panel, a sequencing reaction mixture further comprises a labeled non-specific exopeptidase 320 comprising a luminescent label that is different than that of labeled affinity reagent 310. In some embodiments, labeled non-specific exopeptidase 320 is present in the mixture at a concentration that is less than that of labeled affinity reagent 310. In some embodiments, labeled non-specific exopeptidase 320 displays broad specificity such that it cleaves most or all types of terminal amino acids. Accordingly, a dynamic sequencing approach can involve monitoring affinity reagent binding at a terminus of a polypeptide over the course of a degradation reaction catalyzed by exopeptidase cleavage activity.

As illustrated by the progress of signal output 300, in some embodiments, terminal amino acid cleavage by labeled non-specific exopeptidase 320 gives rise to a signal pulse, and these events occur with lower frequency than the binding pulses of a labeled affinity reagent 310. In this way, amino acids of a polypeptide may be counted and/or identified in a real-time sequencing process. As further illustrated in signal output 300, in some embodiments, a plurality of labeled affinity reagents may be used, each with a diagnostic pulsing pattern (e.g., characteristic pattern) which may be used to identify a corresponding terminal amino acid. For example, in some embodiments, different characteristic patterns (as illustrated by each of lysine, phenylalanine, and glutamine in signal output 300) correspond to the association of more than one labeled affinity reagent with different types of terminal amino acids. As described herein, it should be appreciated that a single affinity reagent that associates with more than one type of amino acid may be used in accordance with the application. Accordingly, in some embodiments, different characteristic patterns correspond to the association of one labeled affinity reagent with different types of terminal amino acids.

As described herein, signal pulse information may be used to identify an amino acid based on a characteristic pattern in a series of signal pulses. In some embodiments, a characteristic pattern comprises a plurality of signal pulses, each signal pulse comprising a pulse duration. In some embodiments, the plurality of signal pulses may be characterized by a summary statistic (e.g., mean, median, time decay constant) of the distribution of pulse durations in a characteristic pattern. In some embodiments, the mean pulse duration of a characteristic pattern is between about 1 millisecond and about 10 seconds (e.g., between about 1 ms and about 1 s, between about 1 ms and about 100 ms, between about 1 ms and about 10 ms, between about 10 ms and about 10 s, between about 100 ms and about 10 s, between about 1 s and about 10 s, between about 10 ms and about 100 ms, or between about 100 ms and about 500 ms). In some embodiments, different characteristic patterns corresponding to different types of amino acids in a single polypeptide may be distinguished from one another based on a statistically significant difference in the summary statistic. For example, in some embodiments, one characteristic pattern may be distinguishable from another characteristic pattern based on a difference in mean pulse duration of at least 10 milliseconds (e.g., between about 10 ms and about 10 s, between about 10 ms and about 1 s, between about 10 ms and about 100 ms, between about 100 ms and about 10 s, between about 1 s and about 10 s, or between about 100 ms and about 1 s). It should be appreciated that, in some embodiments, smaller differences in mean pulse duration between different characteristic patterns may require a greater number of pulse durations within each characteristic pattern to distinguish one from another with statistical confidence.

As detailed above, a real-time sequencing process as illustrated by FIG. 3A can generally involve cycles of terminal amino acid recognition and terminal amino acid cleavage, where the relative occurrence of recognition and cleavage can be controlled by a concentration differential between a labeled affinity reagent 310 and a labeled non-specific exopeptidase 320. In some embodiments, the concentration differential can be optimized such that the number of signal pulses detected during recognition of an individual amino acid provides a desired confidence interval for identification. For example, if an initial sequencing reaction provides signal data with too few signal pulses between cleavage events to permit determination of characteristic patterns with a desired confidence interval, the sequencing reaction can be repeated using a decreased concentration of non-specific exopeptidase relative to affinity reagent.

In some embodiments, polypeptide sequencing in accordance with the application may be carried out by contacting a polypeptide with a sequencing reaction mixture comprising one or more amino acid recognition molecules (e.g., affinity reagents) and/or one or more cleaving reagents (e.g., exopeptidases). In some embodiments, a sequencing reaction mixture comprises an amino acid recognition molecule at a concentration of between about 10 nM and about 10 µM. In some embodiments, a sequencing reaction mixture comprises a cleaving reagent at a concentration of between about 500 nM and about 500 µM.

In some embodiments, a sequencing reaction mixture comprises an amino acid recognition molecule at a concentration of between about 100 nM and about 10 µM, between about 250 nM and about 10 µM, between about 100 nM and about 1 µM, between about 250 nM and about 1 µM, between about 250 nM and about 750 nM, or between about 500 nM and about 1 µM. In some embodiments, a sequencing reaction mixture comprises an amino acid recognition molecule at a concentration of about 100 nM, about 250 nM, about 500 nM, about 750 nM, or about 1 µM.

In some embodiments, a sequencing reaction mixture comprises a cleaving reagent at a concentration of between about 500 nM and about 250 M, between about 500 nM and about 100 µM, between about 1 µM and about 100 µM, between about 500 nM and about 50 µM, between about 1 µM and about 100 µM, between about 10 µM and about 200 µM, or between about 10 µM and about 100 µM. In some embodiments, a sequencing reaction mixture comprises a cleaving reagent at a concentration of about 1 µM, about 5 µM, about 10 µM, about µM, about 50 µM, about 70 µM, or about about 100 µM.

In some embodiments, a sequencing reaction mixture comprises an amino acid recognition molecule at a concentration of between about 10 nM and about 10 µM, and a cleaving reagent at a concentration of between about 500 nM and about 500 µM. In some embodiments, a sequencing reaction mixture comprises an amino acid recognition molecule at a concentration of between about 100 nM and about 1 µM, and a cleaving reagent at a concentration of between about 1 µM and about 100 µM. In some embodiments, a sequencing reaction mixture comprises an amino acid recognition molecule at a concentration of between about 250 nM and about 1 µM, and a cleaving reagent at a concentration of between about 10 M and about 100 µM. In some embodiments, a sequencing reaction mixture comprises an amino acid recognition molecule at a concentration of about 500 nM, and a cleaving reagent at a concentration of between about 25 M and about 75 µM.

In some embodiments, a sequencing reaction mixture comprises an amino acid recognition molecule and a cleaving reagent in a ratio of about 500:1, about 400:1, about 300:1, about 200:1, about 100:1, about 75:1, about 50:1, about 25:1, about 10:1, about 5:1, about 2:1, or about 1:1. In some embodiments, a sequencing reaction mixture comprises an amino acid recognition molecule and a cleaving reagent in a ratio of between about 10:1 and about 200:1. In some embodiments, a sequencing reaction mixture comprises an amino acid recognition molecule and a cleaving reagent in a ratio of between about 50:1 and about 150:1.

While the example illustrated by FIG. 3A relates to a sequencing process using a labeled cleaving reagent, the sequencing process is not intended to be limited in this respect. As described elsewhere herein, the inventors have demonstrated single-molecule sequencing using an unlabeled cleaving reagent. In some embodiments, the approximate frequency with which a cleaving reagent removes successive terminal amino acids is known, e.g., based on a known activity and/or concentration of the enzyme being used. In some embodiments, terminal amino acid cleavage by the reagent is inferred, e.g., based on signal detected for amino acid recognition or a lack of signal detected. The inventors have recognized further techniques for controlling real-time sequencing reactions, which may be used in combination with, or alternatively to, the concentration differential approach as described.

An example of a temperature-dependent real-time sequencing process is shown in FIG. 3B. Panels (I) through (III) illustrate a sequencing reaction involving cycles of temperature-dependent terminal amino acid recognition and terminal amino acid cleavage. Each cycle of the sequencing reaction is carried out over two temperature ranges: a first temperature range ("$T_1$") that is optimal for affinity reagent activity over exopeptidase activity (e.g., to promote terminal amino acid recognition), and a second temperature range ("$T_2$") that is optimal for exopeptidase activity over affinity reagent activity (e.g., to promote terminal amino acid cleavage). The sequencing reaction progresses by alternating the reaction mixture temperature between the first temperature range $T_1$ (to initiate amino acid recognition) and the second temperature range $T_2$ (to initiate amino acid cleavage). Accordingly, progression of a temperature-dependent sequencing process is controllable by temperature, and alternating between different temperature ranges (e.g., between $T_1$ and $T_2$) may be carried through manual or automated processes. In some embodiments, affinity reagent activity (e.g., binding affinity ($K_D$) for an amino acid) within the first temperature range $T_1$ as compared to the second temperature range $T_2$ is increased by at least 10-fold, at least 100-fold, at least 1,000-fold, at least 10,000-fold, at least 100,000-fold, or more. In some embodiments, exopeptidase activity (e.g., rate of substrate conversion to cleavage product) within the second temperature range $T_2$ as compared to the first temperature range $T_1$ is increased by at least 2-fold, 10-fold, at least 25-fold, at least 50-fold, at least 100-fold, at least 1,000-fold, or more.

In some embodiments, the first temperature range $T_1$ is lower than the second temperature range $T_2$. In some embodiments, the first temperature range $T_1$ is between about 15° C. and about 40° C. (e.g., between about 25° C. and about 35° C., between about 15° C. and about 30° C., between about 20° C. and about 30° C.). In some embodiments, the second temperature range $T_2$ is between about 40° C. and about 100° C. (e.g., between about 50° C. and about 90° C., between about 60° C. and about 90° C., between about 70° C. and about 90° C.). In some embodiments, the first temperature range $T_1$ is between about 20° C. and about 40° C. (e.g., approximately 30° C.), and the second temperature range $T_2$ is between about 60° C. and about 100° C. (e.g., approximately 80° C.).

In some embodiments, the first temperature range $T_1$ is higher than the second temperature range $T_2$. In some embodiments, the first temperature range $T_1$ is between about 40° C. and about 100° C. (e.g., between about 50° C. and about 90° C., between about 60° C. and about 90° C., between about 70° C. and about 90° C.). In some embodiments, the second temperature range $T_2$ is between about 15° C. and about 40° C. (e.g., between about 25° C. and about 35° C., between about 15° C. and about 30° C., between about 20° C. and about 30° C.). In some embodiments, the first temperature range $T_1$ is between about 60° C. and about 100° C. (e.g., approximately 80° C.), and the second temperature range $T_2$ is between about 20° C. and about 40° C. (e.g., approximately 30° C.).

Panel (I) depicts a sequencing reaction mixture at a temperature that is within a first temperature range $T_1$ which is optimal for affinity reagent activity over exopeptidase activity. For illustrative purposes, a polypeptide of amino acid sequence "KFVAG . . . " is shown. When the reaction mixture temperature is within the first temperature range $T_1$, labeled affinity reagents in the mixture are activated (e.g., renatured) to initiate amino acid recognition by associating with the polypeptide terminus. Also within the first temperature range $T_1$, labeled exopeptidases in the mixture are inactivated (e.g., denatured) to prevent amino acid cleavage during recognition. In panel (I), a first affinity reagent is shown reversibly associating with lysine at the polypeptide terminus, while a labeled exopeptidase (e.g., Pfu aminopeptidase I (Pfu API)) is shown denatured. In some embodiments, amino acid recognition occurs for a predetermined duration of time before initiating cleavage of the amino acid. In some embodiments, amino acid recognition occurs for a duration of time required to reach a desired confidence interval for identification before initiating cleavage of the amino acid. Following amino acid recognition, the reaction proceeds by changing the temperature of the mixture to within a second temperature range $T_2$.

Panel (II) depicts the sequencing reaction mixture at a temperature that is within a second temperature range $T_2$ which is optimal for exopeptidase activity over affinity reagent activity. For illustrative purposes of this example, the second temperature range $T_2$ is higher than the first temperature range $T_1$, although it should be appreciated that reagent activity may be optimized for any desired temperature range. Accordingly, progression from panel (I) to panel (II) is carried out by raising the reaction mixture temperature using a suitable source of heat. When the reaction mixture reaches a temperature that is within the second temperature range $T_2$, labeled exopeptidases in the mixture are activated (e.g., renatured) to initiate terminal amino acid cleavage by exopeptidase activity. Also within the second temperature range $T_2$, labeled affinity reagents in the mixture are inactivated (e.g., denatured) to prevent amino acid recognition during cleavage. In panel (II), a labeled exopeptidase is shown cleaving the terminal lysine residue, while labeled affinity reagents are denatured. In some embodiments, amino acid cleavage occurs for a predetermined duration of time before initiating recognition of a successive amino acid at the polypeptide terminus. In some embodiments, amino acid cleavage occurs for a duration of time required to detect cleavage before initiating recognition of a successive amino acid. Following amino acid cleavage, the reaction proceeds by changing the temperature of the mixture to within the first temperature range $T_1$.

Panel (III) depicts the beginning of the next cycle in the sequencing reaction, wherein the reaction mixture temperature has been reduced back to within the first temperature range $T_1$. Accordingly, in this example, progression from panel (II) to panel (III) can be carried out by removing the reaction mixture from the source of heat or otherwise cooling the reaction mixture (e.g., actively or passively) to within the first temperature range $T_1$. As shown, labeled affinity reagents are renatured, including a second affinity reagent that reversibly associates with phenylalanine at the polypeptide terminus, while the labeled exopeptidase is shown denatured. The sequencing reaction continues by further cycling between amino acid recognition and amino acid cleavage in a temperature-dependent fashion as illustrated by this example.

Accordingly, a dynamic sequencing approach can involve reaction cycling that is controlled at the level of protein activity or function of one or more proteins within a reaction mixture. It should be appreciated that the temperature-dependent polypeptide sequencing process depicted in FIG. 3B and described above may be illustrative of a general approach to polypeptide sequencing by controllable cycling of condition-dependent recognition and cleavage. For example, in some embodiments, the application provides a luminescence-dependent sequencing process using luminescence-activated reagents. In some embodiments, a luminescence-dependent sequencing process involves cycles of luminescence-dependent amino acid recognition and cleavage. Each cycle of the sequencing reaction may be carried out by exposing a sequencing reaction mixture to two different luminescent conditions: a first luminescent condition that is optimal for affinity reagent activity over exopeptidase activity (e.g., to promote amino acid recognition), and a second luminescent condition that is optimal for exopeptidase activity over affinity reagent activity (e.g., to promote amino acid cleavage). The sequencing reaction progresses by alternating between exposing the reaction mixture to the first luminescent condition (to initiate amino acid recognition) and exposing the reaction mixture to the second luminescent condition (to initiate amino acid cleavage). By way of example and not limitation, in some embodiments, the two different luminescent conditions comprise a first wavelength and a second wavelength.

In some aspects, the application provides methods of polypeptide sequencing in real-time by evaluating binding interactions of one or more labeled affinity reagents with terminal and internal amino acids and binding interactions of a labeled non-specific exopeptidase with terminal amino acids. FIG. 4 shows an example of a method of sequencing in which the method described and illustrated for the approach in FIGS. 3A-3B is modified by using a labeled affinity reagent 410 that selectively binds to and dissociates from one type of amino acid (shown here as lysine) at both terminal and internal positions (FIG. 4, inset panel). As described in the previous approach, the selective binding gives rise to a series of pulses in signal output 400. In this approach, however, the series of pulses occur at a rate that is determined by the number of the type of amino acid throughout the polypeptide. Accordingly, in some embodiments, the rate of pulsing corresponding to binding events would be diagnostic of the number of cognate amino acids currently present in the polypeptide.

As in the previous approach, a labeled non-specific peptidase 420 would be present at a relatively lower concentration than labeled affinity reagent 410, e.g., to give optimal time windows in between cleavage events (FIG. 4, inset panel). Additionally, in certain embodiments, uniquely identifiable luminescent label of labeled non-specific peptidase 420 would indicate when cleavage events have occurred. As the polypeptide undergoes iterative cleavage, the rate of pulsing corresponding to binding by labeled affinity reagent 410 would drop in a step-wise manner whenever a terminal amino acid is cleaved by labeled non-specific peptidase 420. This concept is illustrated by plot 402, which generally depicts pulse rate as a function of time, with cleavage events in time denoted by arrows. Thus, in some embodiments, amino acids may be identified—and polypeptides thereby sequenced—in this approach based on a pulsing pattern and/or on the rate of pulsing that occurs within a pattern detected between cleavage events.

In some embodiments, terminal polypeptide sequence information (e.g., determined as described herein) can be combined with polypeptide sequence information obtained from one or more other sources. For example, terminal polypeptide sequence information could be combined with internal polypeptide sequence information. In some embodiments, internal polypeptide sequence information can be obtained using one or more amino acid recognition molecules that associate with internal amino acids, as described herein. Internal or other polypeptide sequence information can be obtained before or during a polypeptide degradation process. In some embodiments, sequence information obtained from these methods can be combined with polypeptide sequence information using other techniques, e.g., sequence information obtained using one or more internal amino acid recognition molecules.

Shielded Recognition Molecules

In accordance with embodiments described herein, single-molecule polypeptide sequencing methods can be carried out by illuminating a surface-immobilized polypeptide with excitation light, and detecting luminescence produced by a label attached to an amino acid recognition molecule (e.g., a labeled affinity reagent). In some cases, radiative and/or non-radiative decay produced by the label can result in photodamage to the polypeptide. For example, FIG. 5A illustrates an example sequencing reaction in which a recognition molecule is shown associated with a polypeptide immobilized to a surface.

In the presence of excitation illumination, the label can produce fluorescence through radiative decay which results in a detectable association event. However, in some cases, the label produces non-radiative decay which can result in the formation of reactive oxygen species 500. The reactive oxygen species 500 can eventually damage the immobilized peptide, such that the reaction ends before obtaining complete sequence information for the polypeptide. This photodamage can occur, for example, at the exposed polypeptide terminus (top open arrow), at an internal position (middle open arrow), or at the surface linker attaching the polypeptide to the surface (bottom open arrow).

The inventors have found that photodamage can be mitigated and recognition times extended by incorporation of a shielding element into an amino acid recognition molecule. FIG. 5B illustrates an example sequencing reaction using a shielded recognition molecule that includes a shield 502. Shield 502 forms a covalent or non-covalent linkage group that provides increased distance between the label and polypeptide, such that damaging effects from reactive oxygen species 500 can be reduced due to free radical decay over the label-polypeptide separation distance. Shield 502 can also provide a steric barrier that shields the polypeptide from the label by absorbing damage from reactive oxygen species 500 and radiative and/or non-radiative decay.

Without wishing to be bound by theory, it is thought that a shield, positioned between a recognition component and a label component, can absorb, deflect, or otherwise block radiative and/or non-radiative decay emitted by the label component. In some embodiments, the shield prevents or limits the extent to which one or more labels (e.g., luminescent labels) interact with one or more amino acid recognition molecules. In some embodiments, the shield prevents or limits the extent to which one or more labels interact with one or more molecules associated with an amino acid recognition molecule (e.g., a polypeptide associated with the recognition molecule). Accordingly, in some embodiments, the term shield can generally refer to a protective or shielding effect that is provided by some portion of a linkage group formed between a recognition component and a label component.

In some embodiments, a shield is attached to one or more amino acid recognition molecules (e.g., a recognition component) and to one or more labels (e.g., a label component). In some embodiments, the recognition and label components are attached at non-adjacent sites on the shield. For example, one or more amino acid recognition molecules can be attached to a first side of the shield, and one or more labels can be attached to a second side of the shield, where the first and second sides of the shield are distant from each other. In some embodiments, the attachment sites are on approximately opposite sides of the shield.

The distance between the site at which a shield is attached to a recognition molecule and the site at which the shield is attached to a label can be a linear measurement through space or a non-linear measurement across the surface of the shield. The distance between the recognition molecule and label attachment sites on a shield can be measured by modeling the three-dimensional structure of the shield. In some embodiments, this distance can be at least 2 nm, at least 4 nm, at least 6 nm, at least 8 nm, at least 10 nm, at least 12 nm, at least 15 nm, at least 20 nm, at least 30 nm, at least 40 nm, or more. Alternatively, the relative positions of the recognition molecule and label on a shield can be described by treating the structure of the shield as a quadratic surface (e.g., ellipsoid, elliptic cylinder). In some embodiments, the recognition molecule and label attachment sites are separated by a distance that is at least one eighth of the distance around an ellipsoidal shape representing the shield. In some embodiments, the recognition molecule and label are separated by a distance that is at least one quarter of the distance around an ellipsoidal shape representing the shield. In some embodiments, the recognition molecule and label are separated by a distance that is at least one third of the distance around an ellipsoidal shape representing the shield. In some embodiments, the recognition molecule and label are separated by a distance that is one half of the distance around an ellipsoidal shape representing the shield.

The size of a shield should be such that a label is unable or unlikely to directly contact the polypeptide when the amino acid recognition molecule is associated with the polypeptide. The size of a shield should also be such that an attached label is detectable when the amino acid recognition molecule is associated with the polypeptide. For example, the size should be such that an attached luminescent label is within an illumination volume to be excited.

It should be appreciated that there are a variety of parameters by which a practitioner could evaluate shielding effects. Generally, the effects of a shielding element can be evaluated by conducting a comparative assessment between a composition having the shielding element and a composition lacking the shielding element. For example, a shielding element can increase recognition time of an amino acid recognition molecule. In some embodiments, recognition time refers to the length of time in which association events between the recognition molecule and a polypeptide are observable in a polypeptide sequencing reaction as described herein. In some embodiments, recognition time is increased by about 10-25%, 25-50%, 50-75%, 75-100%, or more than 100%, for example by about 2-fold, 3-fold, 4-fold, 5-fold, or more, relative to a polypeptide sequencing reaction performed under the same conditions, with the exception that the amino acid recognition molecule lacks the shielding element but is otherwise similar or identical. In some embodiments, a shielding element can increase sequencing accuracy and/or sequence read length (e.g., by at least 5%, at least 10%, at least 15%, at least 25% or more, relative to a sequencing reaction performed under comparative conditions as described above).

Accordingly, in some aspects, the application provides shielded recognition molecules comprising at least one amino acid recognition molecule, at least one detectable label, and a shielding element (e.g., a "shield") that forms a covalent or non-covalent linkage group between the recognition molecule and label. In some embodiments, a shielding element is at least 2 nm, at least 5 nm, at least 10 nm, at least 12 nm, at least 15 nm, at least 20 nm, or more, in length (e.g., in an aqueous solution). In some embodiments, a shielding element is between about 2 nm and about 100 nm in length (e.g., between about 2 nm and about 50 nm, between about 10 nm and about 50 nm, between about 20 nm and about 100 nm).

In some embodiments, a shield (e.g., shielding element) forms a covalent or non-covalent linkage group between one or more amino acid recognition molecules (e.g., a recognition component) and one or more labels (e.g., a label component). As used herein, in some embodiments, covalent and non-covalent linkages or linkage groups refer to the nature of the attachments of the recognition and label components to the shield.

In some embodiments, a covalent linkage, or a covalent linkage group, refers to a shield that is attached to each of the recognition and label components through a covalent bond or a series of contiguous covalent bonds. Covalent attachment one or both components can be achieved by covalent conjugation methods known in the art. For example, in some embodiments, click chemistry techniques (e.g., copper-catalyzed, strain-promoted, copper-free click chemistry, etc.) can be used to attach one or both components to the shield. Such methods generally involve conjugating one reactive moiety to another reactive moiety to form one or more covalent bonds between the reactive moieties. Accordingly, in some embodiments, a first reactive moiety of a shield can be contacted with a second reactive moiety of a recognition or label component to form a covalent attachment. Examples of reactive moieties include, without limitation, reactive amines, azides, alkynes, nitrones, alkenes (e.g., cycloalkenes), tetrazines, tetrazoles, and other reactive moieties suitable for click reactions and similar coupling techniques.

In some embodiments, a non-covalent linkage, or a non-covalent linkage group, refers to a shield that is attached to one or both of the recognition and label components through one or more non-covalent coupling means, including but not limited to receptor-ligand interactions and oligonucleotide strand hybridization. Examples of receptor-ligand interactions are provided herein and include, without limitation, protein-protein complexes, protein-ligand complexes, protein-aptamer complexes, and aptamer-nucleic acid complexes. Various configurations and strategies for oligonucleotide strand hybridization are described herein and are known in the art (see, e.g., U.S. Patent Publication No. 2019/0024168).

In some embodiments, shield 502 comprises a polymer, such as a biomolecule or a dendritic polymer. FIG. 5C depicts examples of polymer shields and configurations of shielded recognition molecules of the application. A first shielded construct 504 shows an example of a protein shield 530. In some embodiments, protein shield 530 forms a covalent linkage group between a recognition molecule and a label. For example, in some embodiments, protein shield 530 is attached to each of the recognition molecule and label through one or more covalent bonds, e.g., by covalent attachment through a side-chain of a natural or unnatural amino acid of protein shield 530. In some embodiments, protein shield 530 forms a non-covalent linkage group between a recognition molecule and a label. For example, in some embodiments, protein shield 530 is a monomeric or multimeric protein comprising one or more ligand-binding sites. In some embodiments, a non-covalent linkage group is formed through one or more ligand moieties bound to the one or more ligand-binding sites. Additional examples of non-covalent linkages formed by protein shields are described elsewhere herein.

A second shielded construct 506 shows an example of a double-stranded nucleic acid shield comprising a first oligonucleotide strand 532 hybridized with a second oligonucleotide strand 534. As shown, in some embodiments, the double-stranded nucleic acid shield can comprise a recognition molecule attached to first oligonucleotide strand 532, and a label attached to second oligonucleotide strand 534. In this way, the double-stranded nucleic acid shield forms a non-covalent linkage group between the recognition molecule and the label through oligonucleotide strand hybridization. In some embodiments, a recognition molecule and a label can be attached to the same oligonucleotide strand, which can provide a single-stranded nucleic acid shield or a double-stranded nucleic acid shield through hybridization with another oligonucleotide strand. In some embodiments, strand hybridization can provide increased rigidity within a linkage group to further enhance separation between the recognition molecule and the label.

Where shielding element 502 comprises a nucleic acid, the separation distance between a label and a recognition molecule can be measured by the distance between attachment sites on the nucleic acid (e.g., direct attachment or indirect attachment, such as through one or more additional shield polymers). In some embodiments, the distance between attachment sites on a nucleic acid can be measured by the number of nucleotides within the nucleic acid that occur between the label and the recognition molecule. It should be understood that the number of nucleotides can refer to either the number of nucleotide bases in a single-stranded nucleic acid or the number of nucleotide base pairs in a double-stranded nucleic acid.

Accordingly, in some embodiments, the attachment site of a recognition molecule and the attachment site of a label can be separated by between 5 and 200 nucleotides (e.g., between 5 and 150 nucleotides, between 5 and 100 nucleotides, between 5 and 50 nucleotides, between 10 and 100 nucleotides). It should be appreciated that any position in a nucleic acid can serve as an attachment site for a recognition molecule, a label, or one or more additional polymer shields. In some embodiments, an attachment site can be at or approximately at the 5' or 3' end, or at an internal position along a strand of the nucleic acid.

The non-limiting configuration of second shielded construct 506 illustrates an example of a shield that forms a non-covalent linkage through strand hybridization. A further example of non-covalent linkage is illustrated by a third shielded construct 508 comprising an oligonucleotide shield 536. In some embodiments, oligonucleotide shield 536 is a nucleic acid aptamer that binds a recognition molecule to form a non-covalent linkage. In some embodiments, the recognition molecule is a nucleic acid aptamer, and oligonucleotide shield 536 comprises an oligonucleotide strand that hybridizes with the aptamer to form a non-covalent linkage.

A fourth shielded construct 510 shows an example of a dendritic polymer shield 538. As used herein, in some embodiments, a dendritic polymer refers generally to a polyol or a dendrimer. Polyols and dendrimers have been described in the art, and may include branched dendritic structures optimized for a particular configuration. In some embodiments, dendritic polymer shield 538 comprises polyethylene glycol, tetraethylene glycol, poly(amidoamine), poly(propyleneimine), poly(propyleneamine), carbosilane, poly(L-lysine), or a combination of one or more thereof.

A dendrimer, or dendron, is a repetitively branched molecule that is typically symmetric around the core and that may adopt a spherical three-dimensional morphology. See, e.g., Astruc et al. (2010) Chem. Rev. 110:1857. Incorporation of such structures into a shield of the application can provide for a protective effect through the steric inhibition of contacts between a label and one or more biomolecules associated therewith (e.g., a recognition molecule and/or a polypeptide associated with the recognition molecule). Refinement of the chemical and physical properties of the dendrimer through variation in primary structure of the molecule, including potential functionalization of the dendrimer surface, allows the shielding effects to be adjusted as desired. Dendrimers may be synthesized by a variety of techniques using a wide range of materials and branching reactions, as is known in the art. Such synthetic variation allows the properties of the dendrimer to be customized as necessary. Examples of polyol and dendrimer compounds which can be used in accordance with shields of the application include, without limitation, compounds described in U.S. Patent Publication No. 20180346507.

FIG. 5D depicts further example configurations of shielded recognition molecules of the application. A protein-nucleic acid construct 512 shows an example of a shield comprising more than one polymer in the form of a protein and a double-stranded nucleic acid. In some embodiments, the protein portion of the shield is attached to the nucleic acid portion of the shield through a covalent linkage. In some embodiments, the attachment is through a non-covalent linkage. For example, in some embodiments, the protein portion of the shield is a monovalent or multivalent protein that forms at least one non-covalent linkage through a ligand moiety attached to a ligand-binding site of the monovalent or multivalent protein. In some embodiments, the protein portion of the shield comprises an avidin protein.

In some embodiments, a shielded recognition molecule of the application is an avidin-nucleic acid construct 514. In some embodiments, avidin-nucleic acid construct 514 includes a shield comprising an avidin protein 540 and a double-stranded nucleic acid. As described herein, avidin protein 540 may be used to form a non-covalent linkage between one or more amino acid recognition molecules and one or more labels, either directly or indirectly, such as through one or more additional shield polymers described herein.

Avidin proteins are biotin-binding proteins, generally having a biotin binding site at each of four subunits of the avidin protein. Avidin proteins include, for example, avidin, streptavidin, traptavidin, tamavidin, bradavidin, xenavidin, and homologs and variants thereof. In some cases, the monomeric, dimeric, or tetrameric form of the avidin protein can be used. In some embodiments, the avidin protein of an avidin protein complex is streptavidin in a tetrameric form (e.g., a homotetramer). In some embodiments, the biotin binding sites of an avidin protein provide attachment sites for one or more amino acid recognition molecules, one or more labels, and/or one or more additional shield polymers described herein.

An illustrative diagram of an avidin protein complex is shown in the inset panel of FIG. 5D. As shown in the inset panel, avidin protein 540 can include a binding site 542 at each of four subunits of the protein which can be bound to a biotin moiety (shown as white circles). The multivalency of avidin protein 540 can allow for various linkage configurations, which are generally shown for illustrative purposes. For example, in some embodiments, a biotin linkage moiety 544 can be used to provide a single point of attachment to avidin protein 540. In some embodiments, a bis-biotin linkage moiety 546 can be used to provide two points of attachment to avidin protein 540. As illustrated by avidin-nucleic acid construct 514, an avidin protein complex may be formed by two bis-biotin linkage moieties, which form a trans-configuration to provide an increased separation distance between a recognition molecule and a label.

Various further examples of avidin protein shield configurations are shown. A first avidin construct 516 shows an example of an avidin shield attached to a recognition molecule through a bis-biotin linkage moiety and to two labels through separate biotin linkage moieties. A second avidin construct 518 shows an example of an avidin shield attached to two recognition molecules through separate biotin linkage moieties and to a label through a bis-biotin linkage moiety. A third avidin construct 520 shows an example of an avidin shield attached to two recognition molecules through separate biotin linkage moieties and to a labeled nucleic acid through a biotin linkage moiety of each strand of the nucleic acid. A fourth avidin construct 522 shows an example of an avidin shield attached to a recognition molecule and to a labeled nucleic acid through separate bis-biotin linkage moieties. As shown, the label is further shielded from the recognition molecule by a dendritic polymer between the label and nucleic acid.

It should be appreciated that the example configurations of shielded recognition molecules shown in FIGS. 5A-5D are provided for illustrative purposes. The inventors have conceived of various other shield configurations using one or more different polymers that form a covalent or non-covalent linkage between recognition and label components of a shielded recognition molecule. By way of example, FIG. 5E illustrates the modularity of shield configuration in accordance with the application.

As shown at the top of FIG. 5E, a shielded recognition molecule generally comprises a recognition component 550, a shielding element 552, and a label component 554. For ease of illustration, recognition component 550 is depicted as one amino acid recognition molecule, and label component 554 is depicted as one label. It should be appreciated that shielded recognition molecules of the application can comprise shielding element 552 attached to one or more amino acid recognition molecules and one or more labels. Where recognition component 550 comprises more than one recognition molecule, each recognition molecule can be attached to shielding element 552 at one or more attachment sites on shielding element 552. Where label component 554 comprises more than one label, each label can be attached to shielding element 552 at one or more attachment sites on shielding element 552.

In some embodiments, shielding element 552 comprises a protein 560. In some embodiments, protein 560 is a monovalent or multivalent protein. In some embodiments, protein 560 is a monomeric or multimeric protein, such as a protein homodimer, protein heterodimer, protein oligomer, or other proteinaceous molecule. In some embodiments, shielding element 552 comprises a protein complex formed by a protein non-covalently bound to at least one other molecule. For example, in some embodiments, shielding element 552 comprises a protein-protein complex 562. In some embodiments, protein-protein complex 562 comprises one proteinaceous molecule specifically bound to another proteinaceous molecule. In some embodiments, protein-protein complex 562 comprises an antibody or antibody fragment (e.g., scFv) bound to an antigen. In some embodiments, protein-protein complex 562 comprises a receptor bound to a protein ligand. Additional examples of protein-protein complexes include, without limitation, trypsin-aprotinin, barnase-barstar, and colicin E9-Im9 immunity protein.

In some embodiments, shielding element 552 comprises a protein-ligand complex 564. In some embodiments, protein-ligand complex 564 comprises a monovalent protein and a non-proteinaceous ligand moiety. For example, in some embodiments, protein-ligand complex 564 comprises an enzyme bound to a small-molecule inhibitor moiety. In some embodiments, protein-ligand complex 564 comprises a receptor bound to a non-proteinaceous ligand moiety.

In some embodiments, shielding element 552 comprises a multivalent protein complex formed by a multivalent protein non-covalently bound to one or more ligand moieties. In some embodiments, shielding element 552 comprises an avidin protein complex formed by an avidin protein non-covalently bound to one or more biotin linkage moieties. Constructs 566, 568, 570, and 572 provide illustrative examples of avidin protein complexes, any one or more of which may be incorporated into shielding element 552.

In some embodiments, shielding element 552 comprises a two-way avidin complex 566 comprising an avidin protein bound to two bis-biotin linkage moieties. In some embodiments, shielding element 552 comprises a three-way avidin complex 568 comprising an avidin protein bound to two biotin linkage moieties and a bis-biotin linkage moiety. In some embodiments, shielding element 552 comprises a four-way avidin complex 570 comprising an avidin protein bound to four biotin linkage moieties.

In some embodiments, shielding element 552 comprises an avidin protein comprising one or two non-functional binding sites engineered into the avidin protein. For example, in some embodiments, shielding element 552 comprises a divalent avidin complex 572 comprising an avidin protein bound to a biotin linkage moiety at each of two subunits, where the avidin protein comprises a non-functional ligand-binding site 548 at each of two other subunits. As shown, in some embodiments, divalent avidin complex 572 comprises a trans-divalent avidin protein, although a cis-divalent avidin protein may be used depending on a desired implementation. In some embodiments, the avidin protein is a trivalent avidin protein. In some embodiments, the trivalent avidin protein comprises non-functional ligand-binding site 548 at one subunit and is bound to three biotin linkage moieties, or one biotin linkage moiety and one bis-biotin linkage moiety, at the other subunits.

In some embodiments, shielding element 552 comprises a dendritic polymer 574. In some embodiments, dendritic polymer 574 is a polyol or a dendrimer, as described elsewhere herein. In some embodiments, dendritic polymer 574 is a branched polyol or a branched dendrimer. In some embodiments, dendritic polymer 574 comprises a monosaccharide-TEG, a disaccharide, an N-acetyl monosaccharide, a TEMPO-TEG, a trolox-TEG, or a glycerol dendrimer. Examples of polyols useful in accordance with shielded recognition molecules of the application include polyether polyols and polyester polyols, e.g., polyethylene glycol, polypropylene glycol, and similar such polymers well known in the art. In some embodiments, dendritic polymer 574 comprises a compound of the following formula: —(CH$_2$CH$_2$O)$_n$—, where n is an integer from 1 to 500, inclusive. In some embodiments, dendritic polymer 574 comprises a compound of the following formula: —(CH$_2$CH$_2$O)$_n$—, wherein n is an integer from 1 to 100, inclusive.

In some embodiments, shielding element 552 comprises a nucleic acid. In some embodiments, the nucleic acid is single-stranded. In some embodiments, label component 554 is attached directly or indirectly to one end of the single-stranded nucleic acid (e.g., the 5' end or the 3' end) and recognition component 550 is attached directly or indirectly to the other end of the single-stranded nucleic acid (e.g., the 3' end or the 5' end). For example, the single-stranded nucleic acid can comprise a label attached to the 5' end of the nucleic acid and an amino acid recognition molecule attached to the 3' end of the nucleic acid.

In some embodiments, shielding element 552 comprises a double-stranded nucleic acid 576. As shown, in some embodiments, double-stranded nucleic acid 576 can form a non-covalent linkage between recognition component 550 and label component 554 through strand hybridization. However, in some embodiments, double-stranded nucleic acid 576 can form a covalent linkage between recognition component 550 and label component 554 through attachment to the same oligonucleotide strand. In some embodiments, label component 554 is attached directly or indirectly to one end of the double-stranded nucleic acid and recognition component 550 is attached directly or indirectly to the other end of the double-stranded nucleic acid. For example, the double-stranded nucleic acid can comprise a label attached to the 5' end of one strand and an amino acid recognition molecule attached to the 5' end of the other strand.

In some embodiments, shielding element 552 comprises a nucleic acid that forms one or more structural motifs which can be useful for increasing steric bulk of the shield. Examples of nucleic acid structural motifs include, without limitation, stem-loops, three-way junctions (e.g., formed by two or more stem-loop motifs), four-way junctions (e.g., Holliday junctions), and bulge loops.

In some embodiments, shielding element 552 comprises a nucleic acid that forms a stem-loop 578. A stem-loop, or hairpin loop, is an unpaired loop of nucleotides on an oligonucleotide strand that is formed when the oligonucleotide strand folds and forms base pairs with another section of the same strand. In some embodiments, the unpaired loop of stem-loop 578 comprises three to ten nucleotides. Accordingly, stem-loop 578 can be formed by two regions of an oligonucleotide strand having inverted complementary sequences that hybridize to form a stem, where the two regions are separated by the three to ten nucleotides that form the unpaired loop.

In some embodiments, the stem of stem-loop 578 can be designed to have one or more G/C nucleotides, which can provide added stability with the addition hydrogen bonding interaction that forms compared to A/T nucleotides. In some embodiments, the stem of stem-loop 578 comprises G/C nucleotides immediately adjacent to an unpaired loop sequence. In some embodiments, the stem of stem-loop 578 comprises G/C nucleotides within the first 2, 3, 4, or 5 nucleotides adjacent to an unpaired loop sequence. In some embodiments, an unpaired loop of stem-loop 578 comprises one or more attachment sites. In some embodiments, an attachment site occurs at an abasic site in the unpaired loop. In some embodiments, an attachment site occurs at a base of the unpaired loop.

In some embodiments, stem-loop 578 is formed by a double-stranded nucleic acid. As described herein, in some embodiments, the double-stranded nucleic acid can form a non-covalent linkage group through strand hybridization of first and second oligonucleotide strands. However, in some embodiments, shielding element 552 comprises a single-stranded nucleic acid that forms a stem-loop motif, e.g., to provide a covalent linkage group. In some embodiments, shielding element 552 comprises a nucleic acid that forms two or more stem-loop motifs. For example, in some embodiments, the nucleic acid comprises two stem-loop motifs. In some embodiments, a stem of one stem-loop motif is adjacent to the stem of the other such that the motifs together form a three-way junction. In some embodiments, shielding element 552 comprises a nucleic acid that forms a four-way junction 578. In some embodiments, four-way junction 578 is formed through hybridization of two or more oligonucleotide strands (e.g., 2, 3, or 4 oligonucleotide strands).

In some embodiments, shielding element 552 comprises one or more polymers selected from 560, 562, 564, 566, 568, 570, 572, 574, 576, 578, and 580 of FIG. 5E. It should be appreciated that the linkage moieties and attachment sites shown on each of 560, 562, 564, 566, 568, 570, 572, 574, 576, 578, and 580 are shown for illustrative purposes and are not intended to depict a preferred linkage or attachment site configuration.

In some aspects, the application provides an amino acid recognition molecule of Formula (I):

$$A\text{-}(Y)_n\text{-}D \qquad (I),$$

wherein: A is an amino acid binding component comprising at least one amino acid recognition molecule; each instance of Y is a polymer that forms a covalent or non-covalent linkage group; n is an integer from 1 to 10, inclusive; and D is a label component comprising at least one detectable label. In some embodiments, the application provides a composition comprising a soluble amino acid recognition molecule of Formula (I).

In some embodiments, A comprises a plurality of amino acid recognition molecules. In some embodiments, each amino acid recognition molecule of the plurality is attached to a different attachment site on Y. In some embodiments, at least two amino acid recognition molecules of the plurality are attached to a single attachment site on Y. In some embodiments, the amino acid recognition molecule is a recognition protein or a nucleic acid aptamer, e.g., as described elsewhere herein.

In some embodiments, the detectable label is a luminescent label or a conductivity label. In some embodiments, the luminescent label comprises at least one fluorophore dye molecule. In some embodiments, D comprises 20 or fewer fluorophore dye molecules. In some embodiments, the ratio of the number of fluorophore dye molecules to the number of amino acid recognition molecules is between 1:1 and 20:1. In some embodiments, the luminescent label comprises at least one FRET pair comprising a donor label and an acceptor label. In some embodiments, the ratio of the donor label to the acceptor label is 1:1, 2:1, 3:1, 4:1, or 5:1. In some embodiments, the ratio of the acceptor label to the donor label is 1:1, 2:1, 3:1, 4:1, or 5:1.

In some embodiments, D is less than 200 Å in diameter. In some embodiments, —(Y)$_n$— is at least 2 nm in length.

In some embodiments, —(Y)$_n$— is at least 5 nm in length. In some embodiments, —(Y)$_n$— is at least 10 nm in length. In some embodiments, each instance of Y is independently a biomolecule, a polyol, or a dendrimer. In some embodiments, the biomolecule is a nucleic acid, a polypeptide, or a polysaccharide.

In some embodiments, the amino acid recognition molecule is of one of the following formulae:

A-Y$^1$—(Y)$_m$-D or A-(Y)$_m$—Y$^1$-D, wherein: Y$^1$ is a nucleic acid or a polypeptide; and m is an integer from 0 to 10, inclusive.

In some embodiments, the nucleic acid comprises a first oligonucleotide strand. In some embodiments, the nucleic acid comprises a second oligonucleotide strand hybridized with the first oligonucleotide strand. In some embodiments, the nucleic acid forms a covalent linkage through the first oligonucleotide strand. In some embodiments, the nucleic acid forms a non-covalent linkage through the hybridized first and second oligonucleotide strands.

In some embodiments, the polypeptide is a monovalent or multivalent protein. In some embodiments, the monovalent or multivalent protein forms at least one non-covalent linkage through a ligand moiety attached to a ligand-binding site of the monovalent or multivalent protein. In some embodiments, A, Y, or D comprises the ligand moiety.

In some embodiments, the amino acid recognition molecule is of one of the following formulae:

A-(Y)$_m$—Y$^2$-D or A-Y$^2$—(Y)$_m$-D, wherein: Y$^2$ is a polyol or dendrimer; and m is an integer from 0 to 10, inclusive. In some embodiments, the polyol or dendrimer comprises polyethylene glycol, tetraethylene glycol, poly(amidoamine), poly(propyleneimine), poly(propyleneamine), carbosilane, poly(L-lysine), or a combination of one or more thereof.

In some aspects, the application provides an amino acid recognition molecule of Formula (II):

A-Y$^1$-D (II), wherein: A is an amino acid binding component comprising at least one amino acid recognition molecule; Y$^1$ is a nucleic acid or a polypeptide; D is a label component comprising at least one detectable label. In some embodiments, when Y$^1$ is a nucleic acid, the nucleic acid forms a covalent or non-covalent linkage group. In some embodiments, when Y$^1$ is a polypeptide, the polypeptide forms a non-covalent linkage group characterized by a dissociation constant ($K_D$) of less than $50 \times 10^{-9}$ M.

In some embodiments, Y$^1$ is a nucleic acid comprising a first oligonucleotide strand. In some embodiments, the nucleic acid comprises a second oligonucleotide strand hybridized with the first oligonucleotide strand. In some embodiments, A is attached to the first oligonucleotide strand, and wherein D is attached to the second oligonucleotide strand. In some embodiments, A is attached to a first attachment site on the first oligonucleotide strand, and wherein D is attached to a second attachment site on the first oligonucleotide strand. In some embodiments, each oligonucleotide strand of the nucleic acid comprises fewer than 150, fewer than 100, or fewer than 50 nucleotides.

In some embodiments, Y$^1$ is a monovalent or multivalent protein. In some embodiments, the monovalent or multivalent protein forms at least one non-covalent linkage through a ligand moiety attached to a ligand-binding site of the monovalent or multivalent protein. In some embodiments, at least one of A and D comprises the ligand moiety. In some embodiments, the polypeptide is an avidin protein (e.g., avidin, streptavidin, traptavidin, tamavidin, bradavidin, xenavidin, or a homolog or variant thereof). In some embodiments, the ligand moiety is a biotin moiety.

In some embodiments, the amino acid recognition molecule is of one of the following formulae:

A-Y$^1$—(Y)$_n$-D or A-(Y)$_n$—Y$^1$-D, wherein: each instance of Y is a polymer that forms a covalent or non-covalent linkage group; and n is an integer from 1 to 10, inclusive. In some embodiments, each instance of Y is independently a biomolecule, a polyol, or a dendrimer.

In other aspects, the application provides an amino acid recognition molecule comprising: a nucleic acid; at least one amino acid recognition molecule attached to a first attachment site on the nucleic acid; and at least one detectable label attached to a second attachment site on the nucleic acid. In some embodiments, the nucleic acid forms a covalent or non-covalent linkage group between the at least one amino acid recognition molecule and the at least one detectable label.

In some embodiments, the nucleic acid is a double-stranded nucleic acid comprising a first oligonucleotide strand hybridized with a second oligonucleotide strand. In some embodiments, the first attachment site is on the first oligonucleotide strand, and wherein the second attachment site is on the second oligonucleotide strand. In some embodiments, the at least one amino acid recognition molecule is attached to the first attachment site through a protein that forms a covalent or non-covalent linkage group between the at least one amino acid recognition molecule and the nucleic acid. In some embodiments, the at least one detectable label is attached to the second attachment site through a protein that forms a covalent or non-covalent linkage group between the at least one detectable label and the nucleic acid. In some embodiments, the first and second attachment sites are separated by between 5 and 100 nucleotide bases or nucleotide base pairs on the nucleic acid.

In yet other aspects, the application provides an amino acid recognition molecule comprising: a multivalent protein comprising at least two ligand-binding sites; at least one amino acid recognition molecule attached to the protein through a first ligand moiety bound to a first ligand-binding site on the protein; and at least one detectable label attached to the protein through a second ligand moiety bound to a second ligand-binding site on the protein.

In some embodiments, the multivalent protein is an avidin protein comprising four ligand-binding sites. In some embodiments, the ligand-binding sites are biotin binding sites, and wherein the ligand moieties are biotin moieties. In some embodiments, at least one of the biotin moieties is a bis-biotin moiety, and wherein the bis-biotin moiety is bound to two biotin binding sites on the avidin protein. In some embodiments, the at least one amino acid recognition molecule is attached to the protein through a nucleic acid comprising the first ligand moiety. In some embodiments, the at least one detectable label is attached to the protein through a nucleic acid comprising the second ligand moiety.

As described elsewhere herein, shielded recognition molecules of the application may be used in a polypeptide sequencing method in accordance with the application, or any method known in the art. For example, in some embodiments, a shielded recognition molecule provided herein may be used in an Edman-type degradation reaction provided herein, or conventionally known in the art, which can involve iterative cycling of multiple reaction mixtures in a polypeptide sequencing reaction. In some embodiments, a shielded recognition molecule provided herein may be used in a dynamic sequencing reaction of the application, which involves amino acid recognition and degradation in a single reaction mixture.

Sequencing by Degradation of Labeled Polypeptides

In some aspects, the application provides a method of sequencing a polypeptide by identifying a unique combination of amino acids corresponding to a known polypeptide sequence. For example, FIG. 6 shows a method of sequencing by detecting selectively labeled amino acids of a labeled polypeptide 600. In some embodiments, labeled polypeptide 600 comprises selectively modified amino acids such that different amino acid types comprise different luminescent labels. As used herein, unless otherwise indicated, a labeled polypeptide refers to a polypeptide comprising one or more selectively labeled amino acid sidechains. Methods of selective labeling and details relating to the preparation and analysis of labeled polypeptides are known in the art (see, e.g., Swaminathan, et al. *PLoS Comput Biol.* 2015, 11(2): e1004080).

As shown, in some embodiments, labeled polypeptide 600 is immobilized and exposed to an excitation source. An aggregate luminescence from labeled polypeptide 600 is detected and, in some embodiments, exposure to luminescence over time results in a loss in detected signal due to luminescent label degradation (e.g., degradation due to photobleaching). In some embodiments, labeled polypeptide 600 comprises a unique combination of selectively labeled amino acids that give rise to an initial detected signal. As generically illustrated, degradation of luminescent labels over time results in a corresponding decrease in a detected signal for the photobleached labeled polypeptide 602. In some embodiments, the signal can be deconvoluted by analysis of one or more luminescence properties (e.g., signal deconvolution by luminescence lifetime analysis). In some embodiments, the unique combination of selectively labeled amino acids of labeled polypeptide 600 have been computationally precomputed and empirically verified—e.g., based on known polypeptide sequences of a proteome. In some embodiments, the combination of detected amino acid labels are compared against a database of known sequences of a proteome of an organism to identify a particular polypeptide of the database corresponding to labeled polypeptide 600.

In some embodiments, the approach illustrated in FIG. 6 may be modified by determining an optimal sample concentration for performing a sequencing reaction that maximizes sampling in massively parallel analysis. In some embodiments, the concentration is selected so that a desired fraction of the sample wells of an array (e.g., 30%) are occupied at any given time. Without wishing to be bound by theory, it is thought that while a polypeptide is bleached over a period of time, the same well continues to be available for further analysis. Through diffusion, approximately 30% of the sample wells of an array can be used for analysis every 3 minutes. As an illustrative example, in a million sample well chip, 6,000,000 polypeptides per hour may be sampled, or 24,000,000 over a 4 hour period.

In some aspects, the application provides a method of sequencing a polypeptide by detecting luminescence of a labeled polypeptide which is subjected to repeated cycles of terminal amino acid modification and cleavage. For example, FIG. 7 shows a method of sequencing a labeled polypeptide by Edman degradation in accordance with the application. In some embodiments, the method generally proceeds as described herein for other methods of sequencing by Edman degradation. For example, in some embodiments, steps (1) and (2) shown in FIG. 7 may be performed as described elsewhere herein for terminal amino acid modification and terminal amino acid cleavage, respectively, in an Edman degradation reaction.

As shown in the example depicted in FIG. 7, in some embodiments, the method comprises a step of (1) modifying the terminal amino acid of a labeled polypeptide. As described elsewhere herein, in some embodiments, modifying comprises contacting the terminal amino acid with an isothiocyanate (e.g., PITC) to form an isothiocyanate-modified terminal amino acid. In some embodiments, an isothiocyanate modification 710 converts the terminal amino acid to a form that is more susceptible to removal by a cleaving reagent (e.g., a chemical or enzymatic cleaving reagent, as described herein). Accordingly, in some embodiments, the method comprises a step of (2) removing the modified terminal amino acid using chemical or enzymatic means detailed elsewhere herein for Edman degradation.

In some embodiments, the method comprises repeating steps (1) through (2) for a plurality of cycles, during which luminescence of the labeled polypeptide is detected, and cleavage events corresponding to the removal of a labeled amino acid from the terminus may be detected as a decrease in detected signal. In some embodiments, no change in signal following step (2) as shown in FIG. 7 identifies an amino acid of unknown type. Accordingly, in some embodiments, partial sequence information may be determined by evaluating a signal detected following step (2) during each sequential round by assigning an amino acid type by a determined identity based on a change in detected signal or identifying an amino acid type as unknown based on no change in a detected signal.

In some aspects, a method of sequencing a polypeptide in accordance with the application comprises sequencing by processive enzymatic cleavage of a labeled polypeptide, as generally illustrated in FIGS. 8A-8C. As shown, in some embodiments, a labeled polypeptide is subjected to degradation using a modified processive exopeptidase that continuously cleaves a terminal amino acid from one terminus to another terminus. Exopeptidases are described in detail elsewhere herein. FIG. 8A depicts an example in which a labeled polypeptide 800 is subjected to degradation by an immobilized processive exopeptidase 810. FIG. 8B depicts an example in which an immobilized labeled polypeptide 820 is subjected to degradation by a processive exopeptidase 830.

FIG. 8C schematically illustrates an example of a real-time sequencing process performed in accordance with the method depicted in FIG. 8B. As shown, panels (I) through (IV) show a progression of labeled polypeptide degradation, with a corresponding signal trace over time shown below each panel. As shown, each cleavage event corresponding to a labeled amino acid gives rise to a concomitant drop in signal. In some embodiments, the rate of processivity of processive exopeptidase 830 is known, such that the timing between a detected decrease in signal may be used to calculate the number of unlabeled amino acids between each detection event. For example, if a polypeptide of 40 amino acids was cleaved in such a way that an amino acid was removed every second, a labeled polypeptide having 3 signals would show all 3 initially (panel (I)), then 2 (panel (II)), then 1 (panel (III)), and finally no signal. In this way, the order of the labeled amino acids can be determined. Accordingly, these methods may be used to determine partial sequence information, e.g., for proteomic analysis based on polypeptide fragment sequencing.

In some embodiments, single molecule protein sequencing can be achieved using an ATP-based Förster resonance energy transfer (FRET) scheme (e.g., with one or more labeled cofactors), for example as illustrated in FIG. 9. In some embodiments, sequencing by cofactor-based FRET can be performed using an immobilized ATP-dependent protease, donor-labeled ATP, and acceptor-labeled amino acids of a polypeptide substrate. In some embodiments, amino acids can be labeled with acceptors, and the one or more cofactors can be labeled with donors.

For example, in some embodiments, extracted proteins are denatured, and cysteines and lysines are labeled with fluorescent dyes. In some embodiments, an engineered version of a protein translocase (e.g., bacterial ClpX) is used to bind to individual substrate proteins, unfold them, and translocate them through its nano-channel. In some embodiments, the translocase is labeled with a donor dye, and FRET occurs between the donor on the translocase and two or more distinct acceptor dyes on a substrate when the substrate passes through the nano-channel. The order of the labeled amino acids can then be determined from the FRET signal. In some embodiments, one or more of the following non-limiting labeled ATP analogues shown in Table 5 can be used.

TABLE 5

Non-limiting examples of labeled ATP analogues.

Phosphate-labeled ATP:

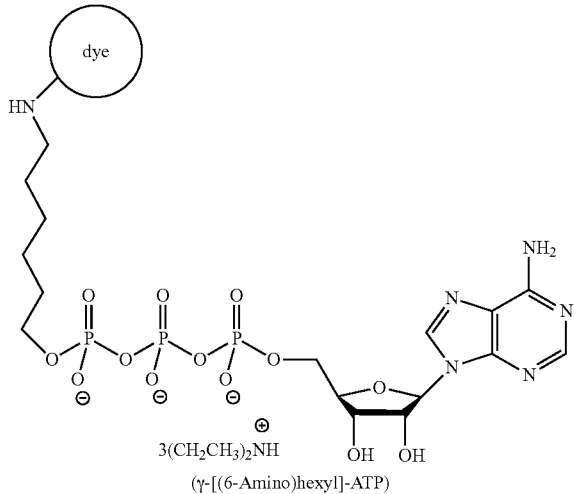

(γ-[(6-Amino)hexyl]-ATP)

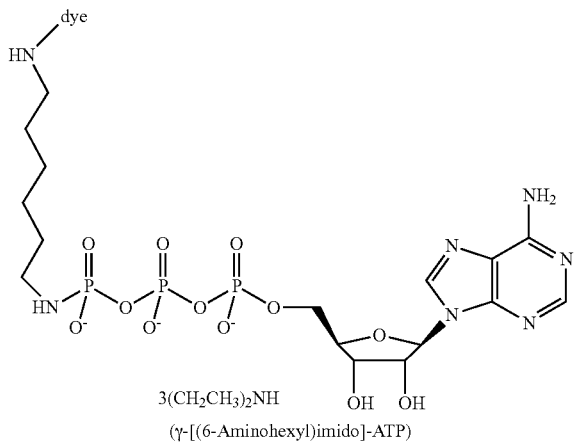

(γ-[(6-Aminohexyl)imido]-ATP)

TABLE 5-continued
Non-limiting examples of labeled ATP analogues.
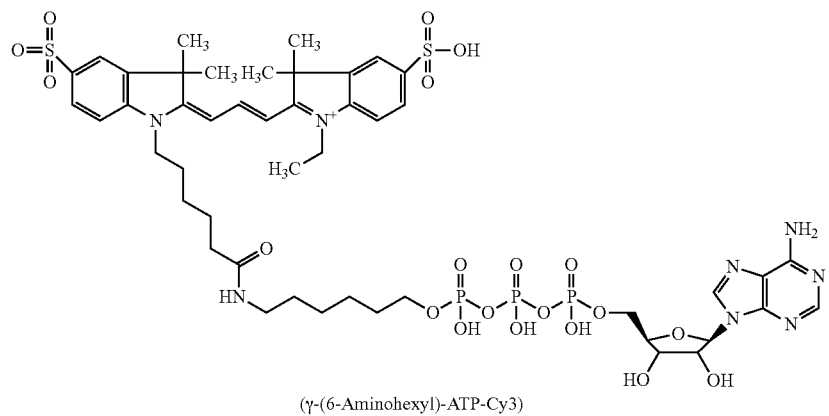
(γ-(6-Aminohexyl)-ATP-Cy3)
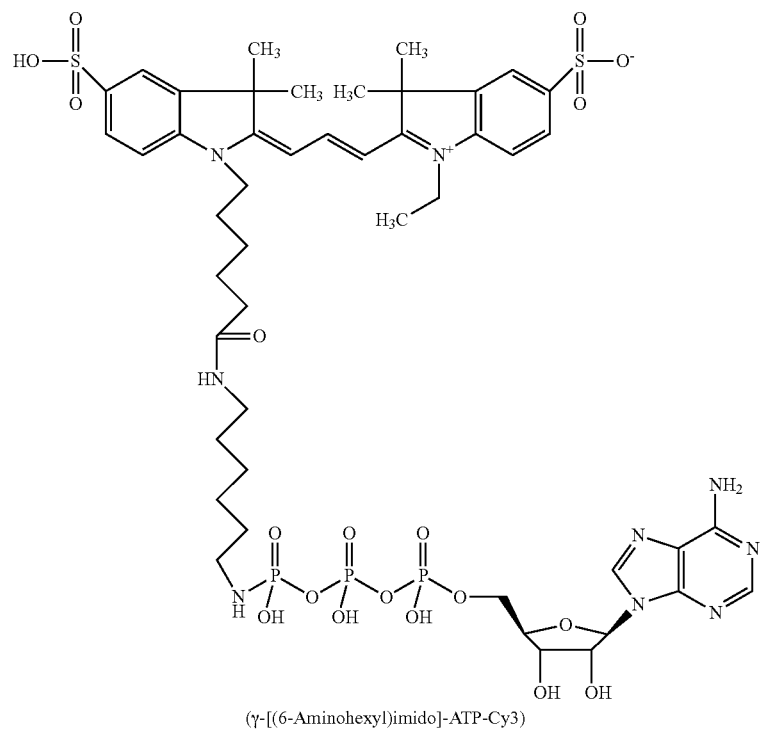
(γ-[(6-Aminohexyl)imido]-ATP-Cy3)
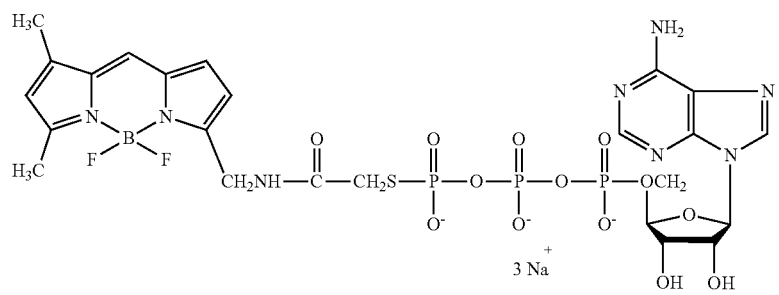
(BODIPY FL ATPγS)

TABLE 5-continued
Non-limiting examples of labeled ATP analogues.
Ribose-labeled ATP:
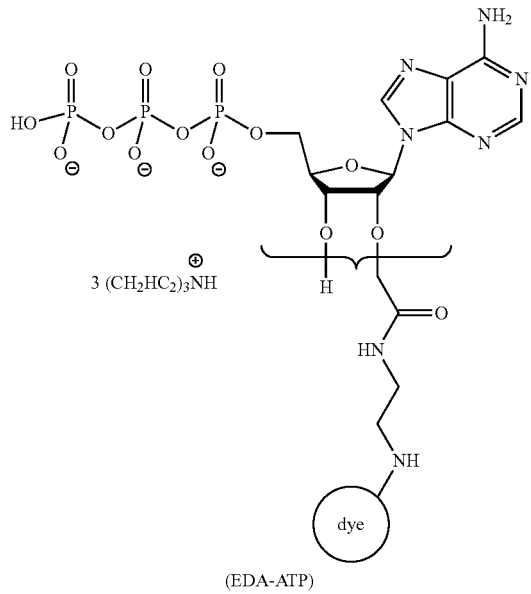
(EDA-ATP)
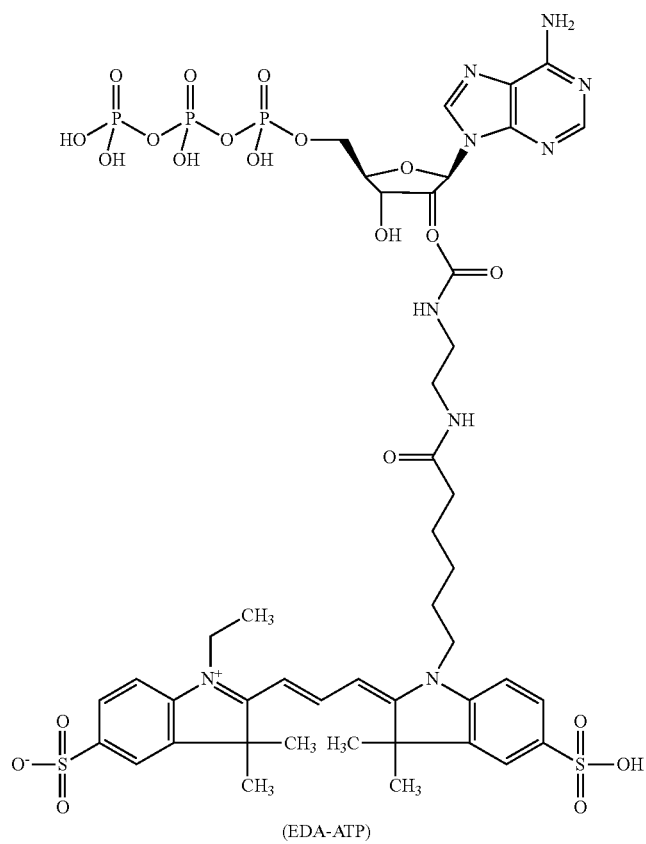
(EDA-ATP)

TABLE 5-continued
Non-limiting examples of labeled ATP analogues.
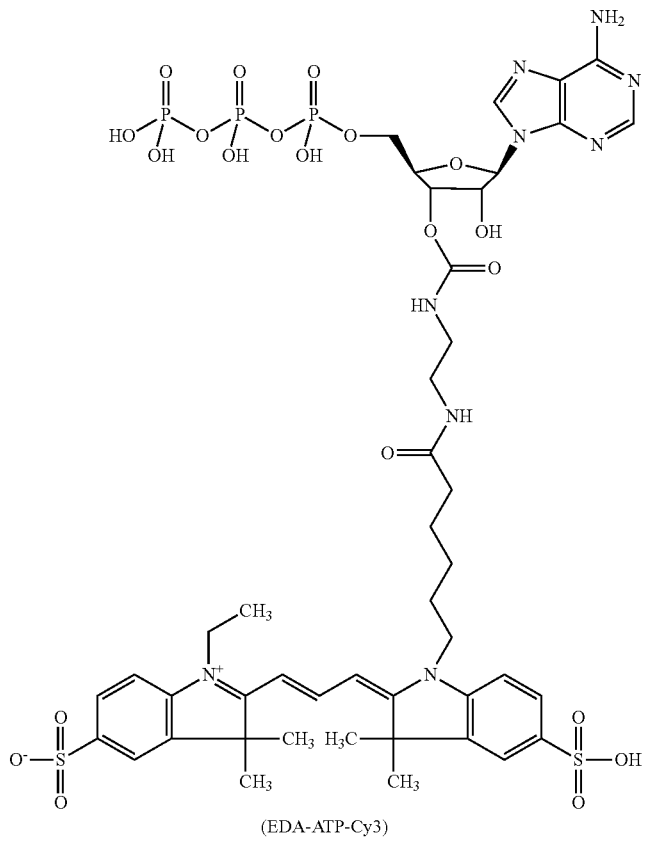
(EDA-ATP-Cy3)
Base-labeled ATP:
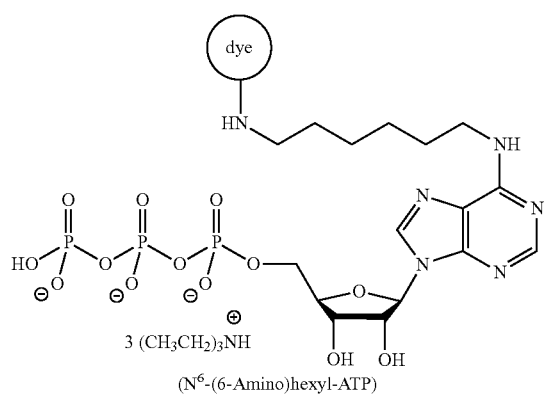
($N^6$-(6-Amino)hexyl-ATP)

TABLE 5-continued

Non-limiting examples of labeled ATP analogues.

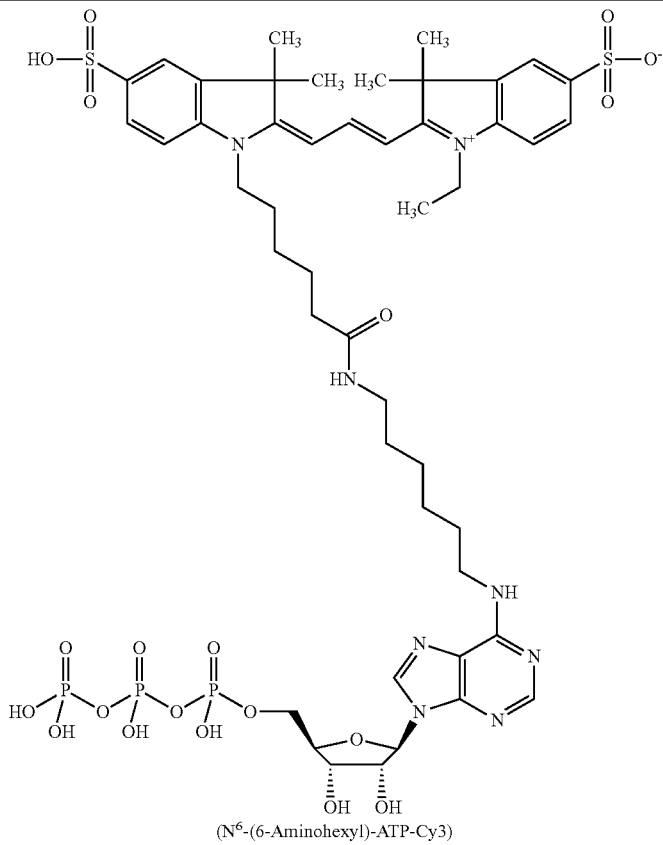

(N⁶-(6-Aminohexyl)-ATP-Cy3)

Preparation of Samples for Sequencing

A polypeptide sample can be modified prior to sequencing. In some embodiments, the N-terminal amino acid or the C-terminal amino acid of a polypeptide is modified. FIG. 10A illustrates a non-limiting example of terminal end modification for preparing terminally modified polypeptides from a protein sample. In step (1), protein sample 1000 is fragmented to produce polypeptide fragments 1002. A polypeptide can be fragmented by cleaving (e.g., chemically) and/or digesting (e.g., enzymatically, for example using a peptidase, for example trypsin) a polypeptide of interest. Fragmentation can be performed before or after labeling. In some embodiments, fragmentation is performed after labeling of whole proteins. One or more amino acids can be labeled before or after cleavage to produce labeled polypeptides. In some embodiments, polypeptides are size selected after chemical or enzymatic fragmentation. In some embodiments, smaller polypeptides (e.g., <2 kDa) are removed and larger polypeptides are retained for sequence analysis. Size selection can be achieved using a technique such as gel filtration, SEC, dialysis, PAGE gel extraction, microfluidic tension flow, or any other suitable technique. In step (2), the N-termini or C-termini of polypeptide fragments 1002 are modified to produce terminally modified polypeptides 1004. In some embodiments, modification comprises adding an immobilization moiety. In some embodiments, modification comprises adding a coupling moiety.

Accordingly, provided herein are methods of modifying terminal ends of proteins and polypeptides with moieties that enable immobilization to a surface (e.g., a surface of a sample well on a chip used for protein analysis). In some embodiments, such methods comprise modifying a terminal end of a labeled polypeptide to be analyzed in accordance with the application. In yet other embodiments, such methods comprise modifying a terminal end of a protein or enzyme that degrades or translocates a protein or polypeptide substrate in accordance with the application.

In some embodiments, a carboxy-terminus of a protein or polypeptide is modified in a method comprising: (i) blocking free carboxylate groups of the protein or polypeptide; (ii) denaturing the protein or polypeptide (e.g., by heat and/or chemical means); (iii) blocking free thiol groups of the protein or polypeptide; (iv) digesting the protein or polypeptide to produce at least one polypeptide fragment comprising a free C-terminal carboxylate group; and (v) conjugating (e.g., chemically) a functional moiety to the free C-terminal carboxylate group. In some embodiments, the method further comprises, after (i) and before (ii), dialyzing a sample comprising the protein or polypeptide.

In some embodiments, a carboxy-terminus of a protein or polypeptide is modified in a method comprising: (i) denaturing the protein or polypeptide (e.g., by heat and/or chemical means); (ii) blocking free thiol groups of the protein or polypeptide; (iii) digesting the protein or polypeptide to produce at least one polypeptide fragment comprising a free C-terminal carboxylate group; (iv) blocking the free C-terminal carboxylate group to produce at least one polypeptide fragment comprising a blocked C-terminal carboxylate group; and (v) conjugating (e.g., enzymatically) a functional moiety to the blocked C-terminal carboxylate group. In some embodiments, the method further comprises, after (iv) and before (v), dialyzing a sample comprising the protein or polypeptide.

In some embodiments, blocking free carboxylate groups refers to a chemical modification of these groups which alters chemical reactivity relative to an unmodified carboxylate. Suitable carboxylate blocking methods are known in the art and should modify side-chain carboxylate groups to be chemically different from a carboxy-terminal carboxylate group of a polypeptide to be functionalized. In some embodiments, blocking free carboxylate groups comprises esterification or amidation of free carboxylate groups of a polypeptide. In some embodiments, blocking free carboxylate groups comprises methyl esterification of free carboxylate groups of a polypeptide, e.g., by reacting the polypeptide with methanolic HCl. Additional examples of reagents and techniques useful for blocking free carboxylate groups include, without limitation, 4-sulfo-2,3,5,6-tetrafluorophenol (STP) and/or a carbodiimide such as N-(3-Dimethylaminopropyl)-N'-ethylcarbodiimide hydrochloride (EDAC), uronium reagents, diazomethane, alcohols and acid for Fischer esterification, the use of N-hydroxylsuccinimide (NHS) to form NHS esters (potentially as an intermediate to subsequent ester or amine formation), or reaction with carbonyldiimidazole (CDI) or the formation of mixed anhydrides, or any other method of modifying or blocking carboxylic acids, potentially through the formation of either esters or amides.

In some embodiments, blocking free thiol groups refers to a chemical modification of these groups which alters chemical reactivity relative to an unmodified thiol. In some embodiments, blocking free thiol groups comprises reducing and alkylating free thiol groups of a protein or polypeptide. In some embodiments, reduction and alkylation is carried out by contacting a polypeptide with dithiothreitol (DTT) and one or both of iodoacetamide and iodoacetic acid. Examples of additional and alternative cysteine-reducing reagents which may be used are well known and include, without limitation, 2-mercaptoethanol, Tris (2-carboxyehtyl) phosphine hydrochloride (TCEP), tributylphosphine, dithiobutylamine (DTBA), or any reagent capable of reducing a thiol group. Examples of additional and alternative cysteine-blocking (e.g., cysteine-alkylating) reagents which may be used are well known and include, without limitation, acrylamide, 4-vinylpyridine, N-Ethylmalemide (NEM), N-ε-maleimidocaproic acid (EMCA), or any reagent that modifies cysteines so as to prevent disulfide bond formation.

In some embodiments, digestion comprises enzymatic digestion. In some embodiments, digestion is carried out by contacting a protein or polypeptide with an endopeptidase (e.g., trypsin) under digestion conditions. In some embodiments, digestion comprises chemical digestion. Examples of suitable reagents for chemical and enzymatic digestion are known in the art and include, without limitation, trypsin, chemotrypsin, Lys-C, Arg-C, Asp-N, Lys-N, BNPS-Skatole, CNBr, caspase, formic acid, glutamyl endopeptidase, hydroxylamine, iodosobenzoic acid, neutrophil elastase, pepsin, proline-endopeptidase, proteinase K, staphylococcal peptidase I, thermolysin, and thrombin.

In some embodiments, the functional moiety comprises a biotin molecule. In some embodiments, the functional moiety comprises a reactive chemical moiety, such as an alkynyl. In some embodiments, conjugating a functional moiety comprises biotinylation of carboxy-terminal carboxymethyl ester groups by carboxypeptidase Y, as known in the art.

In some embodiments, a solubilizing moiety is added to a polypeptide. FIG. 10B illustrates a non-limiting example of a solubilizing moiety added to a terminal amino acid of a polypeptide, for example using a process of conjugating a solubilizing linker to the polypeptide.

In some embodiments, a terminally modified polypeptide 1010 comprising a linker conjugating moiety 1012 is conjugated to a solubilizing linker 1020 comprising a polypeptide conjugating moiety 1022. In some embodiments, the solubilizing linker comprises a solubilizing polymer, such as a biomolecule (e.g., shown as stippled shape). In some embodiments, a resulting linker-conjugated polypeptide 1030 comprising a linkage 1032 formed between 1012 and 1022 further comprises a surface conjugating moiety 1034. Accordingly, in some embodiments methods and compositions provided herein are useful for modifying terminal ends of polypeptides with moieties that increase their solubility. In some embodiments, a solubilizing moiety is useful for small polypeptides that result from fragmentation (e.g., enzymatic fragmentation, for example using trypsin) and that are relatively insoluble. For example, in some embodiments, short polypeptides in a polypeptide pool can be solubilized by conjugating a polymer (e.g., a short oligo, a sugar, or other charged polymer) to the polypeptides.

In some embodiments, one or more surfaces of a sample well (e.g., sidewalls of a sample well) can be modified. A non-limiting example of passivation and/or antifouling of a sample well sidewall is shown in FIG. 10C where an example schematic of a sample well is illustrated with modified surfaces which may be used to promote single molecule immobilization to a bottom surface. In some embodiments, 1040 is $SiO_2$. In some embodiments, 1042 is a polypeptide conjugating moiety (e.g., TCO, tetrazine, $N_3$, alkyne, aldehyde, NCO, NHS, thiol, alkene, DBCO, BCN, TPP, biotin, or other suitable conjugating moiety). In some embodiments, 1050 is $TiO_2$ or $Al_2O_3$. In some embodiments, 1052 is a hydrophobic $C_{4-18}$ molecule, a polytetrafluoroethylene compound (e.g., $(CF_2)_{4-12}$), a polyol, such as a polyethylene glycol (e.g., $PEG_{3-100}$), polypropylene glycol, polyoxyethylene glycol, or combinations or variations thereof, or a zwitterion, such as sulfobetaine. In some embodiments, 1060 is Si. In some embodiments, 1070 is Al. In some embodiments, 1080 is TiN.

Luminescent Labels

As used herein, a luminescent label is a molecule that absorbs one or more photons and may subsequently emit one or more photons after one or more time durations. In some embodiments, the term is used interchangeably with "label" or "luminescent molecule" depending on context. A luminescent label in accordance with certain embodiments described herein may refer to a luminescent label of a labeled affinity reagent, a luminescent label of a labeled peptidase (e.g., a labeled exopeptidase, a labeled non-specific exopeptidase), a luminescent label of a labeled peptide, a luminescent label of a labeled cofactor, or another labeled composition described herein. In some embodiments, a luminescent label in accordance with the application refers to a labeled amino acid of a labeled polypeptide comprising one or more labeled amino acids.

In some embodiments, a luminescent label may comprise a first and second chromophore. In some embodiments, an excited state of the first chromophore is capable of relaxation via an energy transfer to the second chromophore. In some embodiments, the energy transfer is a Förster resonance energy transfer (FRET). Such a FRET pair may be useful for providing a luminescent label with properties that make the label easier to differentiate from amongst a plurality of luminescent labels in a mixture—e.g., as illustrated and described herein for labeled aptamer 106 of FIG. 1C. In yet other embodiments, a FRET pair comprises a first chromophore of a first luminescent label and a second chromophore of a second luminescent label—e.g., as illustrated and described herein for sequencing of labeled peptides using a labeled cofactor (see, e.g., FIG. 9). In certain embodiments, the FRET pair may absorb excitation energy in a first spectral range and emit luminescence in a second spectral range.

In some embodiments, a luminescent label refers to a fluorophore or a dye. Typically, a luminescent label comprises an aromatic or heteroaromatic compound and can be a pyrene, anthracene, naphthalene, naphthylamine, acridine, stilbene, indole, benzindole, oxazole, carbazole, thiazole, benzothiazole, benzoxazole, phenanthridine, phenoxazine, porphyrin, quinoline, ethidium, benzamide, cyanine, carbocyanine, salicylate, anthranilate, coumarin, fluoroscein, rhodamine, xanthene, or other like compound.

In some embodiments, a luminescent label comprises a dye selected from one or more of the following: 5/6-Carboxyrhodamine 6G, 5-Carboxyrhodamine 6G, 6-Carboxyrhodamine 6G, 6-TAMRA, Abberior® STAR 440SXP, Abberior® STAR 470SXP, Abberior® STAR 488, Abberior® STAR 512, Abberior® STAR 520SXP, Abberior® STAR 580, Abberior® STAR 600, Abberior® STAR 635, Abberior® STAR 635P, Abberior® STAR RED, Alexa Fluor®350, Alexa Fluor®405, Alexa Fluor®430, Alexa Fluor®480, Alexa Fluor®488, Alexa Fluor®514, Alexa Fluor®532, Alexa Fluor®546, Alexa Fluor®555, Alexa Fluor®568, Alexa Fluor®594, Alexa Fluor®610-X, Alexa Fluor®633, Alexa Fluor®647, Alexa Fluor®660, Alexa Fluor®680, Alexa Fluor®700, Alexa Fluor®750, Alexa Fluor®790, AMCA, ATTO 390, ATTO 425, ATTO 465, ATTO 488, ATTO 495, ATTO 514, ATTO 520, ATTO 532, ATTO 542, ATTO 550, ATTO 565, ATTO 590, ATTO 610, ATTO 620, ATTO 633, ATTO 647, ATTO 647N, ATTO 655, ATTO 665, ATTO 680, ATTO 700, ATTO 725, ATTO 740, ATTO Oxa12, ATTO Rho101, ATTO Rho11, ATTO Rho12, ATTO Rho13, ATTO Rho14, ATTO Rho3B, ATTO Rho6G, ATTO Thio12, BD Horizon™ V450, BODIPY® 493/501, BODIPY® 530/550, BODIPY® 558/568, BODIPY® 564/570, BODIPY® 576/589, BODIPY® 581/591, BODIPY® 630/650, BODIPY® 650/665, BODIPY® FL, BODIPY® FL-X, BODIPY® R6G, BODIPY® TMR, BODIPY® TR, CAL Fluor® Gold 540, CAL Fluor® Green 510, CAL Fluor® Orange 560, CAL Fluor® Red 590, CAL Fluor® Red 610, CAL Fluor® Red 615, CAL Fluor® Red 635, Cascade® Blue, CF™350, CF™405M, CF™405S, CF™488A, CF™514, CF™532, CF™543, CF™546, CF™555, CF™568, CF™594, CF™620R, CF™633, CF™633-V1, CF™640R, CF™640R-V1, CF™640R-V2, CF™660C, CF™660R, CF™680, CF™680R, CF™680R-V1, CF™750, CF™770, CF™790, Chromeo™ 642, Chromis 425N, Chromis 500N, Chromis 515N, Chromis 530N, Chromis 550A, Chromis 550C, Chromis 550Z, Chromis 560N, Chromis 570N, Chromis 577N, Chromis 600N, Chromis 630N, Chromis 645A, Chromis 645C, Chromis 645Z, Chromis 678A, Chromis 678C, Chromis 678Z, Chromis 770A, Chromis 770C, Chromis 800A, Chromis 800C, Chromis 830A, Chromis 830C, Cy®3, Cy®3.5, Cy®3B, Cy®5, Cy®5.5, Cy®7, DyLight® 350, DyLight® 405, DyLight® 415-Col, DyLight® 425Q, DyLight® 485-LS, DyLight® 488, DyLight® 504Q, DyLight® 510-LS, DyLight® 515-LS, DyLight® 521-LS, DyLight® 530-R2, DyLight® 543Q, DyLight® 550, DyLight® 554-R0, DyLight® 554-R1, DyLight® 590-R2, DyLight® 594, DyLight® 610-B1, DyLight® 615-B2, DyLight® 633, DyLight® 633-B1, DyLight® 633-B2, DyLight® 650, DyLight® 655-B1, DyLight® 655-B2, DyLight® 655-B3, DyLight® 655-B4, DyLight® 662Q, DyLight® 675-B1, DyLight® 675-B2, DyLight® 675-B3, DyLight® 675-B4, DyLight® 679-C5, DyLight® 680, DyLight® 683Q, DyLight® 690-B1, DyLight® 690-B2, DyLight® 696Q, DyLight® 700-B1, DyLight® 700-B1, DyLight® 730-B1, DyLight® 730-B2, DyLight® 730-B3, DyLight® 730-B4, DyLight® 747, DyLight® 747-B1, DyLight® 747-B2, DyLight® 747-B3, DyLight® 747-B4, DyLight® 755, DyLight® 766Q, DyLight® 775-B2, DyLight® 775-B3, DyLight® 775-B4, DyLight® 780-B1, DyLight® 780-B2, DyLight® 780-B3, DyLight® 800, DyLight® 830-B2, Dyomics-350, Dyomics-350XL, Dyomics-360XL, Dyomics-370XL, Dyomics-375XL, Dyomics-380XL, Dyomics-390XL, Dyomics-405, Dyomics-415, Dyomics-430, Dyomics-431, Dyomics-478, Dyomics-480XL, Dyomics-481XL, Dyomics-485XL, Dyomics-490, Dyomics-495, Dyomics-505, Dyomics-510XL, Dyomics-511XL, Dyomics-520XL, Dyomics-521XL, Dyomics-530, Dyomics-547, Dyomics-547P1, Dyomics-548, Dyomics-549, Dyomics-549P1, Dyomics-550, Dyomics-554, Dyomics-555, Dyomics-556, Dyomics-560, Dyomics-590, Dyomics-591, Dyomics-594, Dyomics-601XL, Dyomics-605, Dyomics-610, Dyomics-615, Dyomics-630, Dyomics-631, Dyomics-632, Dyomics-633, Dyomics-634, Dyomics-635, Dyomics-636, Dyomics-647, Dyomics-647P1, Dyomics-648, Dyomics-648P1, Dyomics-649, Dyomics-649P1, Dyomics-650, Dyomics-651, Dyomics-652, Dyomics-654, Dyomics-675, Dyomics-676, Dyomics-677, Dyomics-678, Dyomics-679P1, Dyomics-680, Dyomics-681, Dyomics-682, Dyomics-700, Dyomics-701, Dyomics-703, Dyomics-704, Dyomics-730, Dyomics-731, Dyomics-732, Dyomics-734, Dyomics-749, Dyomics-749P1, Dyomics-750, Dyomics-751, Dyomics-752, Dyomics-754, Dyomics-776, Dyomics-777, Dyomics-778, Dyomics-780, Dyomics-781, Dyomics-782, Dyomics-800, Dyomics-831, eFluor® 450, Eosin, FITC, Fluorescein, HiLyte™ Fluor 405, HiLyte™ Fluor 488, HiLyte™ Fluor 532, HiLyte™ Fluor 555, HiLyte™ Fluor 594, HiLyte™ Fluor 647, HiLyte™ Fluor 680, HiLyte™ Fluor 750, IRDye® 680LT, IRDye® 750, IRDye® 800CW, JOE, LightCycler® 640R, LightCycler® Red 610, LightCycler® Red 640, LightCycler® Red 670, LightCycler® Red 705, Lissamine Rhodamine B, Napthofluorescein, Oregon Green® 488, Oregon Green® 514, Pacific Blue™, Pacific Green™, Pacific Orange™, PET, PF350, PF405, PF415, PF488, PF505, PF532, PF546, PF555P, PF568, PF594, PF610, PF633P, PF647P, Quasar®570, Quasar®670, Quasar®705, Rhodamine 123, Rhodamine 6G, Rhodamine B, Rhodamine Green, Rhodamine Green-X, Rhodamine Red, ROX, Seta™ 375, Seta™ 470, Seta™ 555, Seta™ 632, Seta™ 633, Seta™ 650, Seta™ 660, Seta™ 670, Seta™ 680, Seta™ 700, Seta™ 750, Seta™ 780, Seta™ APC-780, Seta™ PerCP-680, Seta™ R-PE-670, Seta™ 646, SeTau 380, SeTau 425, SeTau 647, SeTau 405, Square 635, Square 650, Square 660, Square 672, Square 680, Sulforhodamine 101, TAMRA, TET, Texas Red®, TMR, TRITC, Yakima Yellow™, Zenon®, Zy3, Zy5, Zy5.5, and Zy7.

Luminescence

In some aspects, the application relates to polypeptide sequencing and/or identification based on one or more luminescence properties of a luminescent label. In some embodiments, a luminescent label is identified based on luminescence lifetime, luminescence intensity, brightness, absorption spectra, emission spectra, luminescence quantum yield, or a combination of two or more thereof. In some embodiments, a plurality of types of luminescent labels can be distinguished from each other based on different luminescence lifetimes, luminescence intensities, brightnesses, absorption spectra, emission spectra, luminescence quantum yields, or combinations of two or more thereof. Identifying may mean assigning the exact identity and/or quantity of one type of amino acid (e.g., a single type or a subset of types) associated with a luminescent label, and may also mean assigning an amino acid location in a polypeptide relative to other types of amino acids.

In some embodiments, luminescence is detected by exposing a luminescent label to a series of separate light pulses and evaluating the timing or other properties of each photon that is emitted from the label. In some embodiments, information for a plurality of photons emitted sequentially from a label is aggregated and evaluated to identify the label and thereby identify an associated type of amino acid. In some embodiments, a luminescence lifetime of a label is determined from a plurality of photons that are emitted sequentially from the label, and the luminescence lifetime can be used to identify the label. In some embodiments, a luminescence intensity of a label is determined from a plurality of photons that are emitted sequentially from the label, and the luminescence intensity can be used to identify the label. In some embodiments, a luminescence lifetime and luminescence intensity of a label is determined from a plurality of photons that are emitted sequentially from the label, and the luminescence lifetime and luminescence intensity can be used to identify the label.

In some aspects of the application, a single polypeptide molecule is exposed to a plurality of separate light pulses and a series of emitted photons are detected and analyzed. In some embodiments, the series of emitted photons provides information about the single polypeptide molecule that is present and that does not change in the reaction sample over the time of the experiment. However, in some embodiments, the series of emitted photons provides information about a series of different molecules that are present at different times in the reaction sample (e.g., as a reaction or process progresses). By way of example and not limitation, such information may be used to sequence and/or identify a polypeptide subjected to chemical or enzymatic degradation in accordance with the application.

In certain embodiments, a luminescent label absorbs one photon and emits one photon after a time duration. In some embodiments, the luminescence lifetime of a label can be determined or estimated by measuring the time duration. In some embodiments, the luminescence lifetime of a label can be determined or estimated by measuring a plurality of time durations for multiple pulse events and emission events. In some embodiments, the luminescence lifetime of a label can be differentiated amongst the luminescence lifetimes of a plurality of types of labels by measuring the time duration. In some embodiments, the luminescence lifetime of a label can be differentiated amongst the luminescence lifetimes of a plurality of types of labels by measuring a plurality of time durations for multiple pulse events and emission events. In certain embodiments, a label is identified or differentiated amongst a plurality of types of labels by determining or estimating the luminescence lifetime of the label. In certain embodiments, a label is identified or differentiated amongst a plurality of types of labels by differentiating the luminescence lifetime of the label amongst a plurality of the luminescence lifetimes of a plurality of types of labels.

Determination of a luminescence lifetime of a luminescent label can be performed using any suitable method (e.g., by measuring the lifetime using a suitable technique or by determining time-dependent characteristics of emission). In some embodiments, determining the luminescence lifetime of one label comprises determining the lifetime relative to another label. In some embodiments, determining the luminescence lifetime of a label comprises determining the lifetime relative to a reference. In some embodiments, determining the luminescence lifetime of a label comprises measuring the lifetime (e.g., fluorescence lifetime). In some embodiments, determining the luminescence lifetime of a label comprises determining one or more temporal characteristics that are indicative of lifetime. In some embodiments, the luminescence lifetime of a label can be determined based on a distribution of a plurality of emission events (e.g., 1, 2, 3, 4, 5, 6, 7, 8, 9, 10, 11, 12, 13, 14, 15, 16, 17, 18, 19, 20, 30, 40, 50, 60, 70, 80, 90, 100, or more emission events) occurring across one or more time-gated windows relative to an excitation pulse. For example, a luminescence lifetime of a label can be distinguished from a plurality of labels having different luminescence lifetimes based on the distribution of photon arrival times measured with respect to an excitation pulse.

It should be appreciated that a luminescence lifetime of a luminescent label is indicative of the timing of photons emitted after the label reaches an excited state and the label can be distinguished by information indicative of the timing of the photons. Some embodiments may include distinguishing a label from a plurality of labels based on the luminescence lifetime of the label by measuring times associated with photons emitted by the label. The distribution of times may provide an indication of the luminescence lifetime which may be determined from the distribution. In some embodiments, the label is distinguishable from the plurality of labels based on the distribution of times, such as by comparing the distribution of times to a reference distribution corresponding to a known label. In some embodiments, a value for the luminescence lifetime is determined from the distribution of times.

As used herein, in some embodiments, luminescence intensity refers to the number of emitted photons per unit time that are emitted by a luminescent label which is being excited by delivery of a pulsed excitation energy. In some embodiments, the luminescence intensity refers to the detected number of emitted photons per unit time that are emitted by a label which is being excited by delivery of a pulsed excitation energy, and are detected by a particular sensor or set of sensors.

As used herein, in some embodiments, brightness refers to a parameter that reports on the average emission intensity per luminescent label. Thus, in some embodiments, "emission intensity" may be used to generally refer to brightness of a composition comprising one or more labels. In some embodiments, brightness of a label is equal to the product of its quantum yield and extinction coefficient.

As used herein, in some embodiments, luminescence quantum yield refers to the fraction of excitation events at a given wavelength or within a given spectral range that lead to an emission event, and is typically less than 1. In some embodiments, the luminescence quantum yield of a luminescent label described herein is between 0 and about 0.001, between about 0.001 and about 0.01, between about 0.01 and about 0.1, between about 0.1 and about 0.5, between about 0.5 and 0.9, or between about 0.9 and 1. In some embodiments, a label is identified by determining or estimating the luminescence quantum yield.

As used herein, in some embodiments, an excitation energy is a pulse of light from a light source. In some embodiments, an excitation energy is in the visible spectrum. In some embodiments, an excitation energy is in the ultraviolet spectrum. In some embodiments, an excitation energy is in the infrared spectrum. In some embodiments, an excitation energy is at or near the absorption maximum of a luminescent label from which a plurality of emitted photons are to be detected. In certain embodiments, the excitation energy is between about 500 nm and about 700 nm (e.g., between about 500 nm and about 600 nm, between about 600 nm and about 700 nm, between about 500 nm and about 550 nm, between about 550 nm and about 600 nm, between about 600 nm and about 650 nm, or between about 650 nm and about 700 nm). In certain embodiments, an excitation energy may be monochromatic or confined to a spectral range. In some embodiments, a spectral range has a range of between about 0.1 nm and about 1 nm, between about 1 nm and about 2 nm, or between about 2 nm and about 5 nm. In some embodiments, a spectral range has a range of between about 5 nm and about 10 nm, between about 10 nm and about 50 nm, or between about 50 nm and about 100 nm.

Sequencing

Aspects of the application relate to sequencing biological polymers, such as polypeptides and proteins. As used herein, "sequencing," "sequence determination," "determining a sequence," and like terms, in reference to a polypeptide or protein includes determination of partial sequence information as well as full sequence information of the polypeptide or protein. That is, the terminology includes sequence comparisons, fingerprinting, probabalistic fingerprinting, and like levels of information about a target molecule, as well as the express identification and ordering of each amino acid of the target molecule within a region of interest. In some embodiments, the terminology includes identifying a single amino acid of a polypeptide. In yet other embodiments, more than one amino acid of a polypeptide is identified. As used herein, in some embodiments, "identifying," "determining the identity," and like terms, in reference to an amino acid includes determination of an express identity of an amino acid as well as determination of a probability of an express identity of an amino acid. For example, in some embodiments, an amino acid is identified by determining a probability (e.g., from 0% to 100%) that the amino acid is of a specific type, or by determining a probability for each of a plurality of specific types. Accordingly, in some embodiments, the terms "amino acid sequence," "polypeptide sequence," and "protein sequence" as used herein may refer to the polypeptide or protein material itself and is not restricted to the specific sequence information (e.g., the succession of letters representing the order of amino acids from one terminus to another terminus) that biochemically characterizes a specific polypeptide or protein.

In some embodiments, sequencing of a polypeptide molecule comprises identifying at least two (e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, or more) amino acids in the polypeptide molecule. In some embodiments, the at least two amino acids are contiguous amino acids. In some embodiments, the at least two amino acids are non-contiguous amino acids.

In some embodiments, sequencing of a polypeptide molecule comprises identification of less than 100% (e.g., less than 99%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 1% or less) of all amino acids in the polypeptide molecule. For example, in some embodiments, sequencing of a polypeptide molecule comprises identification of less than 100% of one type of amino acid in the polypeptide molecule (e.g., identification of a portion of all amino acids of one type in the polypeptide molecule). In some embodiments, sequencing of a polypeptide molecule comprises identification of less than 100% of each type of amino acid in the polypeptide molecule.

In some embodiments, sequencing of a polypeptide molecule comprises identification of at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100 or more types of amino acids in the polypeptide.

In some embodiments, the application provides compositions and methods for sequencing a polypeptide by identifying a series of amino acids that are present at a terminus of a polypeptide over time (e.g., by iterative detection and cleavage of amino acids at the terminus). In yet other embodiments, the application provides compositions and methods for sequencing a polypeptide by identifying labeled amino content of the polypeptide and comparing to a reference sequence database.

In some embodiments, the application provides compositions and methods for sequencing a polypeptide by sequencing a plurality of fragments of the polypeptide. In some embodiments, sequencing a polypeptide comprises combining sequence information for a plurality of polypeptide fragments to identify and/or determine a sequence for the polypeptide.

In some embodiments, combining sequence information may be performed by computer hardware and software. The methods described herein may allow for a set of related polypeptides, such as an entire proteome of an organism, to be sequenced. In some embodiments, a plurality of single molecule sequencing reactions are performed in parallel (e.g., on a single chip) according to aspects of the present application. For example, in some embodiments, a plurality of single molecule sequencing reactions are each performed in separate sample wells on a single chip.

In some embodiments, methods provided herein may be used for the sequencing and identification of an individual protein in a sample comprising a complex mixture of proteins. In some embodiments, the application provides methods of uniquely identifying an individual protein in a complex mixture of proteins. In some embodiments, an individual protein is detected in a mixed sample by determining a partial amino acid sequence of the protein. In some embodiments, the partial amino acid sequence of the protein is within a contiguous stretch of approximately 5 to 50 amino acids.

Without wishing to be bound by any particular theory, it is believed that most human proteins can be identified using incomplete sequence information with reference to proteomic databases. For example, simple modeling of the human proteome has shown that approximately 98% of proteins can be uniquely identified by detecting just four types of amino acids within a stretch of 6 to 40 amino acids (see, e.g., Swaminathan, et al. *PLoS Comput Biol.* 2015, 11(2):e1004080; and Yao, et al. *Phys. Biol.* 2015, 12(5): 055003). Therefore, a complex mixture of proteins can be degraded (e.g., chemically degraded, enzymatically degraded) into short polypeptide fragments of approximately 6 to 40 amino acids, and sequencing of this polypeptide library would reveal the identity and abundance of each of the proteins present in the original complex mixture. Compositions and methods for selective amino acid labeling and identifying polypeptides by determining partial sequence information are described in detail in U.S. patent application Ser. No. 15/510,962, filed Sep. 15, 2015, titled "SINGLE MOLECULE PEPTIDE SEQUENCING," which is incorporated by reference in its entirety.

Embodiments are capable of sequencing single polypeptide molecules with high accuracy, such as an accuracy of at least about 50%, 60%, 70%, 75%, 80%, 85%, 90%, 95%, 96%, 97%, 98%, 99%, 99.9%, 99.99%, 99.999%, or 99.9999%. In some embodiments, the target molecule used in single molecule sequencing is a polypeptide that is immobilized to a surface of a solid support such as a bottom surface or a sidewall surface of a sample well. The sample well also can contain any other reagents needed for a sequencing reaction in accordance with the application, such as one or more suitable buffers, co-factors, labeled affinity reagents, and enzymes (e.g., catalytically active or inactive exopeptidase enzymes, which may be luminescently labeled or unlabeled).

As described above, in some embodiments, sequencing in accordance with the application comprises identifying an amino acid by determining a probability that the amino acid is of a specific type. Conventional protein identification systems require identification of each amino acid in a polypeptide to identify the polypeptide. However, it is difficult to accurately identify each amino acid in a polypeptide. For example, data collected from an interaction in which a first recognition molecule associates with a first amino acid may not be sufficiently different from data collected from an interaction in which a second recognition molecule associates with a second amino acid to differentiate between the two amino acids. In some embodiments, sequencing in accordance with the application avoids this problem by using a protein identification system that, unlike conventional protein identification systems, does not require (but does not preclude) identification of each amino acid in the protein.

Accordingly, in some embodiments, sequencing in accordance with the application may be carried out using a protein identification system that uses machine learning techniques to identify proteins. In some embodiments, the system operates by: (1) collecting data about a polypeptide of a protein using a real-time protein sequencing device; (2) using a machine learning model and the collected data to identify probabilities that certain amino acids are part of the polypeptide at respective locations; and (3) using the identified probabilities, as a "probabilistic fingerprint" to identify the protein. In some embodiments, data about the polypeptide of the protein may be obtained using reagents that selectively bind amino acids. As an example, the reagents and/or amino acids may be labeled with luminescent labels that emit light in response to application of excitation energy. In this example, a protein sequencing device may apply excitation energy to a sample of a protein (e.g., a polypeptide) during binding interactions of reagents with amino acids in the sample. In some embodiments, one or more sensors in the sequencing device (e.g., a photodetector, an electrical sensor, and/or any other suitable type of sensor) may detect binding interactions. In turn, the data collected and/or derived from the detected light emissions may be provided to the machine learning model. Machine learning models and associated systems and methods are described in detail in U.S. Provisional Patent Appl. No. 62/860,750, filed Jun. 12, 2019, titled "MACHINE LEARNING ENABLED PROTEIN IDENTIFICATION," which is incorporated by reference in its entirety.

Sequencing in accordance with the application, in some aspects, may involve immobilizing a polypeptide on a surface of a substrate (e.g., of a solid support, for example a chip, for example an integrated device as described herein). In some embodiments, a polypeptide may be immobilized on a surface of a sample well (e.g., on a bottom surface of a sample well) on a substrate. In some embodiments, the N-terminal amino acid of the polypeptide is immobilized (e.g., attached to the surface). In some embodiments, the C-terminal amino acid of the polypeptide is immobilized (e.g., attached to the surface). In some embodiments, one or more non-terminal amino acids are immobilized (e.g., attached to the surface). The immobilized amino acid(s) can be attached using any suitable covalent or non-covalent linkage, for example as described in this application. In some embodiments, a plurality of polypeptides are attached to a plurality of sample wells (e.g., with one polypeptide attached to a surface, for example a bottom surface, of each sample well), for example in an array of sample wells on a substrate.

Sequencing in accordance with the application, in some aspects, may be performed using a system that permits single molecule analysis. The system may include an integrated device and an instrument configured to interface with the integrated device. The integrated device may include an array of pixels, where individual pixels include a sample well and at least one photodetector. The sample wells of the integrated device may be formed on or through a surface of the integrated device and be configured to receive a sample placed on the surface of the integrated device. Collectively, the sample wells may be considered as an array of sample wells. The plurality of sample wells may have a suitable size and shape such that at least a portion of the sample wells receive a single sample (e.g., a single molecule, such as a polypeptide). In some embodiments, the number of samples within a sample well may be distributed among the sample wells of the integrated device such that some sample wells contain one sample while others contain zero, two or more samples.

Excitation light is provided to the integrated device from one or more light source external to the integrated device. Optical components of the integrated device may receive the excitation light from the light source and direct the light towards the array of sample wells of the integrated device and illuminate an illumination region within the sample well. In some embodiments, a sample well may have a configuration that allows for the sample to be retained in proximity to a surface of the sample well, which may ease delivery of excitation light to the sample and detection of emission light from the sample. A sample positioned within the illumination region may emit emission light in response to being illuminated by the excitation light. For example, the sample may be labeled with a fluorescent marker, which emits light in response to achieving an excited state through the illumination of excitation light. Emission light emitted by a sample may then be detected by one or more photodetectors within a pixel corresponding to the sample well with the sample being analyzed. When performed across the array of sample wells, which may range in number between approximately 10,000 pixels to 1,000,000 pixels according to some embodiments, multiple samples can be analyzed in parallel.

The integrated device may include an optical system for receiving excitation light and directing the excitation light among the sample well array. The optical system may include one or more grating couplers configured to couple excitation light to the integrated device and direct the excitation light to other optical components. The optical system may include optical components that direct the excitation light from a grating coupler towards the sample well array. Such optical components may include optical splitters, optical combiners, and waveguides. In some embodiments, one or more optical splitters may couple excitation light from a grating coupler and deliver excitation light to at least one of the waveguides. According to some embodiments, the optical splitter may have a configuration that allows for delivery of excitation light to be substantially uniform across all the waveguides such that each of the waveguides receives a substantially similar amount of excitation light. Such embodiments may improve performance of the integrated device by improving the uniformity of excitation light received by sample wells of the integrated device. Examples of suitable components, e.g., for coupling excitation light to a sample well and/or directing emission light to a photodetector, to include in an integrated device are described in U.S. patent application Ser. No. 14/821,688, filed Aug. 7, 2015, titled "INTEGRATED DEVICE FOR PROBING, DETECTING AND ANALYZING MOLECULES," and U.S. patent application Ser. No. 14/543,865, filed Nov. 17, 2014, titled "INTEGRATED DEVICE WITH EXTERNAL LIGHT SOURCE FOR PROBING, DETECTING, AND ANALYZING MOLECULES," both of which are incorporated by reference in their entirety. Examples of suitable grating couplers and waveguides that may be implemented in the integrated device are described in U.S. patent application Ser. No. 15/844,403, filed Dec. 15, 2017, titled "OPTICAL COUPLER AND WAVEGUIDE SYSTEM," which is incorporated by reference in its entirety.

Additional photonic structures may be positioned between the sample wells and the photodetectors and configured to reduce or prevent excitation light from reaching the photodetectors, which may otherwise contribute to signal noise in detecting emission light. In some embodiments, metal layers which may act as a circuitry for the integrated device, may also act as a spatial filter. Examples of suitable photonic structures may include spectral filters, a polarization filters, and spatial filters and are described in U.S. patent application Ser. No. 16/042,968, filed Jul. 23, 2018, titled "OPTICAL REJECTION PHOTONIC STRUCTURES," which is incorporated by reference in its entirety.

Components located off of the integrated device may be used to position and align an excitation source to the integrated device. Such components may include optical components including lenses, mirrors, prisms, windows, apertures, attenuators, and/or optical fibers. Additional mechanical components may be included in the instrument to allow for control of one or more alignment components. Such mechanical components may include actuators, stepper motors, and/or knobs. Examples of suitable excitation sources and alignment mechanisms are described in U.S. patent application Ser. No. 15/161,088, filed May 20, 2016, titled "PULSED LASER AND SYSTEM," which is incorporated by reference in its entirety. Another example of a beam-steering module is described in U.S. patent application Ser. No. 15/842,720, filed Dec. 14, 2017, titled "COMPACT BEAM SHAPING AND STEERING ASSEMBLY," which is incorporated herein by reference. Additional examples of suitable excitation sources are described in U.S. patent application Ser. No. 14/821,688, filed Aug. 7, 2015, titled "INTEGRATED DEVICE FOR PROBING, DETECTING AND ANALYZING MOLECULES," which is incorporated by reference in its entirety.

The photodetector(s) positioned with individual pixels of the integrated device may be configured and positioned to detect emission light from the pixel's corresponding sample well. Examples of suitable photodetectors are described in U.S. patent application Ser. No. 14/821,656, filed Aug. 7, 2015, titled "INTEGRATED DEVICE FOR TEMPORAL BINNING OF RECEIVED PHOTONS," which is incorporated by reference in its entirety. In some embodiments, a sample well and its respective photodetector(s) may be aligned along a common axis. In this manner, the photodetector(s) may overlap with the sample well within the pixel.

Characteristics of the detected emission light may provide an indication for identifying the marker associated with the emission light. Such characteristics may include any suitable type of characteristic, including an arrival time of photons detected by a photodetector, an amount of photons accumulated over time by a photodetector, and/or a distribution of photons across two or more photodetectors. In some embodiments, a photodetector may have a configuration that allows for the detection of one or more timing characteristics associated with a sample's emission light (e.g., luminescence lifetime). The photodetector may detect a distribution of photon arrival times after a pulse of excitation light propagates through the integrated device, and the distribution of arrival times may provide an indication of a timing characteristic of the sample's emission light (e.g., a proxy for luminescence lifetime). In some embodiments, the one or more photodetectors provide an indication of the probability of emission light emitted by the marker (e.g., luminescence intensity). In some embodiments, a plurality of photodetectors may be sized and arranged to capture a spatial distribution of the emission light. Output signals from the one or more photodetectors may then be used to distinguish a marker from among a plurality of markers, where the plurality of markers may be used to identify a sample within the sample. In some embodiments, a sample may be excited by multiple excitation energies, and emission light and/or timing characteristics of the emission light emitted by the sample in response to the multiple excitation energies may distinguish a marker from a plurality of markers.

In operation, parallel analyses of samples within the sample wells are carried out by exciting some or all of the samples within the wells using excitation light and detecting signals from sample emission with the photodetectors. Emission light from a sample may be detected by a corresponding photodetector and converted to at least one electrical signal. The electrical signals may be transmitted along conducting lines in the circuitry of the integrated device, which may be connected to an instrument interfaced with the integrated device. The electrical signals may be subsequently processed and/or analyzed. Processing or analyzing of electrical signals may occur on a suitable computing device either located on or off the instrument.

The instrument may include a user interface for controlling operation of the instrument and/or the integrated device. The user interface may be configured to allow a user to input information into the instrument, such as commands and/or settings used to control the functioning of the instrument. In some embodiments, the user interface may include buttons, switches, dials, and a microphone for voice commands. The user interface may allow a user to receive feedback on the performance of the instrument and/or integrated device, such as proper alignment and/or information obtained by readout signals from the photodetectors on the integrated device. In some embodiments, the user interface may provide feedback using a speaker to provide audible feedback. In some embodiments, the user interface may include indicator lights and/or a display screen for providing visual feedback to a user.

In some embodiments, the instrument may include a computer interface configured to connect with a computing device. The computer interface may be a USB interface, a FireWire interface, or any other suitable computer interface. A computing device may be any general purpose computer, such as a laptop or desktop computer. In some embodiments, a computing device may be a server (e.g., cloud-based server) accessible over a wireless network via a suitable computer interface. The computer interface may facilitate communication of information between the instrument and the computing device. Input information for controlling and/or configuring the instrument may be provided to the computing device and transmitted to the instrument via the computer interface. Output information generated by the instrument may be received by the computing device via the computer interface. Output information may include feedback about performance of the instrument, performance of the integrated device, and/or data generated from the readout signals of the photodetector.

In some embodiments, the instrument may include a processing device configured to analyze data received from one or more photodetectors of the integrated device and/or transmit control signals to the excitation source(s). In some embodiments, the processing device may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof). In some embodiments, the processing of data from one or more photodetectors may be performed by both a processing device of the instrument and an external computing device. In other embodiments, an external computing device may be omitted and processing of data from one or more photodetectors may be performed solely by a processing device of the integrated device.

According to some embodiments, the instrument that is configured to analyze samples based on luminescence emission characteristics may detect differences in luminescence lifetimes and/or intensities between different luminescent molecules, and/or differences between lifetimes and/or intensities of the same luminescent molecules in different environments. The inventors have recognized and appreciated that differences in luminescence emission lifetimes can be used to discern between the presence or absence of different luminescent molecules and/or to discern between different environments or conditions to which a luminescent molecule is subjected. In some cases, discerning luminescent molecules based on lifetime (rather than emission wavelength, for example) can simplify aspects of the system. As an example, wavelength-discriminating optics (such as wavelength filters, dedicated detectors for each wavelength, dedicated pulsed optical sources at different wavelengths, and/or diffractive optics) may be reduced in number or eliminated when discerning luminescent molecules based on lifetime. In some cases, a single pulsed optical source operating at a single characteristic wavelength may be used to excite different luminescent molecules that emit within a same wavelength region of the optical spectrum but have measurably different lifetimes. An analytic system that uses a single pulsed optical source, rather than multiple sources operating at different wavelengths, to excite and discern different luminescent molecules emitting in a same wavelength region can be less complex to operate and maintain, more compact, and may be manufactured at lower cost.

Although analytic systems based on luminescence lifetime analysis may have certain benefits, the amount of information obtained by an analytic system and/or detection accuracy may be increased by allowing for additional detection techniques. For example, some embodiments of the systems may additionally be configured to discern one or more properties of a sample based on luminescence wavelength and/or luminescence intensity. In some implementations, luminescence intensity may be used additionally or alternatively to distinguish between different luminescent labels. For example, some luminescent labels may emit at significantly different intensities or have a significant difference in their probabilities of excitation (e.g., at least a difference of about 35%) even though their decay rates may be similar. By referencing binned signals to measured excitation light, it may be possible to distinguish different luminescent labels based on intensity levels.

According to some embodiments, different luminescence lifetimes may be distinguished with a photodetector that is configured to time-bin luminescence emission events following excitation of a luminescent label. The time binning may occur during a single charge-accumulation cycle for the photodetector. A charge-accumulation cycle is an interval between read-out events during which photo-generated carriers are accumulated in bins of the time-binning photodetector. Examples of a time-binning photodetector are described in U.S. patent application Ser. No. 14/821,656, filed Aug. 7, 2015, titled "INTEGRATED DEVICE FOR TEMPORAL BINNING OF RECEIVED PHOTONS," which is incorporated herein by reference. In some embodiments, a time-binning photodetector may generate charge carriers in a photon absorption/carrier generation region and directly transfer charge carriers to a charge carrier storage bin in a charge carrier storage region. In such embodiments, the time-binning photodetector may not include a carrier travel/capture region. Such a time-binning photodetector may be referred to as a "direct binning pixel." Examples of time-binning photodetectors, including direct binning pixels, are described in U.S. patent application Ser. No. 15/852,571, filed Dec. 22, 2017, titled "INTEGRATED PHOTODETECTOR WITH DIRECT BINNING PIXEL," which is incorporated herein by reference.

In some embodiments, different numbers of fluorophores of the same type may be linked to different reagents in a sample, so that each reagent may be identified based on luminescence intensity. For example, two fluorophores may be linked to a first labeled affinity reagent and four or more fluorophores may be linked to a second labeled affinity reagent. Because of the different numbers of fluorophores, there may be different excitation and fluorophore emission probabilities associated with the different affinity reagents. For example, there may be more emission events for the second labeled affinity reagent during a signal accumulation interval, so that the apparent intensity of the bins is significantly higher than for the first labeled affinity reagent.

The inventors have recognized and appreciated that distinguishing nucleotides or any other biological or chemical samples based on fluorophore decay rates and/or fluorophore intensities may enable a simplification of the optical excitation and detection systems. For example, optical excitation may be performed with a single-wavelength source (e.g., a source producing one characteristic wavelength rather than multiple sources or a source operating at multiple different characteristic wavelengths). Additionally, wavelength discriminating optics and filters may not be needed in the detection system. Also, a single photodetector may be used for each sample well to detect emission from different fluorophores. The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

Computational Techniques

Aspects of the present application relate to computational techniques for analyzing the data generated by the polypeptide sequencing techniques described herein. As discussed above, for example in connection with FIGS. 1A and 1B, the data generated by using these sequencing techniques may include a series of signal pulses indicative of instances where an amino acid recognition molecule is associated with an amino acid exposed at the terminus of the polypeptide being sequenced. The series of signal pulses may have varying one or more features (e.g., pulse duration, interpulse duration, change in magnitude), depending on the type of amino acid presently at the terminus, over time as the degradation process proceeds in removing successive amino acids. The resulting signal trace may include characteristic patterns, which arise from the varying one or more features, associated with respective amino acids. The computational techniques described herein may be implemented as part of analyzing such data obtained using these sequencing techniques to identify an amino acid sequence.

Some embodiments may involve obtaining data during a degradation process of a polypeptide, analyzing the data to determine portions of the data corresponding to amino acids that are sequentially exposed at a terminus of the polypeptide during the degradation process, and outputting an amino acid sequence representative of the polypeptide. FIG. 11 is a diagram of an illustrative processing pipeline 1100 for identifying an amino acid sequence by analyzing data obtained using the polypeptide sequencing techniques described herein. As shown in FIG. 11, analyzing sequencing data 1102 may involve using association event identification technique 1104 and amino acid identification technique 1106 to output amino acid sequence(s) 1108.

As discussed herein, sequencing data 1102 may be obtained during a degradation process of a polypeptide. In some embodiments, the sequencing data 1102 is indicative of amino acid identity at the terminus of the polypeptide during the degradation process. In some embodiments, the sequencing data 1102 is indicative of a signal produced by one or more amino acid recognition molecules binding to different types of terminal amino acids at the terminus during the degradation process. Exemplary sequencing data is shown in FIGS. 1A and 1B, which are discussed above.

Depending on how signals are generated during the degradation process, sequencing data 1102 may be indicative of one or more different types of signals. In some embodiments, sequencing data 1102 is indicative of a luminescent signal generated during the degradation process. For example, a luminescent label may be used to label an amino acid recognition molecule, and luminescence emitted by the luminescent label may be detected as the amino acid recognition molecule associates with a particular amino acid, resulting in a luminescent signal. In some embodiments, sequencing data 1102 is indicative of an electrical signal generated during the degradation process. For example, a polypeptide molecule being sequenced may be immobilized to a nanopore, and an electrical signal (e.g., changes in conductance) may be detected as an amino acid recognition molecule associates with a particular amino acid.

Some embodiments involve analyzing sequencing data 1102 to determine portions of sequencing data 1102 corresponding to amino acids that are sequentially exposed at a terminus of the polypeptide during the degradation process. As shown in FIG. 11, association event identification technique 1104 may access sequencing data 1102 and analyze sequencing data to identify portions of sequencing data 1102 that correspond to association events. The association events may correspond to characteristic patterns, such as $CP_1$ and $CP_2$ shown in FIG. 1B, in the data. In some embodiments, association event identification technique 1104 may involve detecting a series of cleavage events and determining portions of sequencing data 1102 between successive cleavage events. As an example, a cleavage event between $CP_1$ and $CP_2$ shown in FIG. 1B may be detected such that a first portion of the data corresponding to $CP_1$ may be identified as a first association event and a second portion of the data corresponding $CP_2$ may be identified as a second association event.

Some embodiments involve identifying a type of amino acid for one or more of the determined portions of sequencing data 1102. As shown in FIG. 11, amino acid identification technique 1106 may be used to determine a type of amino acid for one or more of the association events identified by association event identification technique 1104. In some embodiments, the individual portions of data identified by association event identification technique 1104 may include a pulse pattern, and amino acid identification technique 1106 may determine a type of amino acid for one or more of the portions based on its respective pulse pattern. Referring to FIG. 1B, amino acid identification technique 1106 may identify a first type of amino acid for $CP_1$ and a second type of amino acid for $CP_2$. In some embodiments, determining the type of amino acid may include identifying an amount of time within a portion of data, such as a portion identified using association event identification technique 1104, when the data is above a threshold value and comparing the amount of time to a duration of time for the portion of data. For example, identifying a type of amino acid for $CP_1$ may include determining an amount of time within $CP_1$ where the signal is above a threshold value, such as time period, pd, where the signal is above $M_L$, and comparing it to a total duration of time for $CP_1$. In some embodiments, determining the type of amino acid may involve identifying one or more pulse durations for one or more portions of data identified by association event identification technique 1102. For example, identifying a type of amino acid for $CP_1$ may include determining a pulse duration for $CP_1$, such as time period, pd. In some embodiments, determining the type of amino acid may involve identifying one or more interpulse durations for one or more portions of the data identified using association event identification technique 1104. For example, identifying a type of amino acid for $CP_1$ may include identifying an interpulse duration, such as ipd.

By identifying a type of amino acid for successive portions of sequencing data 1102, amino acid identification technique 1106 may output amino acid sequence(s) 1108 representative of the polypeptide. In some embodiments, the amino acid sequence includes a series of amino acids corresponding to the portions of data identified using association event identification technique 1104.

FIG. 12 is a flow chart of an illustrative process 1200 for determining an amino acid sequence of a polypeptide molecule, in accordance with some embodiments of the technology described herein. Process 1200 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, association event identification technique 1104 and amino acid identification technique 1106 may perform some or all of process 1200 to determine amino acid sequence(s).

Process 1200 begins at act 1202, which involves contacting a single polypeptide molecule with one or more terminal amino acid recognition molecules. Next, process 1200 proceeds to act 1104, which involves detecting a series of signal pulses indicative of association of the one or more terminal amino acid recognition molecules with successive amino acids exposed at a terminus of the single polypeptide while the single polypeptide is being degraded. The series of pulses may allow for sequencing of the single polypeptide molecule, such as by using association event identification technique 1104 and amino acid identification technique 1106.

In some embodiments, process 1200 may include act 1206, which involves identifying a first type of amino acid in the single polypeptide molecule based on a first characteristic pattern in the series of signal pulses, such as by using amino acid identification technique 1106.

FIG. 13 is a flow chart of an illustrative process 1300 for determining an amino acid sequence representative of a polypeptide, in accordance with some embodiments of the technology described herein. Process 1300 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, association event identification technique 1104 and amino acid identification technique 1106 may perform some or all of process 1300 to determine amino acid sequence(s).

Process 1300 begins at act 1302, where data during a degradation process of a polypeptide is obtained. In some embodiments, the data is indicative of amino acid identity at the terminus of the polypeptide during the degradation process. In some embodiments, the data is indicative of a signal produced by one or more amino acid recognition molecules binding to different types of terminal amino acids at the terminus during the degradation process. In some embodiments, the data is indicative of a luminescent signal generated during the degradation process. In some embodiments, the data is indicative of an electrical signal generated during the degradation process.

Next, process 1300 proceeds to act 1304, where the data is analyzed to determine portions of the data corresponding to amino acids that are sequentially exposed at a terminus of the polypeptide during the degradation process, such as by using association event identification technique 1104 and amino acid identification technique 1106. In some embodiments, analyzing the data further comprises detecting a series of cleavage events and determining the portions of the data between successive cleavage events, such as by using association event identification technique 1104.

In some embodiments, analyzing the data further comprises determining a type of amino acid for each of the individual portions, such as by using amino acid identification technique 1106. In some embodiments, each of the individual portions comprises a pulse pattern, and analyzing the data further comprises determining a type of amino acid for one or more of the portions based on its respective pulse pattern. In some embodiments, determining the type of amino acid further comprises identifying an amount of time within a portion when the data is above a threshold value and comparing the amount of time to a duration of time for the portion. In some embodiments, determining the type of amino acid further comprises identifying at least one pulse duration for each of the one or more portions. In some embodiments, determining the type of amino acid further comprises identifying at least one interpulse duration for each of the one or more portions.

Next, process 1300 proceeds to act 1306, where an amino acid sequence representative of the polypeptide is outputted, such as via a user interface. In some embodiments, the amino acid sequence includes a series of amino acids corresponding to the portions.

An illustrative implementation of a computer system 1400 that may be used in connection with any of the embodiments of the technology described herein is shown in FIG. 14. The computer system 1400 includes one or more processors 1410 and one or more articles of manufacture that comprise non-transitory computer-readable storage media (e.g., memory 1420 and one or more non-volatile storage media 1430). The processor 1410 may control writing data to and reading data from the memory 1420 and the non-volatile storage device 1430 in any suitable manner, as the aspects of the technology described herein are not limited in this respect. To perform any of the functionality described herein, the processor 1410 may execute one or more processor-executable instructions stored in one or more non-transitory computer-readable storage media (e.g., the memory 1420), which may serve as non-transitory computer-readable storage media storing processor-executable instructions for execution by the processor 1410.

Computing device 1400 may also include a network input/output (I/O) interface 1440 via which the computing device may communicate with other computing devices (e.g., over a network), and may also include one or more user I/O interfaces 1450, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

EXAMPLES

Example 1. Edman Degradation by Chemical Cleavage

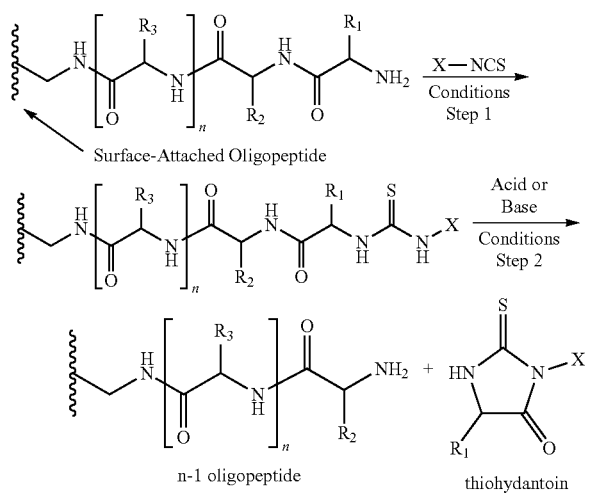

Surface-Attached Oligopeptide n-1 oligopeptide    thiohydantoin

A surface-attached oligopeptide of approximately 3 to approximately 30 amino acids (n=3-30) is provided, where amino acid residues $R_1$-$R_3$ can be any of the common 20 amino acids or an endogenously modified amino acid (e.g., modified by a post-translational modification). In the isothiocyanate N-terminal reaction, Step 1, an isothiocyanate X-NCS is added to a vessel containing the surface-attached oligopeptide, where X is phenyl (Ph), 4-$NO_2$Ph, 4-$SO_3$Ph, napthyl, benzyl, alkyl, or a derivative thereof. Step 1 is carried out under the following Conditions to afford the X-NCS derivatized N-terminal amino acid: aqueous buffer pH 4-10, MeOH or EtOH or IPA alcoholic co-solvents, trialkylamines in organic solvents (DCM, THF, MeCN, DMF, and the like), 20° C. to 50° C. In the thiourea cleavage reaction, Step 2, an Acid or a Base is added to a vessel containing the X-NCS derivatized N-terminal amino acid, where the Acid is acetic acid, formic acid, trichloroacetic acid, trifluoroacetic acid, phosphoric acid, or hydrochloric acid, as neat or aqueous solutions, or where the Base is a trialkylamine or a buffered trialkylamine (e.g., $Et_3NH^+$ $AcO^-$). Step 2 is carried out under the following Conditions to afford the n-1 oligopeptide and thiohydantoin byproduct: neat acid or with aqueous/organic co-solvents of any ratio, 20° C. to 50° C.

Example 2. Solubilizing Linkers for Peptide Surface Immobilization

Seeking to improve oligopeptide solubility in aqueous buffer, it was determined that peptide fragments could be conjugated with oligonucleotide linkers to both improve aqueous solubility and provide a functional moiety for surface immobilization of peptides at the single molecule level. Different peptide-linker conjugates were synthesized, with example structures depicted in FIG. 15A for a peptide-DNA conjugate and a peptide-PEG conjugate. Linker conjugation was observed to greatly enhance peptide solubility in aqueous solution for each of the different peptide-linker conjugates evaluated.

The peptide-linker conjugates were evaluated for amino acid cleavage at peptide N-termini by N-terminal aminopeptidases (Table 6, below).

TABLE 6

Terminal amino acid cleavage of peptide-linker conjugates.

| Entry | Peptide | SEQ ID NO. | Class | Linker | Cleaved by Rat APN | Cleaved by PIP |
|---|---|---|---|---|---|---|
| 1 | KF | 70 | positive | oligo | No | |
| 2 | KKMKKM{LYS(N3)} | 71 | positive | oligo | No | |
| 3 | KKMKKM{LYS(N3)} | 71 | positive | oligo-PEG | No | |
| 4 | KKMKKM{LYS(N3)} | 71 | positive | PEG4 | Yes | |
| 5 | DDMDDMILYS(N3)} | 72 | negative | oligo | Yes | |
| 6 | FFMFFM{LYS(N3)} | 73 | aromatic | oligo | Yes | |
| 7 | AAMAAM{LYS(N3)} | 74 | hydrophobic | oligo | Yes | |

TABLE 6-continued

Terminal amino acid cleavage of peptide-linker conjugates.

| Entry | Peptide | SEQ ID NO. | Class | Linker | Cleaved by Rat APN | Cleaved by PIP |
|---|---|---|---|---|---|---|
| 8 | FPFPFP{LYS(N3)} | 75 | aromatic | oligo | | Yes |
| 9 | DPDPDP{LYS(N3)} | 76 | negative | oligo | | Yes |
| 10 | KPKPKP{LYS(N3)} | 77 | positive | oligo | | No |
| 11 | KPKPKP{LYS(N3)} | 77 | positive | PEG4 | | Yes |

The peptide-linker conjugates shown in Table 6 were incubated with either proline iminopeptidase ("PIP") or rat aminopeptidase N ("Rat APN"), and peptide cleavage was monitored by LCMS. An example of an LCMS demonstrating cleavage of Entry 5 from Table 6 is shown in FIG. 15B. All other cleavage reactions were measured in a similar manner. As shown in Table 6, while positively charged peptide-DNA conjugates ("oligo" and "oligo-PEG" linkers) were not cleaved by the aminopeptidases tested, all other conjugate classes (negatively charged, aromatic, hydrophobic) with DNA oligonucleotide linkers were cleaved. By comparison, the positively charged peptide-PEG conjugates were shown to be cleaved by at least one of the aminopeptidases.

Using labeled peptide-linker conjugates, it was shown that peptides of different compositions could be immobilized to individual sample well surfaces for single molecule analysis. For these experiments, the DNA linker was labeled with a dye (e.g., as depicted in FIG. 15A for the peptide-DNA conjugate), and loading of different peptide-DNA conjugates into individual sample wells was measured by dye fluorescence. An example loading experiment is shown in FIG. 15C. By measuring fluorescence emission of a labeled peptide-DNA conjugate (50 pM), it was determined that at least 18% of sample wells on a chip were loaded at single occupancy per sample well with a surface-immobilized conjugate. These experiments demonstrated that peptide-linker conjugates display enhanced aqueous solubility compared to non-conjugated peptide counterpart, that conjugated linkers do not prevent terminal amino acid cleavage of peptides by different aminopeptidases, and that peptide-linker conjugates of different compositions can be immobilized to chip surfaces at the single molecule level.

Example 3. Exopeptidase Cleavage of Polypeptide Substrates

The cleavage capabilities of various aminopeptidases were tested. The conditions and results for a set of cleavage assay experiments are shown in Table 7, including concentration of peptide substrate, concentration of enzyme, buffer conditions, temperature, and incubation time. Cleavage of peptide substrates by the indicated enzymes was assayed using High Performance Liquid Chromatography (HPLC). The "HPLC assay conv" value in Table 7 indicates the percentage of the peptide substrate that was converted to cleavage product. To determine the "HPLC assay conv" value, two solutions were prepared containing the same starting concentration of peptide. One solution was subjected to enzymatic digestion, while the other solution did not contain any enzyme, but was diluted with an equivalent amount of buffer used to store the enzyme. The reactions were quenched at the time indicated. The amount of reactant converted to product was determined by dividing the area of the peak obtained by HPLC of the starting material remaining after enzymatic digestion by the peak area of the control solution of undigested peptide, and then multiplying this ratio by 100. In Table 7, "NH2" indicates an amine group, "yPIP" refers to $Y.\ pestis$ proline iminopeptidase, "NPEPPS" refers to puromycin-sensitive aminopeptidase, "VPr" refers to $Vibrio\ proteolyticus$ aminopeptidase, and "EDAPN" refers to $L.\ pneumophila$ M1 aminopeptidase.

TABLE 7

Cleavage of peptide substrates by aminopeptidases.

| Enzyme | Peptide Substrate | Conditions | Temp/ Time | HPLC Assay Conv | Pdt |
|---|---|---|---|---|---|
| yPIP | GlyProArgPro (SEQ ID NO: 84) | 5 mM peptide, 50 nM enzyme, 10 mM MgCl$_2$, 10 mM Tris, 0.02% Tween-20 pH 8.0 | 30° C./ 1 hr | 100% | ProArgPro |
| yPIP | DDPDDP{LYSN3}NH2 (SEQ ID NO: 85) | 1 mM peptide, 700 nM enzyme, 10 mM MgCl$_2$, 10 mM Tris, 0.02% Tween-20 pH 8.0 | 30° C./ 6 hrs | 0% | n/a |
| yPIP | AAMAAM{LYSN3}NH2 (SEQ ID NO: 74) | 1 mM peptide, 700 nM enzyme, 10 mM MgCl$_2$, 10 mM Tris, 0.02% Tween-20 pH 8.0 | 30° C./ 6 hrs | 0% | n/a |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| yPIP | YPYPYP{LYSN3}NH2 (SEQ ID NO: 86) | 600 mM peptide, 7 mM enzyme, 10 mM MgCl$_2$, 10 mM Tris, 0.02% Tween-20 pH 8.0 | 30° C./ 1 hr | 100% | PYPYP{LYSN3}NH2 (SEQ ID NO: 87) |
| yPIP | FPFPFP{LYSN3}NH2 (SEQ ID NO: 75) | 600 mM peptide, 7 mM enzyme, 10 mM MgCl$_2$, 10 mM Tris, 0.02% Tween-20 pH 8.0 | 30° C./ 1 hr | 100% | PFPFP{LYSN3}NH2 (SEQ ID NO: 88) |
| NPEPPS | LeuTyr 5 mM | 700 nM enzyme, 25 mM HEPES, 1 mM Mg(OAc)$_2$, 1 mM DTT, pH 7.5 | 30° C./ 1 hr | 5% | Tyr |
| (Cy3B)n-yPIP | FPFPFP{LYSN3}NH2 (SEQ ID NO: 75) | 1 mM peptide, 14 mM enzyme, 10 mM MgCl$_2$, 10 mM Tris, 0.02% Tween-20 pH 8.0 | 30° C./ 15 min | 100% | PFPFP{LYSN3}NH2 (SEQ ID NO: 88) |
| (Cy3B)n-yPIP | FPFPFP{LYSN3}NH2 (SEQ ID NO: 75) | 1 mM peptide, 14 mM enzyme, 200 mM Bis-tris Propane, 30 mM KOAc, 25 mM Mg(OAc)$_2$, 23 mM 3,4 Dihydroxy-benzoic acid and 12 mM Nitrobenzoic acid | 30° C./ 15 min | 100% | PFPFP{LYSN3}NH2 (SEQ ID NO: 88) |
| P. falciparum M1 | MetTyr | 1 mM peptide, 1 mM enzyme, 2.5 mM ZnCl$_2$ 25 mM Tris pH 8.0 | 30° C./ 1 hr | 7% | Tyr |
| (Atto647 N)n-yPIO | FPFPFP{LYSN3}NH2 (SEQ ID NO: 75) | 1 mM peptide, 14 mM enzyme, 10 mM MgCl$_2$, 10 mM Tris, 0.02% Tween-20 pH 8.0 | 30° C./ 1 hr | 100% | PFPFP{LYSN3}NH2 (SEQ ID NO: 88) |
| Rat APN | KKMKKMLys-Triazole-PEG4 Biotin (SEQ ID NO: 89) | 1 mM peptide, 150 nM enzyme, 2.5 mM ZnCl$_2$ 25 mM Tris pH 8.0 | 30° C./ 1 hr | >90% | |
| yPIP | FPFPFP{LYSN3}NH2 (SEQ ID NO: 75) | 1 mM peptide, 7 mM enzyme, 10 mM MgCl$_2$, 10 mM Tris, 0.02% Tween-20 pH 8.0 | 30° C./ 1 hr | 100% | PFPFP{LYSN3}NH2 (SEQ ID NO: 88) |
| yPIP | BCN PEG23 Biotin conjugate | 1 mM peptide, 7 mM enzyme, 10 mM MgCl$_2$, 10 mM Tris, 0.02% Tween-20 pH 8.0 | 30° C./ 1 hr | 100% | PFPFP{LYSN3}NH2 (SEQ ID NO: 88) |
| P. horikoshii Tet | DDMDDM{LYSN3}NH2 (SEQ ID NO: 72) | 1 mM peptide, 1 mM enzyme, 2.5 mM ZnCl$_2$, 25 mM Tris 8.0 | 70° C./ 1 hr | 60% | |
| GluAsp-APN | DDMDDM{LYSN3}NH2 (SEQ ID NO: 72) | 1 mM peptide, 1 mM enzyme, 2.5 mM ZnCl$_2$, 25 mM Tris 8.0 | 30° C./ 1 hr | 100% | |
| P. horikoshii Tet | YYPYYP{LYSN3}NH2 (SEQ ID NO: 92) | 1 mM peptide, 1 mM enzyme, 2.5 mM ZnCl$_2$, 25 mM Tris 8.0 | 70° C./ 1 hr | 100% | YPYYP{LYSN3}NH2 (SEQ ID NO: 93) |
| P. horikoshii Tet | FFPFFP{LYSN3}NH2 (SEQ ID NO: 94) | 1 mM peptide, 1 mM enzyme, 2.5 mM ZnCl$_2$, 25 mM Tris 8.0 | 70° C./ 1 hr | 100% | FPFFP{LYSN3}NH2 (SEQ ID NO: 95) |
| Rat APN | RRPRRP{LYSN3}NH2 (SEQ ID NO: 96) | 1 mM peptide, 50 mM enzyme, 2.5 mM ZnCl$_2$, 25 mM Tris 8.0 | 30° C./ 1 hr | 55% | RPRRP{LYSN3}NH2 (SEQ ID NO: 97) |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| Rat APN | AAPAAP{LYSN3}NH2 (SEQ ID NO: 98) | 1 mM peptide, 50 mM enzyme, 2.5 mM ZnCl$_2$, 25 mM Tris 8.0 | 30° C./ 1 hr | 100% | APAAP{LYSN3}NH2 (SEQ ID NO: 99) |
| Rat APN | KKPKKP{LYSN3}NH2 (SEQ ID NO: 100) | 1 mM peptide, 50 mM enzyme, 2.5 mM ZnCl$_2$, 25 mM Tris 8.0 | 30° C./ 1 hr | 85% | KPKKP{LYSN3}NH2 (SEQ ID NO: 101) |
| Rat APN | KKMKKM{LYSN3}NH2 (SEQ ID NO: 71) | 1 mM peptide, 50 mM enzyme, 2.5 mM ZnCl$_2$, 25 mM Tris 8.0 | 30° C./ 1 hr | 50% | KMKKM{LYSN3}NH2 (SEQ ID NO: 102) |
| VPr | RRPRRP{LYSN3}NH2 (SEQ ID NO: 96) | 1 mM peptide, 2 mM enzyme, 2.5 mM ZnCl$_2$, 25 mM Tris 8.0 | 30° C./ 1 hr | 100% | |
| VPr | AAPAAP{LYSN3}NH2 (SEQ ID NO: 98) | 1 mM peptide, 2 mM enzyme, 2.5 mM ZnCl$_2$, 25 mM Tris 8.0 | 30° C./ 1 hr | 100% | APAAP{LYSN3}NH2 (SEQ ID NO: 99) |
| VPr | KKPKKP{LYSN3}NH2 (SEQ ID NO: 100) | 1 mM peptide, 2 mM enzyme, 2.5 mM ZnCl$_2$, 25 mM Tris 8.0 | 30° C./ 1 hr | 100% | KPKKP{LYSN3}NH2 (SEQ ID NO: 101) |
| VPr | YYPYYP{LYSN3}NH2 (SEQ ID NO: 92) | 1 mM peptide, 2 mM enzyme, 2.5 mM ZnCl$_2$, 25 mM Tris 8.0 | 30° C./ 1 hr | 50% | YPYYP{LYSN3}NH2 (SEQ ID NO: 93) |
| VPr | FFPFFP{LYSN3}NH2 (SEQ ID NO: 94) | 1 mM peptide, 2 mM enzyme, 2.5 mM ZnCl$_2$, 25 mM Tris 8.0 | 30° C./ 1 hr | 100% | FPFFP{LYSN3}NH2 (SEQ ID NO: 95) |
| VPr | AAMAAM{LYSN3}NH2 (SEQ ID NO: 74) | 1 mM peptide, 2 mM enzyme, 2.5 mM ZnCl$_2$, 25 mM Tris 8.0 | 30° C./ 1 hr | 100% | multiple pdts |
| VPr | KKMKKM{LYSN3}NH2 (SEQ ID NO: 89) | 1 mM peptide, 2 mM enzyme, 2.5 mM ZnCl$_2$, 25 mM Tris 8.0 | 30° C./ 1 hr | 100% | multiple pdts |
| VPr | YYMYYM{LYSN3}NH2 (SEQ ID NO: 103) | 1 mM peptide, 2 mM enzyme, 2.5 mM ZnCl$_2$, 25 mM Tris 8.0 | 30° C./ 1 hr | >90% | multiple pdts |
| yPIP | Attor6g-1kPEG-DPAAAFK{LYSN3}-1kPEG-Biotin (SEQ ID NO: 104) | 44 mM Peptide, 7 mM enzyme, 200 mM Bis-tris Propane, 30 mM KOAc, 25 mM Mg(OAc)$_2$, 32 mM 3,4 Dihydroxy-benzoic acid and 12 mM Nitrobenzoic acid + PCD + TXV | 30° C./ 0.5 hr | <10% | PAAAFK-1kPEG-Biotin (SEQ ID NO: 105) |
| PfuPIP | FPFPFP{LYSN3}NH2 (SEQ ID NO: 75) | 1 mM Peptide, 1 µM enzyme, 1 mM CoCl$_2$, 50 mM HEPES, 50 mM KCl | 80° C./ 0.5 hr | 100% | PFPFP{LYSN3}NH2 (SEQ ID NO: 88) |
| PfuPIP | Attor6g-1kPEG-DPAAAFK{LysN3}-1kPEG-Biotin (SEQ ID NO: 104) | 1 mM Peptide, 1 µM enzyme, 1 mM CoCl$_2$, 50 mM HEPES, 50 mM KCl | 80° C./ 0.5 hr | 40% | PAAAFK-1kPEG-Biotin (SEQ ID NO: 105) |
| yPIP | Attor6g-1kPEG-ODN-DD60-Biotin | 20 µM Q24 conjugate, 30 µM ypip, 1x Mg buffer | 30° C./ 0.3 hr | 100% | PAAAFK-1kPEG-Biotin (SEQ ID NO: 105) |
| yPIP | FPFPFP{LYSN3}NH2 (SEQ ID NO: 75) | 1 mM Peptide, 7 µM Enzyme, 50 mM MOPS, 10 mM Mg(OAc)$_2$ pH 8.0 | 37° C./ 0.5 hr | 100% | PFPFP{LYSN3}NH2 (SEQ ID NO: 88) |
| yPIP | Attor6g-1kPEG-ODN-DD60-Biotin | 10 µM Peptide, 7 µM Enzyme, 50 mM MOPS, 10 mM Mg(OAc)$_2$ pH 8.0 | 37° C./ 0.5 hr | 100% | PAAAFK-1kPEG-Biotin (SEQ ID NO: 105) |

TABLE 7-continued

Cleavage of peptide substrates by aminopeptidases.

| Enzyme | Peptide Substrate | Conditions | Temp/Time | HPLC Assay Conv | Pdt |
|---|---|---|---|---|---|
| PfuPIP | FPFPFP{LYSN3}NH2 (SEQ ID NO: 75) | 1 mM Peptide, 1 μM Enzyme, 50 mM MOPS, 10 mM Mg(OAc)$_2$ pH 8.0 | 80° C./ 0.5 hr | 40% | PFPFP{LYSN3}NH2 (SEQ ID NO: 88) |
| yPIP-Q24-Cy3B | FPFPFP{LYSN3}NH2 (SEQ ID NO: 75) | 1 mM Peptide, 2.1 μM Enzyme, 50 mM MOPS, 10 mM Mg(OAc)$_2$ pH 8.0 | 37° C./ 0.5 hr | 100% | PFPFP{LYSN3}NH2 (SEQ ID NO: 88) |
| yPIP-Q24-Rho6G | YPYPYP{LYSN3}NH2 (SEQ ID NO: 86) | 1 mM Peptide, 100 nM Enzyme, 1X CB2 | 37° C./ 0.5 hr | 100%+ | YPYYP{LYSN3}NH2 (SEQ ID NO: 93) |
| yPIP-Q24Dark | YPYPYP{LYSN3}NH2 (SEQ ID NO: 86) | 1 mM Peptide, ~5 μM Enzyme, 1X CB2 | 37° C./ 0.5 hr | <15% | YPYYP{LYSN3}NH2 (SEQ ID NO: 93) |
| Rat APN | QP5-Atto649N (KAAAAAAFK{LYSN3}NH2) (SEQ ID NO: 106) | 37 μM Peptide, 100 nM Enzyme, 2.5 mM ZnCl$_2$, 25 mM Tris pH 8.0 | 37° C./ 0.5 hr | >95% | |
| VPr | QP5-Atto649N (KAAAAAAFK{LYSN3}NH2) (SEQ ID NO: 106) | 37 μM Peptide, 8 μM Enzyme, 2.5 mM ZnCl$_2$, 25 mM Tris pH 8.0 | 37° C./ 0.5 hr | 100% | |
| K287pAzF-Cy3 yPIP | YPYPYP{LYSN3}NH2 (SEQ ID NO: 86) | 1 mM Peptide, 8 μM Enzyme, 50 mM MOPS, 10 mM Mg(OAc)$_2$ pH 8.0 | 37° C./ 1 hr | 100% | PYPYPK (SEQ ID NO: 83) |
| V. cholera APT | AAPAAP{LYSN3}NH2 (SEQ ID NO: 98) | 1 mM Peptide, 1 μM Enzyme, 2.5 mM ZnCl$_2$, 25 mM Tris pH 8.0 | 37° C./ 1 hr | ~5% | |
| Bst M28 | AAPAAP{LYSN3}NH2 (SEQ ID NO: 98) | 1 mM Peptide, 1 μM Enzyme, 2.5 mM ZnCl$_2$, 25 mM Tris pH 8.0 | 37° C./ 1 hr | 100% | |
| Taq APT | AAPAAP{LYSN3}NH2 (SEQ ID NO: 98) | 1 mM Peptide, 1 μM Enzyme, 2.5 mM ZnCl$_2$, 25 mM Tris pH 8.0 | 37° C./ 1 hr | >90% | |
| V. cholera APT | YYPYYP{LYSN3}NH2 (SEQ ID NO: 92) | 1 mM Peptide, 1 μM Enzyme, 2.5 mM ZnCl$_2$, 25 mM Tris pH 8.0 | 37° C./ 1 hr | 5% | |
| Bst M28 | YYPYYP{LYSN3}NH2 (SEQ ID NO: 92) | 1 mM Peptide, 1 μM Enzyme, 2.5 mM ZnCl$_2$, 25 mM Tris pH 8.0 | 37° C./ 1 hr | 10% | |
| Taq APT | YYPYYP{LYSN3}NH2 (SEQ ID NO: 92) | 1 mM Peptide, 1 μM Enzyme, 2.5 mM ZnCl$_2$, 25 mM Tris pH 8.0 | 37° C./ 1 hr | 30% | |
| V. cholera APT | FFPFFP{LYSN3}NH2 (SEQ ID NO: 94) | 1 mM Peptide, 1 μM Enzyme, 2.5 mM ZnCl$_2$, 25 mM Tris pH 8.0 | 37° C./ 1 hr | >95% | |
| Bst M28 | FFPFFP{LYSN3}NH2 (SEQ ID NO: 94) | 1 mM Peptide, 1 μM Enzyme, 2.5 mM ZnCl$_2$, 25 mM Tris pH 8.0 | 37° C./ 1 hr | 30% | |
| Taq APT | FFPFFP{LYSN3}NH2 (SEQ ID NO: 94) | 1 mM Peptide, 1 μM Enzyme, 2.5 mM ZnCl$_2$, 25 mM Tris pH 8.0 | 37° C./ 1 hr | 60% | |
| V. cholera APT | YYMYYM{LYSN3}NH2 (SEQ ID NO: 103) | 1 mM Peptide, 1 μM Enzyme, 2.5 mM ZnCl$_2$, 25 mM Tris pH 8.0 | 37° C./ 1 hr | 30% | |
| Bst M28 | YYMYYM{LYSN3}NH2 (SEQ ID NO: 103) | 1 mM Peptide, 1 μM Enzyme, 2.5 mM ZnCl$_2$, 25 mM Tris pH 8.0 | 37° C./ 1 hr | >50% | multiple (N-1, -2, -3, etc.) |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| Taq APT | YYMYYM{LYSN3}NH2 (SEQ ID NO: 103) | 1 mM Peptide, 1 µM Enzyme, 2.5 mM ZnCl$_2$, 25 mM Tris pH 8.0 | 37° C./ 1 hr | 85% | multiple (N-1, -2, -3, etc.) |
| Cy3B-Q24-pAzF-yPIP | YPYPYP{LYSN3}NH2 (SEQ ID NO: 86) | 1 mM Peptide, 7 µM Enzyme, 10 mM MgCl$_2$, 50 mM MOPS | 37° C./ 0.5 hr | 100% | |
| Cy3B-BstTET | FFPFFP{LYSN3}NH2 (SEQ ID NO: 94) | 1 mM Peptide, 10 µM Enzyme, 2.5 mM ZnCl$_2$, 25 mM Tris pH 8.0 | 37° C./ 0.5 hr | 50% | |
| Cy3B-taqAPT 2nd peak | FFPFFP{LYSN3}NH2 (SEQ ID NO: 94) | 1 mM Peptide, 20 µM Enzyme, 2.5 mM ZnCl$_2$, 25 mM Tris pH 8.0 | 37° C./ 0.5 hr | 100% | |
| Cy3B-taqAPT 4th peak | FFPFFP{LYSN3}NH2 (SEQ ID NO: 94) | 1 mM Peptide, 20 µM Enzyme, 2.5 mM ZnCl$_2$, 25 mM Tris pH 8.0 | 37° C./ 0.5 hr | 100% | |
| PhaloM28 | RRPRRP{LYSN3}NH2 (SEQ ID NO: 96) | 1 mM Peptide, 1 µM Enzyme, 2.5 mM ZnCl$_2$, 25 mM Tris pH 8.0 | 37° C./ 0.5 hr | 30% | multiple, even higher mass |
| yPAP | RRPRRP{LYSN3}NH2 (SEQ ID NO: 96) | 1 mM Peptide, 1 µM Enzyme, 2.5 mM ZnCl$_2$, 25 mM Tris pH 8.0 | 37° C./ 0.5 hr | 100% | |
| yPAP | AAPAAP{LYSN3}NH2 (SEQ ID NO: 98) | 1 mM Peptide, 1 µM Enzyme, 2.5 mM ZnCl$_2$, 25 mM Tris pH 8.0 | 37° C./ 0.5 hr | 100% | |
| yPAP | KKPKKP{LYSN3}NH2 (SEQ ID NO: 100) | 1 mM Peptide, 1 µM Enzyme, 2.5 mM ZnCl$_2$, 25 mM Tris pH 8.0 | 37° C./ 0.5 hr | 100% | |
| yPAP | YYPYYP{LYSN3}NH2 (SEQ ID NO: 92) | 1 mM Peptide, 1 µM Enzyme, 2.5 mM ZnCl$_2$, 25 mM Tris pH 8.0 | 37° C./ 0.5 hr | 100% | |
| PhaloM28 | FFPFFP{LYSN3}NH2 (SEQ ID NO: 94) | 1 mM Peptide, 1 µM Enzyme, 2.5 mM ZnCl$_2$, 25 mM Tris pH 8.0 | 37° C./ 0.5 hr | >80% | |
| yPAP | FFPFFP{LYSN3}NH2 (SEQ ID NO: 94) | 1 mM Peptide, 1 µM Enzyme, 2.5 mM ZnCl$_2$, 25 mM Tris pH 8.0 | 37° C./ 0.5 hr | >80% | |
| *V. cholera* APT | QP5-Atto649N (KAAAAAAFK{LYSN3} NH2) (SEQ ID NO: 106) | 1 mM Peptide, 5 µM Enzyme, 2.5 mM ZnCl$_2$, 25 mM Tris pH 8.0 | 37° C./ 0.5 hr | 100% | |
| yPAP | YYPYYP{LYSN3}NH2 (SEQ ID NO: 92) | 1 mM Peptide, 2 µM Enzyme, 2.5 mM ZnCl$_2$, 25 mM Tris pH 8.0 | 37° C./ 0.5 hr | 10% | |
| *V. anguillarum* APN | RRPRRP{LYSN3}NH2 (SEQ ID NO: 96) | 1 mM peptide, 2 µM enzyme, 2.5 mM ZnCl$_2$, 25 mM Tris pH 8.0 | 30° C./ 1 hr | >90% | |
| *V. anguillarum* APN | AAPAAP{LYSN3}NH2 (SEQ ID NO: 98) | 1 mM peptide, 2 µM enzyme, 2.5 mM ZnCl$_2$, 25 mM Tris pH 8.0 | 30° C./ 1 hr | 50% | |
| *V. anguillarum* APN | KKPKKP{LYSN3}NH2 (SEQ ID NO: 100) | 1 mM peptide, 2 µM enzyme, 2.5 mM ZnCl$_2$, 25 mM Tris pH 8.0 | 30° C./ 1 hr | <5% | |
| VPr | FYPLPWPDDDY {LYSN3}NH2 (SEQ ID NO: 107) | 300 µM Peptide, 4 µM enzyme, 10 mM MgCl$_2$, 50 mM MOPS pH 8.0 | 37° C./ 0.5 hr | 100% | |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| yPIP | YPLPWPDDDY{LYSN3}NH2 (SEQ ID NO: 108) | 300 µM Peptide, 7 µM enzyme, 10 mM MgCl$_2$, 50 mM MOPS pH 8.0 | 37° C./ 0.5 hr | 100% | |
| VPr | PLPWPDDDY{LYSN3}NH2 (SEQ ID NO: 109) | 300 µM Peptide, 4 µM enzyme, 10 mM MgCl$_2$, 50 mM MOPS pH 8.0 | 37° C./ 0.5 hr | 100% | |
| yPIP | LPWPDDDY{LYSN3}NH2 (SEQ ID NO: 108) | 300 µM Peptide, 7 µM enzyme, 10 mM MgCl$_2$, 50 mM MOPS pH 8.0 | 37° C./ 0.5 hr | 100% | |
| hTET | FYPLPWPDDDY{LYSN3}NH2 (SEQ ID NO: 107) | 200 µM Peptide, 2 µM enzyme, 2.5 mM ZnCl$_2$, 25 mM Tris pH 8.0 | 37° C./ 1 hr | 55% | YPLPWPDDDY{LYSN3}NH2 (SEQ ID NO: 108) |
| hTET | FYPLPWPDDDY{LYSN3}NH2 (SEQ ID NO: 107) | 200 µM Peptide, 2 µM enzyme, 10 mM MgCl$_2$, 50 mM MOPS pH 8.0 | 37° C./ 1 hr | 55% | YPLPWPDDDY{LYSN3}NH2 (SEQ ID NO: 108) |
| ProVPrA mbr | FYPLPWPDDDY{LYSN3}NH2 (SEQ ID NO: 107) | 200 µM Peptide, 2.2 µM enzyme, 10 mM MgCl$_2$, 50 mM MOPS pH 8.0 | 37° C./ 1 hr | 6% | YPLPWPDDDY{LYSN3}NH2 (SEQ ID NO: 108) |
| ThrCut-ProVPrA mbr | FYPLPWPDDDY{LYSN3}NH2 (SEQ ID NO: 107) | 200 µM Peptide, 2.1 µM enzyme, 10 mM MgCl$_2$, 50 mM MOPS pH 8.0 | 37° C./ 1 hr | 40% | YPLPWPDDDY{LYSN3}NH2 (SEQ ID NO: 108) |
| VPr | FYPLPWPDDDY{LYSN3}NH2 (SEQ ID NO: 107) | 200 µM Peptide, 4 µM enzyme, 10 mM MgCl$_2$, 50 mM MOPS pH 8.0 | 37° C./ 0.5 hr | 100% | YPLPWPDDDY{LYSN3}NH2 (SEQ ID NO: 108) |
| ProVPrA mbr | FYPLPWPDDDY{LYSN3}NH2 (SEQ ID NO: 107) | 200 µM Peptide, 4 µM enzyme, 10 mM MgCl$_2$, 50 mM MOPS pH 8.0 | 37° C./ 0.5 hr | 50% | YPLPWPDDDY{LYSN3}NH2 (SEQ ID NO: 108) |
| ThrCut-ProVPrA mbr | FYPLPWPDDDY{LYSN3}NH2 (SEQ ID NO: 107) | 200 µM Peptide, 4 µM enzyme, 10 mM MgCl$_2$, 50 mM MOPS pH 8.0 | 37° C./ 0.5 hr | 40% | YPLPWPDDDY{LYSN3}NH2 (SEQ ID NO: 108) |
| Vpr | FWPLPWPDDDY{LYSN3}NH2 (SEQ ID NO: 107) | 200 µM Peptide, 4 µM enzyme, 10 mM MgCl$_2$, 50 mM MOPS pH 8.0 | 37° C./ 1 hr | 100% | |
| VPr pAzF | FWPLPWPDDDY{LYSN3}NH2 (SEQ ID NO: 107) | 200 µM Peptide, 4 µM enzyme, 10 mM MgCl$_2$, 50 mM MOPS pH 8.0 | 37° C./ 1 hr | 96% | |
| ThrCut-ProVPrA mbr Cy3 clicked | FWPLPWPDDDY{LYSN3}NH2 (SEQ ID NO: 107) | 200 µM Peptide, 6.4 µM enzyme, 10 mM MgCl$_2$, 50 mM MOPS pH 8.0 | 37° C./ 1 hr | 100% | |
| hETE | PLPWPDDDY{LYSN3}NH2 (SEQ ID NO: 109) | 200 µM Peptide, 4 µM enzyme, 10 mM MgCl$_2$, 50 mM MOPS pH 8.0 | 37° C./ 1 hr | 100% | |
| VPr | FWPLPWPDDDY{LYSN3}NH2 (SEQ ID NO: 107) | 400 µM Peptide, 8 µM enzyme, 50 mM HEPES pH 8.0, 300 mM NaCl, 1 mM DTT, 5% Glycerol, 32 mM PCA | 37° C./ 1 hr | 100% | |
| VPr | FYPLPWPDDDY{LYSN3}NH2 (SEQ ID NO: 107) | 200 µM Peptide, 8 µM enzyme, 10 mM MgCl$_2$, 50 mM MOPS pH 5.0 | RT/ 1 hr | 100% | YPLPWPDDDY{LYSN3}NH2 (SEQ ID NO: 108) |
| VPr | FYPLPWPDDDY{LYSN3}NH2 (SEQ ID NO: 107) | 200 µM Peptide, 8 µM enzyme, 10 mM MgCl$_2$, 50 mM MOPS pH 5.0 | RT/ 0.5 hr | 100% | YPLPWPDDDY{LYSN3}NH2 (SEQ ID NO: 108) |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| VPr | FYPLPWPDDDY{LYSN3}NH2 (SEQ ID NO: 107) | 200 µM Peptide, 8 µM enzyme, 10 mM MgCl$_2$, 50 mM MOPS pH 5.0 | RT/ 1 hr | 100% | YPLPWPDDDY{LYSN3}NH2 (SEQ ID NO: 108) |
| VPr | FYPLPWPDDDY{LYSN3}NH2 (SEQ ID NO: 107) | 200 µM Peptide, 8 µM enzyme, 10 mM MgCl$_2$, 50 mM MOPS pH 5.0 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: 107) | 600 µM Peptide, 0.8 µM enzyme, 10 mM Mg(OAc)$_2$, 50 mM MOPS pH 5.5 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: 107) | 600 µM Peptide, 0.8 µM enzyme, 10 mM Mg(OAc)$_2$, 50 mM MOPS pH 6.5 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: 107) | 600 µM Peptide, 0.8 µM enzyme, 10 mM Mg(OAc)$_2$, 50 mM MOPS pH 7.5 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: 107) | 600 µM Peptide, 0.8 µM enzyme, 10 mM Mg(OAc)$_2$, 50 mM MOPS pH 8.5 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: 107) | 1200 µM Peptide, 0.08 µM enzyme, 10 mM Mg(OAc)$_2$, 50 mM MOPS pH 5.5 | RT/ 0.5 hr | 50% | YPLPWPDDDY{LYSN3}NH2 (SEQ ID NO: 108) |
| VPr | FYPLPWPDDDY{LYSN3}NH2 (SEQ ID NO: 107) | 1200 µM Peptide, 0.08 µM enzyme, 10 mM Mg(OAc)$_2$, 50 mM MOPS pH 6.5 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: 107) | 1200 µM Peptide, 0.08 µM enzyme, 10 mM Mg(OAc)$_2$, 50 mM MOPS pH 7.5 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: X) | 1200 µM Peptide, 0.08 µM enzyme, 10 mM Mg(OAc)$_2$, 50 mM MOPS pH 8.5 | RT/ 0.5 hr | 100% | YPLPWPDDDY{LYSN3}NH2 (SEQ ID NO: 108) |
| VPr | QP15 FYPLPWPDDDY{LYSN3}NH2 (SEQ ID NO: 107) | 1200 µM Peptide, 0.008 µM enzyme, 10 mM Mg(OAc)$_2$, 50 mM MOPS pH 5.5 | RT/ 0.5 hr | 1.40% | YPLPWPDDDY{LYSN3}NH2 (SEQ ID NO: 108) |
| VPr | QP15 FYPLPWPDDDY{LYSN3}NH2 (SEQ ID NO: 107) | 1200 µM Peptide, 0.008 µM enzyme, 10 mM Mg(OAc)$_2$, 50 mM MOPS pH 6.5 | RT/ 0.5 hr | 56% | YPLPWPDDDY{LYSN3}NH2 (SEQ ID NO: 108) |
| VPr | FYPLPWPDDDY{LYSN3}NH2 (SEQ ID NO: 107) | 1200 µM Peptide, 0.008 µM enzyme, 10 mM Mg(OAc)$_2$, 50 mM MOPS pH 7.5 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: 107) | 1200 µM Peptide, 0.008 µM enzyme, 10 mM Mg(OAc)$_2$, 50 mM MOPS pH 8.5 | RT/ 0.5 hr | 100% | YPLPWPDDDY{LYSN3}NH2 (SEQ ID NO: 108) |
| VPr | FYPLPWPDDDY{LYSN3}NH2 (SEQ ID NO: 107) | 1200 µM Peptide, 800 pM enzyme, 10 mM Mg(OAc)$_2$, 50 mM MOPS pH 7.5 | RT/ 0.5 hr | 2.70% | YPLPWPDDDY{LYSN3}NH2 (SEQ ID NO: 108) |
| VPr | FYPLPWPDDDY{LYSN3}NH2 (SEQ ID NO: 107) | 1200 µM Peptide, 800 pM enzyme, 10 mM Mg(OAc)$_2$, 50 mM MOPS pH 8.5 | RT/ 0.5 hr | 6.80% | YPLPWPDDDY{LYSN3}NH2 (SEQ ID NO: 108) |
| VPr | FAAAWPDDDF1 (SEQ ID NO: 11) | 600 µM Peptide, 8 µM enzyme, 10 mM Mg(OAc)$_2$, 50 mM MOPS pH 8 | RT/ 0.5 hr | 100% | WPDDF1 (SEQ ID NO: 112 |

TABLE 7-continued

Cleavage of peptide substrates by aminopeptidases.

| Enzyme | Peptide Substrate | Conditions | Temp/Time | HPLC Assay Conv | Pdt |
|---|---|---|---|---|---|
| VPr | WAAAFPDDDF1 (SEQ ID NO: 13) | 600 µM Peptide, 8 µM enzyme, 10 mM Mg(OAc)$_2$, 50 mM MOPS pH 8 | RT/ 0.5 hr | 100% | FPDDF1 (SEQ ID NO: 114) |
| VPr | WAAAFPDDDF1 (SEQ ID NO: 13) | 300 µM Peptide, 8 µM enzyme, 10 mM Mg(OAc)$_2$, 50 mM MOPS pH 8 | RT/ 0.5 hr | 100% | FPDDF1 (SEQ ID NO: 114) |
| VPr | WAAAFPDDDF1 (SEQ ID NO: 13) | 300 µM Peptide, 8 µM enzyme, 10 mM Mg(OAc)$_2$, 50 mM MOPS pH 8, 0.2% Tween20 | RT/ 0.5 hr | 100% | FPDDF1 (SEQ ID NO: 114) |
| VPr | WAAAFPDDDF1 (SEQ ID NO: 13) | 300 µM Peptide, 8 µM enzyme, 50/50 MOPS Mg buffer/RB1 | RT/ 0.5 hr | 30% | 70%-3, 30%-4 |
| VPr | WAAAFPDDDF1 (SEQ ID NO: 13) | 300 µM Peptide, 8 µM enzyme, RB2 + Mg | RT/ 0.5 hr | 5% | Almost all -1, -2 and -3 products |
| VPr | WAAAFPDDDF1 (SEQ ID NO: 13) | 300 µM Peptide, 8 µM enzyme, RB4 | RT/ 0.5 hr | 100% | FPDDF1 (SEQ ID NO: 114) |
| VPr | WAAAFPDDDF1 (SEQ ID NO: 13) | 300 µM Peptide, 8 µM enzyme, 10 mM Mg(OAc)$_2$, 50 mM MOPS pH 8, 60 mM KOAc | RT/ 0.5 hr | 70% | 70%-3, 30%-4 |
| VPr | WAAAFPDDDF1 (SEQ ID NO: 13) | 300 µM Peptide, 8 µM enzyme, 10 mM Mg(OAc)$_2$, 50 mM MOPS pH 8, 60 mM KOAc | RT/ 2 hr | 100% | FPDDF1 (SEQ ID NO: 114) |
| VPr | WAAAFPDDDF1 (SEQ ID NO: 13) | 300 µM Peptide, 8 µM enzyme, 10 mM Mg(OAc)$_2$, 50 mM MOPS pH 8, 60 mM KOAc | 37° C./ 2 hr | 100% | FPDDF1 (SEQ ID NO: 114) |
| VPr | FAAAYPDDDF1 (SEQ ID NO: 11) | 600 µM Peptide, 8 µM enzyme, 10 mM Mg(OAc)$_2$, 50 mM MOPS pH 8, 60 mM KOAc | RT/ 0.5 hr | 100% | YPDDF1 (SEQ ID NO: 115) |
| VPr | FAAAYPDDDF1 (SEQ ID NO: 11) | 600 µM Peptide, 0.8 µM enzyme, 10 mM Mg(OAc)$_2$, 50 mM MOPS pH 8, 60 mM KOAc | RT/ 0.5 hr | 50% | YPDDF1 (SEQ ID NO: 115) |
| VPr | FAAAYPDDDF1 (SEQ ID NO: 11) | 600 µM Peptide, 0.08 µM enzyme, 10 mM Mg(OAc)$_2$, 50 mM MOPS pH 8, 60 mM KOAc | RT/ 0.5 hr | 5% | YPDDF1 (SEQ ID NO: 115) |
| VPr | RRPF11 (SEQ ID NO: 116) | 1 mM Peptide, 1 µM enzyme, 10 mM Mg(OAc)$_2$, 50 mM MOPS pH 8, 60 mM KOAc | RT/ 0.5 hr | 79% | RPFQQ (SEQ ID NO: 117) |
| VPr | AAPFQQ (SEQ ID NO: 118) | 1 mM Peptide, 1 µM enzyme, 10 mM Mg(OAc)$_2$, 50 mM MOPS pH 8, 60 mM KOAc | RT/ 0.5 hr | 100% | APFQQ (SEQ ID NO: 119) |
| VPr | KKPFQQ (SEQ ID NO: 120) | 1 mM Peptide, 1 µM enzyme, 10 mM Mg(OAc)$_2$, 50 mM MOPS pH 8, 60 mM KOAc | RT/ 0.5 hr | 32% | KPFQQ (SEQ ID NO: 121) |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| VPr | YYPFQQ (SEQ ID NO: 122) | 1 mM Peptide, 1 µM enzyme, 10 mM Mg(OAc)$_2$, 50 mM MOPS pH 8, 60 mM KOAc | RT/ 0.5 hr | 56% | YPFQQ (SEQ ID NO: 123) |
| VPr | FFPFQQ (SEQ ID NO: 124) | 1 mM Peptide, 1 uM enzyme, 10 mM Mg(OAc)$_2$, 50 mM MOPS pH 8, 60 mM KOAc | RT/ 0.5 hr | 100% | FPFQQ (SEQ ID NO: 125) |
| VPr | DDPFQQ (SEQ ID NO: 126) | 1 mM Peptide, 1 uM enzyme, 10 mM Mg(OAc)$_2$, 50 mM MOPS pH 8, 60 mM KOAc | RT/ 0.5 hr | 0% | DPFQQ (SEQ ID NO: 127) |
| VPr | EEPFQQ (SEQ ID NO: 128) | 1 mM Peptide, 1 uM enzyme, 10 mM Mg(OAc)$_2$, 50 mM MOPS pH 8, 60 mM KOAc | RT/ 0.5 hr | 0% | EPFQQ (SEQ ID NO: 129) |
| VPr | NNPFQQ (SEQ ID NO: 130) | 1 mM Peptide, 1 uM enzyme, 10 mM Mg(OAc)$_2$, 50 mM MOPS pH 8, 60 mM KOAc | RT/ 0.5 hr | 15% | NPFQQ (SEQ ID NO: 131) |
| VPr | QQPFQQ (SEQ ID NO: 132) | 1 mM Peptide, 1 uM enzyme, 10 mM Mg(OAc)$_2$, 50 mM MOPS pH 8, 60 mM KOAc | RT/ 0.5 hr | 66% | QPFQQ (SEQ ID NO: 133) |
| VPr | VVPFQQ (SEQ ID NO: 134) | 1 mM Peptide, 1 uM enzyme, 10 mM Mg(OAc)$_2$, 50 mM MOPS pH 8, 60 mM KOAc | RT/ 0.5 hr | 100% | VPFQQ (SEQ ID NO: 135) |
| VPr | IIPFQQ (SEQ ID NO: 136) | 1 mM Peptide, 1 uM enzyme, 10 mM Mg(OAc)$_2$, 50 mM MOPS pH 8, 60 mM KOAc | RT/ 0.5 hr | 100% | IPFQQ (SEQ ID NO: 137) |
| VPr | LLPFQQ (SEQ ID NO: 138) | 1 mM Peptide, 1 uM enzyme, 10 mM Mg(OAc)$_2$, 50 mM MOPS pH 8, 60 mM KOAc | RT/ 0.5 hr | 100% | LPFQQ (SEQ ID NO: 139) |
| VPr | SSPFQQ (SEQ ID NO: 140) | 1 mM Peptide, 1 uM enzyme, 10 mM Mg(OAc)$_2$, 50 mM MOPS pH 8, 60 mM KOAc | RT/ 0.5 hr | 48% | SPFQQ (SEQ ID NO: 141) |
| VPr | TTPFQQ (SEQ ID NO: 142) | 1 mM Peptide, 1 uM enzyme, 10 mM Mg(OAc)$_2$, 50 mM MOPS pH 8, 60 mM KOAc | RT/ 0.5 hr | 100% | TPFQQ (SEQ ID NO: 143) |
| VPr | CCPFQQ (SEQ ID NO: 144) | 1 mM Peptide, 1 uM enzyme, 10 mM Mg(OAc)$_2$, 50 mM MOPS pH 8, 60 mM KOAc | RT/ 0.5 hr | 70% | CPFQQ (SEQ ID NO: 145) |
| VPr | WWPFQQ (SEQ ID NO: 146) | 1 mM Peptide, 1 uM enzyme, 10 mM Mg(OAc)$_2$, 50 mM MOPS pH 8, 60 mM KOAc | RT/ 0.5 hr | 82% | WPFQQ (SEQ ID NO: 147) |
| VPr | MMPFQQ (SEQ ID NO: 148) | 1 mM Peptide, 1 uM enzyme, 10 mM Mg(OAc)$_2$, 50 mM MOPS pH 8, 60 mM KOAc | RT/ 0.5 hr | 100% | MPFQQ (SEQ ID NO: 149) |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| VPr | PPPFQQ (SEQ ID NO: 150) | 1 mM Peptide, 1 uM enzyme, 10 mM Mg(OAc)$_2$, 50 mM MOPS pH 8, 60 mM KOAc | RT/ 0.5 hr | 0% | PPFQQ (SEQ ID NO: 151) |
| VPr | GGPFQQ (SEQ ID NO: 152) | 1 mM Peptide, 1 µM enzyme, 10 mM Mg(OAc)$_2$, 50 mM MOPS pH 8, 60 mM KOAc | RT/ 0.5 hr | 8% | GPFQQ (SEQ ID NO: 153) |
| VPr | HHPFQQ (SEQ ID NO: 154) | 1 mM Peptide, 1 µM enzyme, 10 mM Mg(OAc)$_2$, 50 mM MOPS pH 8, 60 mM KOAc | RT/ 0.5 hr | 12% | HPFQQ (SEQ ID NO: 155) |
| yPIP pAzF | RRPFQQ (SEQ ID NO: 116) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | AAPFQQ (SEQ ID NO: 118) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | KKPFQQ (SEQ ID NO: 120) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | YYPFQQ (SEQ ID NO: 122) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | FFPFQQ (SEQ ID NO: 124) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | DDPFQQ (SEQ ID NO: 126) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | EEPFQQ (SEQ ID NO: 128) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | NNPFQQ (SEQ ID NO: 130) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | QQPFQQ (SEQ ID NO: 132) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | VVPFQQ (SEQ ID NO: 134) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | IIPFQQ (SEQ ID NO: 136) | 1 mM Peptide, 1 uM enzyme, 10 mM Mg(OAc)$_2$, 50 mM MOPS pH 8, 60 mM KOAc | RT/ 0.5 hr | 0% | N/A |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| yPIP pAzF | LLPFQQ (SEQ ID NO: 138) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | SSPFQQ (SEQ ID NO: 140) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | TTPFQQ (SEQ ID NO: 142) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | CCPFQQ (SEQ ID NO: 144) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | WWPFQQ (SEQ ID NO: 146) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | MMPFQQ (SEQ ID NO: 148) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | PPPFQQ (SEQ ID NO: 150) | 1 mM Peptide, 1 μM enzyme, 10 mM Mg(OAc)$_2$, 50 mM MOPS pH 8, 60 mM KOAc | RT/ 0.5 hr | 26% | multiple |
| yPIP pAzF | GGPFQQ (SEQ ID NO: 152) | 1 mM Peptide, 1 uM enzyme, 10 mM Mg(OAc)$_2$, 50 mM MOPS pH 8, 60 mM KOAc | RT/ 0.5 hr | 0% | N/A |
| yPIP pAzF | HHPFQQ (SEQ ID NO: 154) | 1 mM Peptide, 1 uM enzyme, 10 mM Mg(OAc)$_2$, 50 mM MOPS pH 8, 60 mM KOAc | RT/ 0.5 hr | 0% | N/A |
| hTET | RRPFQQ (SEQ ID NO: 116) | 1 mM Peptide, 1 uM enzyme, 10 mM Mg(OAc)$_2$, 50 mM MOPS pH 8, 60 mM KOAc | RT/ 0.5 hr | 0% | |
| hTET | AAPFQQ (SEQ ID NO: 118) | 1 mM Peptide, 1 μM enzyme, 10 mM Mg(OAc)$_2$, 50 mM MOPS pH 8, 60 mM KOAc | RT/ 0.5 hr | 100% | |
| hTET | KKPFQQ (SEQ ID NO: 120) | 1 mM Peptide, 1 uM enzyme, 10 mM Mg(OAc)$_2$, 50 mM MOPS pH 8, 60 mM KOAc | RT/ 0.5 hr | 0% | |
| hTET | YYPFQQ (SEQ ID NO: 122) | 1 mM Peptide, 1 μM enzyme, 10 mM Mg(OAc)$_2$, 50 mM MOPS pH 8, 60 mM KOAc | RT/ 0.5 hr | 99% | |
| hTET | FFPFQQ (SEQ ID NO: 124) | 1 mM Peptide, 1 μM enzyme, 10 mM Mg(OAc)$_2$, 50 mM MOPS pH 8, 60 mM KOAc | RT/ 0.5 hr | 100% | |

TABLE 7-continued

Cleavage of peptide substrates by aminopeptidases.

| Enzyme | Peptide Substrate | Conditions | Temp/Time | HPLC Assay Conv | Pdt |
|---|---|---|---|---|---|
| hTET | DDPFQQ (SEQ ID NO: 126) | 1 mM Peptide, 1 µM enzyme, 10 mM Mg(OAc)$_2$, 50 mM MOPS pH 8, 60 mM KOAc | RT/0.5 hr | 4% | |
| hTET | EEPFQQ (SEQ ID NO: 128) | 1 mM Peptide, 1 uM enzyme, 10 mM Mg(OAc)$_2$, 50 mM MOPS pH 8, 60 mM KOAc | RT/0.5 hr | 0% | |
| hTET | NNPFQQ (SEQ ID NO: 130) | 1 mM Peptide, 1 µM enzyme, 10 mM Mg(OAc)$_2$, 50 mM MOPS pH 8, 60 mM KOAc | RT/0.5 hr | 69% | |
| hTET | QQPFQQ (SEQ ID NO: 132) | 1 mM Peptide, 1 µM enzyme, 10 mM Mg(OAc)$_2$, 50 mM MOPS pH 8, 60 mM KOAc | RT/0.5 hr | 63% | |
| hTET | VVPFQQ (SEQ ID NO: 134) | 1 mM Peptide, 1 µM enzyme, 10 mM Mg(OAc)$_2$, 50 mM MOPS pH 8, 60 mM KOAc | RT/0.5 hr | 100% | |
| hTET | IIPFQQ (SEQ ID NO: 136) | 1 mM Peptide, 1 µM enzyme, 10 mM Mg(OAc)$_2$, 50 mM MOPS pH 8, 60 mM KOAc | RT/0.5 hr | 100% | |
| hTET | LLPFQQ (SEQ ID NO: 138) | 1 mM Peptide, 1 µM enzyme, 10 mM Mg(OAc)$_2$, 50 mM MOPS pH 8, 60 mM KOAc | RT/0.5 hr | 100% | |
| hTET | SSPFQQ (SEQ ID NO: 140) | 1 mM Peptide, 1 µM enzyme, 10 mM Mg(OAc)$_2$, 50 mM MOPS pH 8, 60 mM KOAc | RT/0.5 hr | 100% | |
| hTET | TTPFQQ (SEQ ID NO: 142) | 1 mM Peptide, 1 µM enzyme, 10 mM Mg(OAc)$_2$, 50 mM MOPS pH 8, 60 mM KOAc | RT/0.5 hr | 100% | |
| hTET | CCPFQQ (SEQ ID NO: 144) | 1 mM Peptide, 1 µM enzyme, 10 mM Mg(OAc)$_2$, 50 mM MOPS pH 8, 60 mM KOAc | RT/0.5 hr | 32% | |
| hTET | WWPFQQ (SEQ ID NO: 146) | 1 mM Peptide, 1 µM enzyme, 10 mM Mg(OAc)$_2$, 50 mM MOPS pH 8, 60 mM KOAc | RT/0.5 hr | 4% | |
| hTET | MMPFQQ (SEQ ID NO: 148) | 1 mM Peptide, 1 uM enzyme, 10 mM Mg(OAc)$_2$, 50 mM MOPS pH 8, 60 mM KOAc | RT/0.5 hr | 0% | |
| hTET | PPPFQQ (SEQ ID NO: 150) | 1 mM Peptide, 1 uM enzyme, 10 mM Mg(OAc)$_2$, 50 mM MOPS pH 8, 60 mM KOAc | RT/0.5 hr | 0% | |
| hTET | GGPFQQ (SEQ ID NO: 152) | 1 mM Peptide, 1 µM enzyme, 10 mM Mg(OAc)$_2$, 50 mM MOPS pH 8, 60 mM KOAc | RT/0.5 hr | 33% | |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| hTET | HHPFQQ (SEQ ID NO: 154) | 1 mM Peptide, 1 µM enzyme, 10 mM Mg(OAc)$_2$, 50 mM MOPS pH 8, 60 mM KOAc | RT/ 0.5 hr | 26% | |
| PfuTET | RRPFQQ (SEQ ID NO: 116) | 1 mM Peptide, 1 µM enzyme, 10 mM Mg(OAc)$_2$, 50 mM MOPS pH 8, 60 mM KOAc | RT/ 0.5 hr | 100% | |
| PfuTET | AAPFQQ (SEQ ID NO: 118) | 1 mM Peptide, 1 µM enzyme, 10 mM Mg(OAc)$_2$, 50 mM MOPS pH 8, 60 mM KOAc | RT/ 0.5 hr | 100% | |
| PfuTET | KKPFQQ (SEQ ID NO: 120) | 1 mM Peptide, 1 µM enzyme, 10 mM Mg(OAc)$_2$, 50 mM MOPS pH 8, 60 mM KOAc | RT/ 0.5 hr | 100% | |
| PfuTET | YYPFQQ (SEQ ID NO: 122) | 1 mM Peptide, 1 µM enzyme, 10 mM Mg(OAc)$_2$, 50 mM MOPS pH 8, 60 mM KOAc | RT/ 0.5 hr | 100% | |
| PfuTET | FFPFQQ (SEQ ID NO: 124) | 1 mM Peptide, 1 µM enzyme, 10 mM Mg(OAc)$_2$, 50 mM MOPS pH 8, 60 mM KOAc | RT/ 0.5 hr | 65% | |
| PfuTET | DDPFQQ (SEQ ID NO: 126) | 1 mM Peptide, 1 µM enzyme, 10 mM Mg(OAc)$_2$, 50 mM MOPS pH 8, 60 mM KOAc | RT/ 0.5 hr | 86% | |
| PfuTET | EEPFQQ (SEQ ID NO: 128) | 1 mM Peptide, 1 µM enzyme, 10 mM Mg(OAc)$_2$, 50 mM MOPS pH 8, 60 mM KOAc | RT/ 0.5 hr | 93% | |
| PfuTET | NNPFQQ (SEQ ID NO: 130) | 1 mM Peptide, 1 µM enzyme, 10 mM Mg(OAc)$_2$, 50 mM MOPS pH 8, 60 mM KOAc | RT/ 0.5 hr | 81% | |
| PfuTET | QQPFQQ (SEQ ID NO: 132) | 1 mM Peptide, 1 µM enzyme, 10 mM Mg(OAc)$_2$, 50 mM MOPS pH 8, 60 mM KOAc | RT/ 0.5 hr | 100% | |
| PfuTET | VVPFQQ (SEQ ID NO: 134) | 1 mM Peptide, 1 uM enzyme, 10 mM Mg(OAc)$_2$, 50 mM MOPS pH 8, 60 mM KOAc | RT/ 0.5 hr | 0% | |
| PfuTET | IIPFQQ (SEQ ID NO: 136) | 1 mM Peptide, 1 uM enzyme, 10 mM Mg(OAc)$_2$, 50 mM MOPS pH 8, 60 mM KOAc | RT/ 0.5 hr | 0% | |
| PfuTET | LLPFQQ (SEQ ID NO: 138) | 1 mM Peptide, 1 µM enzyme, 10 mM Mg(OAc)$_2$, 50 mM MOPS pH 8, 60 mM KOAc | RT/ 0.5 hr | 99% | |
| PfuTET | SSPFQQ (SEQ ID NO: 140) | 1 mM Peptide, 1 µM enzyme, 10 mM Mg(OAc)$_2$, 50 mM MOPS pH 8, 60 mM KOAc | RT/ 0.5 hr | 90% | |

TABLE 7-continued

Cleavage of peptide substrates by aminopeptidases.

| Enzyme | Peptide Substrate | Conditions | Temp/Time | HPLC Assay Conv | Pdt |
|---|---|---|---|---|---|
| PfuTET | TTPFQQ (SEQ ID NO: 142) | 1 mM Peptide, 1 µM enzyme, 10 mM Mg(OAc)$_2$, 50 mM MOPS pH 8, 60 mM KOAc | RT/0.5 hr | 100% | |
| PfuTET | CCPFQQ (SEQ ID NO: 144) | 1 mM Peptide, 1 µM enzyme, 10 mM Mg(OAc)$_2$, 50 mM MOPS pH 8, 60 mM KOAc | RT/0.5 hr | 72% | |
| PfuTET | WWPFQQ (SEQ ID NO: 146) | 1 mM Peptide, 1 µM enzyme, 10 mM Mg(OAc)$_2$, 50 mM MOPS pH 8, 60 mM KOAc | RT/0.5 hr | 37% | |
| PfuTET | MMPFQQ (SEQ ID NO: 148) | 1 mM Peptide, 1 µM enzyme, 10 mM Mg(OAc)$_2$, 50 mM MOPS pH 8, 60 mM KOAc | RT/0.5 hr | 100% | |
| PfuTET | PPPFQQ (SEQ ID NO: 150) | 1 mM Peptide, 1 uM enzyme, 10 mM Mg(OAc)$_2$, 50 mM MOPS pH 8, 60 mM KOAc | RT/0.5 hr | 0% | |
| PfuTET | GGPFQQ (SEQ ID NO: 152) | 1 mM Peptide, 1 uM enzyme, 10 mM Mg(OAc)$_2$, 50 mM MOPS pH 8, 60 mM KOAc | RT/0.5 hr | 0% | |
| PfuTET | HHPFQQ (SEQ ID NO: 154) | 1 mM Peptide, 1 µM enzyme, 10 mM Mg(OAc)$_2$, 50 mM MOPS pH 8, 60 mM KOAc | RT/0.5 hr | 19% | |
| EDAPN (Glu/Asp APN) | RRPFQQ (SEQ ID NO: 116) | 1 mM Peptide, 1.3 uM enzyme, 10 mM Mg(OAc)$_2$, 50 mM MOPS pH 8, 60 mM KOAc | RT/0.5 hr | 0% | |
| EDAPN (Glu/Asp APN) | AAPFQQ (SEQ ID NO: 118) | 1 mM Peptide, 1.3 uM enzyme, 10 mM Mg(OAc)$_2$, 50 mM MOPS pH 8, 60 mM KOAc | RT/0.5 hr | 0% | |
| EDAPN (Glu/Asp APN) | KKPFQQ (SEQ ID NO: 120) | 1 mM Peptide, 1.3 uM enzyme, 10 mM Mg(OAc)$_2$, 50 mM MOPS pH 8, 60 mM KOAc | RT/0.5 hr | 0% | |
| EDAPN (Glu/Asp APN) | YYPFQQ (SEQ ID NO: 122) | 1 mM Peptide, 1.3 uM enzyme, 10 mM Mg(OAc)$_2$, 50 mM MOPS pH 8, 60 mM KOAc | RT/0.5 hr | 0% | |
| EDAPN (Glu/Asp APN) | FFPFQQ (SEQ ID NO: 124) | 1 mM Peptide, 1.3 uM enzyme, 10 mM Mg(OAc)$_2$, 50 mM MOPS pH 8, 60 mM KOAc | RT/0.5 hr | 0% | |
| EDAPN (Glu/Asp APN) | DDPFQQ (SEQ ID NO: 126) | 1 mM Peptide, 1.3 µM enzyme, 10 mM Mg(OAc)$_2$, 50 mM MOPS pH 8, 60 mM KOAc | RT/0.5 hr | 21% | |
| EDAPN (Glu/Asp APN) | EEPFQQ (SEQ ID NO: 128) | 1 mM Peptide, 1.3 µM enzyme, 10 mM Mg(OAc)$_2$, 50 mM MOPS pH 8, 60 mM KOAc | RT/0.5 hr | 31% | |

TABLE 7-continued

Cleavage of peptide substrates by aminopeptidases.

| Enzyme | Peptide Substrate | Conditions | Temp/ Time | HPLC Assay Conv | Pdt |
|---|---|---|---|---|---|
| EDAPN (Glu/Asp APN) | NNPFQQ (SEQ ID NO: 130) | 1 mM Peptide, 1.3 uM enzyme, 10 mM Mg(OAc)$_2$, 50 mM MOPS pH 8, 60 mM KOAc | RT/ 0.5 hr | 0% | |
| EDAPN (Glu/Asp APN) | QQPFQQ (SEQ ID NO: 132) | 1 mM Peptide, 1.3 uM enzyme, 10 mM Mg(OAc)$_2$, 50 mM MOPS pH 8, 60 mM KOAc | RT/ 0.5 hr | 0% | |
| EDAPN (Glu/Asp APN) | VVPFQQ (SEQ ID NO: 134) | 1 mM Peptide, 1.3 uM enzyme, 10 mM Mg(OAc)$_2$, 50 mM MOPS pH 8, 60 mM KOAc | RT/ 0.5 hr | 0% | |
| EDAPN (Glu/Asp APN) | IIPFQQ (SEQ ID NO: 136) | 1 mM Peptide, 1.3 µM enzyme, 10 mM Mg(OAc)$_2$, 50 mM MOPS pH 8, 60 mM KOAc | RT/ 0.5 hr | 42% | |
| EDAPN (Glu/Asp APN) | LLPFQQ (SEQ ID NO: 138) | 1 mM Peptide, 1.3 uM enzyme, 10 mM Mg(OAc)$_2$, 50 mM MOPS pH 8, 60 mM KOAc | RT/ 0.5 hr | 0% | |
| EDAPN (Glu/Asp APN) | SSPFQQ (SEQ ID NO: 140) | 1 mM Peptide, 1.3 uM enzyme, 10 mM Mg(OAc)$_2$, 50 mM MOPS pH 8, 60 mM KOAc | RT/ 0.5 hr | 0% | |
| EDAPN (Glu/Asp APN) | TTPFQQ (SEQ ID NO: 142) | 1 mM Peptide, 1.3 uM enzyme, 10 mM Mg(OAc)$_2$, 50 mM MOPS pH 8, 60 mM KOAc | RT/ 0.5 hr | 0% | |
| EDAPN (Glu/Asp APN) | CCPFQQ (SEQ ID NO: 144) | 1 mM Peptide, 1.3 uM enzyme, 10 mM Mg(OAc)$_2$, 50 mM MOPS pH 8, 60 mM KOAc | RT/ 0.5 hr | 0% | |
| EDAPN (Glu/Asp APN) | WWPFQQ (SEQ ID NO: 146) | 1 mM Peptide, 1.3 uM enzyme, 10 mM Mg(OAc)$_2$, 50 mM MOPS pH 8, 60 mM KOAc | RT/ 0.5 hr | 0% | |
| PfuTET | YAAFAAWADDDW1 (SEQ ID NO: 156) | 1 mM Peptide, 1.0 µM enzyme, 10 mM Mg(OAc)$_2$, 50 mM MOPS pH 8, 60 mM KOAc | RT/ 0.5 hr | Distribution | Mainly ADDDWK (SEQ ID NO: 157) |
| hTET | YAAFAAWADDDW1 (SEQ ID NO: 156) | 1 mM Peptide, 1.0 µM enzyme, 10 mM Mg(OAc)$_2$, 50 mM MOPS pH 8, 60 mM KOAc | RT/ 0.5 hr | 100% | WADDDWK (SEQ ID NO: 158) |
| VPr | YAAFAAWADDDW1 (SEQ ID NO: 156) | 1 mM Peptide, 1.2 µM enzyme, 10 mM Mg(OAc)$_2$, 50 mM MOPS pH 8, 60 mM KOAc | RT/ 0.5 hr | Distribution | Mainly ADDDWK (SEQ ID NO: 157) |

A summary of amino acid cleavage activities for select exopeptidases of Table 7 is shown in FIG. 16. Specific cleavage activities are shown for the following enzymes: "cVPr" (*V. proteolyticus* aminopeptidase), "yPIP" (*Y. pestis* proline iminopeptidase), "D/E APN" (*L. pneumophila* M1 Aminopeptidase), hTET (*Pyrococcus horikoshii* TET aminopeptidase), and Pfu API ("PfuTET" in Table 7). Specific activities with respect to terminal amino acids are classified as shown, with single-letter abbreviations used for amino acids ("XP—" represents any terminal amino acid (X) having an adjacent, or penultimate, proline (P) residue).

Example 4. Terminal Amino Acid Cleavage of Immobilized Peptides at Single Molecule Level Assays for on-chip amino acid cleavage of immobilized peptides were developed using labeled peptide conjugates. The assays were designed to provide a method for determining enzymatic recognition and cleavage activity of exopeptidases toward immobilized peptides, which could permit measurement of kinetic binding parameters and general binding affinities.

To evaluate N-terminal amino acid cleavage of a peptide, a dye labeled peptide was designed and synthesized which contained an N-terminal aspartate that was attached to the dye by way of a PEG spacer. This peptide also contained a proline residue adjacent to the modified aspartate that is recognized specifically by the enzyme proline iminopeptidase (from *Yersinia pestis*, known elsewhere and referred to herein as "yPIP"). The enzyme yPIP should cleave only an N-terminal amino acid upstream from a proline residue.

After showing that this and other labeled peptides were efficiently cut by yPIP in bulk (e.g., as described in Example 2), an on-chip dye/peptide conjugate assay was developed to observe N-terminal amino acid cleavage at the single molecule level. FIG. 17A shows a general scheme for the dye/peptide conjugate assay (inset panel). As shown, a peptide having a label attached to an N-terminal amino acid via a spacer is immobilized to a surface by way of a linker. After being exposed to peptidase, N-terminal amino acid cleavage results in the removal of the labeled residue from a detectable observation volume and is measured by a concomitant loss in signal from the label. The enzyme-peptide complex to the right of the inset panel generically depicts the N-terminal cleavage site.

FIG. 17A shows a labeled peptide construct (at bottom) that was designed and synthesized for use in the dye/peptide conjugate assay. In these experiments, a rhodamine dye (ATTO Rho6G) was attached to an N-terminal aspartate residue of a peptide having a penultimate proline residue at the N-terminus. As shown, the peptide was further conjugated to a solubilizing DNA linker with a biotin moiety for surface immobilization.

The labeled peptide conjugate was loaded onto a glass chip having an array of sample wells. Images of the chip were acquired before and after loading to determine the percent loading of sample wells at single occupancy by rhodamine fluorescence. The enzyme yPIP was then introduced onto the loaded chip and allowed to incubate for two hours at 37° C. An image of the chip following the introduction of yPIP was taken and the percentage of green dyes lost were calculated to evaluate N-terminal amino acid cleavage. FIG. 17B shows imaging results from an experiment which displayed 6-7% loading in the loading stage and 91% loss of signal in previously loaded wells after incubation with yPIP, which was indicative of N-terminal amino acid cleavage. FIG. 17C shows representative signal traces from these experiments, which demonstrate a detected increase in dye signal upon loading of labeled peptide and a detected loss in dye signal following exposure to yPIP.

As further confirmation of N-terminal amino acid cleavage at the single molecule level, on-chip FRET assays were developed to evaluate exopeptidase recognition and cleavage activity. FIG. 18A generically depicts a FRET peptide conjugate assay (panel A) and a FRET enzyme conjugate assay (panel B). In the FRET peptide conjugate assay (panel A), an immobilized peptide construct includes a FRET donor label attached to the linker and a FRET acceptor label attached at the N-terminus. N-terminal amino acid cleavage is detected by a loss in signal from the FRET acceptor label when exposed to peptidase. Additionally, this design permits monitoring loading of the peptide conjugate throughout an experiment by following emission from the FRET donor label.

In the FRET enzyme conjugate assay (panel B), an immobilized peptide construct includes a first label of a FRET pair attached to the linker and a peptidase is labeled with a second label of the FRET pair. N-terminal amino acid cleavage is detected by an enhancement in fluorescence attributable to FRET interactions, which would occur with sufficient proximity of peptidase to peptide and with sufficient residence time at the N-terminus. Additionally, this assay permits evaluating processive amino acid cleavage by a processive exopeptidase by detecting an increasing FRET signal over time with processive cleavage.

FIG. 18A also shows a FRET peptide construct under panel A that was designed and synthesized for use in the FRET peptide conjugate assay of panel A. As shown, the FRET peptide construct included a rhodamine dye (ATTO 647N) attached to an N-terminal aspartate residue of a peptide having a penultimate proline residue at the N-terminus. The peptide was further conjugated to a solubilizing DNA linker which was attached to a cyanine dye (Cy3B) for FRET and a biotin moiety for surface immobilization.

In this experiment, the FRET peptide construct was loaded onto a glass chip having an array of sample wells, and collected light was filtered first by a green filter and then a red filter. Loading of the FRET peptide construct was detected by measuring a signal passing through both the green and red filters. Terminal amino acid cleavage was detected when the signal was measurable only in the green filter, which indicated that the red dye conjugated N-terminal amino acid from the FRET peptide construct was cleaved by yPIP. This detection pattern is illustrated in panel C. As shown, if both dyes are detectable before the addition of yPIP, and only the green dye is visible after incubation with yPIP, it can be reasonably concluded this change in detection pattern is due to cleavage of the peptide and not photobleaching or loss of the peptide as a whole. Additionally, an increase in fluorescence from the lone green dye would be expected, as its emissions are no longer absorbed by the red dye.

Following loading of the FRET peptide construct onto the chip, which had been modified by surface passivation using phosphonic acid and silane, yPIP was introduced and images were obtained at several time points. To assess the overall cleaving trend, the ratio of (green)/(green+red) was computed for each experiment. This ratio increases with the extent of cleaving that occurs. FIG. 18B is a plot of FRET emission ratio across all apertures at different time points of incubation with yPIP. As shown, the green dye contribution to the ratio of fluorescence emissions increases over time during incubation with yPIP, indicating that more N-terminal aspartate residues have been cut, leaving behind the truncated peptide with just the green dye.

Cutting efficiency was then evaluated at different time points by determining at which time points dye fluorescence was observed. This was done with simple thresholding—e.g., if the average dye emission signal was >2.5 during excitation, the dyes were determined to be present (when each corresponding filter was applied). Apertures exhibiting cutting would then display both green and red dyes during the loading phase of the experiment, but only green dye at time points exposed to yPIP. As shown in FIG. 18C, progressively more cutting was observed as the chip was exposed to longer incubation times with yPIP. Example signal traces showing cutting displayed at each of the three yPIP-treated time points are shown in FIG. 18D.

Additional experiments were performed with yPIP and other peptidases using chips that had been modified by surface passivation using dextran, which produced similar results showing an increase in terminal amino acid cleavage over time following introduction of peptidase onto chips. FIG. 18E is a plot of FRET emission ratio across loaded apertures at different time points of incubation with yPIP. FIG. 18F is a plot of FRET emission ratio across loaded apertures at different time points of incubation with an aminopeptidase. Overall, the experiments here demonstrate that N-terminal amino acid cleavage is detectable in real-time at the single molecule level using different exopeptidases and different labeling strategies.

Example 5. Terminal Amino Acid Discrimination by Labeled Affinity Reagent

An adaptor protein involved in proteolytic pathways was identified as a potential candidate for use as a labeled affinity reagent for detecting N-terminal aromatic residues. The adaptor protein, ClpS2 from an α-proteobacterium (*A. tumefaciens*), was expressed and labeled at an exposed cysteine residue. FIG. 19A shows a crystal structure of the ClpS2 protein, with the exposed cysteine residue shown as sticks. The exposed cysteine residue was labeled with a rhodamine dye (ATTO 532).

Peptides having different N-terminal aromatic residues were prepared to test whether the labeled ClpS2 was capable of N-terminal amino acid discrimination at the single molecule level. Example single molecule intensity traces from these experiments are shown in FIG. 19B. As shown, the signal traces demonstrate residue-specific on-off binding patterns corresponding to the labeled affinity reagent reversibly binding the N-terminus of peptides having either: an N-terminal phenylalanine residue (F, top signal trace), an N-terminal tyrosine residue (Y, middle signal trace), or an N-terminal tryptophan residue (W, bottom signal trace).

Further analyses of the single molecule trajectories were carried out, with the results shown in FIGS. 19C-19E. FIG. 19C is a plot showing discriminant pulse durations (time duration of signal peaks) among the three N-terminal residues when reversibly bound by labeled ClpS2. FIG. 19D is a plot showing discriminant interpulse durations (time duration between signal pulses) among the three N-terminal residues. FIG. 19E shows plots which further illustrate the discriminant pulse durations among phenylalanine, tyrosine, and tryptophan at peptide N-termini. Mean pulse duration for the different N-terminal residues is visualized by histograms (A)-(B) and layered histogram (C).

Another adaptor protein, ClpS from *Thermosynochoccus elongatus* (teClpS) was evaluated for use as a labeled affinity reagent for leucine recognition. The data obtained from dwell time analysis, shown in FIGS. 19F-19H, demonstrated that the labeled teClpS protein produces detectable binding interactions with a terminal leucine residue of polypeptides with a mean pulse duration of 0.71 seconds. The amino acid sequence of the teClpS protein used in these experiments is shown in Table 1.

Similar experiments were carried out to evaluate *A. tumefaciens* ClpS1 and *S. elongatus* ClpS2 as potential reagents for leucine recognition, and GID4 as a potential reagent for proline recognition. FIG. 19I shows example results from dwell time analysis which showed differentiable recognition of phenylalanine, leucine, tryptophan, and tyrosine by *A. tumefaciens* ClpS1. FIG. 19J shows example results from dwell time analysis demonstrating leucine recognition by *S. elongatus* ClpS2. FIGS. 19K-19L show example results from dwell time analysis demonstrating proline recognition by GID4.

Example 6. Polypeptide Sequencing by Recognition During Degradation

Experiments were conducted to evaluate peptide sequencing by N-terminal amino acid recognition during an ongoing degradation reaction. Example results from these experiments are shown in FIGS. 20A-20D, which show single molecule intensity traces obtained over two independent polypeptide sequencing reactions conducted in real-time using a labeled ClpS2 protein and an aminopeptidase in the same reaction mixture. In each reaction, a polypeptide of sequence YAAWAAFADDDWK (SEQ ID NO: 78) was immobilized to a chip surface through the C-terminal lysine residue by loading the peptide composition (10 pM) onto chips for 20 minutes, and the immobilized peptide was monitored in the presence of a labeled affinity reagent (ATTO 542-labeled *A. Tumefaciens* ClpS2-V1 at 500 nM) and an aminopeptidase cleaving reagent (VPr at 8 µM).

FIGS. 20A and 20C show signal trace data for two different sequencing runs, with the top panel (panel 1 in FIG. 20A, panel 2 in FIG. 20C) showing a full trace, and the bottom panels (Y, W, F) showing zoomed-in regions corresponding to each of the highlighted regions in the full trace. FIGS. 20B and 20D show pulse duration statistics in histograms for the trace data of the corresponding panels as labeled in FIGS. 20A and 20C, respectively. As shown in the full signal trace of each sequencing run (panels 1, 2), three separate time intervals of signal pulses were observed over the course of the reaction. As highlighted by the zoomed-in regions (panels Y, W, F), the three intervals are visually distinguishable from one another based on an observable difference in pattern of signal pulses.

To further analyze the signal pulse data, pulse duration statistics were determined for each time interval (FIGS. 20B and 20D). The differences in pulse duration distribution were determined to correspond to those observed for these amino acids individually in steady-state on-chip binding assays with ClpS2, and the signal pulse information was phenotypically consistent between intervals from sequencing runs and the individual amino acid binding assays.

As confirmed by the analysis of signal pulse information, the three time intervals of signal pulses observed over the progression of each sequencing run correspond to recognition patterns of Y, W, and F, respectively (panels 1, 2). The intervening time period between signal pulse patterns is due to the selectivity of ClpS2-V1, which does not bind to N-terminal alanine residues. As illustrated by the full signal trace, the first interval corresponds to Y recognition, which is followed by a pause as VPr peptidase cuts Y and two alanine residues, followed by the second interval corresponding to W recognition, which is followed by another pause as VPr peptidase cuts W and two alanine residues, and finally the third interval corresponding to F recognition before VPr peptidase cuts off the F and stops at the remaining ADDDWK (SEQ ID NO: 157) peptide. These results show that pulse duration information, which was obtained by terminal amino acid recognition during an ongoing degradation reaction, can be used to determine characteristic patterns that discriminate between different types of terminal amino acids.

Example 7. Terminal Amino Acid Identification and Cleavage by Labeled Exopeptidase Studies were performed to investigate the potential for a single reagent that is capable of both identifying a terminal amino acid of a peptide and cleaving the terminal amino acid from the peptide. As a single reagent, an exopeptidase must be able to bind to the peptide while retaining cleavage activity toward a terminal residue. Accordingly, an initial approach employing traditional labeling strategies was carried out by targeting the native surface-exposed amino acids of different exopeptidases. In these experiments, surface-exposed cysteine (—SH) or lysine (—NH$_2$) residues were labeled with fluorescent dyes, which proved to be a robust methodology for exopeptidase labeling. In certain cases, however, this approach produced a heterogeneous population of proteins that are labeled with one or more dyes.

In order to more precisely control where labeling occurs on exopeptidases and ensure that each exopeptidase molecule is labeled with a single fluorescent dye (as well as eliminate off-target reactivity of the dye), a new labeling strategy was investigated. In these experiments, labeled exopeptidases were prepared using a site-specific labeling strategy in which an unnatural amino acid containing a reactive functional group is introduced into the exopeptidase (see, e.g., Chin, J. W., et al. J Am Chem Soc. 2002 Aug. 7; 124(31):9026-9027).

The proline iminopeptidase from *Yersinia pestis* (yPIP) was modified by mutation of a lysine residue at position 287 to a residue having a para-azidophenylalanine (pAzF) side chain. FIG. 21A shows a crystal structure of yPIP, with the mutation indicated by the chemical structure of pAzF shown with the K287 sidechain shown as sticks. This mutation site was selected based on the stability provided by the alpha helix at this position and to ensure that the new azido functional group is solvent exposed.

A pEVOL plasmid containing the mutant amino tRNA synthetase and the mutant tRNA necessary to incorporate pAzF into the amino acid chain was obtained. The amber stop codon (TAG), which is necessary for the specific incorporation of pAzF, was then introduced into the cDNA using the QuickChange II mutagenesis kit. The cDNA was then sequenced and the TAG codon position was confirmed. This was followed by co-transfection of both the pET21b+ plasmid containing the yPIP amber mutant and the pEVOL plasmid containing the cellular machinery to charge the tRNA for the amber codon with pAzF. The co-transfected cells were then grown to 0.8 ODU, induced with 0.02% arabinose and 1 mM IPTG in the presence of 2 mM pAzF in 2 L of LB, and harvested using chemolysis. Purification was carried out using a 5 mL affinity chromatography column, and the protein was eluted in 100 mM imidazole. The resulting protein was then dialyzed and concentrated into 50 mM HEPES pH 8.0 and 0.5 M KCl, aliquoted, and flash frozen prior to storage at −20° C.

To confirm the presence of the azido group in the purified protein, DBCO-Cy3 (2 mM) was reacted with the pAzF-yPIP variant (220 µM) (Reaction Conditions: 50 mM HEPES pH 8.0, 0.5 mM KCl, 20% DMSO; 10 hours at 37° C., 48 hours at room temperature). The protein reaction product was purified by size-exclusion chromatography, and it was determined that the resulting protein was 100% labeled with the azide-reactive DBCO-Cy3 reagent (FIG. 21B), indicating robust incorporation of the unnatural amino acid.

Protein labeling and purity of the final product was confirmed by SDS-PAGE analysis of the unlabeled and labeled pAzF variant. FIG. 21C shows a picture of SDS-PAGE gel confirming Cy3-labeling of pAzF-yPIP (overexposed image of gel shown in FIG. 21D to show ladder). FIG. 21E shows a picture of Coomassie-stained gel confirming that both dye and protein co-migrate and are pure.

The dye-labeled pAzF-yPIP variant was used in an activity assay to confirm that the enzyme was still active after labeling and purification. As shown in FIG. 21F, Cy3-pAzF-yPIP was able to hydrolyze 100% of the peptide substrate in 1 hour using 1000-fold excess substrate, as measured by HPLC. These experiments demonstrate a methodology which allows site-specific modification and labeling of an exopeptidase with minimal perturbation of the native protein structure/function.

Example 8. Recognition of Modified Amino Acids in Polypeptide Sequencing

Experiments were performed to evaluate recognition of amino acids containing specific post-translation modifications. A triple-mutant variant (T8V, S10A, K15L) of the Src Homology 2 (SH2) domain from Fyn, a tyrosine kinase, was tested as a potential recognition molecule for phosphorylated tyrosine residues in peptide sequencing. The variant protein was immobilized to the bottom of sample wells, and single-molecule signal traces were collected upon addition of a fluorescently-labeled peptide containing N-terminal phospho-tyrosine. Peptide binding by the immobilized protein was detected during these experiments, as shown by the representative traces in FIG. 22A. Pulse duration data collected during these experiments is shown in FIG. 22B (top, middle, and bottom plots corresponding to the top, middle, and bottom traces of FIG. 22A, respectively). Pulse duration and interpulse duration statistics are shown in FIG. 22C (top and bottom panels, respectively).

Control experiments were performed to confirm that the Fyn protein was specific for the phosphorylated tyrosine. The experiments were repeated for each of three different peptides: a first peptide containing N-terminal unmodified tyrosine (Y; FIG. 22D), a second peptide containing N-terminal and penultimate unmodified tyrosines (YY; FIG. 22E), and a third peptide containing N-terminal phosphoserine (FIG. 22F). As shown, binding was not detected with any of the peptides used in the negative control experiments.

Example 9. Recognition of Penultimate Amino Acids in Polypeptide Sequencing

Experiments were performed to determine the effects of penultimate amino acids on pulse duration for A. *Tumefaciens* ClpS2-V1. Forty-nine different fluorescently-labeled peptides were prepared containing unique dipeptide sequences at the N-terminus, where the N-terminal amino acid was F, W, or Y, and the penultimate position was one of the 20 natural amino acids. For each experiment, ClpS2-V1 was immobilized at the bottom of sample wells, and single-molecule signal traces were collected for $10^{-20}$ minutes upon addition of one of the fluorescently-labeled peptides. Pulse duration data was collected for a minimum of 50 sample wells for each peptide.

FIG. 23 shows the median pulse duration for each of the 50 peptides, with data points grouped by penultimate amino acid (x-axis) and N-terminal amino acids represented with different symbols.

Example 10. Simultaneous Amino Acid Recognition with Multiple Recognition Molecules Single-molecule peptide recognition experiments were performed to demonstrate terminal amino acid recognition of an immobilized peptide by more than one labeled recognition molecule. Single peptide molecules containing N-terminal phenylalanine (FYPLPWPDDDY (SEQ ID NO: 79)) were immobilized in sample wells of a chip. Buffer containing 500 nM each of atClpS1 (*Agrobacterium tumifaciens* ClpS1; sequence provided in Table 1) and atClpS2-V1 (*Agrobacterium tumifaciens* ClpS2 variant 1; sequence provided in Table 1) was added, where atClpS1 and atClpS2-V1 were labeled with Cy3 and Cy3B, respectively. Since the intensity of Cy3B is higher than Cy3, atClpS2-V1 binding events were readily distinguishable from atClpS1 binding events.

FIGS. 24A-24C shows the results of the experiments showing single-molecule peptide recognition with differentially labeled recognition molecules. A representative trace is displayed in FIG. 24A. The pulse duration distributions were distinct for each binder (FIG. 24B) and corresponded to their kinetic profiles as observed in single-binder experiments. Mean pulse duration was 1.3 seconds for atClpS1 and 1.0 seconds for atClpS2-V1 (FIG. 24C). Pulse rate was also distinct: 8.1 pulses/min for atClpS1 and 14.1 pulses/min for atClp2-V1 (FIG. 24C). Thus, when more than one recognition molecule is included for dynamic recognition of immobilized peptides, the binding characteristics of each recognition molecule (including pulse duration, interpulse duration, and pulse rate) can simultaneously provide information about peptide sequence.

Example 11. Enhancing Photostability with Recognition Molecule Linkers

Experiments were performed to evaluate the photostability of immobilized peptides during single-molecule sequencing. The dye-labeled atClpS2-V1 described in Example 5 was added to sample wells containing immobilized peptide substrates in the presence of excitation light at 532 nm to monitor recognition by emission from ATTO 532. A representative trace is shown in FIG. 25A. As shown in the top panel, recognition was observed to cease at approximately 600 seconds into the experiment. The bottom panel is a zoomed view showing signal pulses at approximately 180-430 seconds into the reaction.

FIG. 25B shows a visualization of the crystal structure of the ClpS2 protein used in these experiments. As shown, the cysteine residue that serves as the dye conjugation site is approximately 2 nm from the terminal amino acid binding site. It was hypothesized that photodamage to the peptide was caused by proximity of the dye to the N-terminus of peptide during binding. To mitigate the potential photodamaging effects of dye proximity, the ClpS2 protein was dye-labeled through a linker that increased distance between the dye and N-terminus of peptide by more than 10 nm. The linker included streptavidin and a double-stranded nucleic acid; the double-stranded nucleic acid was labeled with two Cy3B dye molecules and attached to streptavidin through a bis-biotin moiety, and a ClpS2 protein was attached to each of the remaining two binding sites on streptavidin through a biotin moiety. A representative trace using this dye-shielded ClpS2 molecule is shown in FIG. 25C. As shown in the top panel, recognition time was extended to approximately 6,000 seconds into the experiment. The bottom panel is a zoomed view showing signal pulses at approximately 750-930 seconds into the reaction.

A DNA-streptavidin recognition molecule was generated with a linker containing a double-stranded nucleic acid labeled with two Cy3B dye molecules and attached to streptavidin through a bis-biotin moiety, and a single ClpS2 protein attached to the remaining two binding sites on streptavidin through a bis-biotin moiety. This construct was used in a single-molecule peptide sequencing reaction, and representative traces from these experiments are shown in FIGS. 26A-26D.

The sequencing experiments described in example 6 were repeated, with the reaction conditions changed as follows: the DNA-streptavidin ClpS2 recognition molecule was used in combination with hTET amino acid cleaving reagent. A representative signal trace is shown in FIG. 27.

Example 12. Sequencing by Recognition During Degradation by Multiple Exopeptidases Experiments were performed to evaluate the use of multiple types of exopeptidases with differential cleavage specificities in a single-molecule peptide sequencing reaction mixture. Single peptide molecules (YAAWAAFADDDWK (SEQ ID NO: 78)) were immobilized through a C-terminal lysine residue in sample wells of a chip. Buffer containing atClpS2-V1 for amino acid recognition and hTET for amino acid cleavage was added. A representative trace is displayed in FIG. 28A, with expanded views of pulse pattern regions shown in FIG. 28B.

An experiment was carried out to evaluate sequencing reactions in the presence of two types of exopeptidases with differential specificities. Single peptide molecules (FYPLPWPDDDYK (SEQ ID NO: 80)) were immobilized through a C-terminal lysine residue in sample wells of a chip. Buffer containing atClpS2-V1 for amino acid recognition, and both hTET and yPIP for amino acid cleavage was added. A representative trace is displayed in FIG. 28C, with expanded views of pulse pattern regions shown in FIG. 28D. Additional representative traces from these reaction conditions are shown in FIG. 28E.

Further experiments were carried out to evaluate sequencing reactions in the presence of two types of exopeptidases with differential specificities. Single peptide molecules (YPLPWPDDDYK (SEQ ID NO: 81)) were immobilized through a C-terminal lysine residue in sample wells of a chip. In one experiment, buffer containing atClpS2-V1 for amino acid recognition, and both hTET and yPIP for amino acid cleavage was added. A representative trace is displayed in FIG. 28F, with expanded views of pulse pattern regions shown in FIG. 28G. Additional representative traces from these reaction conditions are shown in FIG. 28H. In a further experiment, buffer (50 mM MOPS, 60 mM KOAc, 200 µM Co(OAc)$_2$) containing atClpS2-V1 for amino acid recognition, and both PfuTET and yPIP for amino acid cleavage was added. A representative trace is displayed in FIG. 28I, with expanded views of pulse pattern regions shown in FIG. 28J.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the application describes "a composition comprising A and B," the application also contemplates the alternative embodiments "a composition consisting of A and B" and "a composition consisting essentially of A and B."

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

What is claimed is:

1. A method of polypeptide sequencing, the method comprising:
    (a) detecting a first series of signal pulses indicative of association of one or more amino acid recognition molecules with a first amino acid at a terminus of a single polypeptide molecule;
    (b) removing the first amino acid from the terminus of the single polypeptide molecule, wherein a second amino acid is exposed at the terminus of the single polypeptide molecule; and
    (c) identifying the second amino acid based at least in part on a first characteristic pattern in the first series of signal pulses, wherein each signal pulse of the first characteristic pattern is indicative of an individual association event between an amino acid recognition molecule and the first amino acid prior to (b).

2. The method of claim 1, wherein the detecting and the removing are performed in a single reaction mixture.

3. The method of claim 2, wherein the single reaction mixture comprises the one or more amino acid recognition molecules and a cleaving reagent that removes one or more amino acids from the terminus of the single polypeptide molecule.

4. The method of claim 3, wherein the first amino acid is removed by the cleaving reagent.

5. The method of claim 3, wherein the single reaction mixture comprises an amino acid recognition molecule and the cleaving reagent in a ratio of between about 10:1 and about 200:1.

6. The method of claim 3, wherein the single reaction mixture comprises an amino acid recognition molecule and the cleaving reagent in a ratio of between about 50:1 and about 150:1.

7. The method of claim 1, further comprising identifying the first amino acid based on the first characteristic pattern in the first series of signal pulses.

8. The method of claim 1, wherein each of the one or more amino acid recognition molecules comprises a recognition protein or a nucleic acid aptamer.

9. The method of claim 8, wherein the recognition protein is a degradation pathway protein, a peptidase, an antibody, an aminotransferase, a tRNA synthetase, or an SH2 domain-containing protein or fragment thereof.

10. The method of claim 1, wherein each of the one or more amino acid recognition molecules comprises a detectable label.

11. The method of claim 10, wherein the detectable label is a luminescent label or a conductivity label.

12. The method of claim 1, wherein the single polypeptide molecule is immobilized to a surface.

13. The method of claim 1, wherein the first series of signal pulses is a series of real-time signal pulses.

14. The method of claim 1, wherein signal pulses of the first series of signal pulses comprise a mean pulse duration of between about 1 millisecond and about 10 seconds.

15. The method of claim 14, wherein the mean pulse duration is between about 10 milliseconds and about 100 milliseconds or between about 100 milliseconds and about 500 milliseconds.

16. The method of claim 1, wherein the first and second amino acids are contiguous amino acids of a different type.

17. The method of claim 1, wherein the first and second amino acids are contiguous amino acids of the same type.

18. The method of claim 1, wherein (c) comprises identifying that the second amino acid comprises a post-translational modification.

19. The method of claim 18, wherein the post-translational modification is selected from acetylation, ADP-ribosylation, caspase cleavage, citrullination, formylation, N-linked glycosylation, O-linked glycosylation, hydroxylation, methylation, myristoylation, neddylation, nitration, oxidation, palmitoylation, phosphorylation, prenylation, S-nitrosylation, sulfation, sumoylation, and ubiquitination.

20. The method of claim 18, wherein the second amino acid has a side chain comprising the post-translational modification.

21. The method of claim 20, wherein the side chain comprising the post-translational modification is phospho-tyrosine or phospho-serine.

22. The method of claim 1, further comprising repeating steps (a)-(c) one or more times to determine an amino acid sequence of the single polypeptide molecule.

* * * * *